US009758805B2

(12) United States Patent
De Kruif et al.

(10) Patent No.: US 9,758,805 B2
(45) Date of Patent: *Sep. 12, 2017

(54) METHODS AND MEANS FOR THE PRODUCTION OF IG-LIKE MOLECULES

(71) Applicant: Merus N.V., Utrecht (NL)

(72) Inventors: Cornelis Adriaan De Kruif, Utrecht (NL); Linda Johanna Aleida Hendriks, Utrecht (NL); Ton Logtenberg, Utrecht (NL)

(73) Assignee: Merus N.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,581

(22) Filed: Dec. 18, 2015

(65) Prior Publication Data

US 2016/0177364 A1    Jun. 23, 2016

Related U.S. Application Data

(63) Continuation of application No. 13/866,756, filed on Apr. 19, 2013, now Pat. No. 9,248,182.

(60) Provisional application No. 61/635,935, filed on Apr. 20, 2012.

(51) Int. Cl.
| | | |
|---|---|---|
| *C12N 15/00* | (2006.01) | |
| *C12N 5/07* | (2010.01) | |
| *C12P 21/04* | (2006.01) | |
| *C12P 21/00* | (2006.01) | |
| *C07K 16/12* | (2006.01) | |
| *C07K 16/26* | (2006.01) | |
| *C07K 16/36* | (2006.01) | |
| *C07K 16/46* | (2006.01) | |
| *C07K 16/18* | (2006.01) | |
| *C07K 16/28* | (2006.01) | |
| *A61K 39/395* | (2006.01) | |
| *A61K 39/40* | (2006.01) | |
| *A61K 39/00* | (2006.01) | |

(52) U.S. Cl.
CPC .......... *C12P 21/005* (2013.01); *A61K 39/395* (2013.01); *A61K 39/3955* (2013.01); *A61K 39/40* (2013.01); *C07K 16/12* (2013.01); *C07K 16/1278* (2013.01); *C07K 16/1282* (2013.01); *C07K 16/18* (2013.01); *C07K 16/26* (2013.01); *C07K 16/28* (2013.01); *C07K 16/283* (2013.01); *C07K 16/2809* (2013.01); *C07K 16/2866* (2013.01); *C07K 16/2896* (2013.01); *C07K 16/36* (2013.01); *C07K 16/468* (2013.01); *A61K 2039/507* (2013.01); *C07K 2317/14* (2013.01); *C07K 2317/31* (2013.01); *C07K 2317/526* (2013.01); *C07K 2317/56* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,801,687 A | 1/1989 | Ngo |
| 4,816,567 A | 3/1989 | Cabilly et al. |
| 5,151,504 A | 9/1992 | Croze |
| 5,223,409 A | 6/1993 | Ladner et al. |
| 5,385,839 A | 1/1995 | Stinski |
| 5,627,037 A | 5/1997 | Ward et al. |
| 5,631,169 A | 5/1997 | Lakowicz et al. |
| 5,641,640 A | 6/1997 | Hanning |
| 5,667,988 A | 9/1997 | Barbas et al. |
| 5,731,168 A | 3/1998 | Carter et al. |
| 5,733,779 A | 3/1998 | Reff |
| 5,770,429 A | 6/1998 | Lonberg et al. |
| 5,772,997 A | 6/1998 | Hudziak et al. |
| 5,783,186 A | 7/1998 | Arakawa et al. |
| 5,789,208 A | 8/1998 | Sharon |
| 5,834,237 A | 11/1998 | Jacobs et al. |
| 5,885,827 A | 3/1999 | Wabl et al. |
| 5,888,789 A | 3/1999 | Rodriguez |
| 5,965,371 A | 10/1999 | Marasco et al. |
| 6,004,940 A | 12/1999 | Marasco et al. |
| 6,054,297 A | 4/2000 | Carter et al. |
| 6,080,560 A | 6/2000 | Russell et al. |
| 6,114,598 A | 9/2000 | Kucherlapati et al. |
| 6,180,357 B1 | 1/2001 | Young et al. |
| 6,207,446 B1 | 3/2001 | Szostak et al. |
| 6,265,150 B1 | 7/2001 | Terstappen et al. |
| 6,291,740 B1 | 9/2001 | Bremel et al. |
| 6,303,341 B1 | 10/2001 | Hiatt et al. |

(Continued)

FOREIGN PATENT DOCUMENTS

| | | |
|---|---|---|
| AU | 2003250074 A1 | 2/2004 |
| CA | 2405961 A1 | 11/2001 |

(Continued)

OTHER PUBLICATIONS

Atwell, S. et al., "Stable Heterodimers from Remodeling the Domain Interface of a Homodimer using a Phage Display Library," JMB, vol. 270, pp. 26-35 (1997).

Baeuerle, P., et al., "Bispecific T-Cell Engaging Antibodies for Cancer Therapy," Cancer Research, vol. 69(12), pp. 4941-4944 (2009).

Bogan, A., et. al., "Anatomy of Hot Spots in Protein Interfaces," JMB, vol. 280, pp. 1-9 (1998).

Carter, P., "Bispecific human IgG by design," Journal of Immunological Methods, vol. 248, pp. 7-15, (2001).

Carter, P., et al., "Toward the Production of Bispecific Antibody Fragments for Clinical Applications," Journal of Hematotherapy, vol. 4, pp. 463-470 (1995).

(Continued)

*Primary Examiner* — Michael Burkhart
(74) *Attorney, Agent, or Firm* — Nelson Mullins Riley & Scarborough LLP; Jane E. Remillard, Esq.; Cynthia L. Kanik

(57) ABSTRACT

The invention provides means and methods for producing one or more Ig-like molecules in a single host cell. Novel CH3 mutations enabling the production of monospecific and/or bispecific Ig-like molecules of interest are also provided.

43 Claims, 46 Drawing Sheets

(56) References Cited

U.S. PATENT DOCUMENTS

| | | |
|---|---|---|
| 6,335,163 B1 | 1/2002 | Sharon |
| 6,596,541 B2 | 7/2003 | Murphy et al. |
| 7,067,284 B1 | 6/2006 | Barbas et al. |
| 7,105,348 B2 | 9/2006 | Murphy et al. |
| 7,183,076 B2 | 2/2007 | Arathoon et al. |
| 7,262,028 B2 | 8/2007 | Van Berkel et al. |
| 7,329,530 B2 | 2/2008 | Houtzager et al. |
| 7,429,486 B2 | 9/2008 | Van Berkel et al. |
| 7,491,516 B2 | 2/2009 | Collinson et al. |
| 7,579,446 B2 | 8/2009 | Bakker et al. |
| 7,642,228 B2 | 1/2010 | Carter et al. |
| 7,696,330 B2 | 4/2010 | Meulen et al. |
| 7,740,852 B2 | 6/2010 | Bakker et al. |
| 7,777,010 B2 | 8/2010 | Logtenberg |
| 7,858,086 B2 | 12/2010 | Geuijen et al. |
| 7,901,919 B2 | 3/2011 | Houtzager et al. |
| 7,919,257 B2 | 4/2011 | Hoogenboom et al. |
| 7,927,834 B2 | 4/2011 | Van Berkel et al. |
| 7,932,360 B2 | 4/2011 | Van Berkel et al. |
| 7,960,518 B2 | 6/2011 | Throsby et al. |
| 7,968,092 B2 | 6/2011 | Throsby et al. |
| 8,052,974 B2 | 11/2011 | Throsby et al. |
| 8,106,170 B2 | 1/2012 | Ter Meulen et al. |
| 8,148,497 B2 | 4/2012 | Bakker et al. |
| 8,192,927 B2 | 6/2012 | Van Den Brink et al. |
| 8,211,431 B2 | 7/2012 | Throsby et al. |
| 8,241,631 B2 | 8/2012 | Throsby et al. |
| 8,268,756 B2 | 9/2012 | Logtenberg et al. |
| 8,470,327 B2 | 6/2013 | Throsby et al. |
| 8,592,562 B2 | 11/2013 | Kannan et al. |
| 8,911,738 B2 | 12/2014 | Throsby et al. |
| 9,012,371 B2 | 4/2015 | Logtenberg et al. |
| 9,248,181 B2 | 2/2016 | De Kruif et al. |
| 9,248,182 B2 | 2/2016 | De Kruif et al. |
| 9,358,286 B2 | 6/2016 | De Kruif et al. |
| 2002/0088016 A1 | 7/2002 | Bruggemann |
| 2002/0138857 A1 | 9/2002 | Ghayur |
| 2003/0039958 A1 | 2/2003 | Holt et al. |
| 2003/0077739 A1 | 4/2003 | Simmons et al. |
| 2003/0091561 A1 | 5/2003 | van de Winkel et al. |
| 2003/0093820 A1 | 5/2003 | Green et al. |
| 2003/0096225 A1 | 5/2003 | Logtenberg |
| 2003/0194403 A1 | 10/2003 | van de Winkel et al. |
| 2003/0207346 A1 | 11/2003 | Arathoon et al. |
| 2003/0219829 A1 | 11/2003 | Logtenberg et al. |
| 2003/0224408 A1 | 12/2003 | Hoogenboom et al. |
| 2005/0014261 A1 | 1/2005 | Houtzager et al. |
| 2005/0037001 A1 | 2/2005 | Germeraad et al. |
| 2005/0170398 A1 | 8/2005 | Van Berkel et al. |
| 2006/0015949 A1 | 1/2006 | Lonberg et al. |
| 2006/0015957 A1 | 1/2006 | Lonberg et al. |
| 2006/0088520 A1 | 4/2006 | Germeraad et al. |
| 2006/0117699 A1 | 6/2006 | Di Trapani |
| 2006/0160184 A1 | 7/2006 | Hoogenboom et al. |
| 2006/0205077 A1 | 9/2006 | Schwenk et al. |
| 2006/0257397 A1 | 11/2006 | Throsby et al. |
| 2007/0054362 A1 | 3/2007 | Van Berkel et al. |
| 2007/0059766 A1 | 3/2007 | Logtenberg et al. |
| 2007/0280945 A1 | 12/2007 | Stevens et al. |
| 2008/0070799 A1 | 3/2008 | Bakker et al. |
| 2008/0241166 A1 | 10/2008 | Tomlinson et al. |
| 2009/0017521 A1 | 1/2009 | Houtzager et al. |
| 2009/0054254 A1 | 2/2009 | Throsby et al. |
| 2009/0074765 A1 | 3/2009 | Carmeliet et al. |
| 2009/0130652 A1 | 5/2009 | Throsby et al. |
| 2009/0181855 A1 | 7/2009 | Vasquez et al. |
| 2009/0182127 A1 | 7/2009 | Kjaergaard et al. |
| 2009/0263864 A1 | 10/2009 | Van Berkel et al. |
| 2010/0015133 A1 | 1/2010 | Igawa et al. |
| 2010/0069614 A1 | 3/2010 | Houtzager et al. |
| 2010/0146647 A1 | 6/2010 | Logtenberg et al. |
| 2010/0172917 A1 | 7/2010 | Ter Meulen et al. |
| 2010/0286374 A1 | 11/2010 | Kannan et al. |
| 2010/0297153 A1 | 11/2010 | Geuijen et al. |
| 2010/0310572 A1 | 12/2010 | Bakker et al. |
| 2010/0310586 A1 | 12/2010 | Dolcetti et al. |
| 2010/0331527 A1 | 12/2010 | Davis et al. |
| 2011/0177073 A1 | 7/2011 | Van Berkel et al. |
| 2011/0195454 A1 | 8/2011 | McWhirter et al. |
| 2011/0268739 A1 | 11/2011 | Throsby et al. |
| 2012/0021409 A1 | 1/2012 | McWhirter et al. |
| 2012/0039898 A1 | 2/2012 | Throsby et al. |
| 2012/0058907 A1 | 3/2012 | Logtenberg et al. |
| 2012/0076794 A1 | 3/2012 | Throsby et al. |
| 2012/0093823 A1 | 4/2012 | Van Den Brink et al. |
| 2012/0141493 A1 | 6/2012 | Throsby et al. |
| 2012/0177637 A1 | 7/2012 | Hoogenboom et al. |
| 2012/0192300 A1 | 7/2012 | Babb et al. |
| 2012/0276115 A1 | 11/2012 | Van Den Brink et al. |
| 2012/0315278 A1 | 12/2012 | Throsby et al. |
| 2013/0115208 A1 | 5/2013 | Ho et al. |
| 2013/0336981 A1 | 12/2013 | De Kruif et al. |
| 2014/0072579 A1 | 3/2014 | De Kruif et al. |
| 2014/0120096 A1 | 5/2014 | Bakker et al. |
| 2014/0140999 A1 | 5/2014 | De Kruif et al. |
| 2014/0314755 A1 | 10/2014 | Logtenberg et al. |
| 2014/0317766 A1 | 10/2014 | Logtenberg et al. |
| 2015/0139996 A1 | 5/2015 | De Kruif et al. |
| 2015/0196637 A1 | 7/2015 | De Kruif et al. |
| 2016/0177364 A1* | 6/2016 | De Kruif .............. C07K 16/12 424/136.1 |
| 2016/0238600 A1 | 8/2016 | Hoogenboom et al. |

FOREIGN PATENT DOCUMENTS

| | | |
|---|---|---|
| CA | 2445255 A1 | 10/2002 |
| EP | 0120694 A2 | 10/1984 |
| EP | 171142 A1 | 2/1986 |
| EP | 0307667 A2 | 3/1989 |
| EP | 0314161 A1 | 5/1989 |
| EP | 0402029 A2 | 12/1990 |
| EP | 0445625 A1 | 9/1991 |
| EP | 0469025 A1 | 2/1992 |
| EP | 0469897 A2 | 2/1992 |
| EP | 0481790 A2 | 4/1992 |
| EP | 0523949 A1 | 1/1993 |
| EP | 0666868 A1 | 8/1995 |
| EP | 0724639 A1 | 8/1996 |
| EP | 0814159 A2 | 12/1997 |
| EP | 1325932 A2 | 7/2003 |
| EP | 1349234 A2 | 10/2003 |
| EP | 1439234 A1 | 7/2004 |
| EP | 1870459 A1 | 12/2007 |
| EP | 2 147594 A1 | 1/2010 |
| FR | 2817875 A1 | 6/2002 |
| JP | H08-116978 A | 5/1996 |
| JP | H 11-500915 A | 1/1999 |
| JP | 2001/523971 A | 11/2001 |
| JP | 2004/524841 A | 8/2004 |
| JP | 2006-109711 A | 4/2006 |
| JP | 2008/538912 A | 11/2008 |
| JP | 2010/505418 A | 2/2010 |
| JP | 2010512749 A | 4/2010 |
| JP | 2011/508604 A | 3/2011 |
| JP | 2013-004215 A | 1/2013 |
| RU | 2236127 C2 | 9/2004 |
| WO | 90/02809 A1 | 3/1990 |
| WO | 90/12878 A1 | 11/1990 |
| WO | 91/00906 A1 | 1/1991 |
| WO | 91/08216 A1 | 6/1991 |
| WO | 91/17271 A1 | 11/1991 |
| WO | 92/01047 A1 | 1/1992 |
| WO | 92/03918 A1 | 3/1992 |
| WO | 92/09690 A2 | 6/1992 |
| WO | 9215679 A1 | 9/1992 |
| WO | 92/18619 A1 | 10/1992 |
| WO | 92/20791 A1 | 11/1992 |
| WO | 93/01288 A1 | 1/1993 |
| WO | 93/12227 A1 | 6/1993 |
| WO | 94/02602 A1 | 2/1994 |
| WO | 94/02610 A1 | 2/1994 |
| WO | 94/23046 A1 | 10/1994 |
| WO | 94/25591 A1 | 11/1994 |
| WO | 95/17085 A1 | 6/1995 |

(56) References Cited

FOREIGN PATENT DOCUMENTS

| | | |
|---|---|---|
| WO | 95/17500 A1 | 6/1995 |
| WO | 95/20401 A1 | 8/1995 |
| WO | 96/27011 A1 | 9/1996 |
| WO | 97/42313 A1 | 11/1997 |
| WO | 97/47739 A1 | 12/1997 |
| WO | 98/15627 A1 | 4/1998 |
| WO | 98/15833 A1 | 4/1998 |
| WO | 98/24923 A1 | 6/1998 |
| WO | 98/39416 A1 | 9/1998 |
| WO | 98/41645 A1 | 9/1998 |
| WO | 98/50431 A2 | 11/1998 |
| WO | 98/52976 A1 | 11/1998 |
| WO | 99/15684 A2 | 4/1999 |
| WO | 99/20749 A1 | 4/1999 |
| WO | 99/23221 A2 | 5/1999 |
| WO | 99/26569 A1 | 6/1999 |
| WO | 99/36569 A1 | 7/1999 |
| WO | 99/45962 A1 | 9/1999 |
| WO | 99/50657 A1 | 10/1999 |
| WO | 99/64582 A2 | 12/1999 |
| WO | 00/44777 A1 | 8/2000 |
| WO | 00/63403 A2 | 10/2000 |
| WO | 00/70023 A1 | 11/2000 |
| WO | 00/71694 A1 | 11/2000 |
| WO | 00/76310 A1 | 12/2000 |
| WO | 01/00245 A2 | 1/2001 |
| WO | 01/19394 A2 | 3/2001 |
| WO | 01/27279 A1 | 4/2001 |
| WO | 01/32901 A1 | 5/2001 |
| WO | 01/48485 A2 | 7/2001 |
| WO | 01/64929 A1 | 9/2001 |
| WO | 01/88132 A2 | 11/2001 |
| WO | 02/18948 A2 | 3/2002 |
| WO | 02/43478 A2 | 6/2002 |
| WO | 02/46233 A1 | 6/2002 |
| WO | 02/059297 A2 | 8/2002 |
| WO | 02/066630 A1 | 8/2002 |
| WO | 02/074969 A2 | 9/2002 |
| WO | 02/096948 A2 | 12/2002 |
| WO | 03/002609 A2 | 1/2003 |
| WO | 03/004704 A2 | 1/2003 |
| WO | 03/016501 A2 | 2/2003 |
| WO | 03/033670 A2 | 4/2003 |
| WO | 03/046560 A2 | 6/2003 |
| WO | 03/048306 A2 | 6/2003 |
| WO | 03/052416 A2 | 6/2003 |
| WO | 03/102157 A2 | 12/2003 |
| WO | 03/106674 A2 | 12/2003 |
| WO | 03/106684 A2 | 12/2003 |
| WO | 03/107218 A1 | 12/2003 |
| WO | 2004/003211 A1 | 1/2004 |
| WO | 2004009618 A2 | 1/2004 |
| WO | 2004/061104 A2 | 7/2004 |
| WO | 2004/106375 A1 | 12/2004 |
| WO | 2005/068622 A2 | 7/2005 |
| WO | 2005/118635 A2 | 12/2005 |
| WO | 2006/028936 A2 | 3/2006 |
| WO | 2006106905 A1 | 10/2006 |
| WO | 2006/117699 A2 | 11/2006 |
| WO | 2007/117410 A2 | 10/2007 |
| WO | 2007110205 A2 | 10/2007 |
| WO | 2007147901 A1 | 12/2007 |
| WO | 2008/054606 A2 | 5/2008 |
| WO | 2008/076379 A2 | 6/2008 |
| WO | 2008/119353 A1 | 10/2008 |
| WO | 2009051974 A1 | 4/2009 |
| WO | 2009/080251 A1 | 7/2009 |
| WO | 2009/080252 A1 | 7/2009 |
| WO | 2009/080253 A1 | 7/2009 |
| WO | 2009/089004 A1 | 7/2009 |
| WO | 2009/098596 A2 | 8/2009 |
| WO | 2009/157771 A2 | 12/2009 |
| WO | 2010/084197 A1 | 7/2010 |
| WO | 2010/129304 A2 | 11/2010 |
| WO | 2011/028952 A1 | 3/2011 |
| WO | 2011/028953 A1 | 3/2011 |
| WO | 2011/097603 A1 | 8/2011 |
| WO | 2011143545 A1 | 11/2011 |
| WO | 2012/020096 A1 | 2/2012 |
| WO | 2012023053 A2 | 2/2012 |
| WO | 2012/058768 A1 | 5/2012 |
| WO | 2012/131555 A2 | 10/2012 |
| WO | 2012/141798 A1 | 10/2012 |
| WO | 2012148873 A2 | 11/2012 |
| WO | 2013134263 A1 | 9/2013 |
| WO | 2013184761 A1 | 12/2013 |
| WO | 2014/051433 A1 | 4/2014 |

OTHER PUBLICATIONS

Davies, J. et al., "Antibody VH Domains as Small Recognition Units," BioTechnology, vol. 13, pp. 475-479 (1995).

Davis, J., et al., " SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Engineering, Design &Selection, vol. 23 (4) pp. 195-202 (2010).

Deisenhofer, J., "Crystallographic Refinement and Atomic Models of a Human Fc Fragment and Its Complex with Fragment B of Protein a from *Staphylococcus Aureus* at 2.9- and 2.8-A Resolution," Biochemistry, vol. 20 (9), pp. 2361-2370, (1981).

Ellerson, J.R., et al., "Structure and Function of Immunoglobulin Domains: III. Isolation and Characterization of a Fragment Corresponding to the C y2 Homology Region of Human Immunoglobin G," Journal of Immunology, vol. 116, pp. 510-517 (1976).

Gunasekaran, K. et al., "Enhancing Antibody Fc Heterodimer Formation through Electrostatic Steering Effects, Applications to Bispecific Molecules and Monovalent IgG," Journal of Biological Chemistry, vol. 285 (25), pp. 19637-19646 (2010).

Hendsch, Z., et al., "Preferential Heterodimer Formation via Undercompensated Electrostatic Interactions," J. Am. Chem. Soc., vol. 123 (6), pp. 1264-1265 (2001).

Kumar , R., et al., The Second PDZ Domain of INAD Is a Type I Domain Involved in Binding to Eye Protein Kinase C, Mutational Analysis and Naturally Occurring Variants, The Journal of Biological Chemistry, vol. 276 (27), pp. 24971-24977 (2001).

Marvin, J. et al., "Redesigning an Antibody Fragment for Faster Association with Its Antigen," Biochemistry, vol. 42 (23), pp. 7077-7083, (2003).

McPhee, F. et al., "Engineering human immunodeficiency virus 1 protease heterodimers as macromolecular inhibitors of viral maturation," PNAS, vol. 93, pp. 11477-11481 (1996).

Merchant, A., et al., "An efficient route to human bispecific IgG," Nature Biotechnology, vol. 16, pp. 677-681, (1998).

Merus, "Merus Presents Preclinical Data on its Novel Bispecific Antibody MCLA-117 at EHA 2013,—Clinical Candidate Designed for the Treatment of Acute Myeloid Leukemia (AML)," Press Release, www.merus.nl, 3 pages, dated Jun. 17, 2013.

Merus, "Merus Selects Clinical Candidate for the Treatment of Acute Myeloid Leukemia (AML)," Press Release, www.merus.nl, 2 pages, dated Jan. 7, 2013.

Merus, www.merus.nl, press release, 2 pages, dated Jan. 7, 2013.

Merus, www.merus.nl, press release, 3 pages, dated Jun. 17, 2013.

Miller, S., "Protein-Protein Recognition and the Association of Immunoglobulin Constant Domains," J. Mol. Biol. vol. 216, pp. 965-973 (1990).

Nieba, L et al. "Disrupting the hydrophobic patches at the antibody variable/constant domain interface: improved in vivo folding and physical characterization of an engineered scFv fragment," Protein Engineering, vol. 10, pp. 435-444 (1997).

Nohaile, M.J., et al., "Altering dimerization specificity by changes in surface electrostatics," PNAS, vol. 98(6), pp. 3109-3114 (2001).

Padlan, E., "X-Ray Crystallography of Antibodies," Advances in Protein Chemistry, vol. 49, pp. 57-133 (1996).

Papadea, C., et al., "Human Immunoglobulin G and Immunoglobulin G Subclasses: Biochemical, Genetic, and Clinical Aspects," Critical Reviews in Clinical Laboratory Sciences, vol. 27(1), pp. 27-58 (1989).

(56) References Cited

OTHER PUBLICATIONS

Raffen, R. et al., "Reengineering Immunoglobulin Domain Interactions by Introduction of Charged Residues," Protein Engineering, vol. 11(4), pp. 303-309 (1998).
Ridgway, J. et al., "Knobs-into-holes' Engineering of Antibody CH3 Domains for Heavy Chain Heterodimerization," Protein Engineering, vol. 9 (7) pp. 617-621 (1996).
Sal-Man, N. et al., Arginine Mutations within a Transmembrane Domain of Tar, an *Escherichia coli* Aspartate Receptor, Can Drive Homodimer Dissociation and Heterodimer Association in Vivo, Journal of Biochemistry, vol. 385, pp. 29-36 (2005).
Schiffer, M. et al., "Analysis of Immunoglobulin Domain Interactions Evidence for a Dominant Role of Salt Bridges," JMB, vol. 203, pp. 799-802 (1988).
Selzer, T. et al., "Rational design of faster associating and tighter binding protein complexes," Nature Structural Biology, vol. 7, p. 537-541 (2000).
Sheinerman, F., et al., "Electrostatic aspects of protein-protein interactions," Current Opinion in Structural Biology, vol. 10, pp. 153-159 (2000).
Sinha, N. et al., "Difference in Electrostatic Properties at Antibody-Antigen Binding Sites: Implications for Specificity and Cross-Reactivity," Biophysical Journal, vol. 83, pp. 2946-2968 (2002).
Sinha, N., et al. "Electrostatics in Protein Binding and Function," Current Protein and Peptide Science, vol. 3, pp. 601-614 (2002).
Strelkauskas, A. et al., "Human Monoclonal Antibody: 2. Simultaneous Expression of IgG and IgM with Similar Binding Specificities by a Human Hybrid Clone," Hybridoma, vol. 6 (5), pp. 479-488 (1987).
Van Rhenen, A., et al., "The novel AML stem cell-associated antigen CLL-1 aids in discrimination between normal and leukemic stem cells," Blood, vol. 110 (7), pp. 2659-2666 (2007).
Zhao, X., et al., "Targeting C-type lectin-like molecule-1 for antibody-mediated immunotherapy in acute myeloid leukemia," Haematologica, vol. 95(1), pp. 71-78 (2010).
Zhu, Z. et al., "Remodeling Domain Interfaces to Enhance Heterodimer Formation," Protein Science, vol. 6, pp. 781-788 (1997).
U.S. Appl. No. 13/866,756, filed Apr. 19, 2013, Cornelis A. De Kruif.
U.S. Appl. No. 13/866,747, filed Apr. 19, 2013, Cornelis A. De Kruif.
U.S. Appl. No. 14/081,848, filed Nov. 15, 2013, Cornelis A. De Kruif.
U.S. Appl. No. 14/395,330, filed Oct. 17, 2014, Cornelis A. De Kruif.
U.S. Appl. No. 14/040,023, filed Sep. 27, 2013, Alexander Berthold.
U.S. Appl. No. 14/395,325, filed Oct. 17, 2014, Cornelis A. De Kruif.
Ai-Lazikani, B. et al., "Standard conformations for the canonical structures of immunoglobulins," J Mol Biol., vol. 273 (4):927-948 (1997).
Attaelmannan M. et al., "Understanding and identifying monoclonal gammopathies," Clin. Chem., vol. 46(8 Pt 2):1230-1238 (2000).
Bendig, MM., "The production of foreign proteins in mammalian cells," Genet Eng., (7):91-127 (1988).
Bostrom, J., "Variants of the antibody herceptin that interact with HER2 and VEGF at the antigen binding site," Science, vol. 323(5921):1610-1614 (2009).
Capelle, Ma et al., "Spectroscopic characterization of; antibodies adsorbed to aluminium adjuvants: correlation with antibody vaccine immunogenicity," Vaccine, vol. 23(14):1686-1694 (2005).
Coligan Je, "Commonly used detergents," Curr Protoc Protein Sci., Appendix 1:Appendix 1B (1998).
De Kruif, J. et al., "Generation of stable cell clones expressing mixtures of human antibodies," Biotechnol Bioeng, vol. 106(5): 741-750 (2010).
Devries, SJ. et al., "The HADDOCK web server for data driven biomolecular docking," Nature Protocols, vol. 5(5):883-897 (2010).
Demeule, B., "Characterization of protein aggregation: the case of a therapeutic immunoglobulin," Biochem Biophys. Acta., vol. 1774(1):146-153 (2007).
Demeule, B., "Detection and characterization of protein aggregates by fluorescence microscopy," Int J. Pharm, vol. 329(1-2):37-45 (2007).
Farnan, D. et al., "Multiproduct high-resolution monoclonal antibody charge variant separations by pH gradient ion-axchange chromatography," Anal Chem, vol. 81(21): 8846-8857 (2009).
Dusogie, EE, "Mapping of the C1q binding site on rituxan, a chimeric antibody with a human IgG1 Fc," J Immunol., vol. 164(8):4178-4184 (2000).
Ionescu, RM. et al, "Contribution of variable domains to the stability of humanized IgG1 monoclonal antibodies," J. Pharm Sci., vol. 97(4): 1414-1426 (2008).
Kabat, EA., et al., "Identical V region amino acid sequences and segments of sequences in antibodies of different specificities. Relative contributions of VH and VL genes, mini genes, and complementarity-determining regions to binding of antibody-combining sites," J Immunol., vol. 147(5):1709-1719 (1991).
Lee, B. et al., "The interpretation of protein structures: estimation of static accessibility," J Mol Biol.,vol. 55(3), 379-400 (1971).
Schaefer, G. et al, "A two-in-one antibody against HER3 and EGFR has superior inhibitory activity compared with monospecific antibodies," Cancer Cell, vol. 20(4): 472-486 (2011).
Tahallah, N., "The effect of the source pressure on the abundance of ions of noncovalent protein assemblies in an electrospray ionization orthogonal time-of-flight instrument," Rapid Commun Mass Spectrom, vol. 15(8):596-601 (2001).
Abedi, M.R. et al., "Green fluorescent protein as a scaffold for intracellular presentation of peptides," Nucleic Acids Res., vol. 26(2):623-630 (1998).
Akerstrom, B. et al., "On the interaction between singlechain Fv antibodies and bacterial immunoglobulin-binding proteins," J. Immunol Methods., vol. 177(t-2):151-163 (1994).
Alber, T., KG., "Nucleotide sequence of the triose phosphate isomerase gene of *Saccharomyces cerevisiae*," J. Mol. Appl Genet., vol. 1(5): 419-434 (1982).
Allen, TM "Ligand-Targeted therapeutics in anticancer therapy," Nat Rev Cancer, vol. 2(10):750-763 (2002).
Ammerer, G., "Expression of genes in yeast using the ADCI promoter," Methods Enzymol., vol. 101: 192-201 (1983).
Antica, M. et al., "Thymic stern cells in mouse bone marrow," Blood, vol. 84(1):111-117 (1994).
Appeal Brief filed by Regeneron on Jul. 20, 2015 from U.S. Appl. 13/948,818, 30 pages.
Appel RD,.et al., "A new generation of information retrieval tools for biologists: the example of the ExPASy WWW server," Trends Biochem. Sci., vol. 19: 258-260 (1994).
Arai, Y. et al., "Antibody responses induced by immunization with a Japanese rabies vaccine determined by neutralization test and enzyme-linked immunosorbent assay," Vaccine, vol. 20(19-20): 2448-2453 (2002).
Aranda, A. et al., "Nuclear Hormone Receptors and Gene Expression, " Physiol Rev., vol. 81(3):1269-1304 (2001).
Auerbach, R. et al, "Angiogenesis assays: a critical overview," Clin Chem., vol. 49(1):32-40 (2003).
Barbas, CF. et al., "Assembly of combinatorial antibody libraries on phage surfaces: the gene III site," PNAS, USA, vol. 88(18):7978-7982 (1991).
Barnes, LM. et al.,"Characterization ofthe stability of Recombinant protein production in the GS-NSO expression system," Biotechnol Bioeng., vol. 73(4):261-270 (2001).
Bebbington, CR. et al, "High-level expression of a recombinant antibody from myeloma cells using a glutamine synthetase gene as an amplifiable selectable marker," Biotechnology (NV), vol. 10(2): 169-175 (1992).
Bell, AC. et al., "Insulators and boundaries: versatile regulatory elements in the eukaryotic genome," Science, vol. 291 (5503): 447-450 (2001).
Bertagnolli, M. et al, "IL-12 augments antigen-dependent proliferation of activated T lymphocytes," J. Immunol., vol. 149(12):3778-3783 (1992).

(56) References Cited

OTHER PUBLICATIONS

Bertagnolli, M., et al., "IL-7 supports the generation of cytotoxic T lymphocytes from thymocytes, Multiple lymphokines required for proliferation and cytotoxicity," J. Immunol., vol. 145(6):1706-1712 (1990).
Bertagnolli, MM. et al., "IL-4 supported Induction of Cytolytic T lymphocytes Requires IL-2 and IL-6," Cell Immunol., vol. 133(2):327-341 (1991).
Bhardwaj, N. et al., "Influenza Virus-infected Dendritic Cells Stimulate Strong Proliferative and Cytolytic Responses from Human CD8+ T cells," J Clin Invest., vol. 94(2):797-807 (1994).
Binz, H.K.et al., "Designing repeat proteins: well-expressed, soluble and stable proteins from combinatorial libraries of consensus ankyrin repeat proteins," J Mol Biol., vol. 332(2):489-503 (2003).
Birchmeier, C, et. al., "Met, Metastasis, Motility and more," Nat Rev Mol Cell Biol., vol. 4(12): 915-925 (2003).
Bitter, GA, "Heterologous Gene Expressionin Yeast," Methods Enzymol., vol. 152: 673-684 (1987).
Bode, J. et al.' " The Hitchhiking Principle: Optimizing episomal Vectors for the Use in Gene Therapy and Biotechnology," Gene Ther. and Mol. Biol., vol. 6:33-46 (2001).
Boder, et al., "Yeast surface display for screening combinatorial polypeptide libraries," Nat Biotechnol., vol. 15 (6): 553-557 (1997).
Boel E, et al., "Functional human monoclonal antibodies of all isotypes constructed from phage display library-lerived single-chain Fv antibody fragments," J Immunol Methods, vol. 239(1-2):153-166 (2000).
Bowman, MR., et al., "The cloning of CD70 and its identification as the ligand for CD27," J. Immunol., vol. 152(4): 1756-1761 (1994).
Brezinsky, SC. et al., "A simple method for enriching populations of transfected CHO cells for cells of higher specific productivity," J. Immune! Methods, vol. 277(1-37 2):141-155 (2003).
Brink MF, et al., "Developing Efficient Strategies for the-Generation of Transgenic Cattle which Produce Biopharmaceuticals in milk," Theriogenology, vol. 53(1):139-148 (2000).
Broach, JR. et al. "Transformation in yeast: development of a hybrid cloning vector and isolation of the CAN1 gene," Gene, vol. 8(1),121-133 (1979).
Burger, C. et al., " An integrated strategy for the process development of are combinant antibody ccytokine fusion protein expressed in BHK cells," Appl. Microbiol Biotechnol., vol. 52(3): 345-353 (1999).
Burioni, R. et al., "Nonneutralizing Human Antibody Fragments Against Hepatitis C Virus E2 Glycoprotein Modulate Neutralization of Binding Activity of Human Recombinant," Virology, vol. 288(1): 29-35 (2001).
Campbell KH, et al., "Sheep cloned by nuclear transfer from a cultured cell line," Nature, vol. 380(6569): 64-66 (1996).
Cao, B., et. al., "Neutralizing monoclonal antibodies to hepatocyte growth factor/scatter factor (HGF/SF) display antitumor activity in animal models," PNAS USA, vol. 98(13):7443-7448 (2001).
Carmack, CE, "Influence of a V kappa 8 L chain transgene on endogenous rearrangements and the immune response to the HA(Sb) determinant on influenza virus," J. Immunol.,vol. 147(6):2024-2033 (1991).
Barter, P. et al., "Humanization of an anti-p185HER2 antibody for human cancer therapy," PNAS USA, vol. 89 (10):4285-4289 (2001).
Casellas, R, et al., "Contribution of receptor editing to the antibody repertoire," Science, vol. 291 (5508):1541-1544 (2001).
Champion, JM et al., "The development of monoclonal human rabies virus-neutralizing antibodies as a substitute for pooled human immune globulin in the prophylactic treatment of rabies virus exposure," J Immunol Methods, vol. 235 (1-2):81-90 (2000).
Chan, A., et al., "Genomic Organization of the T Cell Receptor," Cancer Detect Prev., vol. 14(2):261-267(1989).

Chen, Y. et al., "Selection and Analysis of an Optimized Anti-VEGF Antibody: Crystal Structure of an Affinity-matured Fab in Complex with Antigen," J. of Molec. Biology, vol. 293(4):865-881 (1999).
Cheong, HS. et al., "Affinity enhancement of bispecific antibody against two different epitopes in the same antigen," Biochem Biophys. Res Commun., vol. 173(3),795-800 (1990).
Cherrington, J.M. et al., "New paradigms for the treatment of cancer: the role of Anti-Angiogenesis Agents," Adv Cancer Res., vol. 79:1-38 (2000).
Chesnut, J. et al., "Selective Isolation of Transiently Transfected Cells From a Mammalian Cell Population with Vectors Expressing a Membrane Anchored Single-Chain Antibody, " Journal of Immunological Methods, vol. 193 :17-27 (1996).
Cheung, SC. et al, " A recombinant human Fab expressed in *Escherichia coli* neutralizes rabies virus" J ViroL, vol. 56(11):6714-6720 (1992).
Chothia, C., et al., "Canonical structures for the hypervariable regions of immunoglobulins," J Mol Biol, vol. 196(4): 901-917 (1987).
Clackson, T. et al., "Making antibody fragments using phage display libraries," Nature, vol. 352(6336): 624-628 (1991).
Cockett MI, et al.,"High level expression of tissue inhibitor of metalloproteinases in Chinese hamster ovary cells using glutamate synthetase gene amplification," Biotechhology, vol. 8(7): 662-667 (1990).
Conn, G. et al., "Purification of a glycoprotein vascular endothelial cell mitogen from a rat gliomaderived cell line," PNAS; USA, vol. 87(4):1323-1327 (1990).
Conrath, EK., et al., "Camel Single-Domain antibodies as modular building units in bispecific and bivalent antibody constructs," J Biol. Chem., vol. 276(1): 7346-7350 (2001).
Corsaro, CM., "Enhancing the efficiency of DNA-mediated gene transfer in mammalian cells," Somatic Cell Genet., vol. 7(5): 603-616 (1981).
Cvetkovic, B. et al., "Appropriate tissue- and cell-specific expression of a single copy human angiotensinogen transgene specifically targeted upstream of the HPRT locus by homologous recombination," J Biol Chem., vol. 275(2): 1073-1078 (2000).
Dammacco F. et al.," Immunoglobulln secretion by peripheral blood and bone marrow B cells in patients with multiple Myeloma, Studies by the reverse haemolytic plaque assay," Clin Exp. Immunol., vol. 57(3): 743-751 (1984).
Darzynkiewicz, Z. et al., "Features of Apoptotic cells measured by flow cytometry," Cytometry, vol. 13(8):795-808 (1992).
De Haard, H.J. et al., " A large nonimmunized human Fab fragment phage library that permits rapid isolation and cinetic analysis of high affinity antibodies," J Biol Chem., vol. 274(26):18218-18230 (1999).
De Jong, G., et al., "Mammalian artificial chromosome pilot production facility: large-scale isolation of functional satellite DNA-based artificial chromosomes," Cytometry, vol. 35(2): 129-133 (1999).
De Kruif J, et al., "Rapid selection of cell subpopulation-specific human monoclonal antibodies from a synthetic phage antibody library," PNAS, USA, vol. 92(9):3938-3942 (1995).
De Vries, P. et al., "The effect of recombinant mast cell growth factor on purified murine hematopoietic stem cells," J Exp Med, vol. 173(5):1205-1211 (1991).
Decision of UK High Court of Justice (REGN against Kymab Limited; Novo Nordisk) dated Feb. 2, 2016.
Declaration Dr. A. Murphy dated Aug. 31, 2015.
Declaration Martin, Joel in EP2314629.
Declaration of Joel Martin filed May 18, 2016 in EP2314629B.
Declaration of Ton Logtenberg filed Apr. 5, 2016 in EP2314629B.
Degraaf, M. "Expression of scFvs and scFv fusion proteins in eukaryotic cells," Methods Mol Biol., vol. 178:379-387 (2002).
Desmyter, A. et al., Crystal structure of a camel single-domain VH antibody fragment in complex with lysozyme, Nat Struct Biol., vol. 3(9):803-811 (1996).
Dietzschold, B. et al., Delineation of putative mechanisms involved in antibody-mediated clearance of rabies virus from the central nervous system, PNAS, USA, vol. 89(15): 7252-7256 (1992).

(56) References Cited

OTHER PUBLICATIONS

Dinnyes A., et al., "Somatic cell nuclear transfer: recent progress and challenges," Cloning Stem Cells, vol. 4 (1):81-90 (2002).
Flavell, DJ, et al. "Therapy of human Tcell acute lymphoblastic leukaemia with a combination of anti-CD7 and anti-CD38-Saporin immunotoxins is significantly better than therapy with each individual immunotoxin," Br J. Cancer, rol. 84 (4): 571-578 (2001).
Folkman, J., "Angiogenesis in cancer, vascular, rheumatoid and other disease," Nat Med., vol. 1(1):27-31 (1995).
Franconi, R. et al., "Functional expression in bacteria and plants of an scFv antibody fragment against ospoviruses," Immunotechnology, vol. 4 (3-4):189-201 (1999).
French, RR. et al., "Cooperative mixtures of bispecific F(ab')2 antibodies for delivering saporin to lymphoma in vitro and in vivo," Cancer Res., vol. 51(9):2353-2361 (1991).
Frenken, LG. et al., "Isolation of antigen specific llama VHH antibody fragments and their high level secretion by Saccharomyces cerevisiae," J Biotechnol., vol. 78(1):11-21 (2000).
Friedenson, G. et al., "Immunoglobulin G antibodies from an individual rabbit in which several heavy chain variants are paired with one light chain sequence," J Biol Chem., vol. 248(20):7073-7079 (1973).
Frykman, S. et al., "Quantitating secretion rates of individual cells: design of secretion assays," Biotechnol Bioeng., vol. 59(2):214-226 (1998).
Fuchs, P. et al., "Targeting recombinant antibodies to the surface of *Escherichia coli*: fusion to a peptidoglycan associated; lipoprotein," Biotechnology (N V), vol. 9(12):1369-1372 (1991).
Fussenegger, M. et al., "Genetic optimization of recombinant glycoprotein production by mammalian cells," Trends Biotechnol., vol. 17(1):35-42 (1999).
Galy, AH. et al., "Delineation of T- progenitor cell activity within the CD34+ compartment of adult bone marrow," Bood, vol. 85(10):2770-2778 (1985).
Gan, W. et al., "Functional characterization of the internal ribosome entry site of eIF4G mRNA," J Biol Chem., vol. 273 (9): 5006-5012 (1998).
Garber, K. "Biotech industry faces new bottleneck," Nat Biotechnol., vol. 19(3):184-185 (2001).
Garnick, RL., "Peptide mapping for detecting variants in protein products," Dev Biol Stand., vol. 76:117-130 (1992).
Garrard, LJ. et al., "Fab assembly and enrichment in a monovalent phage display system," Biotechnology (N V),vol. 9(12): 1373-1377 (1991).
Gerber. T. et al., "Vascular endothelial growth factor regulates endothelial cell survival through the phosphatidylinositol 3'-kinase/Akt signal transduction pathway Requirement for Flk-1/KDR activation," J. Biol Chem., vol. 273(46):30336-30343 (1998).
Gerstner, RB. et al., "Sequence plasticity in the antigen-binding site of a therapeutic anti-HER2 antibody," J Mol Biol., vol. 321(5):851-862 (2002).
Ghetie, MA. et al., "Homodimerization of tumor-reactive monoclonal antibodies markedly increases their ability to Induce growth arrest or apoptosis of tumor cells," PNAS, USA, vol. 94(14):7509-7514 (1997).
Giddings, G. et al., "Transgenic plants as factories for biopharmaceticals," Nat Biotechnol., vol. 18(11):1151-1155 (2000).
Gluzman, Y. et al., "SV40-transfonned simian Cells support the replication of early SV40 mutants," Cell, vol. 23 (1):175-182 (1981).
Gorczyca, W. et al., "Induction of DNA strand breaks associated with apoptosis during treatment of leukemias," Leukemia, vol. 7(5): 659-670 (1993).
Gorczyca,W.-et al., "DNA strand breaks occurring during apoptosis:their early in situ detection by the terminal deoxynucleotidyl transferase and nick translation assays and prevention by serine protease inhibitors," Int J Oncol., vol. 1(6):639-648 (1993).
Gorman, C. et al., "Site-specific gene targeting for gene expression in eukaryotes," Curr Opin Biotechnol., vol. 11 (5):455-460 (2000).
Graham, FL., et al., "A new technique for the assay of infectivity of human adenovirus 5 DNA," Virology, vol. 52(2), 156-467 (1973).
Gram, H. et al., "In vitro selection and affinity maturation of antibodies from a naive combinatorial immunoglobulin library," PNAS, USA, vol. 89(8): 3576-3580 (1992).
Graslund, T.et al., "Integrated strategy for selective expanded bed ion-exchange- adsorption and site specific protein processing using gene fusion technology," J. Biotechnol., vol. 96(1):93-102 (2002).
Gray, E et al., "Secretion capture and report web: use of affinity derivatized agarose microdroplets for the selection of hybridoma cells," J. Immunol Methods, vol. 182(2):155-163 (1995).
Greenberger, JS. et al., "Demonstration of permanent factor-dependent multipotential(erythroid/neutrophil/pasophil) hematopoietic progenitor cell lines," PNAS USA, vol. 80(10):2931-2935 (1983).
Griffiths, A.D. et al., "Human anti-self antibodies with high specificity from phage display libraries," EMBO J., vol. 12(2): 725-734 (1993).
Griffiths, AD. et al., "Isolation of high affinity human antibodies directly from large synthetic repertoires," EMBO J., vol. 13(14): 3245-3260 (1994).
Groeneveld EH., et al., "Bone morphogenetic proteins in human bone regeneration," Eur J., Endocrinol., vol. 142 :11:9-21 (2000).
Grosveld, F., "Activation by locus control regions?" Curr Opin Genet Dev., vol. 9(2):152-157 (1999).
Guery, JC, "Dendritic cells are the most efficient in presenting endogenous naturally processed self-epitopes to class II- restricted T cells," J Immunol., vol. 154(2): 536-544 (1995).
Hamers-Casterman, C. et al., "Naturally occurring antibodies devoid of light chains," Nature, vol. 363 (6428):446-448 (1993).
Hanes, J. et al "Picomolar affinity antibodies from a fully synthetic naive library selected and evolved by ribosome lisplay," Nat Biotechnol., vol. 18(12):1287-1292 (2000).
Hanes, J. et al., "Selecting and evolving functional proteins in vitro by ribosome display," Methods Enzymol, vol. 328: 404-430 (2000).
Harjunpaa, A. et al., "Rituximab (anti-CD20) therapy of B-cell lymphomas: direct complement killing is superior to aellular effector mechanisms," Scand J Immunol., vol. 51 (6):634-641 (2000).
Hawkins,- RE., et al., "Selection of phage antibodies by binding affinity Mimicking affinity maturation," J Mol Biol., vol. 226(3):889-896 (1992).
Hay, BN. et al., "Bacteriophage cloning and *Escherichia coli* expression of a human IgM Fab," Hum Antibodies Hybridomas, vol. 3(2):81-85 (1992).
Heintges, "Cloning and molecular characterization- of human high affinity antibody fragments against Hepatitis C virus NS3 helicase," J. Virol Methods, vol. 103(1):75-88 (2002).
Hiatt, A. et al., "Production of antibodies in transgenic plants," Nature, vol. 342(6245):76-78 (1989).
Hitzeman, RA. et al., "Isolation and characterization of the yeast 3-phosphoglycerokinase gene (PGK) by an immunological screening technique," J Biol Chem., vol. 255(24):12073-12080 (1980).
Holliger, P. et al., "Diabodies: small bivalent and bispecific antibody fragments," PNAS USA, vol. 90 (14):6444-6448 (1993).
Holmes, R et al., "Improved cell line development by a high throughput affinity capture surface display technique to select; for high secretors," J Immunol. Methods, vol. 230(1-2): 141-147 (1999).
Holt, L.J. et al., "Domain antibodies: proteins for therapy," Trends Biotechnol., vol. 21 (11): 484-490 (2003).
Hoogenboom, et al., "Antibody phage display technology and its applications, " Immunotechnology, vol. 4(1):1-20 (1998).
Hoogenboom, HR. et al., "Bypassing immunisation. Human antibodies from synthetic. repertoires of germ line VH gene segments rearranged in vitro," J Mol. Biol., vol. 227(2): 381-388 (1992).
Hoogenboom, HR., "Designing and optimizing library selection strategies for generating high affinity antibodies," Trends; Biotechnol.,vol. 15(2): 62-70 (1997).
Hoogenboom, HR., et al., "Natural and designer binding sites made by phage display technology," Immunol Today, vol. 21 (8): 371-378 (2000).

(56) References Cited

OTHER PUBLICATIONS

Hoogenboom, HR: et al., "Multisubunit proteins on the surface of filamentous. phage: methodologies for displaying antibody (Fab) heavy and light chains," Nucleic Acids Res., vol. 19(15): 4133-4137 (1991).

Houshmand, H. et al., "Use of bacteriophage T7 displayed peptides for determination of monoclonal.antibody specificity and biosensor analysis of the binding reaction," Anal Biochem., vol. 268(2):363-370 (1999).

Houston, M.E., Jr. et al. "Use of a conformationally restricted secondary structural element to display peptide libraries: a two stranded alpha-helical coiled-coil stabilized by lactam bridges," J. Mol. Biol., vol. 262(2):270-282 (1996).

Huang, AV. et al., "Role of bone marrow-derived cells in presenting MHC class I-restricted tumor antigens," Science, vol. 264(5161): 961-965 (1994).

Hudziak, HM, et al., "p185HER2 monoclonal. antibody has anti proliferative effects in vitro and sensitizes human breast tumor cells to tumor necrosis factor," Mol Cell Biol., vol. 9(3): 1166-1172 (1989).

Huls, G. A.' et al.' "A recombinant, fully human monoclonal antibody with antitumor activity constructed from phage- lisplayed antibody fragments," Nat Biotechnol., vol. 17(3): 276-281 (2002).

Huls, G. A., et al., "Antitumor immune effector mechanisms recruited by phage display-derived fully human IgG1 and gA1 monoclonal antibodies," Cancer Res. ,vol. 59(22):5778-5784 (1999).

Huse, K. et al., "Purification of antibodies by affinity chromatography," J Biochem Biophys Methods, vol. 51 (3)217-231 (2002).

Huse, WD. et al, "Generation of a large combinatorial library of the immunoglobulin repertoire in phage lambda," Science, vol. 246(4935): 1275-1281 (1989).

Hynes, RO., "Cell adhesion: old and new questions," Trends Cell Biol., vol. 9(12): 33-37 (1999).

Inaba, K K et al.' "Dendritic cells pulsed with protein antigens in vitro can prime antigen-specific, restricted T cells in situ," J Exp Med., vol. 172(2): 631-640 (1990).

Inaba, M. et al., "Distinct mechanisms of neonatal tolerance induced by dendritic cells and thymic B cells," J Exp Vied., vol. 173(3):549-559 (1991).

Itoh, N. et al., "The polypeptide encoded by the cDNA for human cell surface antigen Fas can mediate apoptosis," Cell, vol. 66(2):233-243 (1991).

Jakobbvits, A,., "From XenoMouse technology to panitumumab,the first fully human antibody product from ransgenic mice," Nat. Biotechnol, vol. 25(10):1134-1143 (2007).

Jakobovits, A. "The long-awaited magic bullets: therapeutic human monoclonal antibodies from transgenic mice," Expert Opin. Investig Drugs, vol. 7(4):607-614 (1998).

Jakobovits, A. et al., "Germ-line transmission and expression of a human-derived yeast artificial chromosome," Nature, vol. 362(6417):255-258 (1993).

Jakobovits, A. et al., "Analysis of homozygous mutant chimeric mice: deletion of the immunoglobulin heavy-chain joining region blocks B cell development and antibody production," PNAS USA, vol. 90(6): 2551-2555 (1993).

Jeffers, M. et. al., "Enhanced tumorigenicity and invasion metastasis by hepatocyte growth factor/scatter factor-met signalling in human cells concomitant with induction of the urokinase proteolysis network," Mol Cell Biol., vol. 16 3):1115-1125 (1996).

Jespers, LS, et al., "Guiding the selection of human antibodies from phage display repertoires to a single epitope of an. antigen," Biotechnology (NY),vol. 12(9): 899-903 (1994).

Johansson, BM. et al., "Evidence for involvement of activin A and Bone morphogenetic protein 4 in mammalian mesoderm and hematopoietic development," Mol Cell Biol., vol. 15(1): 141-151 (1995).

Jonasson, P. et al., "Genetic design for facilitated production and recovery of recombinant proteins in *Escherichia coli*" Biotechnol Appl. Biochem., vol. 35(Pt 2):91-105 (2002).

Jones, D., et al., "High-level expression of recombinant IgG in the human cell line PER.C™," Biotechnol Prog., vol. 19(1): 163-168 (2003).

Joyner, A.L Handbook, " Gene Targeting: A practical approach," Oxford University press, 1-96 (2000).

Kang, AS. et al., "Linkage of recognition and replication functions by assembling combinatorial antibody Fab libraries along phage surfaces," PNAS USA, vol. 88(10): 4363-4366 (1991).

Kasprzyk, PG. et al., "Therapy of an animal model of human gastric cancer using a combination of anti-erbB-2 monoclonal antibodies," Cancer Res., vol. 52(10):2771-2776 (1992).

Kaufman, R.J., et al., "Amplification and expression of sequences co-transfected with a modular dihydrofolate reductase Complementary DNA gene," J Mol Biol., vol. 159(4), 601-621 (2000).

Kaufman, RJ., "Overview of vector design for mammalian gene expression," Mol Biotechnol., vol. 16(2):151-160 (2000).

Keller, G.et al., "Hematopoietic commitment during embryonic stem cell differentiation in culture," Mol. Cell Biol., vol. 13(1): 473-486 (1993).

Kim, SJ,et al., "Characterization of chimeric antibody producing CHO cells in the course of dihydrofolate reductase-mediated gene amplification and their stability in the absenceof selective pressure," Biotechnol Bioeng., vol. 58(1):73-84 (1998).

Klagsbrun, M., et al., "Vascular endothelial growth factor and its receptors," Cytokine Growth Factor Rev., vol. 7 (3):259-270 (1996).

Kohler, G., et al., "Continuous cultures of fused cells secreting antibody of predefined specificity," Nature, vol. 256 (5517): 495-497 (1975).

Koide, A. et al., "The fibronectin type III domain as a scaffold for novel binding proteins," J Mol Biol.,vol. 284 (4):1141-1151 (1998).

Kontermann, RE., "Dual targeting strategies with bispecific antibodies," mAbs, vol. 4(2):182-197 (2012).

Koochekpour, S. et. al., "Met and hepatocyte growth factor/scatter factor expression in human gliomas" Cancer Res., vol. 57(23):5391-5398 (1997).

Korndorfer, IP. et al.,"Crystallographic analysis of an "anticalin" with tailored specificity for fluorescein reveals nigh structural plasticity of the lipocalin loop region," Proteins, vol. 53(1):121-129 (2003).

Korndorfer, IR. et al., "Structural mechanism of specific ligand recognition by a lipocalin tailored for the aomplexation of digoxigenin" J. Mol Biol., vol. 330(2):385-396 (2003).

Kortt, AA. et al., "Dimeric and trimeric antibodies: high avidity scFvs for cancer targeting," Biomol. Eng., vol. 18(3): 95-108 (2001).

Krebs, et al., "High-throughput generation and engineering of recombinant human antibodies," J. Immunol Methods, vol. 254(1-2):67-84 (2001).

Kroesen, Bj. et al., "Bispecific antibodies for treatment of cancer in experimental animal models and man," Adv Drug Deliv Rev., vol. 31(1-2):105-129 (1998).

Ku, J. et al., "Alternate protein frameworks for molecular recognition," PNAS USA, vol. 92(14):6552-6556 (1995).

Kuhlman, B. et al., "Design of a novel globulatprotein fold with atomic level accuracy," Science, vol. 302 :5649}:1364-1368 (2003).

Kunkel, TA. et al., "Rapid and efficient site-specific mutagenesis without phenotypic selection," Methods Enzymol., vol. 154:367-382 (1987).

Kwaks, TH.et al., "Identification of anti-repressor elements that confer high and stable protein production in mammalian cells" Nat Biotechnol., vol. 21(5):553-558 (2003).

Lang, AB. et.al. "Immunotherapy with human monoclonal antibodiesFragment A specificity of polyclonal; and monoclonal antibodies is crucial for full protection against tetanus toxin," J Immunol., vol. 151(1):466-472 (1993).

Larrick, JW., et al., "Producing proteins in transgenic plants and animals," Curr Opin. BiotechnoL, vol. 12(4): 411-418 (1990).

Lekkerkerker, L. "Phage antibodies against human dendritic cell subpopulations obtained by flow cytometry-Dased selection on freshly isolated cells," J Immunol. Methods, vol. 231(1-2):53-63 (1999).

(56) References Cited

OTHER PUBLICATIONS

Lenz, W., "Expression of heterobispecific antibodies by genes transfected into producer hybridoma cells," Gene, vol. 87(2):213-218 (1990).
Li, T., et al., "Stable expression of three genes from a tricistronic retroviral vector containing a picornavirus and 9-nt aellularinternal ribosome entry site elements," J Virol. Methods, vol. 115(2):137-144 (2004).
Lindhofer, H. et al., "Preferential species-restricted heavy/light chain pairing in rat/mouse quadromas, Implications 'for a single-step purification of bispecific antibodies," J Immunol., vol. 155(1), 219-225 (1995).
Little, M. et al., "Human antibody libraries in *Escherichia coli*," J. Biotechnol., vol. 41(2-3): 187-195 (1995).
Lobato, MN., et al., "Intracellular antibodies and challenges facing their use as therapeutic agents," Trends Mol. Med., vol. 9(9):390-396 (2003).
Logtenberg, "Antibody cocktails: nextgeneration biopharmaceuticals with improved potency," Trends Biotechnol., vol. 25(9): 390-394 (2007).
Lonberg, N., "Fully human antibodies from transgenic mouse and phage display platforms," Curr Opinion Immunol., vol. 20(4): 450-459 (2008).
Lu, D. et al.' "Selection of high affinity human neutralizing antibodies to VEGFR2 from a large antibody phage display library for anti angiogenesis therapy," Int J. Cancer, vol. 97(3): 393-399 (2002).
Lu, D. et al.' "Acquired antagonistic activity of a bispecific diabody directed against two different epitopes on vascular endothelial growth factor receptor 2," J Immunol. Methods, vol. 230(1-2):159-171 (1999).
Lu, D. et al.' "Identification of the residues in the extracellular region of KDR important for interaction with vascular endothelial growth factor arid neutralizing anti-KDR antibodies, " J Biol. Chem., vol. 75(19): 159-171 (1999).
Lu, D.,et. al., Complete inhibition of vascular endothelial growth factor (VEGF) activities with a bifunctional diabody lirected againstboth VEGF kinase receptors, fms-like tyrosine kinase receptor and kinase insert domain containing receptor, Cancer Res., vol. 61(19): 7002-7008 (2001).
Lucas, BK. et al, "High-level production of recombinant proteins in CHO cells using a dicistronic DHFR intron expression vector," Nucleic Acids Res., vol. 24(9):1774-1779 (1996).
Macatonia, SE. et al., "Dendritic cells produce IL-12 and direct the development of Th1 cells from naive CD4+ T mils," J Immunol,vol. 154(10):5071-5079 (1995).
Macatonia, SE. et al., "Primary stimulation by dendritic cells induces antiviral proliferative and cytotoxic Tcell responses in vitro," J.Exp Med., vol. 169(4):1255-1264 (1989).
Macdonald, LE. et al., "Precise and in situ genetic humanization of 6 Mb of mouse immunoglobulin genes," PNAS USA, vol. 111(14):5147-5152 (2014).
Macejak, DG., "Internal initiation of translation mediated by the 5' leader of a cellular RNA," Nature, vol. 353 (6339):90-94 (1991).
Manen, D. et al., "A sensitive reporter gene system using bacterial luciferase based on a series of plasmid cloning rectors compatible with derivatives of pBR322," Gene, vol. 186(2), 197-261(1997).
Marasco,WA., "Intrabodies as antiviral agents," Curr Top Microbiol. Immunol., vol. 260: 247-270 (2001).
Marks, JD. et al.' "By-passing immunization. Human antibodies from V-gene libraries displayed on phage," J Mol Bio., vol. 222(3):581-597 (1991).
Marks, JD., "Deciphering antibody properties that lead to potent botulinum neurotoxin neutralization," Mov Disord.,19 Suppl8, S101-S108 (2004).
Marvin, JS. "Recombinant approaches to IgG-like bispecific antibodies," Acta Pharmacol Sin.,vol. 26(6):649-658 (2005).
Massengale, WT et al., "CD20-negative relapse of cutaneous B-cell lymphoma after anti-CD20 monoclonal antibody therapy," J Am Acad Dermatol., vol. 46(3):441-443 (2002).
Matsuda, F. et al., "The complete nucleotide sequence of the human immunoglobulin heavy chain variable region ocus," J. Exp. Med., vol. 188 (11):2151-2162(1998).
Mattheakis, LC. et al., "An in vitro polysome display system for identifying ligands from very large peptide libraries," PNAS USA, vol. 91(19): 9022-9026 (1994).
Mayer, MP., "A new set of useful cloning and expression vectors derived from BlueScript," Gene, vol. 163(1):41-46 (1995).
McBurney, MW. et al., "Evidence for repeat-induced gene silencing in cultured Mammalian cells: inactivation of tandem repeats of transfected genes," Exp Cell Res.,vol. 274(1):1-8 (2002).
McClanahan, T. et al., "Hematopoietic growth factor receptor genes as markers of lineage commitment during in vitro development of hematopoietic cells," Blood,vol. 81(11):2903-2915 (1993).
McConnell, S.J., et al., "Tendamistat as a scaffold for conformationally constrained phage peptide libraries," J. Mol. Biol., vol. 250(4):460-470 (1995).
Mendel, DB., et al," the angiogenesis inhibitor SU5416 has long-lasting effects on vascular endothelial growth factor eceptor phosphorylation and function," Clin. Cancer Res., vol. 6(12):4848-4858 (2000).
Mendez MJ., et al., "Functional transplant of megabase human immunoglobulin loci recapitulates human antibody esponse in mice," Nat Genet., vol. 15(2):146-156 (1997).
Morimoto, K. et al., "High level expression of a human rabies virus neutralizing monoclonal antibody by a rhabdovirus-based vector," J. Immunol Methods, vol. 252(1-2):199-206 (2001).
Morrison, SL, "Transfectomas provide novel chimeric antibodies," Science, vol. 229(4719):1202-1207 (1985).
Murphy, AJ. et al., "Mice with megabase humanization of their immunoglobulin genes generate antibodies as efficiently as normal mice," PNAS USA,vol. 111(14):5153-5158 (2014).
Muyldermans, S., "Single domain camel antibodies: current status," J. Biotechnol., vol. 74(4):277-302 (2001).
Nahta, R. et al.,"The HER-2-targeting antibodies trastuzumab and pertuzumab synergistically inhibit the survival of breast cancer cells," Cancer Res., vol. 64(7): 2343-2346 (2004).
Nair, S. et al., "Induction of primary, antiviral cytotoxic, and proliferative responses with antigens administered via dendritic celis," J. Virol., vol. 67(7):4062-4069 (1993).
Nanbru, C. et al., "Alternative translation of the proto-oncogene-c-myc by an internal ribosome entry site," J Biol. Chem., 272(51): 32061-32066 (1997).
Nelson, AL et al., "Development trends for human monoclonal antibody therapeutics," Nat Rev Drug Discov., vol. 9 (10): 767-774 (2010).
Nemazee, D., "Receptor editing in B cells," Adv Immunol., vol. 74: 89-126 (2000).
Neufeld, G., et al. "Vascular endothelial growth factor (VEGF) and its receptors," Faseb J.,vol. 13(1):9-22 (1999).
Neumann, E., "Gene transfer into mouse lyoma cells by electroporation in high electric fields," EMBO J., vol. 1 (7):841-845 (1982).
Ngo, T.H. et al., "Identification of functional synergism between monoclonal antibodies. Application to the enhancement of plasminogen activator inhibitor-1 neutralizing effects," FEBS Lett., vol. 416(3):373-376 (1997).
Nguyen, VK. et al.,"Heavy-chain only antibodies derived from dromedary are secreted and displayed by mouse B cells," Immunology, vol. 109(1):93-101 (2003).
Nicholson, IC. et al., "Antibody repertoires of four- and five-feature translocus mice carrying human immunoglobulin heavy chain and kappa and lambda light chain yeast artificial chromosomes," J Immunol., vol. 163(12):6898-6906 (1999).
Nissim A, et al., "Antibody fragments from a 'single pot' phage display library as immunochemical reagents" EMBO J., 13(3):692-698 (1994).
Nord, K. et al., "A combinatorial library of an alpha-helical bacterial receptor domain," Protein Eng.,vol. 8(6):601-608 (1995).
Nord' K. K et al. "Recombinant human factor VIII-specific affinity ligands selected from phage-displayed combinatorial libraries of protein A," Eur J Biochem., vol. 268(15):4269-4277 (2001).

(56) References Cited

OTHER PUBLICATIONS

Norderhaug,-L. et al.,"Balanced expression of single subunits in a multisubunit protein, achieved by cell fusion of individual transfectants," Eur J Biochem., vol. 269(13):3205-3210 (2002).
Nowakowski, A., et al., "Potent neutralization of botulinum neurotoxin by recombinant oligoclonal antibody" PNAS, USA: vol. 99(17):11346-11350 (2002).
Oh, SK., et al., "Homeotic gene Antennapedia mRNA contains 5'-noncoding sequences that confer translational initiation by internal ribosome binding," Genes Dev., vol. 6(9):1643-1653 (1992).
Patel AK, et al., "An improved assay for antibody dependent cellular cytotoxicity based on time resolved fluorometry," .1 Immunol. Methods, vol. 184(1):29-38 (1995).
Pau, M.G. et al., "The human cell line PER.C6 provides a new manufacturing system for the production of influenza vaccines," Vaccine, vol. 19(17-19):2716-2721 (2001).
Peeters, K, et al., "Production of antibodies and antibody fragments in plants," Vaccine, vol. 19(17-19): 2756-2761 :2001).
Perrin, P. et al., "In vitro rabies vaccine potency appraisal by ELISA: advantages of the immunocapture method with a neutralizing anti-glycoprotein monoclonal antibody," Biologicals, vol. 18(4): 321-330 (1990).
Persic, L. et al., "An integrated vector system for the eukaryotic expression of antibodies or their fragments after selection from phage display libraries," Gene, vol. 187(1):9-18 (1997).
Phelps, JL et al, "Expression and characterization of a chimeric bifunctional antibody with therapeutic applications," J. Immunol., vol. 145(4):1200-1204 (1990).
Pluckthun, A et al., "In vitro selection and evolution of proteins," In: Adv. Prot. Chem.,vol. 55: 367-403 (2001).
Pollock DP. et al., "Transgenic milk as a method for the production of recombinant antibodies," J Immunol Methods, vol. 231 (1-2), 147-157 (1999).
Porgador, A. et al., Bone marrow generated dendritic cells pulsed withaclass I-restricted peptide are potent nducers of cytotoxic T lymphocytes, J Exp Med., vol. 182(1):255-260 (1995).
Radic, MC. et al., "Ig Hand L chain contributions to autoimmune specificities," J Immunol., vol. 146(1):176-182 (1991).
Rebar, EJ. et al., "Phage display methods for selecting tinc finger proteins with novel DNA-binding specificities," Methods Enzymol., vol. 267:129-149 (1996).
Rees, S. et al, "Bicistronic vector for the creation of stable mammalian cell lines that predisposes all antibiotic-resistant cells to express recombinant protein," Biotechniques, vol. 20(1):102-110 (1996).
Reiter, Y.et al., "An antibody single-domain phagedisplay library of a native heavychain variable. region isolation of runctional single-domain VH molecules with a unique interface," J. Mol Biol.,vol. 290(3), 685-698 (1999).
Reply of Patent Proprietor to Notice of Opposition under R.79( 1) in EP2314629B, pp. 1-20.
Repp, R. et al., "Phase I clinical trial of the bIspecific antibody MDX-H21 0 (anti-FcgammaRI x anti-HER-2/neu) in combination with Filgrastim (G-CSF) for treatment of advanced breastcancer," Br J Cancer, vol. 89(12):2234-2243 :2003).
Riechmann, L., "Novel folded protein domains generated by combinatorial shuffling of polypeptide segments," PNAS, USA, vol. 97(18): 10068-10073 (2000).
Ritchie, A. et al., "Allelic exclusion and control of endogenous immunoglobulin gene rearrangement in kappa transgenic mice," Nature, vol. 312(6):517-520 (1984).
Roberts, RW., "RNA peptide fusions for the in vitro selection of peptides and proteins," PNAS, USA, vol. 94 (23):97-203 (1997).
Roholt, OA., et al., "Antibodies of limited heterogeneity: L chains of a single mobility," Immunochemistry, vol. 7 (4):329-340 (1970).
Roitt, I.M. et al., "Anti-idiotypes as surrogate antigens: structural considerations," Immunol. Today, vol. 6(9):265-267 (1985).
Rojas, G. et al., "Phage antibody fragments library combining a single human light chain variable region with immune mouse heavy chain variable regions," J. Biotechnol., vol. 94(3):287-298 (2002).
Rong, S. et al., "Tumorigenesis induced by coexpression of human hepatocyte growth factor and the human met protooncogene leads to high levels of expression of the ligand and receptor," Cell Growth Differ., vol. 4(7): 563-569 (1993).
Rong, S. et al., "Tumorigenicity of the met proto-oncogene and the gene for hepatocyte growth factor, " Mol. Cell . Biol. vol. 12(11):5152-5158 (1992).
Rosenberg, A. et al, " T7 Select Phage Display System: A Powerful New Protein Display System Based on 3acteriaophage T7," Innovations, vol. 6:1-6 (1996).
Rottgen, P., et al., "A human pancreatic secretory trypsin inhibitor presenting a hypervariable highly constrained apitope via; monovalent phagemid display," Gene, vol. 164(2): 243-250 (1995).
Sanger, F. et al., "DNA sequencing with chain-terminating inhibitors," PNAS USA, vol. 74(12):5463-5467 (1977).
Santini, C. et al.,"Efficient display of an Hcv cDNA expression library as C-terminal fusion to the capsid protein D of acteriophage lambda," J Mol Biol., vol. 282(1):125-135 (1998).
Schaffitzel, C, et al., "Ribosome display: an in vitro method for selection and evolution of antibodies from libraries," J Immunol. Methods, vol. 231(1-2):119-135 (1999).
Schlehuber, S, "Tuning ligand affinity, specificity, and folding stability of an engineered lipocalin variant—a so-called 'anticalin'—using a molecular random approach," Biophysical Chemistry, vol. 96:213-228 (2002).
Schmitz, U. et al., "Phage display: a molecular tool for the generation of antibodies—a review," Placenta, 21 Suppl A: S106-112 (2000).
Yelverton E, et al., "Rabies virus glycoprotein analogs: biosynthesis in *Escherichia coli*," Science, vol. 219 :4585):614-620 (1983).
Yoo, EM et al., "Structural requirements for polymeric immunoglobulin assembly and association with J chain," J Biol. Chem., vol. 274(47):33771-33777 (1999).
Zacharchuk, CM. et al.,"Programmed T lymphocyte death.Cell activation- and steroid-induced pathways are mutually antagonistic," J. Immunol., vol. 145(12):4037-4045 (1990).
Zahn-Zabal, M. et al., "Development of stable cell lines for production or regulated expression using matrix attachment regions," J Biotechnol., vol. 87:29-42 (2001).
Zamai, L. et al., "Optimal detection of apoptosis by flow cytometry depends on cell morphology," Cytometry, vol. 14(8): 891-897 (1993).
Zhu, Z. et. al., "Inhibition of vascular endothelial growth factor-induced receptor activation with anti-kinase insert domain-containing receptor single-chain antibodies from a phage display library," Cancer Res., vol. 58(15):3209-3214.
Zhu, Z., et al., "Inhibition of tumor growth and metastasis by targeting tumor-associated angiogenesis with antagonists to the receptors of vascular endothelial growth factor," Invest New Drugs, vol. 17(3):195-212 (1999).
Zou, Yr. et al., "Cre-loxP-mediated gene replacement: a mouse strain producing humanized antibodies," Curr Biol., vol. 4(12):1099-1103 (1994).
Neuberger, MS., "Isotype exclusion and transgene down-regulation in immunoglobulin-lambda transgenic mice," Nature, vol. 338(6213): 350-352 (1989).
Nikolic, T. et al, "A subfraction of B220(+) cells in murine bone marrow and spleen; does not belong to the B cell ineage but has dendritic cell characteristics," Eur J. Immunol., vol. 32(3): 686-692 (2002).
Nissim, A. "Antibody fragments from a 'single pot' phage display library as immunochemical reagents," EMBO J., vol. 13(3): 692-698 (1994).
Novobrantseva, TI. et al., "Rearrangement and expression of immunoglobulin light chain genes can precede heavy chain expression during normal B cell development in mice," J Exp; Med., vol. 189(1):75-88 (1999).
O'Brien, RL., "Somatic hypermutation of an immunoglobulin transgene in kappa transgenic mice," Nature, 326 (6111):405-409 (1987).
Odegard, VH., et al., "Targeting of somatic hypermutation," Nat Rev Immunol., vol. 6(8):573-583 (2006).

(56) References Cited

OTHER PUBLICATIONS

Orban, PC. et al, "Tissue-and site-specific DNA recombination in transgenic mice," PNAS USA, vol. 89(15): 6861-6865 (1992).
Padlan, EA., "A possible procedure for reducing the immunogenicity of antibody variable domains while preserving their ligand-binding properties," Mol Immunol., vol. 28(4-5):489-498 (1991).
Pasqualucci, L. et al, "BCL-6 mutations in normal germinal center B cells: evidence of somatic hypermutation acting outside Ig loci," PNAS USA, vol. 95(20):11816-11821 (1998).
Pelanda, R. et al, "A prematurely expressed Ig(kappa) transgene, but not V(kappa)J(kappa) gene segment targeted nto the Ig(kappa) locus, can rescue B cell development in lambda5-deficient mice," Immunity, vol. 5(3): 229-239 (1996).
Jeled, Ju. et al., "The biochemistry of somatic hypermutation," Annu Rev Immunol, vol. 26: 481-511 (2008).
Phan, TG., "High affinity germinal center B cells are actively selected into the plasma cell compartment," J Exp Med., vol. 203(11): 2419-2424 (2006).
Popov, AV., "A human immunoglobulin lambda locus is similarly well expressed in mice and humans," J Exp Med., vol. 189(10): 1611-1619 (1999).
Prak, EL, et al., "Light chain replacement: a new model for antibody gene rearrangement," J Exp Med., vol. 182 (2):541-548 (1995).
Presta, LG., "Engineering of therapeutic antibodies to minimize immunogenicity and optimize function," Adv Drug Deily Rev., vol. 58(5-6): 640-656 (2006).
Queen, C. et al., "A humanized antibody that binds to the interleukin 2 receptor," PNAS USA, vol. 86 (24):10029-10033 (1989).
Rajewsky, K. et al., "Conditional gene targeting," J Clin Invest., vol. 98(3): 600-603 (1996).
Retter, MW., et al., "Receptor editing: genetic reprogramming of autoreactive lymphocytes," Cell Biochem Biophys., vol. 31(1): 81-88 (1999).
Rickert, RC. et al, "B lymphocyte-specific, Cre-mediated mutagenesis in mice," Nucleic Acids Research, vol. 25(6): 1317-1318 (1997).
Ritchie, KA. et al., "Allelic exclusion and control of endogenous immunoglobulin gene rearrangement in kappa ransgenic mice," Nature, vol. 312(5994): 517-520(1984).
Sasaki, Y. et al, "Canonical NF-kappa B activity, dispensable for B cell development, replaces BAFF-receptor signals and promotes B cell proliferation upon activation," Immunity, vol. 24: 729-739 (2006).
Schaffitzel, C. et al. In vitro selection and evolution of protein-ligand interactions by ribosome display. In: Protein Protein Interactions, A Molecular Cloning Manaul , E. Golomis Ed., Cold Spring Harbor Labatory Press, New York: 535-537 (2001).
Seibler, J. et al., "Rapid generation of inducible mouse mutants,"Nucleic Acids Res., vol. 31(4):e12 (2003).
Shaffer, AL. et al., "In vivo occupancy of the kappa light chain enhancers in primary pro-and pre-B cells: a model for kappa locus activation," Immunity, vol. 6(2): 131-143 (1997).
Sharpe, MJ. et al, "Somatic hypermutation of immunoglobulin kappa may depend on sequences 3' of C kappa and 3ccurs on passenger transgenes," EMBO J., vol. 10(8): 2139-2145 (1991).
Shvarts, a. A et al , "A senescence rescue screen identifies BCL6 as an inhibitor of anti-proliferative p19(ARF)-p53 signaling," Genes Dev., vol. 16(6):681-686 (2002).
Sirac, C. et al, "Role of the monoclonal kappa chain V domain and reversibility of renal damage in a transgenic model of acquired Fanconi syndrome," Blood, vol. 108(2):536-543 (2006).
Sirac, C. et al, "Toward understanding renal Fanconi syndrome: step by step advances through experimental models," Contrib Nephrol, vol. 169:247-261 (2011).
Sirac, C. et al., "Light chain inclusion permits terminal B cell differentiation and does not necessarily result in autoreactivity," PNAS USA, vol. 103(20): 7747-7752 (2006).
Smith, EJ. et al., "A novel, native-format bispecific antibody triggering T-cell killing of B-cells is robustly active in mouse tumor models and cynomolgus monkeys," Sci Rep., vol. 5: 17943 12 pages (2015).
Smith-Gill, SJ. et al., "Contributions of immunoglobulin heavy and light chains to antibody specificity for lysozyme and two haptens," J Immunol., vol. 139(12): 4135-4144 (1987).
Soriano, P., "Generalized lacZ expression with the ROSA26 Cre reporter strain," Nat Genet., vol. 21(1):70-71 (1999).
Srinivas, S. et al., "Cre reporter strains produced by targeted insertion of EYFP and ECFP into the ROSA26 locus," BMC Dev Biol., vol. 1:4 (2001).
Stevens, "Human Antibody Discovery, VelocImmune—A novel platform," Pharma Focus Asia, Issue 8: 72-74 (2008).
Storb, U. et al, "Transgenic mice with mu and kappa genes encoding antiphosphorylcholine antibodies," J Exp Med., vol. 164(2):627-641 (1986).
Storb, U. et al., "Immunoglobulin transgenes as targets for somatic hypermutation," Int J Dev Biol., vol. 42 (7):977-982 (1998).
Tan, P. et al., "Superhumanized antibodies: reduction of immunogenic potential by complementarity-determining region grafting with human germline sequences: application to an anti-CD28," The Journal of Immunology, vol. 169:1119-1125 (2002).
Taylor, LD. et aL, "A transgenic mouse that expresses a diversity of human sequence heavy and light chain Immunoglobulins," Nucleic Acids Res., vol. 20(23):6287-6295 (1992).
Taylor, LD., "Human immunoglobulin transgenes undergo rearrangement, somatic mutation and class switching in mice that lack endogenous IgM," Int Immunol.,vol. 6(4): 579-591 (1994).
Thiebe, R. et al., "The variable genes and gene families of the mouse immunoglobulin kappa locus," Eur J Immunol, vol. 29(7):2072-2081 (1999).
Thomas, KR et al., "Site-directed mutagenesis by gene targeting in mouse embryo-derived stem cells," Cell, vol. 51 (3):503-512 (1987).
Throsby, M. et al., "Isolation and characterization of human monoclonal antibodies from individuals infected with Nest Nile Virus," J Virol., vol. 80(14):6982-6992 (2006).
Torres et al., "LoxP-containing transgenes,"Laboratory Protocols for Conditional Gene Targeting, Chapter 10:42-53 (1997).
Neiner, LM., "Fully human therapeutic monoclonal antibodies, "J Immunother., vol. 29(1):1-9 (2006).
Wilson TJ, et al., "The LoxP/CRE system and genome modification," Methods Mol Biol., 158, 83-94 (2001).
Winter, D.B. et al. "Insertion of 2 kb of bacteriophage DNA between an immunoglobulin promoter and leader exon stops somatic hypermutation in a kappa transgene," Mol Immunol, vol. 34(5): 359-366 (1997).
Winter, G. et al., "Making antibodies by phage display technology," Annu Rev Immunol., vo1.12:433-455 (1994).
Wunderlich, FF., "Generation of inducible Cre systems for conditional gene inactivation in mice," PhD thesis, Universitat Köin (2004).
Xiang, Y., et al., "The Downstream Transcriptional Enhancer, Ed, positively regulates mouse Ig kappa gene expression and somatic hypermutation," J Immunol., vol. 180(10): 6725-6732 (2008).
Xu, Y. et al, "Deletion of the Ig kappa light chain intronic enhancer/matrix attachment region impairs but does not abolish V kappa J kappa rearrangement," Immunity, vol. 4(4):377-385 (1996).
Yang, SY., et al, "Control of gene conversion and somatic hypermutation by immunoglobulin promoter and enhancer sequences," J Exp Med., vol. 203(13): 2919-2928 (2006).
Yang, XW. et al., "Homologous recombination based modification in *Escherichia coli* and germline transmission in transgenic mice of a bacterial artificial chromosome," Nat Biotechnol., vol. 15(9): 859-865 (1997).
Yoshio-Hoshino, N. et al., "Establishment of a new interleukin-6 (IL-6) receptor inhibitor applicable to the gene terapy for IL-6-dependent tumor," Cancer Res., vol. 67(3):871-875 (2007).
Zou, YR. et al., "Generation of a mouse strain that produces immunoglobulin kappa chains with human constant regions," Science, vol. 262(5137): 1271-1274 (1993).

(56) References Cited

OTHER PUBLICATIONS

Jechlinger, W., "Optimization and delivery of plasmid DNA for vaccination," Expert Rev Vaccines, vol. 5(6): 803-825 (2006).
Jiang, X. et al., "A novel strategy for generation of monoclonal antibodies from single B cells using rt-PCR technique and in vitro expression," Biotechnol Prog., vol. 22(4): 979-988 (2006).
Jin, A. et al., "A rapid and efficient single-cell manipulation method for screening antigen-specific antibody-secreting ells from human peripheral blood," Nat Med., vol. 15(9): 1088-1092 (2009).
Kato, M. et al., "Cell activation by CpG ODN leads to improved electrofusion in hybridoma production," J Immunol Methods, vol. 373(1-2):102-110 (2011).
Kim, CH. et al., "Subspecialization of CXCR5+ T cells: B helper activity is focused in a germinal center-localized subset of CXCR5+ T cells," J. Exp Med., vol. 193(12):1373-1381 (2001).
Kim, MS. et al., "Comparative analyses of complex formation and binding sites between human tumor necrosis factor alpha and its three antagonists elucidate their different neutralizing mechanisms," J. Mol Biol., vol. 374(5):1374-1388 (2007).
Kwakkenbos, MJ. et al., "Generation of stable monoclonal antibody producing B cell receptor-positive human memory B cells by genetic programming," Nat Med., vol. 16(1):123-128 (2010).
Lai, L. et al, "Mouse cell surface antigens: nomenclature and immunophenotyping," J. Immunol., vol. 160 (8)3861-3868 (1998).
Ling, NR. et al., "Modulation of the murine immune response to human IgG by complexing with monoclonal antibodies. I. Antibody responses to determinants on the constant region of light chains and gamma chains," Immunology, vol. 62(1):1-6 (1987).
Lonberg N. et al. "Human Antigen-specific human antibodies from mice comprising four distinct genetic modifications," Nature, vol. 368(6474):856-859 (1994).
Love JC. et al. "A microengraving method for rapid selection of single cells producing antigen-specific antibodies," Nat Biotechnol., vol. 24(6): 703-707 (2006).
Babcook, JS. et al., "A novel strategy for generating monoclonal antibodies from single, isolated lymphocytes producing antibodies of defined specificities," PNAS USA, vol. 93(15):7843-7848 (1996).
Banchereau, J. et al., "Long-term human B cell lines dependent on interleukin-4 and antibody to CD40," Science, vol. 251(4989): 70-72 (1991).
Bins, AD. et al, "A rapid and potent DNA vaccination strategy defined by in vivo monitoring of antigen expression," Nat Med, vol. 11(8):899-904 (2005).
Chao, G. et al., "Isolating and engineering human antibodies using yeast surface display," Nat Protoc., vol. 1(2): 755-768 (2006).
Clark, M., "Antibody humanization: a case of the 'Emperor's new clothes'?," Immunol Today, vol. 21 (8):397-402 (2000).
Cobaugh, CW., et al., "Synthetic antibody libraries focused towards peptide ligands," J Mol Biol., vol. 378(3): 622-633 (2008).
Crowe, JE Jr., "Recent advances in the study of human antibody responses to influenza virus using optimized iuman hybridoma approaches," Vaccine, vol. 27 Suppl 6:G47-51 (2009).
Ettinger, R. et al., "IL-21 induces differentiation of human naive and memory B cells into antibody-secreting plasma mils," J Immunol, vol. 176(12): 7867-7879 (2005).
Feldhaus, MJ. et al., "Flow-cytometric isolation of human antibodies from a nonimmune *Saccharomyces cerevisiae* surface display library,"Nat Biotechnol., vol. 21(2):163-170 (2003).
Fischer, N., Sequencing antibody repertoires: the next generation, Mabs, vol. 3(1):17-20 (2011).
GE, X. et al., "Rapid construction and characterization of synthetic antibody libraries without DNA amplification," Biotechnol Bioeng, vol. 106(3): 347-357 (2010).
Glanville, J. et al., "Precise determination of the diversity of a combinatorial antibody library gives insight into the human immunoglobulin repertoire," PNAS, vol. 106(48): 20216-20221(2009).
Good, KL. et al. "Kinetics of human B cell behavior and amplification of proliferative responses following stimulation with IL-21," J Immunol., vol. 177(8):5236-5247 (2006).

Gulli, LF et al.' "Epidermal growth factor-induced apoptosis in A431 cells can be reversed by reducing the tyrosine kinase activity," Cell Growth Differ., vol. 7(2):173-178 (1996).
Harding, FA. et al.,"The immunogenicity of humanized and fully human antibodies: residual immunogenicity resides in the CDR regions," MAbs,vol. 2(3), 256-265 (2010).
Harvey, BR. et al., "Anchored periplasmic expression, a versatile technology for the isolation of high-affinity antibodies from *Escherichia coli*-expressed libraries," PNAS USA, vol. 101(25):9193-9198 (2004).
Ishii, KJ. et al., "TANK-binding kinase-1 delineates innate and adaptive immune responses to DNA vaccines," Nature, vol. 451 (7179): 725-729 (2008).
Jacob, J. et al., "Activity of DNA vaccines encoding self or heterologous Her-2/neu in Her-2 or neu transgenic mice," Cell Immunol. vol. 240(2):96-106 (2006).
Manz, RA., et al., "Maintenance of serum antibody levels," Annu Rev Immunol., vol. 23:367-386 (2005).
Mazor, Y. et al.' "Isolation of engineered, full-length antibodies from libraries expressed in *Escherichia coli*," Nat Biotechnol., vol. 25(5):563-565 (2007).
Meijer PJ. et al., "Isolation of human antibody repertoires with preservation of the natural heavy and light chain pairing," J Mol Biol., vol. 358(3):764-772 (2006).
Merus MeMo Description filed by the Applicant at the EPO on Dec. 22, 2011 in European Application No. 09075279.1, (EP 2147594 B1).
Mohapatra, S. et al., "Designer monoclonal antibodies as drugs: the state of the art," Expert Rev Clin Immunol., vol. 4(3): 305-307 (2008).
Ogunniyi, AO. et al., "Screening individual hybridomas by microengraving to discover monoclonal antibodies," Nat Protoc., vol. 4(5):767-782 (2009).
Persson, H. et al., "A focused antibody library for improved hapten recognition," J. Mol. Biol., vol. 357(2): 607-620 ;2006).
Ponsel, D. et al., "High affinity, developability and functional size: the holy grail of combinatorial antibody library jeneration," Molecules, vol. 16(5):3675-3700 (2011).
Poulsen, TR., "Limits for antibody affinity maturation and repertoire diversification in hypervaccinated humans," J. Immunol., vol. 187(8): 4229-4235 (2011).
Quaak, SG. et al., "GMP production of p DERMATT for vaccination against melanoma in a phase I clinical trial," Eur J Pharm Biopharm,vol. 70(2): 429-438 (2008).
Ravn, U. et al., By-passing in vitro screening—next generation sequencing technologies applied to antibody display and in silico candidate selection, Nucleic Acids Res., vol. 38(21):e193 (2010).
Reddy, ST. et al., "Monoclonal antibodies isolated without screening by analyzing the variable-gene repertoire of plasma cells," Nat Biotechnol.,vol. 28(9): 965-969 (2010).
Reddy, ST. et al.' "Systems analysis of adaptive immunity by utilization of high-throughput technologies," Curr Opin. Biotechnol, vol. 22(4): 584-589 (2011).
Ruuls, SR. et al., "Novel human antibody therapeutics: the age of the Umabs," Biotechnol J., vol. 3(9-10): 1157-1171 (2008).
Schmidlin, H. et al., "New insights into the regulation of human B-cell differentiation" Trends Immunol., vol. 30 (6):277-285 (2009).
Shapiro-Shelef, M. et al., "Regulation of plasma-cell development," Nat. Rev. Immunol., vol. 5(3): 230-242 (2005).
Smith, K. et al., "Rapid generation of fully human monoclonal antibodies specific to a vaccinating antigen," Nat. Protoc.,vol. 4(3):372-384 (2009).
Stevenson, FK. et al., "DNA vaccines to attack cancer," PNAS USA, 101 Suppl 2:14646-14652 (2004).
Story, CM. et al., "Profiling antibody responses by multiparametric analysis of primary B cells," PNAS USA, vol. 105 (46):17902-17907 (2008).
Tajiri, K. et al., "Cell-microarray analysis of antigen-specific B-cells:single cell analysis of antigen receptor expression and specificity," Cytometry Part A., vol. 71(11), 961-967 (2007).

(56) References Cited

OTHER PUBLICATIONS

Tiller, T. et al., "Efficient generation of monoclonal antibodies from single human B cells by single cell RT-PCR and expression vector cloning," J Immunol Methods, vol. 329(1-2): 112-124 (2008).
Tokimitsu, Y. et al., "Single lymphocyte analysis with a microwell array chip," Cytometry Part A., vol. 71(12): 1003-1010 (2007).
Traggiai, E et al., "An efficient method to make human monoclonal antibodies from memory B cells: potent neutralization of SARS coronavirus," Nat Med., vol. 10(8): 871-875 (2004).
Neeratna, R. et al., "CPG ODN allows lower dose of antigen against hepatitis B surface antigen in BALB/c mice," Immunol Cell Biol., vol. 81(1):59-62 (2003).
Nhittington, PJ. et al., "DNA vaccination controls Her-2+ tumors that are refractory to targeted therapies," Cancer Res., vol. 68(18): 7502-7511 (2008).
Wrammert, J. et al., "Rapid cloning of high-affinity human monoclonal antibodies against influenza virus," Nature, vol. 453(7195): 667-671 (2008).
Wu, C. et al., "Simultaneous targeting of multiple disease mediators by a dual-variable-domain immunoglobulin," Nat Biotechnol., vol. 25(11):1290-1297 (2007).
Yu, X. et aL, "An optimized electrofusion-based protocol for generating virus-specific human monoclonal antibodies," J Immunol Methods, vol. 336(2):142-151 (2008).
Zubler, RH. et al., "Theoretical and practical aspects of B-cell activation:murine and human systems," Immunol. Rev, vol. 99: 281-299 (1987).
Coligan JE, "Commonly used detergents," Curr Protoc Protein Sci., Appendix 1:Appendix 1B (2001).
Davies, NP. et al., "Creation of mice expressing human antibody light chains by introduction of a yeast artificial Thromosome containing the core region of the human immunoglobulin kappa locus," Biotechnology, vol. 11(8):911-914 (1993).
De Francesco, L. et al, "Big Pharma vies for mice," Nature Biotechnology, News in Brief Article, vol. 25(6): 613 :2007).
De Kruif, J. et al., "Selection and application of human single chain Fv antibody fragments from a semi-synthetic phage antibody display library with designed CDR3 regions," J Mol Biol. vol. 248(11:97-105 (1995).
Decision of US District Court about U.S. Pat. No. 8,502,018, REGN vs. Merus B.V., dated Nov. 2, 2015, 114 pages.
Decl. Anthony De Franco (1st) in the Matter of Australian Patent Application No. 2009263082 (the Opposed Application) in the name of Merus B.v. (the Applicant)—and—Opposition thereto by RegeneronPharmaceuticals, Inc. (the Opponent), Dec. 21, 2014, 56 pages.
Decl. Robert Brink (4th), in the Matter of Australian Patent Application No. 2009263082 (the Opposed Application) in the name of Merus B.v. (the Applicant)—and—Opposition thereto by RegeneronPharmaceuticals, Inc. (the Deponent), Oct. 19, 2016, 19 pages.
European Search Report, EP Application No. 12186010, dated May 22, 2013, 11 pages.
Flavell, DJ, et al. "Therapy of human Tcell acute lymphoblastic leukaemia with a combination of anti-CD7 and anti-CD38-SAPORIN immunotoxins is significantly better than therapy with each individual immunotoxin," Br J. Cancer, vol. 84 (4): 571-578 (2001).
Sen Bank Acc. No. X59315 (human Ig kappa Lc variable region), 13 pages.
Hengstschläger, M. et al, "A lambda 1 transgene under the control of a heavy chain promoter and enhancer foes not undergo somatic hypermutation," Eur J. Immunol., vol. 24(7):1649-1656 (1994).
Hochedlinger, K., et al., "Monoclonal mice generated by nuclear transfer from mature B and T donor cells," Nature, vol. 415(6875): 1035-1038 (2002).
Homig-Holzel, C. et al., "Constitutive CD40 signaling in B cells selectively activates the noncanonical NF-kappaB pathway and promotes lymphomagenesis," J Exp Med., vol. 205(6): 1317-1329 (2008).

Hoogenboom, HR., "Selecting and screening recombinant antibody libraries," Nat Biotechnol., vol. 23(9):1105-1116 :2005).
Hwang, WY., et al., "Immunogenicity of engineered antibodies," Methods, vol. 36(1):3-10 (2005).
ImMunoGeneTics "Cheb_VK" 7 pages. (2012).
Inlay, M. "Essential roles of the kappa light chain intronic enhancer and 3' enhancer in kappa rearrangement and demethylation," Nat Immunol., vol. 3(5):463-468 (2002).
International Preliminary Examination Report, PCT/EP03/07690, dated Nov. 29, 2004, 19 pages.
International Search Report, PCT/EP03/07690, dated Sep. 21, 2004, 9 pages.
International Search Report, PCTJNL2004/000386, dated Nov. 23, 2004, 2 pages.
International Search Report, PCTJNL2005/000036, dated Jan. 16, 2006, 3 pages.
Jacob, JB. et al., " Combining Human and Rat Sequences in Her-2 DNA Vaccines Blunts Immune Tolerance and Drives Antitumor Immunity," Cancer Research, vol. 70(1):119-128 (2010).
Jain, M., et al., "Engineering antibodies for clinical applications," Trends Biotechnol., vol. 25(7): 307-316 (2007).
Janeway C. et al., "Structure if the Antibody Molecule and the Immunoglobin Genes," Immuno Biology the Immune System in Health and Disease, Chapter 3, Garland Science, Fourth Edition, 90-108 (1999).
Janeway C. et al., "The Development and Survival of Lymphocytes, Immuno Biology the Immune System in Health and Disease, " Garland Science, Chapter 6, Fourth Edition, 375-290 (1999).
Janeway C., "Antigen Presentation to T Lymphocytes, Immuno Biology the Immune System in Health and Disease," Garland Science, Chapter 6, Eighth Edition, 31 pages. (2012).
Jolly, CJ., "Rapid methods for the analysis of immunoglobulin gene hypermutation: application to transgenic and jene targeted mice," Nucleic Acids Res., vol. 25(10):1913-1919 (1997).
Jones, PT. et al., "Replacing the complementarity-determining regions in a human antibody with those from a mouse," Nature, vol. 321(6069):522-525 (1986).
Kakitani, M. et al., "A novel transgenic chimaeric mouse system for the rapid functional evaluation of genes encoding secreted proteins," Nucleic Acids Res., 33(9). 8 pages (2005).
Kelly, R. et al., "Antigen Binding Thermodynamics and Antiproliferative Effects of Chimeric and Humazinzed anti-p185 HER2 Antibody Fab Fragments," Biochemistry, vol. 31 :5435-5441 (1992).
Kitamura D., "A B cell-deficient mouse by targeted disruption of the membrane exon of the immunoglobulin mu chain gene," Nature,vol. 350(6317):423-426 (1991).
Kling, J. "Big Pharma vies for mice," Nature Biotechnology, vol. 25(6): 613 (2007).
Klitz, W., et al., "New HLA haplotype frequency reference standards: high resolution and large sample typing of HLA DR-DQ haplotypes in a sample of European Americans," Tissue Antigens, vol. 62(4), 296-307 (2003).
Klotz, EL. et al, "Somatic hypermutation of an artificial test substrate within an Ig kappa transgene," J ImmunoL, vol. 161(2):782-790 (1998).
Klotz, EL. et al., "Somatic hypermutation of a lambda 2 transgene under the control of the lambda enhancer or the heavy chain intron enhancer," J. Immunol, vol. 157(10):4458-4463 (1996).
Klöhn, PC., et al., "IBC's 23rd Annual Antibody Engineering, 10th Annual Antibody Therapeutics International conferences and the 2012 Annual Meeting of The Antibody Society:Dec. 3-6, 2012," San Diego, CA, Mabs, vol. 5 (2): 178-201 (2013).
Kong, Q., "A lambda 3' enhancer drives active and untemplated somatic hypermutation of a lambda 1 transgene," J Immunol., vol. 161(1):294-301 (1998).
Kramer, RA et al., "A novel helper phage that improves phage display selection efficiency by preventing the amplification of phages without recombinant protein,"Nucleic Acids Res., vol. 31(11): 9 pages. (2003).
Kwaks , TH., et al., "Employing epigenetics to augment the expression of therapeutic proteins in mammalian cells," Trends Biotechnol., vol. 24(3) :137-142 (2006).

(56) References Cited

OTHER PUBLICATIONS

Larbouret, C. et al., "In vivo therapeutic synergism of anti-epidermal growth factor receptor and anti-HER2 monoclonal antibodies against pancreatic carcinomas," Clin Cancer Res., vol. 13(11), 3356-3362 (2007).
Lazar, GA. et al.' "A molecular immunology approach to antibody humanization and functional optimization," Mol Immunol., vol. 44(8):1986-1998 (2007).
Lee, CM. et al., "Selection of human antibody fragments by phage display," Nat. Protoc, vol. 2(11): 3001-3008 (2007).
Lefranc, MP., "Nomenclature of the human immunoglobulin kappa (IGK) genes," Exp Clin Immunogenet., vol. 18 (3):161-174 (2001).
Letter of Protest filed by Regeneron against U.S. Appl. No. 15/158,543 on Oct. 14, 2016, 45 pages.
Li, LH. et al "Characterization of PEG-mediated electrofusion of human erythrocytes," Biophys J., vol. 67 (6)2361-2366 (1994).
Lie, YS., et al., "Advances in quantitative PCR technology: 5' nuclease assays," Curr Opin Biotechnol., vol. 9(1): 43-48 (1998).
Lofgren, JA. et al., "Comparing ELISA and surface plasmon resonance for assessing clinical immunogenicity of panitumumab," J Immunol., vol. 178(11): 7467-7472 (2007).
Lonberg, N., "Human antibodies from transgenic animals," Nat Biotechnol., vol. 23(9): 1117-1125 (2005).
Ma, J. et al., "Assembly of monoclonal antibodies with IgG1 and IgA heavy chain domains in transgenic tobacco plants," J. Immunol., vol. 24(1): 131-138 (1999).
Mao, H et al., "Spatially addressed combinatorial protein libraries for recombinant antibody discovery and pptimization," Nat Biotechnol., vol. 28(11):1195-1202 (2010).
Mao, X. et al., "Activation of EGFP expression by Cre-mediated excision in a new ROSA26 reporter mouse strain," Blood, vol. 97(1): 324-326 (2001).
McGinnes, K., "B-lineage colonies from normal, human bone marrow are initiated by B cells and their progenitors," Bood, vol. 77(5):961-970(1991).
Meyer, KB. et al., "The Ig kappa 3'-enhancer triggers gene expression in early B lymphocytes but its activity is enhanced on B cell activation," Int Immunol., vol. 8(10):1561-1568 (1996).
Meyer, KB., et al.,"The importance of the 3'-enhancer region in immunoglobulin kappa gene expression," Nucleic Acids Res., vol. 11, 18(19):5609-5615 (1990).
Middendorp, S. et al., "Impaired precursor B cell differentiation in Bruton's tyrosine kinase-deficient mice," J Immunol., vol. 168(6): 2695-2703 (2002).
Middendorp, S., et al., "Cellular maturation defects in Bruton's tyrosine kinase-deficient immature B cells are amplified by premature B cell receptor expression and reduced by receptor; editing," J Immunol., vol. 172 (3):1371-1379 (2004).
Mirick, GR. et al., "A review of human antiglobulin antibody (HAGA, HAMA, HACA,; HAHA) responses to monoclonal antibodies. Not four letter words,Q J ." Nucl Med Mol Imaging, vol. 48(4), 251-257 (2004).
Moreau, JF. et al., "Leukaemia inhibitory factor is identical to the myeloid growth factor human interleukin for DA cells," Nature,vol. 336(6200):690-692 (1988).
Morrison, SL. et al., "Chimeric human antibody molecules: mouse antigenbinding domains with human constant region domains," PNAS USA, vol. 81(21): 6851-6855 (1984).
Mostoslavsky, R. et al., "A synchronous replication and allelic exclusion in the immune system," Nature, vol. 414 (6860): 221-225 (2001).
Murakami, T. et al., "Splenic CD19-CD35+B220+ cells function as an inducer of follicular dendritic cell network formation," Blood, vol. 110(4):1215-1224 (2007).
Nagle, M. "Press Release Regeneron helps make Sanofi Veloclmmune to its 'weak' pipeline," 2 pages, Dec. 3, 2007.
Nemazee, D., "Receptor editing in lymphocyte development and central tolerance," Nat Rev Immunol., vol. 6 (10):728-740 (2006).
Neuberger, MS et al., "Isotype exclusion and transgene down-regulation in immunoglobulin-lambda transgenic mice," Nature, vol. 338 (6213): 350-352 (1989).
Notice of Opposition from Regeneron in EP 2314629B, Sep. 25, 2014, 1 page.
Opponent's (REGN) submissions filed in the Matter of Australian Patent Application No. 2009263082 (the Opposed Application) in the name of Merus B.v. (the Applicant)—and—Opposition thereto by RegeneronPharmaceuticals, Inc. (the Opponent), Oct. 19, 2016, 4 pages.
Opponent's (REGN) submissions filed in the Matter of Australian Patent Application No. 2009263082 (the Opposed Application) in the name of Merus B.v. (the Applicant)—and—Opposition thereto by RegeneronPharmaceuticals, Inc. :the Opponent), Oct. 5, 2016, 7 pages.
Opponent's submissions filed on May 1, 2016 (oppo JP5749161).
Opponent's submissions filed on Jan. 15, 2016 (oppo JP5749161) 55 pages.
Opposition (EP), notice filed by Regeneron, EP Application No. 09075279.1 dated Sep. 25, 2014, 1 page.
Opposition (EP), reply by Opponent, EP Application No. 09075279.1, dated Apr. 2, 2015, 32 pages.
Pokorna, D. et al. "DNA-vaccination via tattooing induces stronger humoral and cellular immune response than intramuscular delivery supported by molecular adjuvants," Genet Vaccines Ther., vol. 6(4):198-208 (2008).
Protest and Submission (1st) filed by Regeneron in Candian Patent Application No. 2,729,095, Apr. 8, 2014, 16 pages.
Protest and Submission (2nd) filed by Regeneron in Candian Patent Application No. 2,729,095, Sep. 16, 2015, 15 pages.
Reiter, MW. et al., "Receptor editing occurs frequently during normal B cell development," J Exp Med, vol. 188 (7):1231-1238 (1998).
Roitt, A. et al., "Immunology," Moscow "MIR" 2000, 5 pages.
Singer, M. et aL, "The Logic and Machinery of Gene Expression," Genes & Genomes, Chapter 3.3: 133-145 (1991).
WHO Technical Series Report, vol. 848, p. 8 (1994).
Claims filed in European Application No. 14163642.3 on Jun. 10, 2015, 2 pages.
Decl. Andrew Murphy dated Aug. 31, 2015, 5 pages.
Decl. Anthony De Franco (3rd) filed in the Matter of Australian Patent Application No. 2009263082 (the Opposed Application) in the name of Merus B.v. (the Applicant)—and—Opposition thereto by RegeneronPharmaceuticals, Inc. (the Opponent), Oct. 10, 2016, 41 pages.
Decl. Anthony De Franco (4th) filed in the Matter of Australian Patent Application No. 2009263082 (the Opposed Application) in the name of Merus B.v. (the Applicant)—and—Opposition thereto by RegeneronPharmaceuticals, Inc. (the Opponent), Oct. 18, 2016, 10 pages.
Extended European Search Report, EP Application No. 10189886A, dated Nov. 20, 2012, 6 pages.
Final written Submission by Opponent filing in European Application No. 10186063.3 dated, May 20, 2016, 14 pages.
Gen Bank Acc. No. AAF20450, dated Jul. 26, 2016, 2 pages.
Gen Bank Acc. No. NG_005838, Dec. 25, 2015, 4 pages.
International Preliminary Report on Patentability, PCT/NL2009/050381, dated Jan. 5, 2011, 11 pages.
International Search Report, PCT/NL2009/050381, dated Dec. 12, 2009, 6 pages.
Letter of the Patent Proprietor Opposition proceedings in Ep:2314629B, Jul. 27, 2016, 337 pages.
Letter to the European Patent Office filed in EP Application No. 12173456.0 (EP2505654) dated Apr. 12, 2013, 12 pages.
Office Action issued in European Application No. 14163642.3 on Jan. 29, 2016, 3 pages.
Office Action Response filed in U.S. Appl. No. 12/932,719, filed Jun. 11, 2014, 12 pages.
Office Action Response filed in U.S. Appl. No. 12/932,719 on Feb. 27, 2012, 10 pages.
Office Action Response filed in U.S. Appl. No. 12/932,719 on Oct. 8, 2013, 12 pages.

(56) References Cited

OTHER PUBLICATIONS

Opponent's submissions filed on Jan. 15, 2016 (oppo JP5749161), 25 pages.
Opponents Initial Supplementary Submissions the Matter of Australian Patent Application No. 2009263082 (the Opposed Application) in the name of Merus B.v. (the Applicant)—and—Opposition thereto by RegeneronPharmaceuticals, Inc. (the Opponent), Oct. 5, 2016, 7 pages.
Patent Applicant's Outline of Submission filed in the Matter of Australian Patent Application No. 2009263082 (the Opposed Application) in the name of Merus B.v. (the Applicant)—and—Opposition thereto by Regeneron Pharmaceuticals, Inc. (the Opponent), Sep. 9, 2016, 49 pages.
Patent Applicants Outline of Submissions filed in the Matter of Australian Patent Application No. 2009263082 (the Opposed Application) in the name of Mews B.v. (the Applicant)—and—Opposition thereto by Regeneron Pharmaceuticals, Inc. (the Opponent, dated Oct. 19, 2016, 15 pages.
Reply of the Patent Proprietor filed in European Patent Application No. 10186063.3, dated Februart 24, 2015, 22 pages.
Response filed by the Patentee in European Application No. 09075279.1, dated Dec. 22, 2011, 15 pages.
Response to Official Action filed in Canadian Application No. CA 2,729,095, dated May 10, 2016, 12 pages.
Response to Summons to Attend Oral Proceedings filed in European Application No. 1018063.3, dated May 20, 2016, 174 pages.
Submission filed by Patentee (post-filing data) in European Application No. 09075279.1 dated Jun. 13, 2013, 3 pages.
Submission of Apr. 2, 2015 (prosecution file, patent in suit) filed in European Patent No. 2147594, 32 pages.
Teaching of U.S. Appl. No. 12/589,181 (MeMo) dated May 24, 2012, file in U.S. Appl. No. 12/589,181 on Jun. 20, 2012, 30 pages.
U.S. Office Action, U.S. Appl. No. 13/866,747, dated Apr. 10, 2015, 8 pages.
U.S. Office Action, U.S. Appl. No. 13/866,747, dated Sep. 29, 2015, 7 pages.
U.S. Office Action, U.S. Appl. No. 13/866,756, dated Apr. 13, 2015, 9 pages.
U.S. Office Action, U.S. Appl. No. 13/866,756, dated Sep. 18, 2015, 7 pages.
U.S. Office Action, U.S. Appl. No. 14/040,023, dated Nov. 28, 2016, 14 pages.
U.S. Office Action, U.S. Appl. No. 14/081,848, dated Apr. 10, 2015, 9 pages.
U.S. Office Action, U.S. Appl. No. 14/081,848, dated Feb. 12, 2016, 7 pages.
U.S. Office Action, U.S. Appl. No. 15/205,629, dated Nov. 1, 2016, 15 pages.
Smith, GP. et al., "Small binding proteins selected from a combinatorial repertoire of knottins displayed on phage"J Mol Biol., vol. 277(2): 317-332 (1998).
Smith, GP., "Filamentous fusion phage: novel expression vectors that display cloned antigens on the virion surface," Science, 228(4705):1315-1317 (1985).
Spillner, E. et al., "Paratope-based protein identification by antibody and peptide phage display," Anal Biochem., vol. 321 (1):96-104 (2003).
Spiridon CI, et al., "Tartgeting multiple Her-2 epitopes with monoclonal antibodies results in improved antigrowth activity of a; human breast cancer cell line in vitro and in vivo," Clin Cancer Res., vol. 8(6):1720-1730 (2002).
Stein, I. et al., "Translation of vascular endothelial growth factor mRNA by internal ribosome entry: implications for translation under hypoxia," Mol Cell Biol., vol. 18(6): 3112-3119 (1998).
Stijlemans, B. et al., "Efficient targeting of conserved cryptic epitopes of infectious agents by single domain antibodies African trypanosomes as paradigm," J Biol Chem., vol. 279(2):1256-1261 (2004).
Stoneley, M.,et al., "C-Myc 5' untranslated region contains an internal ribosome entry segment," Oncogene, vol. 16 (3):423-428 (1998).
Struhl, K. et al., "High-frequency transformation of yeast: autonomous replication of hybrid DNA molecules," PNAS, USA, vol. 76(3):1035-1039 (1979).
Szabo, A. et al.' "Surface plasmon resonance and its use in biomolecular interaction analysis (BIA),"Curr Opin Struct Biol., vol. 5(5):699-705 (1995).
Tada, H. et al., "Expression and characterization of a chimeric bispecific antibody against fibrin and against urokinase-type plasminogen activator," J Biotechnol, 33(2):157-174 (1994).
Takai, Y. et al., "B cell stimulatory factor-2 is involved in the differentiation of cytotoxic T lymphocytes," J Immunol., vol. 140(2): 508-512 (1988).
Takai, Y. et al., Requirement for three distinct lymphokines for the induction of cytotoxic T lymphocytes; from thymocytes, J Immunol., vol. 137 (11):3494-3500 (1986).
Tanaka, T. et al., "De novo production of diverse intracellular antibody libraries," Nucleic Acids Res., vol. 31 (5): e23 (2003).
Tanha, J. et al., "Selection by phage display of llama conventional V(H) fragments with heavy chain antibody V(H)H properties," J. Immunol Methods, vol. 263(1-2):97-109 (2002).
Thomas, "Large-Scale ite directed mutagenesis by gene targeting in mouse embryo-derived stem cells," Cell, vol. 51(3): 503-512 (1987).
Thomassen, Yet al., "Production of VHH antibody fragments by Saccharomyces cerevisiae," Enzyme Microb. Technol., vol. 3(1):273-278 (2002).
Thotakura, NR., et al., "Glycoprotein hormones:glycobiology of gonadotrophins,thyrotrophin and free alpha subunit," Glycobiol., vol. 5(1):3-10 (1995).
Toki, J.et al., "Analyses of T-Cell differentiation from hemopoietic stem cells in the GO phase by an in vitro method, " PNAS USA, vol. 88(17):7548-7551 (1991).
Transue, TR. et al., "Camel single domain antibody inhibits enzyme by mimicking carbohydrate substrate," Proteins, vol. 32(4):515-522 (1998).
Urlaub, G. et al., "Isolation of Chinese hamster cel/mutants deficient in dihydrofolate reductase activity," PNAS USA, vol. 77(7): 4216-4220 (1980).
Vagner, S., et al., "Alternative translation of human fibroblast growth factor 2 mRNA occurs by internal entry of ribosomes," Mol Cell Biol., vol. 15(1):35-44 (1995).
Vajdos, FF.et al., "Comprehensive functional maps of the antigen binding site of an anti-ErbB2 antibody obtained with shotgun scanning mutagenesis," J Mol Biol., vol. 320(2): 415-428 (2002).
Valenzuela, OM., "High-throughput engineering of the mouse genome coupled with high-resolution expression analysis," Nat Biotechnol, vol. 21 (6):652-659 (2003).
Van Den, B. et al., "Building novel binding ligands to B7.1,and B7.2 based on human antibody Single variable light chain domains," J Mol Biol., vol. 310(3):591-601 (2001).
Van Der Heijden, RW. et al., "Structural and functional studies on a unique linear neutralizing antigenic site (G5) of the rabies virus glycoprotein, " J Gen Virol., vol. 74(Pt 8):1539-1545 (1993).
Van Der Vuurst De Vries A. et al., "Dissecting the human peripheral B-cell compartment with phage display-derived antibodies," Immunology, vol. 98(1):55-62 (1999).
Vaughan T J, "Human antibodies with sub-nanomolar affinities isolated from a large non-immunized phage display ibrary," Nat Biotechnol., vol. 14(3): 309-314 (1996).
Verma, R. et al.,"Antibody engineering: comparison of bacterial, yeast, insect and mammalian expression systems," J Immunol Methods, vol. 216(1-2):165-181 (1998).
Wang, G. et al., "AT cell-independent antitumor response in mice with bone marrow cells retrovirally transduced with an antibody/ Fc-gamma chain chimeric receptor gene recognizing a human ovarian cancer antigen, "Nat Med., vol. 4 (2), 168-172 (1998).
Ward, ES. et al., "Binding activities of a repertoire of single immunoglobulin variable domains secreted from *Escherichia coli*," Nature, 341(6242):544-546 (1989).

(56) References Cited

OTHER PUBLICATIONS

Warnaar, SO. et al., "Purification of bispecific F(ab')2 from murine trinoma OC/TR with specificity for CD3 and ovarian cancer," Hybridoma, 13(6):519-526 (1994).
Weinberger, O. et al., "Cellular interactions in the generation of cytolytic T lymphocyte responses: role of Ia-positive splenic adherent cells in presentation in H-2 antigen," PNAS, USA, vol. 77(10):6091-6095 (1980).
Weinberger, O.et al., "Cellular interactions in the generation of cytolytic T lymphocyte responses. Analysis of the helper Tcell pathway," EurJ.ImmunoL, vol. 11 (5): 405-411 (1981).
Wen, XY,et al., "Tricistronic viral vectors co-expressing interleukin-12 (1L-12) andCD80(B7-1)for the immunotherapy of cancer preclinical studies in myeloma," Cancer Gene Ther, vol. 8(5)368-370 (2001).
Wigler, M. et al., "Biochemical transfer of single-copy eucaryotic genes using total cellular DNA as donor," Cell, vol. 14(3):725-731 (1978).
Wilmut I, et al., "Viable offspring derived from fetal and adult mammalian cells," Nature, vol. 385(6619):810-813 (1997).
Wilmut I., et al., "Basic techniques for transgenesis, " J. Reprod Fertil Suppl., vol. 43:265-275 (1991).
Wright A. et al., "Effect of glycosylation on antibody function: implications for genetic engineering," Trends Biotechnol., vol. 15(1):26-32. (1997).
Ye, X., et al., Ultrabithorax and Antennapedia 5' untranslated regions promote developmentally regulated internal translation initiation, Mol. Cell Biol., 17(3):1714-1721(1997).
Almagro, JC. et al., "Humanization of antibodies," Front Biosci., vol. 13: 1619-1633 (2008).
Arnold, LW., et al., "Development of B-1 cells: segregation of phosphatidyl choline specific; B cells to the B-1 population occurs after immunoglobulin gene expression," J Exp Med., vol. 179(5):1585-1595 (1994).
Aucouturier, P. et al, "Monoclonal Ig L chain and L chain V domain fragment crystallization in myeloma-associated Fanconi's syndrome," J Immunol., vol. 150(8 Pt 1):3561-3568 (1993).
Betz, AG., Elements regulating somatic hypermutation of an immunoglobulin kappa gene: critical role for the intron enhancer/matrix attachment region, Cell, vol. 77(2): 239-248 (1994) Abstract only.
Bogen, B., et al., "A rearranged lambda 2 light gene chain retards but does not exclude kappa and lambda 1 expression," Eur J Immunol., vol. 21(10), 2391-5 (1991).
Brady, JL. et al., "Rapid specific amplification of rat antibody cDNA from nine hybridomas in the presence of myeloma light chains," J Immunol Methods, vol. 315(1-2):61-67 (2006).
Brüggemann, M., "A repertoire of monoclonal antibodies with human heavy chains from transgenic mice," PNAS U.S.A., vol. 86(17):6709-6713 (1989).
Carter, P., "Improving the efficacy of antibody -based cancer therapies," Nat. Rev Cancer, vol. 1(2):118-129 (2001).
Cascalho, M. et al, "A quasi-monoclonal mouse," Science, vol. 272(5268):1649-1652 (1996).
Castelli, FA., "HLA-DP4, the most frequent HLA II molecule, defines a new supertype of peptide-binding specificity," J. Immunol., vol. 169(12):6928-6934 (2002).
CD marker handbook extract, "Human and Mouse," BD biosciences, 4 pages. (2010).
Conrath, KE. et al., "Emergence and evolution of functional heavy-chain antibodies in Camelidae." Dev Comp Immunol., vol. 27(2):87-103 (2003).
De Chiara, T. et al., "VelociMouse: Fully ES Cell-Derived F0-Generation Mice Obtained from the Injection of ES cells into Eight-Cell-Stage Embryos," Chapter 16 of Gene Knockout Protocols: 2nd Ed, vol. 530, Humana Press, 311-324 (2009).
De Kruif, J. et al., Human immunoglobulin repertoires against tetanus toxoid contain a large and diverse fraction of high affinity promiscuous V(H) genes, J Mol. Biol., vol. 387(3):548-558 (2009).
De Wildt, RM et al., "Analysis of heavy and light chain pairings indicates that receptor editing shapes the human antibody repertoire," J Mol Biol., vol. 285(3): 895-901 (1999).
Decl. Andrew Murphy in the Matter of Australian Patent Application no. 2009263082 (the Opposed Application) in the name of Merus B.v. (the Applicant)—and—Opposition thereto by RegeneronPharmaceuticals, Inc. (the Opponent, Dated Dec. 19, 2014, 18 pages.
Decl. Anthony De Franco (2nd) in the Matter of Australian Patent Application No. 2009263082 (the Opposed Application) in the name of Merus B.v. (the Applicant)—and—Opposition thereto by RegeneronPharmaceuticals, Inc. (the Opponent), dated Oct. 18, 2015 , 31 pages.
Decl. Anthony De Franco filed in Opposition file Against EP Patent No. 2147594 on Aug. 24, 2016, 22 pages.
Decl. Christopher Carl Goodnow (2nd), in the Matter of Australian Patent Application No. 2009263082 (the Opposed Application) in the name of Mews B.v. (the Applicant)—and—Opposition thereto by RegeneronPharmaceuticals, Inc. (the Opponent), (1st) Oct. 4, 2016, 13 pages.
Decl. Christopher Carl Goodnow in the Matter of Australian Patent Application No. 2009263082 (the Opposed Application) in the name of Merus B.v. (the Applicant)—and—Opposition thereto by RegeneronPharmaceuticals, Inc. (the Opponent), (1st) Oct. 16, 2015, 81 pages.
Decl. David Tarlinton (2nd) in the Matter of Australian Patent Application No. 2009263082 (the Opposed Application) in the name of Merus B.v. (the Applicant)—and—Opposition thereto by RegeneronPharmaceuticals, Inc. (the Opponent), Oct. 15, 2015, 24 pages.
Decl. John McWhirter incl. Sequence Alignment filed in Opposition file Against EP Patent No. 2147594 on Aug. 2, 2016, 4 pages.
Decl. Peter Hudson (1st) in the Matter of Australian Patent Application No. 2009263082 (the Opposed Application) in the name of Merus B.v. (the Applicant)—and—Opposition thereto by RegeneronPharmaceuticals, Inc. (the opponent), May 1, 2015, 52 pages.
Decl. Peter Hudson (2nd) in the Matter of Australian Patent Application No. 2009263082 (the Opposed Application) in the name of Merus B.v. (the Applicant)—and—Opposition thereto by RegeneronPharmaceuticals, Inc. (the opponent), Jun. 2, 2015, 7 pages.
Decl. Robert Brink (1st) in the Matter of Australian Patent Application No. 2009263082 (the Opposed Application) in the name of Merus B.v. (the Applicant)—and—Opposition thereto by RegeneronPharmaceuticals, Inc. (the Opponent), Apr. 30, 2015, 34 pages.
Decl. Robert Brink (2nd) in the Matter of Australian Patent Application no. 2009263082 (the Opposed Application) in the name of Merus B.v. (the Applicant)—and—Opposition thereto by RegeneronPharmaceuticals, Inc. (the opponent), Jun. 2, 2015, 38 pages.
Decl. Robert Brink (3rd), in the Matter of Australian Patent Application No. 2009263082 (the Opposed Application) in The name of Merus N.V. (the Applicant)—and—Opposition thereto by RegeneronPharmaceuticals, Inc. (the opponent), Oct. 4, 2016, 19 pages.
Decl. Ton Logtenberg filed on Sep. 15, 2015 in U.S. Appl. No. 13/750,753, 4 pages.
Desmet, J. et al., "Anchor profiles of HLA-specific peptides: analysis by a novel affinity scoring method and experimental validation," Proteins, vol. 58(1):53-69 (2005).
Desmet, J. et al., "Computation of the binding of fully flexible peptides to proteins with flexible side chains," FASEB J., vol. 11(2):164-172 (2016).
Desmet, J. et al., "Fast and accurate side-chain topology and energy refinement (FASTER) as a new method for protein structure optimization," Proteins, vol. 48(1):31-43 (2002).
Desmet, J. et al., "The dead-end elimination theorem and its use in protein side-chain positioning," Nature, vol. 356 (6369):539-542 (1992).

(56) References Cited

OTHER PUBLICATIONS

Eggan, K. et al., "Hybrid vigor, fetal overgrowth, and viability of mice derived by nuclear cloning and tetraploid embryo complementation," PNAS, USA, vol. 98(11):6209-6214 (2001).
Eren, R. R et al.' "Preclinical evaluation of two human anti-hepatitis B virus (Hbv) monoclonal antibodies in the Hbv- . mere mouse model and in Hbv chronic carrier chimpanzees," Hepatology, vol. 32(3): 588-596 (2000).
Esposito, G., "Phage display of a human antibody against Clostridium tetani toxin," Gene, vol. 148(1):167-168 (1994).
Ewert, S. et al., "Biophysical properties of human antibody variable domains," J Mol. Biol., vol. 325(3):531-553 (2003).
Fecteau, JF. et al., "A new memory CD27-IgG+ B cell population in peripheral blood expressing VH genes with low frequency of somatic mutation," J Immunol., vol. 177(6): 3728-3736 (2006).
Franklin, MC. et al, "Insights into ErbB signaling from the structure of the ErbB2-pertuzumab complex," Cancer Cell, vol. 5(4):317-328 (2004).
Galun, E et al., "Clinical evaluation (phase I) of a combination of two human monoclonal antibodies to HBV: safety and antiviral properties," Hepatology, vol. 35(3):673-679(2002).
Gascan, H. et al., "Human B cell clones can be induced to proliferate and to switch to IgE and IgG4 synthesis by nterleukin 4 and a signal provided by activated CD4+ T cell clones," J Exp; Med., vol. 173(3): 747-750 (1991).
Gelpi, E., "Biomedical and biochemical applications of liquid chromatography-mass spectrometry," J. Chromatogr A. vol. 703(1-2):59-80 (1995).
Gen Bank Acc. No. ABA26122.
Gen Bank Acc. No. D0187586-1 2005.
Gen Bank Acc. No. M87478 1994.
Gonzalez-Fernandez, A., et al., "Analysis of somatic hypermutation in mouse Peyer's patches using mmunoglobulin kappa light-chain transgenes," PNAS USA, vol. 90(21):9862-9866 (1993).
Gorczyca, W., et al., "Detection of DNA strand breaks in individual apoptotic cells by the in situ terminal deoxynucleotidyl transferase and nick translation assays," Cancer Res., vol. 53(8):1945-1951 (1993).
Goyenechea, B. et al., "Cells strongly expressing Ig(kappa) transgenes show clonal recruitment of hypermutation: a role for both MAR and the enhancers," EMBO J. vol. 16(13): 3987-3994 (1997).
Goyenechea, B., et al, "Modifying the sequence of an immunoglobulin V-gene alters the resulting pattern of hypermutation," PNAS USA, vol. 93(24):13979-13984 (1996).
Green, LL. et al., "Antigen-specific human monoclonal antibodies from mice engineered with human Ig heavy and fight chain YACs," Nat Genet., vol. 7(1):13-21 (1994).
Hardy, R., et al., "B cell development pathways," Annu Rev Immunol., vol. 19:595-621 (2001).
Third Party Pre-Issuance Under 37 C.F.R. § in U.S. Appl. No. 15/090,505, dated Feb. 24, 2017, 30 pages.
Third Party Pre-Issuance Under 37 C.F.R. § in U.S. Appl. No. 15/140,321, dated Feb. 10, 2017, 19 pages.
Communication pursuant to Article 94(3) EPC, European Application No. 13720614.0, dated Mar. 24, 2017, 5 pages.
Third Party Observation in Advance of Oral Proceedings Scheduled for Mar. 24, 2018 filed in European Patent Applicaiton No. 12186010.0, dated Mar. 13, 2017, 8 pages.

\* cited by examiner

Figure 1:
A) schematic representation of construct vector MV1057
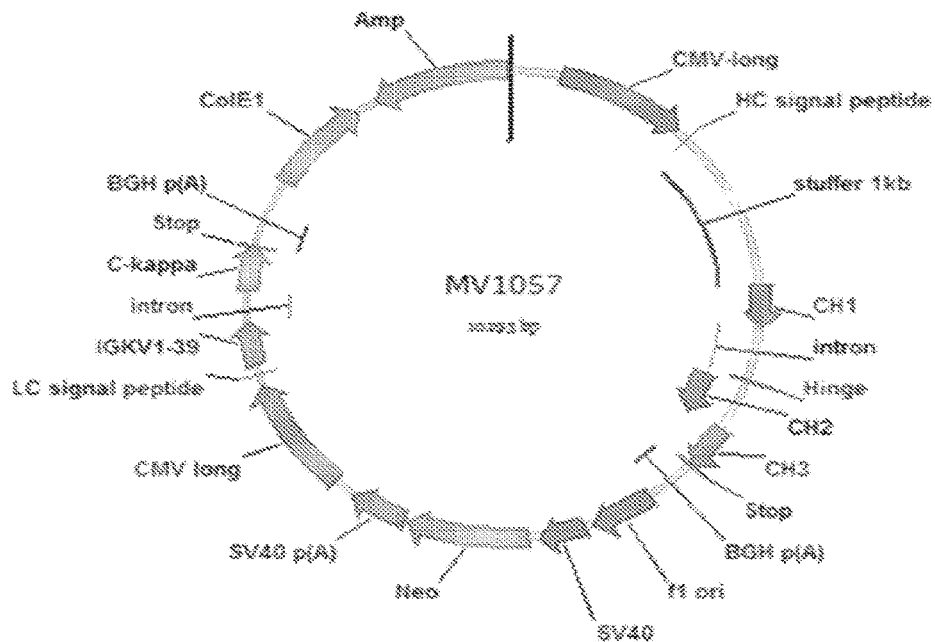
B) schematic representation of phage display vector MV1043
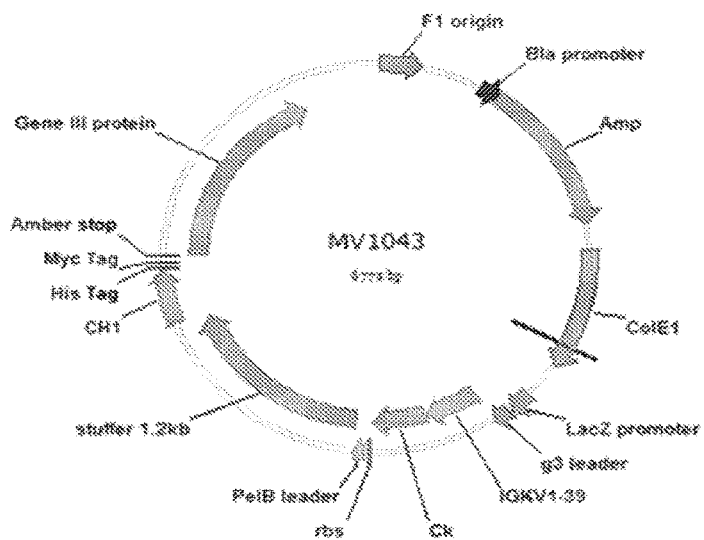

Figure 2: amino acid sequence of wildtype IgG1 Fc, as present in construct vector MV1057 (EU numbering scheme applied)

```
131        141        151        161        171        181
SSKSTSGGTA ALGCLVKDYF PEPVTVSWNS GALTSGVHTF PAVLQSSGLY SLSSVVTVPS
191        201        211        221        231        241
SSLGTQTYIC NVNHKPSNTK VDKRVEPKSC DKTHTCPPCP APELLGGPSV FLFPPKPKDT
251        261        271        281        291        301
LMISRTPEVT CVVVDVSHED PEVKFNWYVD GVEVHNAKTK PREEQYNSTY RVVSVLTVLH
311        321        331        341        351        361
QDWLNGKEYK CKVSNKALPA PIEKTISKAK GQPREPQVYT LPPSREEMTK NQVSLTCLVK
371        381        391        401        411        421
GFYPSDIAVE WESNGQPENN YKTTPPVLDS DGSFFLYSKL TVDKSRWQQG NVFSCSVMHE
431        441
ALHNHYTQKS LSLSPGK
```

Figure 3: nucleotide and amino acid sequences of VH regions used

MF1025_VH
gaggtgcagctggtggagtctgggggaggcttggtacagcctggggggtccctgagactctcctgtgcag
cctctggattcacctttagcagctatgccatgagctgggtccgccaggctccagggaaggggctggagtg
ggtctcagctattagtggtagtggtggtagcacatactacgcagactccgtgaagggccggttcaccatc
tccagagacaattccaagaacacgctgtatctgcaaatgaacagcctgagagccgaggacacggccgtgt
attactgtgcaagggccgattggtgggcgacttttgactactggggccaaggtaccctggtcacc MF1025_VH
EVQLVESGGGLVQPGGSLRLSCAASGFTFSSYAMSWVRQAPGKGLEWVSAISGSGGSTYYADSVKGRFTI
SRDNSKNTLYLQMNSLRAEDTAVYYCARADWWATFDYWGQGTLVT MF1122_VH
gaggtgcagctggtggagtctgggggaggcgtggtccagcctggggaggtccctgagactctcctgtgcag
cctctggattcaccttcagtagctatggcatgcactgggtccgccaggctccaggcaaggggctggagtg
ggtggcagttatatcatatgatggaagtaataaatactatgcagactccgtgaagggccgattcaccatc
tccagagacaattccaagaacacgctgtatctgcaaatgaacagcctgagagctgaggacacggccgtgt
attactgtgcaagagccctcttcacgaccatcgccatggactattggggccaaggtaccctggtcacc MF1122_VH
EVQLVESGGGVVQPGRSLRLSCAASGFTFSSYGMHWVRQAPGKGLEWVAVISYDGSNKYYADSVKGRFTI
SRDNSKNTLYLQMNSLRAEDTAVYYCARALFTTIAMDYWGQGTLVT MF1337 VH
gaggtgcagctggtggagactggggctgaggtgaagaagccgggggcctcagtgaaggtctcctgcaaggcttct
gactacatcttcaccaaatatgacatcaactgggtgcgccaggcccctggacaagggcttgaatggatgggatgg
atgagcgctaacactggaaacacgggctatgcacagaagttccagggcagagtcaccatgaccagggacacgtcc
ataaacacagcctacatggagctgagcagcctgacatctggtgacacggccgtttatttctgtgcgaggagtagt
cttttcaagacagagacggcgccctactatcacttcgctctggacgtctggggccaagggaccacggtcacc MF1337
VHEVQLVETGAEVKKPGASVKVSCKASDYIFTKYDINWVRQAPGQGLEWMGWMSANTGNTGYAQKFQGRVTMTRD
TSINTAYMELSSLTSGDTAVYFCARSSLFKIETAPYYHFALDVWGQGTTVT

A     K409D:K392D/D399'K:E356'K

B     D399K:E356K/D399'K:E356'K

C     K409D:K392D/K409'D:K392'D

Fig 12:
A 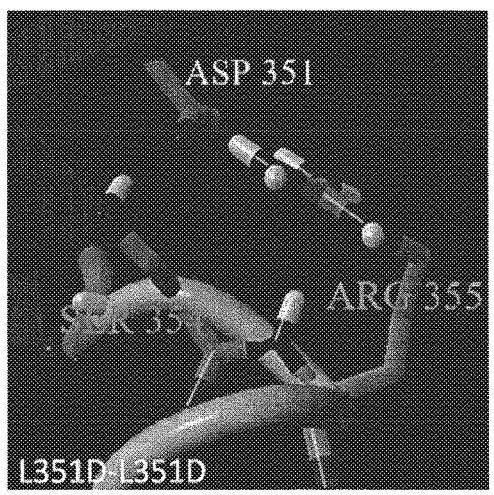 B 

Figure 22:
A
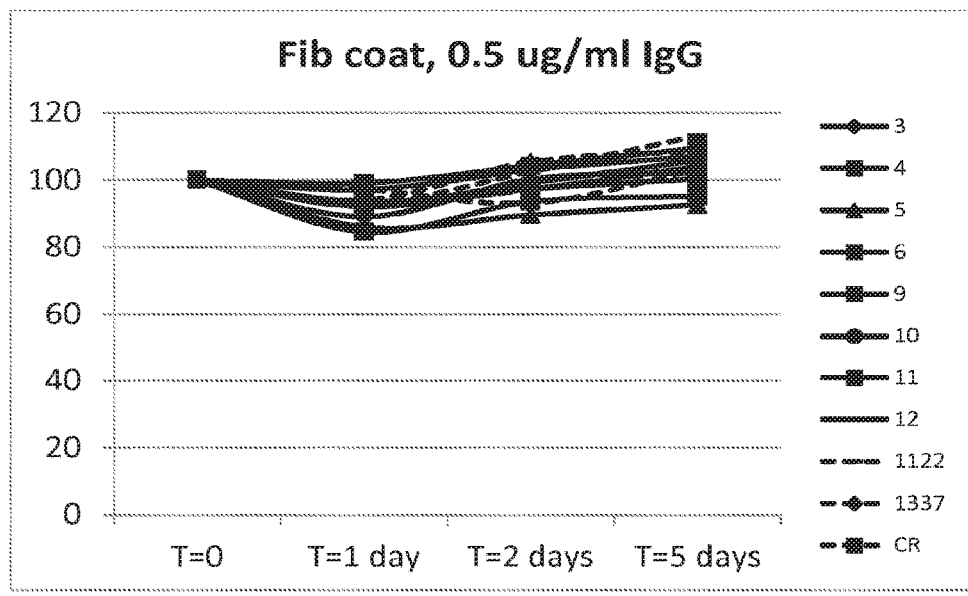
B
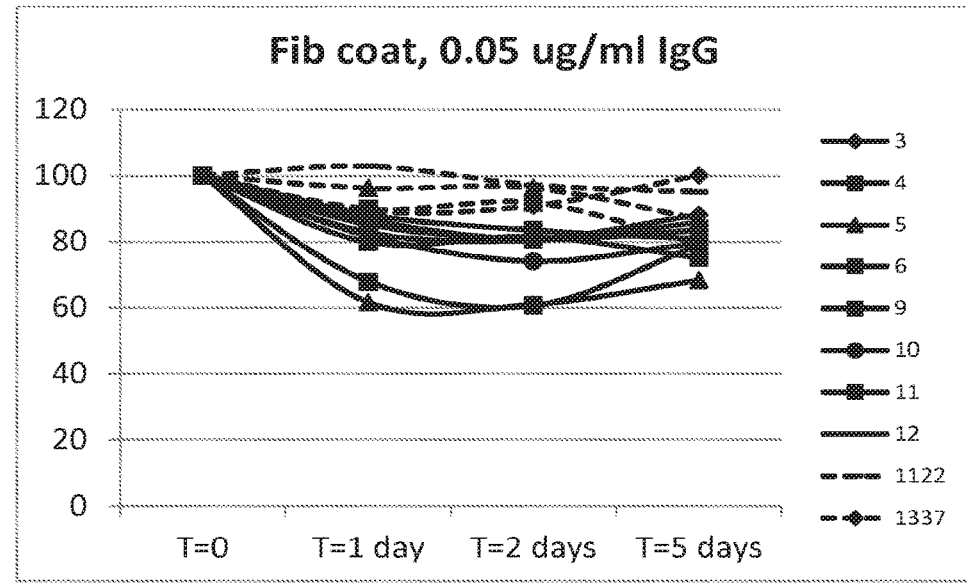

Figure 27B:
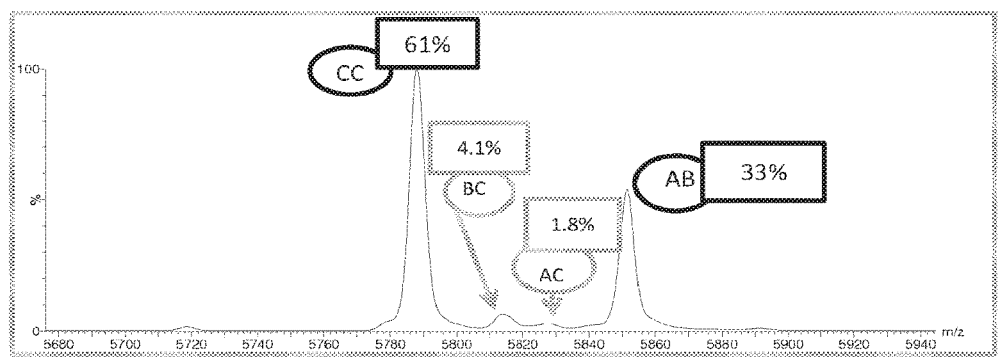
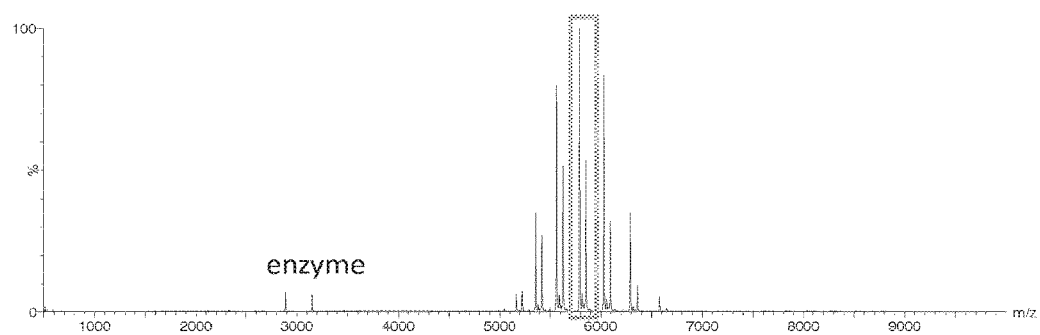

| Protein sample | Stress | Nile red particles | UV 350 nm | LS 400 nm ($10^7$ cps) | Intrinsic fluorescence | | 1,8-ANS fluorescence | | |
|---|---|---|---|---|---|---|---|---|---|
| | | | | | fluo.int. ($10^6$cps) | λ Max. (nm) | 1,8-ANS int. ($10^6$cps) | λ Max. (nm) | Shift (nm) |
| BB | 2d4°C | 0-10 | 0.001 | 0.7 | 4.2 | 335 | | | |
| | 2d50°C | 0-10 | 0.013 | 0.8 | 4.2 | 335 | | | |
| AA | 2d4°C | 10-20 | 0 | 1.2 | 5.7 | 338 | | | |
| | 2d50°C | 10-20 | 0.002 | 1.0 | 5.5 | 338 | | | |
| Wildtype bispecific (AA AB BB) | 2d4°C | 30-50 | 0.003 | 0.9 | 5.1 | 336 | 7.1 | 507 | |
| | 2d50°C | >10000** | 0.007 | 0.9 | 5.0 | 336 | 7.1 | 507 | |
| | 2w4°C | | 0 | 0.9 | 5.0 | 336 | | | |
| | 2w40°C | >2000** | 0 | 0.8 | 5.0 | 336 | | | |
| | T0 | | 0.001 | 0.8 | 5.0 | 336 | | | |
| | 5FT | >2000** | 0.009 | 1.2 | 4.8 | 336 | | | |
| Charge reversal bispecific (E356K,D399K/ K392D,K409D) | 2d4°C | 10-20 | 0.001 | 1.3 | 5.9 | 336 | 7.0 | 507 | |
| | 2d50°C | 10-20 | 0.002 | 1.2 | 5.7 | 336 | 7.0 | 507 | |
| | 2w4°C | >2000** | 0 | 1.1 | 5.5 | 336 | | | |
| | 2w40°C | >2000** | 0.002 | 1.1 | 5.5 | 336 | | | |
| | T0 | | 0.001 | 1.3 | 5.7 | 336 | | | |
| | 5FT | 30-50 | 0.007 | 1.8 | 5.5 | 336 | | | |
| Combi. # 3* | 2d4°C | 30-50 | 0 | 0.9 | 5.0 | 337 | | | |
| | 2d50°C | 30-50 | 0.001 | 0.8 | 4.9 | 337 | | | |
| Combi. # 4 | 2d4°C | 20-30 | 0 | 1.0 | 6.2 | 337 | 7.5 | 505 | |
| | 2d50°C | >3000** | 0.001 | 1.0 | 6.2 | 337 | 7.5 | 505 | |
| | 2w4°C | | 0.001 | 1.0 | 6.3 | 337 | | | |
| | 2w40°C | >2000** | 0.003 | 0.9 | 6.3 | 337 | | | |
| | T0 | | 0.002 | 1.1 | 6.3 | 337 | | | |
| | 5FT | >2000** | 0.003 | 1.2 | 6.0 | 337 | | | |

Figure 30

| | | | | | | | | | |
|---|---|---|---|---|---|---|---|---|---|
| Combi. # 5 | 2d4°C | >2000** | 0.001 | 1.1 | 4.9 | 337 | | | |
| | 2d50°C | >10000** | 0.001 | 0.9 | 5.0 | 337 | | | |
| Combi. # 6 | 2d4°C | 10-20 | 0 | 0.7 | 4.3 | 337 | | | |
| | 2d50°C | 20-30 | 0.001 | 0.7 | 4.3 | 337 | | | |
| Combi. # 9 | 2d4°C | 30-50 | 0 | 1.0 | 5.5 | 337 | 7.5 | 507 | |
| | 2d50°C | 50-100 | 0 | 1.0 | 5.5 | 337 | 8.1 | 500 | -7 |
| | 2w4°C | >2000** | 0 | 0.9 | 5.1 | 337 | | | |
| | 2w40°C | >2000** | 0 | 0.9 | 5.2 | 337 | | | |
| | T0 | | 0.002 | 0.8 | 5.1 | 337 | | | |
| | 5FT | >2000** | 0.007 | 1.4 | 4.9 | 337 | | | |
| Combi. # 10 | 2d4°C | 30-50 | 0.002 | 1.0 | 5.6 | 337 | 7.0 | 505 | |
| | 2d50°C | 150-200 | 0.001 | 1.1 | 5.9 | 337 | 8.7 | 499 | -6 |
| | 2w4°C | >2000** | 0 | 0.9 | 5.2 | 337 | | | |
| | 2w40°C | >2000** | 0 | 0.9 | 5.4 | 337 | | | |
| | T0 | | 0.005 | 1.0 | 5.3 | 337 | | | |
| | 5FT | 20-30 | 0.004 | 1.1 | 5.4 | 337 | | | |
| Combi. # 11 | 2d4°C | 20-30 | 0 | 0.9 | 4.9 | 337 | | | |
| | 2d50°C | 30-50 | 0.002 | 0.9 | 5.1 | 337 | | | |
| | 2w4°C | >2000** | 0 | 0.8 | 5.0 | 337 | | | |
| | 2w40°C | >2000** | 0 | 0.8 | 5.1 | 337 | | | |
| | T0 | | 0.004 | 1.1 | 5.0 | 337 | | | |
| | 5FT | >2000** | 0.002 | 1.2 | 5.0 | 337 | | | |
| Combi. # 12 | 2d4°C | 10-20 | 0.001 | 0.8 | 3.8 | 337 | 6.2 | 511 | |
| | 2d50°C | 10-20 | 0.002 | 0.7 | 3.8 | 337 | 6.5 | 508 | -3 |
| | 2w4°C | >2000** | 0.003 | 0.6 | 3.6 | 337 | | | |
| | 2w40°C | >2000** | 0.001 | 0.5 | 3.5 | 337 | | | |
| | T0 | | 0.005 | 0.6 | 3.7 | 337 | | | |
| | 5FT | | 0.004 | 0.7 | 3.6 | 337 | | | |

Figure 30 - continued

OD450 values from bispecific ELISA

| Tr. # | Detected IgG Species | | |
|---|---|---|---|
| | AB (Tet-Fib) | AC (Tet-Thyr) | BC (Fib-thyr) |
| 1 | 0.989 | 1.792 | 0.438 |
| 2 | 1.085 | 1.852 | 0.418 |
| 3 | 1.419 | 0.775 | 1.547 |
| 4 | 0.205 | 1.795 | 1.22 |
| 5 | 1.367 | 0.047 | 0.057 |
| 6 | 1.359 | 0.043 | 0.06 |
| 7 | 0.054 | 1.779 | 0054 |
| 8 | 0.04 | 1.338 | 0.052 |
| 9 | 1.588 | 0.048 | 0.051 |
| 10 | 0.044 | 1.805 | 0.055 |
| 11 | 0.043 | 1.821 | 0.056 |

Figure 31

| Transfection # 9 | | |
|---|---|---|
| Species* | Mass | Mass difference |
| C | 72464,62 | |
| D | 72684,53 | 219,90 |
| B | 73070,99 | 386,47 |
| A | 73410,46 | 339,47 |
| CC | 144929,2 | 71518,78 |
| CD | 145149,2 | 219,90 |
| DD | 145369,1 | 219,90 |
| BC | 145535,6 | *166,56* |
| BD | 145755,5 | 219,90 |
| AC | 145875,1 | *119,57* |
| AD | 146095 | 219,90 |
| BB | 146142 | *47,00* |
| AB | 146481,5 | 339,47 |
| AA | 146820,9 | 339,47 |
| Transfection # 10 | | |
| Species | Mass | Mass difference |
| C | 72464,62 | |
| D | 72684,53 | 219,90 |
| A | 73410,46 | 725,94 |
| CC | 144929,2 | 71518,78 |
| CD | 145149,2 | 219,90 |
| DD | 145369,1 | 219,90 |
| AC | 145875,1 | 506,03 |
| AD | 146095 | 219,90 |
| AA | 146820,9 | 725,94 |
| Transfection # 11 | | |
| Species | Mass | Mass difference |
| C | 72464,62 | |
| B | 73070,99 | 606,37 |
| A | 73410,46 | 339,47 |
| CC | 144890,95 | 71480,49 |
| BC | 145535,61 | 644,66 |
| AC | 145875,08 | 339,47 |
| BB | 146141,98 | 266,90 |
| AB | 146481,45 | 339,47 |
| AA | 146820,92 | 339,47 |

Figure 32

SEQUENCE LISTING

<160> NUMBER OF SEQ ID NOS: 7

<210> SEQ ID NO 1
<211> LENGTH: 317
<212> TYPE: PRT
<213> ORGANISM: Homo sapiens
<220> FEATURE:
<221> NAME/KEY: misc_feature
<223> OTHER INFORMATION: wildtype IgG1 Fc

<400> SEQUENCE: 1

```
Ser Ser Lys Ser Thr Ser Gly Gly Thr Ala Ala Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Phe Pro Ala Val Leu Gln Ser Ser Gly
        35                  40                  45

Leu Tyr Ser Leu Ser Ser Val Val Thr Val Pro Ser Ser Ser Leu Gly
    50                  55                  60

Thr Gln Thr Tyr Ile Cys Asn Val Asn His Lys Pro Ser Asn Thr Lys
65                  70                  75                  80

Val Asp Lys Arg Val Glu Pro Lys Ser Cys Asp Lys Thr His Thr Cys
                85                  90                  95

Pro Pro Cys Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
        115                 120                 125

Val Thr Cys Val Val Val Asp Val Ser His Glu Asp Pro Glu Val Lys
    130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
        195                 200                 205

Ala Lys Gly Gln Pro Arg Glu Pro Gln Val Tyr Thr Leu Pro Pro Ser
    210                 215                 220

Arg Glu Glu Met Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Leu Tyr Ser Lys Leu Thr Val Asp Lys Ser Arg Trp Gln Gln
        275                 280                 285

Gln Gly Asn Val Phe Ser Cys Ser Val Met His Glu Ala Leu His Asn
    290                 295                 300

His Tyr Thr Gln Lys Ser Leu Ser Leu Ser Pro Gly Lys
305                 310                 315
```

<210> SEQ ID NO 2
<211> LENGTH: 345
<212> TYPE: DNA
<213> ORGANISM: Homo sapiens
<220> FEATURE:

<221> NAME/KEY: misc_feature
<223> OTHER INFORMATION: MF1025_VH

<400> SEQUENCE: 2

```
gaggtgcagc tggtggagtc tgggggaggc ttggtacagc ctgggggtc cctgagactc    60
tcctgtgcag cctctggatt caccttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc aagggccgat   300
tggtgggcga cttttgacta ctggggccaa ggtaccctgg tcacc               345
```

<210> SEQ ID NO 3
<211> LENGTH: 115
<212> TYPE: PRT
<213> ORGANISM: Homo sapiens
<220> FEATURE:
<221> NAME/KEY: misc_feature
<223> OTHER INFORMATION: MF1025_VH

<400> SEQUENCE: 3

```
Glu Val Gln Leu Val Glu Ser Gly Gly Gly Leu Val Gln Pro Gly Gly
 1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ala Asp Trp Trp Ala Thr Phe Asp Tyr Trp Gly Gln Gly Thr
            100                 105                 110
Leu Val Thr
        115
```

<210> SEQ ID NO 4
<211> LENGTH: 348
<212> TYPE: DNA
<213> ORGANISM: Homo sapiens
<220> FEATURE:
<221> NAME/KEY: misc_feature
<223> OTHER INFORMATION: MF1122_VH

<400> SEQUENCE: 4

```
gaggtgcagc tggtggagtc tgggggaggc gtggtccagc ctgggaggtc cctgagactc    60
tcctgtgcag cctctggatt caccttcagt agctatgcca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggccgtgt attactgtgc aagagccctc   300
ttcacgacca tcgccatgga ctattgggcc caaggtaccc tggtcacc             348
```

<210> SEQ ID NO 5
<211> LENGTH: 116
<212> TYPE: PRT

<213> ORGANISM: Homo sapiens
<220> FEATURE:
<221> NAME/KEY: misc_feature
<223> OTHER INFORMATION: MF1122_VH

<400> SEQUENCE: 5

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Phe Thr Thr Ile Ala Met Asp Tyr Trp Gly Gln Gly
            100                 105                 110

Thr Leu Val Thr
        115

<210> SEQ ID NO 6
<211> LENGTH: 372
<212> TYPE: DNA
<213> ORGANISM: Homo sapiens
<220> FEATURE:
<221> NAME/KEY: misc_feature
<223> OTHER INFORMATION: MF1337 VH

<400> SEQUENCE: 6
gaggtgcagc tggtggagac tggggctgag gtgaagaagc cggggggcctc agtgaaggtc    60 tcctgcaagg cttctgacta catcttcacc aaatatgaca tcaactgggt gcgccaggcc   120
cctggacaag ggcttgaatg gatgggatgg atgagcgcta acactggaaa cacgggctat   180
gcacagaagt tccagggcag agtcaccatg accaggaca cgtccataaa cacagcctac   240
atggagctga gcagcctgac atctggtgac acggccgttt atttctgtgc gaggagtagt   300
cttttcaaga cagagacggc gccctactat cacttcgctc tggacgtctg gggccaaggg   360
accacggtca cc                                                        372

<210> SEQ ID NO 7
<211> LENGTH: 126
<212> TYPE: PRT
<213> ORGANISM: Homo sapiens
<220> FEATURE:
<221> NAME/KEY: misc_feature
<223> OTHER INFORMATION: MF1337

<400> SEQUENCE: 7

Val His Glu Val Gln Leu Val Glu Thr Gly Ala Glu Val Lys Lys Pro
1               5                   10                  15

Gly Ala Ser Val Lys Val Ser Cys Lys Ala Ser Asp Tyr Ile Phe Thr
            20                  25                  30

Lys Tyr Asp Ile Asn Trp Val Arg Gln Ala Pro Gly Gln Gly Leu Glu
        35                  40                  45

Trp Met Gly Trp Met Ser Ala Asn Thr Gly Asn Thr Gly Tyr Ala Gln
    50                  55                  60

-continued

```
Lys Phe Gln Gly Arg Val Thr Met Thr Arg Asp Thr Ser Ile Asn Thr
65                  70                  75                  80

Ala Tyr Met Glu Leu Ser Ser Leu Thr Ser Gly Asp Thr Ala Val Tyr
                85                  90                  95

Phe Cys Ala Arg Ser Ser Leu Phe Lys Thr Glu Thr Ala Pro Tyr Tyr
                100                 105                 110

His Phe Ala Leu Asp Val Trp Gly Gln Gly Thr Thr Val Thr
        115                 120                 125
```

METHODS AND MEANS FOR THE PRODUCTION OF IG-LIKE MOLECULES

RELATED APPLICATIONS

This application is a continuation of U.S. Ser. No. 13/866,756, filed on Apr. 19, 2013, which claims priority to U.S. Provisional Application No. 61/635,935, filed on Apr. 20, 2012, the contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Oct. 25, 2013 is named 2013_10_25_MRX_008_ST25.txt and is 8,450 bytes in size.

FIELD

The invention relates to the fields of molecular biology, medicine and biological therapeutics. It particularly relates to the field of therapeutic antibodies for the treatment of various diseases.

BACKGROUND

Many currently used biological therapeutics are isolated recombinant, human or humanized monoclonal antibodies that enhance the ability of the body's immune system to neutralize or eliminate cells and/or molecules involved in disease processes or to eradicate invading pathogens or infectious agents. Monoclonal antibodies bind to a single specific area, or epitope, of an antigen and, for use in therapy, are often selected for a desirable functional property such as for example killing of tumor cells, blocking of receptor-ligand interactions or virus neutralization. Nowadays, there are about 30 FDA approved monoclonal antibodies, which are typically produced at large quantities and their biophysical and biochemical characteristics can be analyzed in great detail to ensure batch-to-batch consistency, which facilitates regulatory acceptability. Despite these favorable characteristics, monoclonal antibodies have several disadvantages, some of which relate to their monospecific nature and the complexity of diseases. Diseases processes are often multifactorial in nature, and involve redundant or synergistic action of disease mediators or up-regulation of different receptors, including crosstalk between their signaling networks. Consequently, blockade of multiple, different factors and pathways involved in pathology may result in improved therapeutic efficacy. By nature of their monospecificity, monoclonal antibodies can only interfere with a single step within the complex disease processes which often does not have an optimal effect. In addition to not fully addressing multiple aspects of a disease process, it has become clear that targeting a single epitope on a single cellular or soluble protein or pathogen often will not suffice to efficiently treat disease because the target epitope may no longer be available for the monoclonal antibody to bind to and exert the desired effect. As an example, tumor cells often escape from monoclonal antibody therapy by down-regulation, mutation or shielding of the target epitope present on a growth factor receptor. By activating alternative receptors and/or their ligands, tumor cells than may exploit a different path leading to continued growth and metastasis. Similarly, viruses and other pathogens frequently mutate and lose or shield the target epitope, thereby escaping monoclonal antibody treatment. Monoclonal antibodies that bind to a single epitope often do not recruit the full spectrum of effector mechanisms evoked by polyclonal antibodies, including, amongst other things, opsonization (enhancing phagocytosis of antigens), steric hindrance (antigens coated with antibodies are prevented from attaching to host cells or mucosal surfaces), toxin neutralization, agglutination or precipitation (antibodies binding several soluble antigens cause aggregation and subsequent clearance), activation of complement and antibody-dependent cellular cytotoxicity (antibodies enable the killing of target cells by natural killer cells and neutrophils).

Polyclonal antibodies for therapeutic applications may be obtained from pooled human serum. Such serum-derived therapeutic polyclonal antibodies may for example be used to treat or prevent infections caused by viruses such as the rabies virus, cytomegalovirus and respiratory syncytial virus, to neutralize toxins such as tetanus toxin and botulinum toxin or to prevent Rhesus D allograft immunization. A more widespread use of serum-derived polyclonal antibody preparations has been prevented by the fact that source plasma is only available for a limited range of targets such as infectious diseases and toxins. Moreover, the products are highly dependent on donor blood availability, both in terms of quantity and suitability, resulting in considerable variation between batches. In addition, screening technologies fail to keep up with constantly evolving viruses, thus, immunoglobulin products carry a potential risk of infectious disease transmission. Finally, the long process of blood collection, screening and immunoglobulin purification means plasma-derived immunoglobulins are expensive to produce.

Mixtures of monoclonal antibodies may improve the efficacy of monoclonal antibodies while avoiding the limitations associated with serum-derived polyclonal antibodies. In the art, combinations of two human or humanized monoclonal antibodies have been tested in preclinical models and in clinical trials (for example mixtures of 2 monoclonal antibodies against the HER2 receptor, mixtures of 2 antibodies against the EGFR receptor and, 2 monoclonal antibodies against the rabies virus).

In the art, it has been shown that combinations of 2 monoclonal antibodies may have additive or synergistic effects and recruit effector mechanisms that are not associated with either antibody alone. For example, mixtures of 2 monoclonal antibodies against the EGFR or HER2 were shown to more potently kill tumor cells based on a combination of activities including enhanced receptor internalization, improved blockade of signalling pathways downstream of the receptors as well as enhanced immune effector-mediated cytotoxicity. For combination therapies based on 2 monoclonal antibodies, the component antibodies may be produced separately and combined at the protein level. A drawback of this approach is the staggering cost of developing the 2 antibodies individually in clinical trials and (partially) repeating that process with the combination. This would lead to unacceptable cost of treatments based on antibody combinations. Alternatively, the 2 recombinant cell lines producing the component monoclonal antibodies may be mixed in a fermentor and the resultant mixture of antibodies may be purified as a single preparation (WO 2004/061104). A drawback of this approach is the poor control over the composition and hence reproducibility of the resulting recombinant polyclonal antibody preparation, especially when considering that such compositions may change over time as the cells are being cultured.

During the past decade, bispecific antibodies have emerged as an alternative to the use of combinations of 2 antibodies. Whereas a combination of 2 antibodies represents a mixture of 2 different immunoglobulin molecules that bind to different epitopes on the same or different targets, in a bispecific antibody this is achieved through a single immunoglobulin molecule. By binding to 2 epitopes on the same or different targets, bispecific antibodies may have similar effects as compared to a combination of 2 antibodies binding to the same epitopes. Furthermore, since bispecific antibodies of the IgG format combine 2 different monovalent binding regions in a single molecule and mixtures of 2 IgG antibodies combine 2 different bivalent binding molecules in a single preparation, different effects of these formats have been observed as well. From a technological and regulatory perspective, this makes development of a single bispecific antibody less complex because manufacturing, preclinical and clinical testing involve a single, molecule. Thus, therapies based on a single bispecific antibody are facilitated by a less complicated and cost-effective drug development process while providing more efficacious antibody therapies.

Bispecific antibodies based on the IgG format, consisting of 2 heavy and two light chains have been produced by a variety of methods. For instance, bispecific antibodies may be produced by fusing two antibody-secreting cell lines to create a new cell line or by expressing two antibodies in a single cell using recombinant DNA technology. These approaches yield multiple antibody species as the respective heavy chains from each antibody may form monospecific dimers (also called homodimers), which contain two identical paired heavy chains with the same specificity, and bispecific dimers (also called heterodimers) which contain two different paired heavy chains with different specificity. In addition, light chains and heavy chains from each antibody may randomly pair to form inappropriate, non-functional combinations. This problem, known as heavy and light chain miss-pairings, can be solved by choosing antibodies that share a common light chain for expression as bispecific. But even when a common light chain is used, expression of two heavy chains and one common light chain in a single cell will result in 3 different antibody species, i.e. two monospecific 'parental' antibodies and the bispecific antibody so that the bispecific antibody of interest needs to be purified from the resulting antibody mixture. Although technologies have been employed to further increase the percentage of bispecific antibodies in the mixtures of parental and bispecific antibodies and to decrease the percentage of miss-paired heavy and light chains, there remains a need for bispecific formats that eliminate or minimize some of the disadvantages mentioned above.

Taken together, the art provides a variety of technologies and methods for generating monoclonal antibodies, bispecific antibodies, mixtures of monoclonal antibodies, or mixtures of monospecific and bispecific antibodies that can subsequently be used for therapeutic application in patients. However, as discussed above, each of these existing technologies and methods have their drawbacks and limitations.

There is thus a need for improved and/or alternative technologies for producing biological therapeutics in the form of mixtures or bispecific approaches for targeting multiple disease-modifying molecules

DESCRIPTION OF THE INVENTION

The invention provides methods and means for improved and/or alternative technologies for producing biological therapeutics in the form of mixtures or bispecific approaches for targeting multiple disease-modifying molecules, as well as products and uses resulting from these methods and means.

Various approaches are described in the art in order to promote the formation of a certain bispecific antibody of interest, thereby reducing the content of undesired antibodies in the resulting mixture.

For antibodies, it is well-known that the CH3-CH3 interaction is the primary driver for Fc dimerization (Ellerson J R., et al., J. Immunol 1976 (116) 510-517; Deisenhofer J. biochemistry 1981 (20) 2361-2370). It is furthermore well-known that when two CH3 domains interact with each other they meet in a protein-protein interface which comprises "contact" residues (also called contact amino acids, interface residues or interface amino acids). Contact amino acids of a first CH3 domain interact with one or more contact amino acids of a second CH3 domain. Contact amino acids are typically within 5.5 Å (preferably within 4.5 Å) of each other in the three-dimensional structure of an antibody. The interaction between contact residues from one CH3 domain and contact residues from a different CH3 domain may for instance be via Van der Waals forces, hydrogen bonds, water-mediated hydrogen bonds, salt bridges or other electrostatic forces, attractive interactions between aromatic side chains, disulfide bonds, or other forces known to one skilled in the art. It was previously shown that approximately one-third of the contact amino acid side chains at the human IgG1 CH3 domain interface can account for the majority of contributions to domain folding and association. It can further be envisaged that other (neighbouring) amino acid residues may affect the interactions in the protein-protein interface.

Approaches to interfere with the dimerization of antibody heavy chains have been employed in the art. Specific engineering in the CH3 domains was applied in order to favour heterodimerization over homodimerization. Examples of such engineering of the CH3-CH3 interface include the introduction of complementary protuberance and cavity mutations, also known as 'knob-into-hole' approaches as described for instance in WO1998/050431, Ridgeway et al., 1996 and Merchant et al. 1998.

Generally, the method involves introducing a protuberance at the interface of a first polypeptide and a corresponding cavity in the interface of a second polypeptide, such that the protuberance can be positioned in the cavity so as to promote heteromultimer formation and hinder homomultimer formation. "Protuberances" or "knobs" are constructed by replacing small amino acid side chains from the interface of the first polypeptide with larger side chains (e.g. tyrosine or tryptophan). Compensatory "cavities" or "holes" of identical or similar size to the protuberances are created in the interface of the second polypeptide by replacing large amino acid side chains with smaller ones (e.g. alanine or threonine) The protuberance and cavity can be made by synthetic means such as altering the nucleic acid encoding the polypeptides or by peptide synthesis.

Using the knob-into-hole technology alone, the proportion of a bispecific antibody of interest is at best 87% of the mixture of the 2 parental and bispecific antibodies. Merchant et al., succeeded in raising the proportion of bispecific antibodies to 95% of the mixture by introduction of an additional disulfide bond between the two CH3 domains in the CH3-CH3 interface. Still, in order to use such bispecific antibody as a medicament, the bispecific antibody has to be purified (separated) from the homodimers and formulated into a pharmaceutically acceptable diluent or excipient.

Purification of heterodimers from such mixtures poses a major challenge because of the similarity in physico-chemical properties of the homodimers and heterodimers. It is one object of the present invention to provide methods for producing a bispecific antibody in a single cell clone with a further improved proportion of the bispecific antibody in the mixture. According to the invention, knob-into-hole technology can thus be used as one of the means, alone or together with other means, to achieve said further improved bispecific proportion in a mixture.

Another example of such engineering of the CH3-CH3 interface is provided by a heterodimeric Fc technology that supports the design of bispecific and asymmetric fusion proteins by devising strand-exchange engineered domain (SEED) CH3 heterodimers. These SEED CH3 heterodimers are derivatives of human IgG and IgA CH3 domains that are composed of alternating segments of human IgA and IgG CH3 sequences which results in pairs of complementary human SEED CH3 heterodimers, the so-called SEED-bodies (Davis J H. Et al., Protein Engineering, Design & Selection 2010 (23)195-202; WO2007/110205).

Yet another approach for the production of a given bispecific antibody of interest is based on electrostatic engineering of contact residues within the CH3-CH3 interface that are naturally charged, as for example described in EP01870459 or US2010/0015133, WO2007/147901, WO2010/129304, Gunasekaran et al (2010) and WO 2009/089004. These publications describe mutations in the CH3 domains of heavy chains wherein naturally occurring charged amino acid contact residues are replaced by amino acid residues of opposite charge (i.e. a charge reversal strategy). This creates an altered charge polarity across the Fc dimer interface such that co-expression of electrostatically matched Fc chains support favorable attractive interactions thereby promoting desired Fc heterodimer formation, whereas unfavorable repulsive charge interactions suppress unwanted Fc homodimer formation.

It was described that within the CH3-CH3 interface four unique charges residue pairs are involved in the domain-domain interaction. These are D356/K439', E357/K370', K392/D399' and D399/K409' (numbering according to Kabat (1991) where residues in the first chain are separated from residues in the second chain by '1' and where the prime (') indicates the residue numbering in the second chain). As the CH3-CH3 interface displays a 2-fold symmetry, each unique charge pair is represented twice in intact IgG (i.e., also K439/D356', K370/E357', D399/K392' and K409/D399' charge interactions are present in the interface). Taking advantage of this two-fold symmetry, it was demonstrated that a single charge reversion, e.g. K409D in the first chain, or D399'K in the second chain resulted in diminished homodimer formation due to repulsion of identical charges. Combining different charge reversions further enhanced this repulsive effect. It was demonstrated that expression of different CH3 domains comprising different, complementary charge reversions, could drive heterodimerization, resulting in an increased proportion of the bispecific species in the mixture.

Using the approach described above, it is possible to produce a bispecific antibody in a single cell with proportions ranging between about 76% and about 96%. It is an object of the present invention to provide methods for producing a bispecific antibody in a single cell with a further improved percentage of desired bispecific antibodies. According to the present invention, electrostatic engineering technology can be used as one of the means, alone or together with other means, e.g knob-into-hole approaches, to achieve said further improved percentages of desired (bispecific) antibodies.

In one aspect, the present invention provides a method for producing at least two different Ig-like molecules from a single host cell, wherein each of said two Ig-like molecules comprises two CH3 domains that are capable of forming an interface, said method comprising providing in said cell a) a first nucleic acid molecule encoding a $1^{st}$ CH3 domain-comprising polypeptide chain, b) a second nucleic acid molecule encoding a $2^{nd}$ CH3 domain-comprising polypeptide chain, c) a third nucleic acid molecule encoding a $3^{rd}$ CH3 domain-comprising polypeptide chain, and d) a fourth nucleic acid molecule encoding a $4^{th}$ CH3 domain-comprising polypeptide chain, wherein at least two of said nucleic acid molecules are provided with means for preferential pairing of said $1^{st}$ and $2^{nd}$ CH3 domain-comprising polypeptides and said $3^{rd}$ and $4^{th}$ CH3-domain comprising polypeptides, said method further comprising the step of culturing said host cell and allowing for expression of said at least four nucleic acid molecules and harvesting said at least two different Ig-like molecules from the culture.

It is often desired to produce more than one (bispecific) antibody, for instance in order to more efficiently interfere with multiple biological pathways involved in a disease process or with the invasion, replication and/or spreading of a pathogen.

A mixture of more than one bispecific antibody is also particularly useful for the treatment of certain diseases. For example, tumor cells use many different strategies to develop resistance during treatment with antibodies or small molecule drugs. Resistance may involve multiple cell surface receptors and soluble molecules and it is considered beneficial to develop antibody-based treatments for cancers that address multiple such disease-and escape-associated molecules simultaneously. In case more than 2 such disease- and escape-related target molecules or epitopes are involved, a mixture of bispecific antibodies provides an innovative and attractive therapeutic format. Preferably, such mixtures of bispecific antibodies are produced by a single cell to facilitate a drug development process that is less complicated from a regulatory point of view and cost-effective and feasible from a drug manufacturing and clinical development point of view. In a single cell-based approach, it is desirable to use methods that allow controlled and efficient production of the bispecific antibodies, thus reducing or even completely abrogating the need of separating the desired mixture of bispecific IgG molecules from non-desired monospecific IgG molecules. In the prior art, mixtures of monospecific and bispecific antibodies have been produced by a single cell (WO2004/009618), but these mixtures represent complex concoctions of several different bispecific and monospecific antibody species. It is a further object of the present invention to provide means and methods for producing defined mixtures of bispecific antibodies in single cells. Preferably, methods are provided which result in mixtures of (bispecific) antibodies with a proportion of at least 95%, at least 97% or even more than 99% of dimeric IgG molecules, irrespective of the amount of monomeric by-products, see herein below. Typically, in a cell where multiple intact IgG molecules are produced, half molecules (monomeric by-products) may be present that can be simply removed by size exclusion chromatography known in the art.

In one embodiment the present invention provides methods for producing a defined mixture of at least two different Ig-like molecules in single cells, instead of a single (bispecific) antibody of interest, wherein the formation of other, undesired dimeric antibody species is diminished or even absent. The resulting mixture is well defined and its composition is controlled by the design of CH3 domain mutants. Furthermore, regulation of expression levels and/or different transfection ratios used for expression affects the composition of the mixture. In a method according to the invention, a first nucleic acid molecule encodes a CH3 domain which preferentially pairs with a CH3 domain encoded by a second nucleic acid molecule, and a third nucleic acid molecules encodes a CH3 domain which preferentially pairs with a CH3 domain encoded by a fourth nucleic acid molecule. The present invention also provides mixtures of at least two different Ig-like molecules obtainable by the methods of the invention.

As used herein, the term "preferential pairing of said $1^{st}$ and $2^{nd}$ CH3 domain-comprising polypeptides" means that essentially all the resulting dimers comprising the $1^{st}$ CH3 domain-comprising polypeptide and/or the $2^{nd}$ CH3 domain-comprising polypeptide will be dimers consisting of one $1^{st}$ CH3 domain-comprising polypeptide paired with one $2^{nd}$ CH3 domain-comprising polypeptide. Likewise, the term "preferential pairing of said $3^{rd}$ and $4^{th}$ CH3 domain-comprising polypeptides" means that essentially all of the resulting dimers comprising the $3^{rd}$ CH3 domain-comprising polypeptide and/or the $4^{th}$ CH3 domain-comprising polypeptide will be dimers consisting of one $3^{rd}$ CH3 domain-comprising polypeptide paired with one $4^{th}$ CH3 domain-comprising polypeptide. As a result, when nucleic acid molecules encoding four different (A, B, C, D) CH3 domain-comprising polypeptides are introduced in a single cell, instead of a mixture of 10 different Ig-like dimers (AA, AB, AC, AD, BB, BC, BD, CC, CD and DD), a mixture of predominantly two specific Ig-like molecules is produced.

As explained herein below in more detail, in a preferred embodiment said first CH3-domain comprising polypeptide chain comprises the amino acid substitution T366K, and said second CH3-domain comprising polypeptide chain comprises the amino acid substitution L351D. These amino acid changes are preferred means for preferential pairing of said first and second CH3-domain comprising polypeptide chains. Said first CH3-domain comprising polypeptide chain preferably further comprises the amino acid substitution L351K. Moreover, said second CH3-domain comprising polypeptide chain preferably further comprises an amino acid substitution selected from the group consisting of Y349E, Y349D and L368E, most preferably L368E. In yet another preferred embodiment, said third CH3-domain comprising polypeptide chain comprises the amino acid substitutions E356K and D399K, and said fourth CH3-domain comprising polypeptide chain comprises the amino acid substitutions K392D and K409D.

In a method according to the present invention, each of the CH3-domain comprising polypeptide chains preferably further comprises a variable region recognizing a target epitope. The variable regions that are part of the CH3-domain comprising polypeptide chains preferably share a common light chain. In that case only the VHs of the variable regions differ whereas the VL in all variable regions is essentially the same. Hence, in a preferred aspect a method according to the invention is provided, which further comprises providing said host cell with a nucleic acid molecule encoding a common light chain. In one particularly preferred embodiment, each of said 4 variable regions of the 4 CH3-domain comprising polypeptide chains recognizes a different target epitope. For instance, if the first nucleic acid molecule encodes a heavy chain that further contains a variable domain with specificity for antigen A, the second nucleic acid molecule encodes a heavy chain that further contains a variable domain with specificity for antigen B, the third nucleic acid molecule encodes a heavy chain that further contains a variable domain with specificity for antigen C, and the fourth nucleic acid molecule encodes a heavy chain that further contains a variable domain with specificity for antigen D, a mixture will then be produced containing bispecific Ig-like molecules that are specific for AB and bispecific Ig-like molecules that are specific for CD. The formation of monospecific antibodies (with AA, BB, CC or DD specificity) or bispecific antibodies with specificity for AC, AD, BC or BD is lowered or even absent due to the means for preferential pairing of said $1^{st}$ and $2^{nd}$ CH3 domain-comprising polypeptides and said $3^{rd}$ and $4^{th}$ CH3 domain-comprising polypeptides. It is, of course, possible to use further nucleic acid molecules, for instance encoding a $5^{th}$ and a $6^{th}$ CH3 domain-comprising polypeptide, in order to produce defined mixtures comprising more than two different Ig-like molecules.

Of note, the ratio of the nucleic acids used in a method according to the invention does not need to be 1:1:1:1 and the ratio of the resulting Ig-like molecules that are expressed does not need to be 1:1. It is possible to use means known in the art to produce mixtures of antibodies with optimized ratios. For instance, expression levels of nucleic acid molecules and hence the ratios of the resulting Ig-like molecules produced may be regulated by using different genetic elements such as promoters, enhancers and repressors or by controlling the genomic integration site of copy number of the DNA constructs encoding antibodies.

Said means for preferential pairing preferably may comprise engineered complementary knob-into-hole mutations, disulfide bridges, charge mutations including charge reversal mutations, or combinations thereof. The skilled person will appreciate that said means for preferential pairing may be chosen within a certain type of mutations, i.e. all at least 4 nucleic acid molecules encoding CH3-domain comprising polypeptide chains may for example comprise charge mutations as means for preferential pairing. Additionally, also non-engineered wildtype CH3 may in certain instances be used for preferential pairing of two wildtype CH3-domain comprising polypeptide chains. In a particularly preferred embodiment, said means for preferential pairing comprise at least one CH3 mutation selected from Table B, as explained elsewhere in this application. One preferred embodiment thus provides a method according to the present invention, wherein all 4 of said nucleic acid molecules are provided with means for preferential pairing of said $1^{st}$ and $2^{nd}$ CH3 domain-comprising polypeptides and said $3^{rd}$ and $4^{th}$ CH3-domain comprising polypeptides, wherein said means for preferential pairing of said $1^{st}$ and $2^{nd}$ CH3 domain-comprising polypeptides are different from those means for preferential pairing of said $3^{rd}$ and $4^{th}$ CH3-domain comprising polypeptides.

One aspect of the present invention provides a method according to the invention, wherein said means for preferential pairing of said $1^{st}$ and $2^{nd}$ CH3 domain-comprising polypeptides are different from said means for preferential pairing of said $3^{rd}$ and $4^{th}$ CH3-domain comprising polypeptides. By 'different' it is meant that the means for preferential pairing of said $1^{st}$ and $2^{nd}$ CH3 domain comprising polypeptides are designed such that preferential pairing of the $1^{st}$ and $2^{nd}$ chain is favoured. The design is such that essentially no interaction between the $1^{st}$ and the $3^{rd}$ and/or $4^{th}$ CH3 domain comprising polypeptide chain will take place. In other words, dimerization between said $1^{st}$ CH3 domain comprising polypeptide and said $3^{rd}$ or $4^{th}$ polypeptide is reduced to essentially zero and so forth. The $3^{rd}$ and the $4^{th}$ CH3 domain-comprising polypeptides may either be wildtype or may comprise means for preferential pairing that are different from the means for preferential pairing of the $1^{st}$ and $2^{nd}$ CH3 domains. Current studies have focused on the production of a single bispecific antibody, using for instance the knob-into-hole technology or mutations (reversions) of charged contact amino acids present in CH3 domains. Production of defined mixtures of at least two (bispecific) Ig-like molecules, without significant co-production of other dimeric by-products, has, however, not been realized prior to the present invention.

The present invention provides methods for the efficient and controlled production of a well-defined mixture of Ig-like molecules, with a high proportion of bispecifics in the mixture. Even a proportion of (two) bispecifics of at least 95%, at least 97% or more is obtained in a system where two bispecifics are desired. This means that only at most 5%, at most 3% or less monospecific bivalent by-products are obtained. Of note, the amount of monomeric by-products, i.e. half molecules, is less important since these half-molecules are easily separated from dimers using their size difference.

In another preferred embodiment, the variable regions of the $1^{st}$ and the $2^{nd}$ CH3-domain comprising polypeptide chains recognize different target epitopes, whereas the variable regions of the $3^{rd}$ and the $4^{th}$ CH3-domain comprising polypeptide chains recognize the same target epitopes. This will result in the predominant production of one kind of bispecific Ig-like molecule and one kind of monospecific Ig-like molecule. For instance, if the variable regions of the $1^{st}$ and the $2^{nd}$ CH3-domain comprising polypeptide chains recognize different target epitopes and if the variable regions of the $3^{rd}$ and the $4^{th}$ CH3-domain comprising polypeptide chains both recognize the same target epitope which is different from the target epitopes recognized by the $1^{st}$ and the $2^{nd}$ CH3-domains, a mixture of Ig-like molecules having specificity for AB or CC will be formed. Further provided is therefore a method according to the invention, wherein the target epitope recognized by the variable regions of the $3^{rd}$ and $4^{th}$ CH3 domain comprising polypeptide chain is the same, but different from the target epitope recognized by the variable region of the $1^{st}$ or the $2^{nd}$ CH3-domain comprising polypeptide chain.

Alternatively, when the variable regions of the $1^{st}$ and the $2^{nd}$ CH3-domain comprising polypeptide chains recognize different target epitopes and when the variable regions of the $3^{rd}$ and the $4^{th}$ CH3-domain comprising polypeptide chains both recognize the same epitope as the $1^{st}$ or the $2^{nd}$ CH3-domain comprising polypeptide chains, a mixture of Ig-like molecules having specificity for AB and AA, or AB and BB will be formed. A method according to the invention, wherein the target epitope recognized by the variable regions of the $3^{rd}$ and $4^{th}$ CH3 domain comprising polypeptide chain is the same as the target epitope recognized by the variable region of the $1^{st}$ or the $2^{nd}$ CH3-domain comprising polypeptide chain is therefore also herewith provided.

It is another object of the present invention to provide means and methods for producing defined mixtures of bispecific antibodies and monospecific antibodies in a single cell culture. A non-limiting example of such well-defined mixture is a mixture of bispecific antibodies with specificity AB and monospecific antibodies with specificity AA. Another example is a mixture of bispecific antibodies with specificity AB and monospecific antibodies with specificity BB. Yet another example is a mixture of bispecific antibodies with specificity AB and monospecific antibodies with specificity CC. Again, preferably means and methods are provided which yield mixtures of antibodies of interest with at least 90%, more preferably at least 95% and most preferably at least 97% or even more than 99% of desired antibodies.

In yet another embodiment, a method according to the invention is provided wherein the variable regions of the $1^{st}$ and the $2^{nd}$ CH3-domain comprising polypeptide chains recognize the same target epitope, whereas the variable regions of the $3^{rd}$ and the $4^{th}$ CH3-domain comprising polypeptide chains recognize a second target epitope which differs from the target epitope recognized by said $1^{st}$ and $2^{nd}$ variable regions. This will result in the predominant production of monospecific Ig-like molecules having either specificity for AA or specificity for BB. The formation of bispecific Ig-like molecules is diminished or even avoided. In several embodiments it is preferred to produce mixtures of monospecific antibodies in a single cell, rather than mixtures of bispecific antibodies. For instance when cross-linking of two identical target molecules is desired, or when two targets are located too far away from each other so that they cannot be bound by a single bispecific antibody. It can also be advantageous to produce mixtures of monospecific antibodies in a single cell as the mixture can be regarded as a single therapeutic product. In the art, the therapeutic efficacy and safety of various monospecific antibodies has already been proven and market authorisation has been obtained. Production of mixtures of monospecific antibodies in a single cell will thus facilitate the testing for efficacy and safety of several of such mixtures and will reduce the efforts and costs for regulatory approval and manufacturing. There are, however, currently no methods available for producing specific mixtures of monospecific antibodies in a single cell wherein the formation of bispecific by-products is reduced to below 5%. It is another object of the present invention to provide means and methods for producing such well-defined homodimeric antibody mixtures in single cells wherein the formation of bispecific antibodies is reduced to below 5%.

Hence, a method according to the present invention is suitable for the production of any desired mixture of bispecific and/or monospecific Ig-like molecules. Again, it is possible to use further nucleic acid molecules, for instance encoding a $5^{th}$ and a $6^{th}$ (and $7^{th}$ and $8^{th}$ and so forth) CH3 domain-comprising polypeptide, in order to produce defined mixtures comprising more than two different Ig-like molecules.

Preferably, in a method according to the present invention at least two CH3 domains are used that comprise at least one combination of mutations provided by the present invention. Through these mutations novel specific interactions are formed between two CH3 domains. These mutations according to the present invention are discussed below in more detail.

The term 'Ig-like molecule' as used herein means a proteinaceous molecule that possesses at least one immunoglobulin (Ig) domain. Said Ig-like molecule comprises a sequence comprising the function of at least an immunoglobulin CH3 domain, preferably the sequence comprises an IgG1 CH3 domain. Proteinaceous molecules that possess at least a CH3 domain can be further equipped with specific binding moieties. The CH3 domains of the present invention, containing means for preferential pairing, can thus be used for preferential pairing of two CH3-domain comprising proteinaceous molecules to design desired heterodimeric binding molecules or mixtures of binding molecules. Binding moieties that can be engineered to the CH3-domain comprising proteinaceous molecules can be any binding agent, including, but not limited to, single chain Fvs, single chain or Tandem diabodies (TandAb®), VHHs, Anticalins®, Nanobodies®, a BiTE®, a Fab, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins® or a KALBITOR®. In a preferred embodiment, the binding moieties are antibody variable regions (i.e. VH/VL combinations). Variable regions that are part of the CH3-domain comprising polypeptide chains preferably share a common light chain. In that case, only the VHs of the variable regions differ whereas the VL in all variable regions is essentially the same.

Alternatively, or in addition, other molecules can be engineered to the CH3 domains of the present invention, including cytokines, hormones, soluble ligands, receptors and/or peptides.

In a more preferred embodiment, said Ig-like molecule comprises a full length Fc backbone. In a most preferred embodiment, the Ig-like molecules are antibodies. The variable regions of these antibodies preferably share a common light chain, but they may differ in their VH regions. The term 'antibody' as used herein means a proteinaceous molecule belonging to the immunoglobulin class of proteins, containing one or more domains that bind an epitope on an antigen, where such domains are derived from or share sequence homology with the variable region of an antibody. Antibodies are known in the art and include several isotypes, such as IgG1, IgG2, IgG3, IgG4, IgA, IgD, IgE, and IgM. An antibody according to the invention may be any of these isotypes, or a functional derivative and/or fragment of these. In a preferred embodiment, Ig-like molecules are produced that are antibodies of the IgG isotype because IgG antibodies e.g. have a longer half life as compared to antibodies of other isotypes.

Antibodies produced with methods according to the present invention can have sequences of any origin, including murine and human sequences. Antibodies can consist of sequences from one origin only, such as fully human antibodies, or they can have sequences of more than one origin, resulting for instance in chimeric or humanized antibodies. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is bound by the binding domain. The affinity is a measure for the strength of binding to a particular antigen or epitope. Specific binding is defined as binding with affinities ($K_D$) of at least $1\times10^{-5}$ M, more preferably $1\times10^{-7}$ M, more preferably higher than $1\times10^{-9}$ M. Typically, monoclonal antibodies for therapeutic applications have affinities of up to $1\times10^{-10}$ M or even higher. The term 'antigen' as used herein means a substance or molecule that, when introduced into the body, triggers the production of an antibody by the immune system. An antigen, among others, may be derived from pathogenic organisms, tumor cells or other aberrant cells, from haptens, or even from self structures. At the molecular level, an antigen is characterized by its ability to be bound by the antigen-binding site of an antibody. Also mixtures of antigens can be regarded as 'antigen', i.e. the skilled person would appreciate that sometimes a lysate of tumor cells, or viral particles may be indicated as 'antigen' whereas such tumor cell lysate or viral particle preparation exists of many antigenic determinants. An antigen comprises at least one, but often more, epitopes. The term 'epitope' as used herein means a part of an antigen that is recognized by the immune system, specifically by antibodies, B cells, or T cells. Although epitopes are usually thought to be derived from non-self proteins, sequences derived from the host that can be recognized are also classified as epitopes.

The term 'CH3 domain' is well known in the art. The IgG structure has four chains, two light and two heavy chains; each light chain has two domains, the variable and the constant light chain (VL and CL) and each heavy chain has four domains, the variable heavy chain (VH) and three constant heavy chain domains (CH1, CH2, CH3). The CH2 and CH3 domain region of the heavy chain is called Fc (Fragment crystallizable) portion, Fc fragment, Fc backbone or simply Fc. The IgG molecule is a heterotetramer having two heavy chains that are held together by disulfide bonds (—S—S—) at the hinge region and two light chains. The heavy chains dimerize through interactions at the CH3-CH3 domain interface and through interactions at the hinge region. The number of hinge disulfide bonds varies among the immunoglobulin subclasses (Papadea and Check 1989). The Fc fragment of an immunoglobulin molecule is a dimer of the two C-terminal constant regions, i.e. CH2 and CH3 domains, of the heavy chain. Among its physiological functions are interactions with the complement system and with specific receptors on the surface of a variety of cells.

Interactions between the CH3 domains of two individual heavy chains are known to play an important role in driving heavy chain dimerization. Thus, CH3 domains direct the association of antibody heavy chains, and it is known that the interface between CH3 domains contains more than 20 contact residues from each chain that play a role in the CH3-CH3 interaction (Deisenhofer J., Biochemistry 1981 (20)2361-2370; Miller S., J. Mol. Biol. 1990 (216)965-973; Padlan, Advances in Protein Chemistry 1996 (49) 57-133). The CH3 variants of the present invention can thus be used in association with other antibody domains to generate full length antibodies that are either bispecific or monospecific. The specificity of the antibody as defined by the VH/VL combinations typically does not affect the heavy chain dimerization behaviour that is driven by the CH3 domains.

The terms 'contact residue', 'contact amino acid', 'interface residue' and 'interface amino acid' as used herein typically refers to any amino acid residue present in the CH3 domain that can be involved in interdomain contacts, as can be calculated by technologies known in the art, including calculating solvent accessible surface area (ASA) of the CH3 domain residues in the presence and absence of the second chain (Lee and Richards J. Mol. Biol. 1971 (55)379) where residues that show difference (>1 $Å^2$) in ASA between the two calculations are identified as contact residues. Contact residues that have been identified include residues at positions 347, 349, 350, 351, 352, 353, 354, 355, 356, 357, 360, 364, 366, 368, 370, 390, 392, 394, 395, 397, 399, 400, 405, 407, 409, 439 according to the EU numbering system (Table A).

TABLE A

List of CH3 domain interface residues

| Interface residue in chain A | Contacting residues in chain B |
| --- | --- |
| Q347 | K360 |
| Y349 | S354, D356, E357, K360 |

TABLE A-continued

List of CH3 domain interface residues

| Interface residue in chain A | Contacting residues in chain B |
|---|---|
| T350 | S354, R355 |
| L351 | L351, P352, P353, S354, T366 |
| S354 | Y349, T350, L351 |
| R355 | T350 |
| D356 | Y349, K439 |
| E357 | Y349, K370 |
| K360 | Q347, Y349 |
| S364 | L368, K370 |
| T366 | L351, Y407 |
| L368 | S364, K409 |
| K370 | E357, S364 |
| N390 | S400 |
| K392 | L398, D399, S400, F405 |
| T394 | T394, V397, F405, Y407 |
| P395 | V397 |
| V397 | T394, P395 |
| D399 | K392, K409 |
| S400 | N390, K392 |
| F405 | K392, T394, K409 |
| Y407 | T366, T394, Y407, K409 |
| K409 | L368, D399, F405, Y407 |
| K439 | D356 |

Contact residues within the CH3-CH3 interface can either be amino acids that are charged, or amino acid residues that are neutral. The term 'charged amino acid residue' or 'charged residue' as used herein means amino acid residues with electrically charged side chains. These can either be positively charged side chains, such as present in arginine (Arg, R), histidine (His, H) and lysine (Lys, K) or can be negatively charged side chains, such as present in aspartic acid (Asp, D) and glutamic acid (Glu, E). The term 'neutral amino acid residue' or neutral residue as used herein refers to all other amino acids that do not carry electrically charged side chains. These neutral residues include serine (Ser, S), threonine (Thr, T), asparagine (Asn, N), glutamine (GLu, Q), Cysteine (Cys, C), glycine (Gly, G), proline (Pro, P), alanine (Ala, A), valine (Val, V), isoleucine (Ile, I), leucine (Leu, L), methionine (Met, M), phenylalanine (Phe, F), tyrosine (Tyr, Y), and tryptophan (Trp, T).

The term 'CH3-CH3 domain interface', or 'CH3 interface', 'CH3-CH3 pairing', 'domain interface' or simply 'interface', as used herein, refers to the association between two CH3 domains of separate CH3-domain comprising polypeptides that is a result of interacting amino acid residues, i.e. at least one interaction between an amino acid of a first CH3 domain and an amino acid of a second CH3 domain. Such interaction is for instance via Van der Waals forces, hydrogen bonds, water-mediated hydrogen bonds, salt bridges or other electrostatic forces, attractive interactions between aromatic side chains, the formation of disulfide bonds, or other forces known to one skilled in the art.

As used herein, said means for preferential pairing of the first and second CH3 domain-comprising polypeptides and said third and fourth CH3 domain-comprising polypeptide can be any means known in the art. In one embodiment, at least one nucleic acid molecule encodes a CH3 domain which contains at a contact residue position a large amino acid residue (i.e. a "knob" or "protuberance") such as for instance R, F, Y, W, I or L, whereas at least one other nucleic acid molecule encodes a CH3 domain which contains at a complementary contact residue position a small amino acid residue (i.e. a "hole" or "cavity") such as for instance G, A, S, T or V. The resulting CH3 domains will preferentially pair with each other due to the steric conformation of said contact amino acids. The knob-into-hole technology is described herein before in more detail. In a further embodiment of the present invention, at least one nucleic acid molecule encodes a CH3 domain which contains at a contact residue position that is naturally charged, i.e. a naturally occurring K, H, R, D or E, an amino acid that now carries the opposite charge as compared to wildtype, whereas at least one other nucleic acid molecule encodes a CH3 domain which contains at a complementary contact residue position that is naturally charged, an amino acid that now carries the opposite charge as compared to wildtype. The resulting engineered CH3 domains will preferentially pair with each other due to the opposite charges of said contact amino acids, whereas pairing of identical CH3 domains will be diminished due to electrostatic repulsion. In one embodiment, CH3 mutations as described in EP01870459, WO 2009/089004, Gunasekaran et al (2010), are used. In one embodiment, the means for preferential pairing of said $1^{st}$ and $2^{nd}$ CH3 domain-comprising polypeptides are "knob" and "hole" amino acid residues and the means for preferential pairing of said $3^{th}$ and $4^{th}$ CH3 domain-comprising polypeptides are charge-engineered amino acids. Preferably, both said means for preferential pairing of said $1^{st}$ and $2^{nd}$ CH3 domain-comprising polypeptides and said $3^{th}$ and $4^{th}$ CH3 domain-comprising polypeptides are charge-engineered amino acids. In one embodiment, different amino acid residues are engineered for preferential pairing of said $1^{st}$ and $2^{nd}$ CH3 domain-comprising polypeptides as compared to the amino acid residues that are engineered for preferential pairing of said $3^{th}$ and $4^{th}$ CH3 domain-comprising polypeptides. In a particularly preferred embodiment at least a first and a second nucleic acid molecule encode CH3 domains with novel mutations as provided by the present invention. As described herein below in more detail, the present invention provides novel CH3 mutations which enable the production of certain bispecific Ig-like molecules of interest without a significant amount of undesired (dimeric) by-products. The present invention also provides novel CH3 mutations which enable the production of certain monospecific Ig-like molecules of interest without a significant amount of undesired (dimeric) by-products. The use of at least one of these CH3 mutations according to the present invention is, therefore, preferred.

The term 'polypeptide', 'polypeptide molecule' or 'polypeptide chain' as used herein refers to a chain of amino acids that are covalently joined together through peptide bonds. Proteins are typically made up of one or more polypeptide molecules. One end of every polypeptide, called the amino terminal or N-terminal, has a free amino group. The other end, with its free carboxyl group, is called the carboxyl terminal or C-terminal. Polypeptides according to the present invention may have gone through post-translational modification processes and may e.g. be glycosylated. The CH3 domain-comprising polypeptide chains of the present invention thus refer to polypeptide chains that at least encompass an Ig CH3 domain and that may have gone through post-translational modification processes.

The term "nucleic acid molecule" as used herein is defined as a molecule comprising a chain of nucleotides, more preferably DNA and/or RNA. In one embodiment, double-stranded RNA is used. In other embodiments a nucleic acid molecule of the invention comprises other kinds of nucleic acid structures such as for instance a DNA/RNA helix, peptide nucleic acid (PNA), locked nucleic acid (LNA) and/or a ribozyme. Hence, the term "nucleic acid molecule" also encompasses a chain comprising non-natural nucleotides, modified nucleotides and/or non-nucleotide building blocks which exhibit the same function as natural nucleotides.

The present invention further provides a method for making a host cell for production of at least two different Ig-like molecules, the method comprising the step of introducing into said host cell nucleic acid sequences encoding at least a first, a second, a third and a fourth CH3-domain comprising polypeptide chain, wherein at least two of said nucleic acid sequences are provided with means for preferential pairing of said first and second CH3-domain comprising polypeptides and said third and fourth CH3-domain comprising polypeptides, wherein said nucleic acid sequences are introduced consecutively or concomitantly.

It is a further aspect of the present invention to provide a method for making a host cell for production of a heterodimeric Ig-like molecule, the method comprising the step of introducing into said host cell nucleic acid sequences encoding at least a first and a second CH3-domain comprising polypeptide chain, wherein said first CH3 domain-comprising polypeptide chain comprises at least one substitution of a neutral amino acid residue by a positively charged amino acid residue and wherein said second CH3 domain-comprising polypeptide chain comprises at least one substitution of a neutral amino acid residue by a negatively charged amino acid residue, wherein said nucleic acid sequences are introduced consecutively or concomitantly. Said methods for making said host cells preferably further comprise the step of introducing into said host cell a nucleic acid sequence encoding a common light chain.

Also provided herein is a recombinant host cell comprising nucleic acid sequences encoding at least a first, a second, a third and a fourth CH3-domain comprising polypeptide chain, wherein at least two of said nucleic acid molecules are provided with means for preferential pairing of said first and second CH3-domain comprising polypeptides and said third and fourth CH3-domain comprising polypeptides. The invention furthermore provides a recombinant host cell comprising nucleic acid sequences encoding at least a first and a second CH3-domain comprising polypeptide chain, wherein said first CH3 domain-comprising polypeptide chain comprises at least one substitution of a neutral amino acid residue by a positively charged amino acid residue and wherein said second CH3 domain-comprising polypeptide chain comprises at least one substitution of a neutral amino acid residue by a negatively charged amino acid residue.

A recombinant host cell according to the invention preferably further comprises a nucleic acid sequence encoding a common light chain.

A "host cell" according to the invention may be any host cell capable of expressing recombinant DNA molecules, including bacteria such as for instance *Escherichia* (e.g. *E. coli*), *Enterobacter, Salmonalla, Bacillus, Pseudomonas, Streptomyces*, yeasts such as *S. cerevisiae, K. lactis, P. pastoris, Candida*, or *Yarrowia*, filamentous fungi such as *Neurospora, Aspergillus oryzae, Aspergillus nidulans* and *Aspergillus niger*, insect cells such as *Spodoptera frugiperda* SF-9 or SF-21 cells, and preferably mammalian cells such as Chinese hamster ovary (CHO) cells, BHK cells, mouse cells including SP2/0 cells and NS-0 myeloma cells, primate cells such as COS and Vero cells, MDCK cells, BRL 3A cells, hybridomas, tumor-cells, immortalized primary cells, human cells such as W138, HepG2, HeLa, HEK293, HT1080 or embryonic retina cells such as PER. C6, and the like. Often, the expression system of choice will involve a mammalian cell expression vector and host so that the antibodies can be appropriately glycosylated. A human cell line, preferably PER.C6, can advantageously be used to obtain antibodies with a completely human glycosylation pattern. The conditions for growing or multiplying cells (see e. g. Tissue Culture, Academic Press, Kruse and Paterson, editors (1973)) and the conditions for expression of the recombinant product may differ somewhat, and optimization of the process is usually performed to increase the product proportions and/or growth of the cells with respect to each other, according to methods generally known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991). Expression of antibodies in recombinant host cells has been extensively described in the art (see e.g. EP0120694; EP0314161; EP0481790; EP0523949; U.S. Pat. No. 4,816,567; WO 00/63403). The nucleic acid molecules encoding the light and heavy chains may be present as extrachromosomal copies and/or stably integrated into the chromosome of the host cell, the latter is preferred.

It is a further aspect of the present invention to provide a culture of recombinant host cells according to the invention, or a culture of recombinant host cells obtainable or obtained by a method according to the invention, said culture either producing at least two different Ig-like molecules or a heterodimeric Ig-like molecule.

To obtain expression of nucleic acid sequences encoding the CH3 domain-comprising polypeptides, it is well known to those skilled in the art that sequences capable of driving such expression can be functionally linked to the nucleic acid sequences encoding the CH3 domain-comprising polypeptides. Functionally linked is meant to describe that the nucleic acid sequences encoding the CH3 domain-comprising polypeptides or precursors thereof is linked to the sequences capable of driving expression such that these sequences can drive expression of the CH3 domain-comprising polypeptides or precursors thereof. Useful expression vectors are available in the art, e.g. the pcDNA vector series of Invitrogen. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter. Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter, promoters derived from Simian Virus 40 (SV40), and the like. Suitable promoters can also be derived from eukaryotic cells, such as methallothionein (MT) promoters, elongation factor 1α (EF-1α) promoter, actin promoter, an immunoglobulin promoter, heat shock promoters, and the like. Any promoter or enhancer/promoter capable of driving expression of the sequence of interest in the host cell is suitable in the invention. In one embodiment the sequence capable of driving expression comprises a region from a CMV promoter, preferably the region comprising nucleotides −735 to +95 of the CMV immediate early gene enhancer/promoter. The skilled artisan will be aware that the expression sequences used in the invention may suitably be combined with elements that can stabilize or enhance expression, such as insulators, matrix attachment regions, STAR, elements (WO 03/004704), and the like. This may enhance the stability and/or levels of expression.

Protein production in recombinant host cells has been extensively described, e.g. in Current Protocols in Protein Science, 1995, Coligan J E, Dunn B M, Ploegh H L, Speicher D W, Wingfield P T, ISBN 0-471-11184-8; Bendig, 1988. Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Several culturing conditions can be optimized by methods well known in the art to optimize protein production yields. Culturing can be done for instance in dishes, roller bottles or in bioreactors, using batch, fed-batch, continuous systems, hollow fiber, and the like. In order to achieve large scale (continuous) production of recombinant proteins through cell culture it is preferred in the art to have cells capable of growing in suspension, and it is preferred to have cells capable of being cultured in the absence of animal-or human-derived serum or animal-or human-derived serum components. Thus purification is easier and safety is enhanced due to the absence of additional animal or human proteins derived from the culture medium, while the system is also very reliable as synthetic media are the best in reproducibility.

Ig-like molecules are expressed in host cells and are harvested from the cells or, preferably, from the cell culture medium by methods that are generally known to the person skilled in the art. After harvesting, these Ig-like molecules may be purified by using methods known in the art. Such methods may include precipitation, centrifugation, filtration, size-exclusion chromatography, affinity chromatography, cation-and/or anion-exchange chromatography, hydrophobic interaction chromatography, and the like. For a mixture of antibodies comprising IgG molecules, protein A or protein G affinity chromatography can be suitably used (see e.g. U.S. Pat. Nos. 4,801,687 and 5,151,504).

Ig-like molecules, and/or mixtures thereof, produced with methods according to the present invention preferably have a common light chain. Further provided is, therefore, a method according to the invention, further comprising providing said host cell with a nucleic acid molecule encoding a common light chain. This is a light chain that is capable of pairing with at least two different heavy chains, thereby forming functional antigen binding domains. A functional antigen binding domain is capable of specifically binding to an antigen. Preferably, a common light chain is used that is capable of pairing with all heavy chains produced with a method according to the invention, thereby forming functional antigen binding domains, so that mispairing of unmatched heavy and light chains is avoided. In one aspect, only common light chains with one identical amino acid sequence are used. Alternatively, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. Such variants are thus also capable of binding different heavy chains and forming functional antigen binding domains. The term 'common light chain' as used herein thus refers to light chains which may be identical or have some amino acid sequence differences while retaining the binding specificity of the resulting antibody after pairing with a heavy chain. It is for instance possible to prepare or find light chains that are not identical but still functionally equivalent, e.g. by introducing and testing conservative amino acid changes, and/or changes of amino acids in regions that do not or only partly contribute to binding specificity when paired with the heavy chain, and the like. A combination of a certain common light chain and such functionally equivalent variants is encompassed within the term "common light chain". Reference is made to WO 2004/009618 for a detailed description of the use of common light chains. Preferably, a common light chain is used in the present invention which is a germline-like light chain, more preferably a germline light chain, preferably a rearranged germline human kappa light chain, most preferably either the rearranged germline human kappa light chain IgVκ1-39/Jκ or IGVκ3-20/Jκ.

Alternatively, the skilled person may select, as an alternative to using a common light chain and to avoid mispairing of unmatched heavy and light chains, means for forced pairing of the heavy and light chain, such as for example described in WO2009/080251, WO2009/080252 and/or WO2009/080253.

The present invention provides novel engineered CH3 domains as well as novel combinations of CH3 mutations. Before the present invention, charged contact amino acids of CH3 domains that were known to be involved in CH3-CH3 pairing were substituted by amino acids of opposite charge (charge reversal), thereby influencing the CH3-CH3 pairing. The mutations according to the present invention are an inventive alternative to this approach, because now CH3 amino acids that are non-charged or neutral in wildtype CH3 are substituted with charged residues. The present invention in this embodiment does not exchange charged contact amino acids by amino acids of opposite charge but substitutes non-charged CH3 amino acids for charged ones. The approach of the present invention provides not only a method for efficiently steering the dimerization of CH3 domains but also has the advantage that at least one additional charge-charge interaction in the CH3 interface is created. In view of this additional charge-charge interaction on top of the existing charge-pairs in the CH3-CH3 interface, the dimers according to the invention are generally more stable as compared to the wild type dimers (the wild type dimer is defined as a bispecific IgG (AB) without CH3 engineering in contrast to its parental homodimers (AA or BB)). Moreover, it has surprisingly become possible to increase the proportion of one or more Ig-like molecules of interest in a mixture even further. As described herein before, methods known in the art for preferential production of a bispecific antibody typically involves the production of some undesired dimeric side products. For instance, the proportion of a bispecific antibody of interest using the knob-into-hole technology is at best 87%, whereas the electrostatic engineering approach wherein charged contact amino acids are substituted by amino acids of opposite charge, also results in proportions of up to 96% (see for instance Example 11). Quite surprisingly, the present inventors have succeeded in introducing mutations that further enhance the proportion of an Ig-like molecule of interest in a mixture. For instance, Example 17 discloses a method using mutations according to the present invention, wherein the proportion of a bispecific antibody of interest was raised to such extent that no dimeric by-product was detectable in the resulting mixture at all. Unpaired half-molecules consisting of only a single heavy chain paired with a common light chain were present to some extent in the mixtures, but these are the result of unbalanced expression of the heavy chains and can be easily separated from the mixture by size exclusion chromatography. Hence, with such mutations according to the present invention, a bispecific Ig-like molecule can be produced in a single cell with a high proportion with essentially no contaminating dimeric by-products being present, which is particularly suitable for the production of a pharmaceutical composition.

One preferred embodiment of the present invention therefore provides a method for producing a heterodimeric Ig-like molecule from a single cell, wherein said Ig-like molecule comprises two CH3 domains that are capable of forming an interface, said method comprising providing in said cell a. A first nucleic acid molecule encoding a $1^{st}$ CH3 domain-comprising polypeptide chain, b. A second nucleic acid molecule encoding a $2^{nd}$ CH3 domain-comprising polypeptide chain, wherein said first CH3 domain-comprising polypeptide chain comprises at least one substitution of a neutral amino acid residue by a positively charged amino acid residue and wherein said second CH3 domain-comprising polypeptide chain comprises at least one substitution of a neutral amino acid residue by a negatively charged amino acid residue, said method further comprising the step of culturing said host cell and allowing for expression of said two nucleic acid molecules and harvesting said heterodimeric Ig-like molecule from the culture.

Said method preferably further comprises the step of providing said host cell with a nucleic acid molecule encoding a common light chain, which has advantages as outlined herein before.

The amino acids at position 366 of one CH3 domain and position 351 of a second CH3 domain have been reported to be a pair of contact residues in the CH3-CH3 interface, meaning that they are located sufficiently close to each other in the three-dimensional conformation of the resulting Ig-like molecule in order to be capable of interacting with each other. Hence, the first CH3 domain will preferentially pair with the second CH3 domain.

In one embodiment, threonine (T) at position 366 of a first CH3 domain is replaced by a first charged amino acid and leucine (L) at position 351 of a second CH3 domain is replaced by a second charged amino acid, wherein said first and second charged amino acids are of opposite charge. If the first CH3 domain-comprising polypeptide, that carries a charged residue at position 366, further comprises a variable domain which has specificity for antigen A, and if the second CH3 domain-comprising polypeptide, that carries an oppositely charged residue at position 351, further comprises a variable domain which has specificity for antigen B, bispecific Ig-like molecules with an AB specificity will be predominantly formed. Further provided is therefore a method according to the present invention, wherein said means for preferential pairing of said $1^{st}$ and $2^{nd}$ CH3 domain-comprising polypeptides or said means for preferential pairing of said $3^{rd}$ and $4^{th}$ CH3 domain-comprising polypeptides are a substitution of threonine at position 366 of said $1^{st}$ or $3^{rd}$ CH3 domain by a first charged amino acid and substitution of leucine at position 351 of said $2^{nd}$ or $4^{th}$ CH3 domain by a second charged amino acid, wherein said first and second charged amino acids are of opposite charge.

One preferred combination of mutations according to the present invention is the substitution of threonine (T) by lysine (K) at position 366 of a first CH3 domain-comprising polypeptide which further comprises a variable domain (for instance with specificity A) and the substitution of leucine (L) by asp artic acid (D) at position 351 of a second CH3 domain-comprising polypeptide which further comprises a variable domain (for instance with specificity B). This is denoted as a T366K/L351'D pair mutation. As explained before, the amino acids at position 366 of one CH3 domain and position 351 of a second CH3 domain have been reported to be a pair of contact residues in the CH3-CH3 interface. The lysine that is introduced at position 366 and the aspartic acid introduced at position 351 have opposite charges, so that these amino acids will electrostatically attract each other. Hence, the first CH3 domain will preferentially attract the second CH3 domain and Ig-like molecules comprising a first CH3 domain containing lysine at position 366 paired with a second CH3 domain containing asp artic acid at position 351 will be predominantly formed. If the first CH3 domain-comprising polypeptide has specificity for antigen A, and if the second CH3 domain-comprising polypeptide has specificity for antigen B, bispecific Ig-like molecules with 'AB' specificity will be predominantly formed. Nota bene, in some embodiments the specificity of the variable domains of both said first and second CH3-domain comprising polypeptide chains may be the same, which will result in the formation of monospecific Ig-like molecules (for instance with 'AA' specificity). As mentioned above, one of the advantages of the mutations according to the present invention is the fact that a novel interaction between a newly introduced pair of charged amino acids is created, instead of replacing existing charged amino acid interactions. This was not previously disclosed or suggested. One aspect of the invention therefore provides a method according to the present invention for producing at least two different Ig-like molecules from a single host cell, wherein said $1^{st}$ CH3 domain-comprising polypeptide chain comprises the amino acid substitution T366K, and said $2^{nd}$ CH3 domain-comprising polypeptide chain comprises the amino acid substitution L351D. One embodiment provides a method for producing a heterodimeric Ig-like molecule from a single cell, wherein said Ig-like molecule comprises two CH3 domains that are capable of forming an interface, said method comprising providing in said cell:

a first nucleic acid molecule encoding a $1^{st}$ CH3 domain-comprising polypeptide chain, and a second nucleic acid molecule encoding a $2^{nd}$ CH3 domain-comprising polypeptide chain, wherein said first CH3 domain-comprising polypeptide chain comprises the amino acid substitution T366K and wherein said second CH3 domain comprising polypeptide chain comprises the amino acid substitution L351D, said method further comprising the step of culturing said host cell and allowing for expression of said two nucleic acid molecules and harvesting said heterodimeric Ig-like molecule from the culture.

Using the above mentioned amino acid substitutions according to the present invention, it has become possible to produce a heterodimeric Ig-like molecule from a single cell, whereby the presence of contaminating homodimers is less than 5%, preferably less than 2%, more preferably less than 1%, or, most preferably, whereby contaminating homodimers are essentially absent. One embodiment therefore provides a method for producing a heterodimeric Ig-like molecule from a single cell, wherein said Ig-like molecule comprises two CH3 domains that are capable of forming an interface and wherein the presence of contaminating homodimers is less than 5%, preferably less than 2%, more preferably less than 1%, and most preferably contaminating homodimers are essentially absent, said method comprising providing in said cell:
- a first nucleic acid molecule encoding a 1$^{st}$ CH3 domain-comprising polypeptide chain, and
- a second nucleic acid molecule encoding a 2$^{nd}$ CH3 domain-comprising polypeptide chain, wherein said first CH3 domain-comprising polypeptide chain comprises the amino acid substitution T366K and wherein said second CH3 domain comprising polypeptide chain comprises the amino acid substitution L351D, said method further comprising the step of culturing said host cell and allowing for expression of said at two nucleic acid molecules and harvesting said heterodimeric Ig-like molecule from the culture.

Preferably, a method according to the present invention for producing at least two different Ig-like molecules, or a method according to the invention for producing a heterodimeric Ig-like molecule, is provided wherein said first CH3-domain comprising polypeptide chain further comprises the amino acid substitution L351K. It is further preferred that said second CH3-domain comprising polypeptide chain further comprises an amino acid substitution selected from the group consisting of Y349E, Y349D and L368E. Most preferably said second CH3-domain comprising polypeptide chain further comprises the amino acid substitution L368E.

Thus, in a preferred embodiment the above mentioned T366K/L351'D mutations according to the present invention are further combined with the substitution of leucine (L) by glutamic acid (E) at position 368 of the second CH3 domain. This is, for example, denoted as a T366K/L351'D,L368'E mutation (but alternative ways of denoting are also possible, such as T336K/L351D-L368E or T366K/L351D,L368E or T366K-L351D,L368E). As shown in Example 17, introduction of this mutation according to the invention into a first CH3 domain-comprising polypeptide with specificity for antigen A, and a second CH3 domain-comprising polypeptide with specificity for antigen B results in a particular good proportion of bispecific Ig-like molecules with dual AB specificity. With this mutational pair it has even become possible to obtain bispecific antibody without any detectable amount of homodimers formed. A particularly preferred embodiment therefore provides a method for producing a heterodimeric Ig-like molecule from a single cell, wherein said Ig-like molecule comprises two CH3 domains that are capable of forming an interface and wherein the presence of contaminating homodimers is less than 5%, preferably less than 2%, more preferably less than 1%, and most preferably contaminating homodimers are essentially absent, said method comprising providing in said cell:
- a first nucleic acid molecule encoding a 1$^{st}$ CH3 domain-comprising polypeptide chain, and
- a second nucleic acid molecule encoding a 2$^{nd}$ CH3 domain-comprising polypeptide chain, wherein said first CH3 domain-comprising polypeptide chain comprises the amino acid substitution T366K and wherein said second CH3 domain comprising polypeptide chain comprises the amino acid substitutions L351D and L368E, said method further comprising the step of culturing said host cell and allowing for expression of said at two nucleic acid molecules and harvesting said heterodimeric Ig-like molecule from the culture.

In yet another preferred embodiment, threonine (T) is substituted by lysine (K) at position 366 of a first CH3 domain and leucine (L) is substituted by asp artic acid (D) at position 351 of a second CH3 domain and tyrosine (Y) is substituted by glutamic acid (E) at position 349 of said second CH3 domain. This is for example denoted as a T366K/L351'D,Y349'E mutation but other ways of denoting these mutations may include for example T366K -L351D: Y349E, or T366K/L351D,Y349E or simply T366K/L351DY349E. Residue Y349 is a neighboring residue of the residue at position 351 that may contribute to dimer interactions. According to in silico data, Y349E adds to the stability of the heterodimer (lower in silico scores) as well as to the destabilization of the monodimer (higher in silico scores) and glutamic acid (E) on position 349 is more favorable than asp artic acid (D). Thus, introduction of a second amino acid substitution in the second CH3 domain comprising polypeptide, comprising already the amino acid substitution at position 351, favors heterodimerization further.

A particularly preferred embodiment therefore provides a method for producing a heterodimeric Ig-like molecule from a single cell, wherein said Ig-like molecule comprises two CH3 domains that are capable of forming an interface and wherein contaminating homodimers are less than 5%, more preferably less than 2%, even more preferably less than 1%, and most preferably essentially absent, said method comprising providing in said cell:
- a first nucleic acid molecule encoding a 1$^{st}$ CH3 domain-comprising polypeptide chain, and
- a second nucleic acid molecule encoding a 2$^{nd}$ CH3 domain-comprising polypeptide chain, wherein said first CH3 domain-comprising polypeptide chain comprises the amino acid substitution T366K and wherein said second CH3 domain comprising polypeptide chain comprises the amino acid substitutions L351D and Y349E, said method further comprising the step of culturing said host cell and allowing for expression of said at two nucleic acid molecules and harvesting said heterodimeric Ig-like molecule from the culture.

In yet another preferred embodiment, threonine (T) is substituted by lysine (K) at position 366 of a first CH3 domain and leucine (L) is substituted by asp artic acid (D) at position 351 of a second CH3 domain and tyrosine (Y) is substituted by glutamic acid (E) at position 349 of said second CH3 domain and leucine (L) is substituted by glutamic acid (E) at position 368 of said second CH3 domain. This is denoted as a T366K/L351'D,Y349'E,L368'E mutation. The two residues Y349 and L368 are residues that may contribute to dimer interactions. According to the in silico data, Y349E and L368E add to the stability of the heterodimer (lower in silico scores) as well as to the destabilization of the BB dimer (higher in silico scores) and glutamic acids (E) on positions 349 and 368 are more favorable than aspartic acids (D). Thus, introduction of a second and third amino acid substitution in the B-chain, which already comprises the amino acid substitution at position 351, favors heterodimerization further. A particularly preferred embodiment therefore provides a method for producing a heterodimeric Ig-like molecule from a single cell, wherein said Ig-like molecule comprises two CH3 domains that are capable of forming an interface and wherein contaminating homodimers are less than 5%, more preferably less than 2%, even more preferably less than 1%, and most preferably essentially absent, said method comprising providing in said cell:
- a first nucleic acid molecule encoding a 1$^{st}$ CH3 domain-comprising polypeptide chain, and
- a second nucleic acid molecule encoding a 2$^{nd}$ CH3 domain-comprising polypeptide chain, wherein said first CH3 domain-comprising polypeptide chain comprises the amino acid substitution T366K and wherein said second CH3 domain comprising polypeptide chain comprises the amino acid substitutions L351D and Y349E and L368E, said method further comprising the step of culturing said host cell and allowing for expression of said at two nucleic acid molecules and harvesting said heterodimeric Ig-like molecule from the culture.

In yet another preferred embodiment, threonine (T) is substituted by lysine (K) at position 366 of a first CH3 domain and leucine (L) is substituted by lysine (K) at position 351 of said first CH3 domain and leucine (L) is substituted by aspartic acid (D) at position 351 of a second CH3 domain and leucine (L) is substituted by glutamic acid (E) at position 368 of said second CH3 domain. This is denoted as a T366K,L351K/L351'D,L368'E mutation. This mutation also enhances the proportion of the (bispecific) antibody of interest, as shown in the Examples. Also with this mutation it has become possible to obtain bispecific antibody without any detectable amount of homodimers formed. Further provided is therefore a method for producing a heterodimeric Ig-like molecule from a single cell, wherein said Ig-like molecule comprises two CH3 domains that are capable of forming an interface and wherein contaminating homodimers are less than 5%, preferably less than 2%, more preferably less than 1%, and most preferably essentially absent, said method comprising providing in said cell:

a first nucleic acid molecule encoding a $1^{st}$ CH3 domain-comprising polypeptide chain, and a second nucleic acid molecule encoding a $2^{nd}$ CH3 domain-comprising polypeptide chain, wherein said first CH3 domain-comprising polypeptide chain comprises the amino acid substitutions T366K and L351K, and wherein said second CH3 domain comprising polypeptide chain comprises the amino acid substitutions L351D and L368E, said method further comprising the step of culturing said host cell and allowing for expression of said at two nucleic acid molecules and harvesting said heterodimeric Ig-like molecule from the culture.

In yet another preferred embodiment, threonine (T) is substituted by lysine (K) at position 366 of a first CH3 domain and leucine (L) is substituted by lysine (K) at position 351 of said first CH3 domain and leucine (L) is substituted by aspartic acid (D) at position 351 of a second CH3 domain and tyrosine (Y) is substituted by aspartic acid (D) at position 349 of said second CH3 domain and arginine (R) is substituted by aspartic acid (D) at position 355 of said second CH3 domain. This is denoted as a T366K,L351K/L351'D,Y349'D,R355'D mutation. The T366K-L351K/L351'D-Y349'D pair may be further improved by the R355'D mutation in the B-chain, which results in a higher BB-in silico score, but also the AB in silico score is slightly higher. Further provided is therefore a method for producing a heterodimeric Ig-like molecule from a single cell, wherein said Ig-like molecule comprises two CH3 domains that are capable of forming an interface and wherein contaminating homodimers are less than 5%, more preferably less than 2%, even more preferably less than 1%, and most preferably essentially absent, said method comprising providing in said cell:

a first nucleic acid molecule encoding a $1^{st}$ CH3 domain-comprising polypeptide chain, and a second nucleic acid molecule encoding a $2^{nd}$ CH3 domain-comprising polypeptide chain, wherein said first CH3 domain-comprising polypeptide chain comprises the amino acid substitutions T366K and L351K, and wherein said second CH3 domain comprising polypeptide chain comprises the amino acid substitutions L351D and Y349D and R355D, said method further comprising the step of culturing said host cell and allowing for expression of said at two nucleic acid molecules and harvesting said heterodimeric Ig-like molecule from the culture.

Table B provides an overview of mutations that can be introduced in CH3 domains as preferred means for preferential pairing to create either heterodimers or homodimers.

TABLE B

| AA substitutions in CH3 | Construct # | Preferentially pairs with |
|---|---|---|
| — (wildtype) | — | Wildtype |
| E356K, D399K | 1 | Construct 2 or 3 |
| K392D, K409D | 2 | Construct 1 |
| K392D, K409D, K439D | 3 | Construct 1 |
| K392D, D399K, K409D | 4 | Construct 4 |
| E356K, E357K, K439D, K370D | 5 | Construct 5 |
| T366W | 6 | Construct 7 |
| T366S, L368A, Y407V | 7 | Construct 6 |
| T366K | 43 | Construct 63, 69, 70, 71, 73 |
| L351D | 63 | Construct 43, 68 |
| T366K, L351K | 68 | Construct 63, 69, 70, 71, 72, 75 |
| L351D, L368E | 69 | Construct 43, 68 |
| L351E, Y349E | 70 | Construct 43, 68 |
| L351D, Y349E | 71 | Construct 43, 68 |
| L351D, R355D | 72 | Construct 43, 68 |
| L351D, Y349E, L368E | 73 | Construct 43 |
| L351D, Y349D, R355D | 75 | Construct 68 |

A method according to the present invention for producing at least two different Ig-like molecules, or a method according to the invention for producing a heterodimeric Ig-like molecule, wherein said means for preferential pairing of said $1^{st}$ and $2^{nd}$ CH3 domain-comprising polypeptides and/or said means for preferential pairing of said 3rd and $4^{th}$ CH3 domain-comprising polypeptides comprise at least one combination of mutations as depicted in Table B is therefore also provided herewith. Preferably, said means for preferential pairing of said $1^{st}$ and $2^{nd}$ CH3 domain-comprising polypeptides and said means for preferential pairing of said $3^{rd}$ and $4^{th}$ CH3 domain-comprising polypeptides comprise at least two combinations of mutations as depicted in Table B.

The present invention also provides novel combinations of CH3 mutations with which it has become possible to produce a mixture of at least two monospecific Ig-like molecules in a single cell, wherein contaminating bispecific Ig-like molecules are less than 5%, preferably more than 2%, even more preferably less than 1%, and most preferably even essentially absent. These mutations according to the invention are, therefore, particularly suitable for the production of a mixture of monospecific antibodies, which is for instance advantageous when a high level of crosslinking of two identical target molecules is desired, when the density of antibodies on a target cells needs to be high enough to recruit certain effector functions such as complement-mediated lysis of a tumor cell, or when two targets are located too far away from each order so that they cannot be bound by as single bispecific antibody, or in order to simplify regulatory approval procedures. In such cases, it is often desired to optimize the production platform for such monospecific antibodies. As shown in Example 10, the present invention provides the insight that when lysine (K) at position 392 of a first CH3 domain-comprising polypeptide (for instance having specificity A) is substituted by aspartic acid (D) and when aspartic acid (D) at position 399 of said first CH3 domain-comprising polypeptide is substituted by lysine (K) and when lysine (K) at position 409 of said first CH3 domain-comprising polypeptide is substituted by asp artic acid (D), it has become possible to produce a mixture of at least two different monospecific Ig-like molecules in a single cell, including monospecific Ig-like molecules with specificity AA, wherein the formation of bispecific by-products (bispecific Ig-like molecules) is reduced to below 5%, or even to below 3%, or even essentially not detectable at all. Hence, the above mentioned combination of mutations (denoted herein as K392D, D399K, K409D) is particularly preferred for the production of a mixture of monospecific Ig-like molecules. The skilled person will appreciate that functional variants thereof, i.e., K392E, D399R, K409E, may result in similar effects. Additionally, double mutants comprising D399K and K409D substitutions, or other functional variants such as e.g. K392D and K409D, D399R and K409E and so forth, may also result in similar effects.

The same holds true for a combination of mutations wherein glutamic acid (E) at position 356 of a first CH3 domain-comprising polypeptide is substituted by lysine (K) and wherein glutamic acid (E) at position 357 of said first CH3 domain-comprising polypeptide is substituted by lysine (K) and wherein lysine (K) at position 439 of said first CH3 domain-comprising polypeptide is substituted by asp artic acid (D) and wherein lysine (K) at position 370 of said first CH3 domain-comprising polypeptide is substituted by aspartic acid (D). This combination of mutations (denoted herein as E356K, E357K, K439D, K370D) is also particularly preferred for the production of a mixture of monospecific Ig-like molecules. The skilled person will appreciate that functional variants thereof, i.e., E356R, E357R, K439E, K370E, may result in similar effects. Additionally, triple or double mutants comprising E356K and K439D, and E357K and K370D substitutions, or other functional variants may also result in similar effects. A further embodiment therefore provides a method for producing at least two different monospecific Ig-like molecules from a single host cell, wherein each of said two Ig-like molecules comprises two CH3 domains that are capable of forming an interface, said method comprising providing in said cell a) a first nucleic acid molecule encoding a $1^{st}$ CH3 domain-comprising polypeptide chain having a specificity A, b) a second nucleic acid molecule encoding a $2^{nd}$ CH3 domain-comprising polypeptide chain having a specificity B, wherein said first CH3 domain-comprising polypeptide chain comprises a K392D, D399K, K409D mutation and said second CH3 domain-comprising polypeptide chain comprises either a wildtype CH3 domain or comprises a E356K, E357K, K439D, K370D mutation, said method further comprising the step of culturing said host cell and allowing for expression of said nucleic acid molecules and harvesting said at least two different Ig-like molecules from the culture.

An alternative embodiment provides a method for producing at least two different monospecific Ig-like molecules from a single host cell, wherein each of said two Ig-like molecules comprises two CH3 domains that are capable of forming an interface, said method comprising providing in said cell a) a first nucleic acid molecule encoding a $1^{st}$ CH3 domain-comprising polypeptide chain having a specificity A, b) a second nucleic acid molecule encoding a $2^{nd}$ CH3 domain-comprising polypeptide chain having a specificity B, wherein said first CH3 domain-comprising polypeptide chain comprises either a wildtype CH3 domain or comprises a K392D, D399K, K409D mutation and said second CH3 domain-comprising polypeptide chain comprises a E356K, E357K, K439D, K370D mutation, said method further comprising the step of culturing said host cell and allowing for expression of said nucleic acid molecules and harvesting said at least two different Ig-like molecules from the culture.

As shown in Example 10, two monospecific Ig-like molecules can be produced in a single cell, wherein the formation of bispecific Ig-like molecules is essentially undetectable. The skilled person may select a $3^{rd}$ nucleic acid molecule encoding a wildtype or engineered CH3 domain-comprising polypeptide chain to provide to said host cell such that a mixture of 3 monospecific antibodies is produced, and so forth.

In one aspect of the invention, a method according to the invention for producing at least two different Ig-like molecules or for producing a heterodimeric Ig-like molecule is provided wherein each of the CH3-domain comprising polypeptide chains further comprises a variable region recognizing a different target epitope, wherein the target epitopes are located on the same molecule. This often allows for more efficient counteraction of the (biological) function of said target molecule as compared to a situation wherein only one epitope is targeted. For example, a heterodimeric Ig-like molecule may simultaneously bind to 2 epitopes present on, e.g., growth factor receptors or soluble molecules critical for tumors cells to proliferate, thereby effectively blocking several independent signalling pathways leading to uncontrolled proliferation, and any combination of at least two Ig-like molecules may simultaneously bind to 2, or even 3 or 4 epitopes present on such growth factor receptors or soluble molecules.

In a preferred embodiment, the target molecule is a soluble molecule. In another preferred embodiment, the target molecule is a membrane-bound molecule.

In another aspect of the invention, a method according to the invention for producing at least two different Ig-like molecules or for producing a heterodimeric Ig-like molecule is provided wherein each of the CH3-domain comprising polypeptide chains further comprises a variable region recognizing a target epitope, wherein the target epitopes are located on different molecules. In this case, each of the different target molecules may either be a soluble molecule or a membrane-bound molecule. In one embodiment, the different target molecules are soluble molecules. Alternatively, one target molecule is a soluble molecule whereas the second target molecule is a membrane bound molecule. In yet another alternative, both target molecules are membrane bound molecules. In one embodiment the different target molecules are expressed on the same cells, whereas in other embodiments the different target molecules are expressed on different cells. As a non-limiting example, any heterodimeric Ig-like molecule or any combination of at least two Ig-like molecules may be suitable for simultaneously blocking multiple membrane-bound receptors, neutralizing multiple soluble molecules such as cytokines or growth factors for tumor cells or for neutralizing different viral serotypes or viral strains.

One preferred embodiment provides a method according to the invention for producing at least two different Ig-like molecules or for producing a heterodimeric Ig-like molecule, wherein at least one of said target epitopes is located on a tumor cell. Alternatively, or additionally, at least one of said target epitopes is located on the surface of an effector cell. This is for instance suitable for recruitment of T cells or NK cells for tumor cell killing. For instance, at least one Ig-like molecule is produced with a method according to the invention that is capable of recruiting immune effector cells, preferably human immune effector cells, by specifically binding to a target molecule located on immune effector cells. In a further embodiment, said immune effector cell is activated upon binding of the Ig-like molecule to the target molecule. Recruitment of effector mechanisms may for instance encompass the redirection of immune modulated cytotoxicity by administering an Ig-like molecule produced by a method according to the invention that is capable of binding to a cytotoxic trigger molecule such as the T cell receptor or an Fc gamma receptor, thereby activating downstream immune effector pathways. The term 'immune effector cell' or 'effector cell' as used herein refers to a cell within the natural repertoire of cells in the mammalian immune system which can be activated to affect the viability of a target cell. Immune effector cells include cells of the lymphoid lineage such as natural killer (NK) cells, T cells including cytotoxic T cells, or B cells, but also cells of the myeloid lineage can be regarded as immune effector cells, such as monocytes or macrophages, dendritic cells and neutrophilic granulocytes. Hence, said effector cell is preferably an NK cell, a T cell, a B cell, a monocyte, a macrophage, a dendritic cell or a neutrophilic granulocyte.

Target antigens present on immune effector cells may include CD3, CD16, CD25, CD28, CD64, CD89, NKG2D and NKp46. Further provided is therefore a method according to the invention for producing at least two different Ig-like molecules or for producing a heterodimeric Ig-like molecule, wherein said target epitope is located on a CD3, CD16, CD25, CD28, CD64, CD89, NKG2D or a NKp46 molecule.

The viability of a target cell may include cell survival, proliferation and/or ability to interact with other cells.

In one aspect the present invention thus provides methods according to the invention for producing a heterodimeric Ig-like molecule, wherein each of the CH3-domain comprising polypeptide chains further comprises a variable region recognizing a target epitope. In one embodiment, each of the 2 variable regions of the CH3-domain comprising polypeptide chains recognizes the same target epitope but with different affinities. In another embodiment, each of the 2 variable regions of the CH3-domain comprising polypeptide chains recognizes a different target epitope. In another embodiment, the different target epitopes are located on the same target molecule, which can be either a membrane-bound molecule or a soluble molecule. In another embodiment, the different target epitopes are located on different target molecules, which can be either expressed on the same cells or on different cells. Alternatively, the different target molecules can be soluble molecules, or one target molecule can be a soluble molecule whereas the second target molecule is a membrane bound molecule. In a preferred embodiment, at least one of the target molecules of the heterodimeric Ig-like molecule is located on a tumor cell. In yet another preferred embodiment, at least one of the target molecules of the heterodimeric Ig-like molecule is located on an effector cell (i.e. an NK cell, a T cell, a B cell, a monocyte, a macrophage, a dendritic cell or a neutrophilic granulocyte, and said target epitope may be located on a CD3, CD16, CD25, CD28, CD64, CD89, NKG2D or a NKp46 molecule).

In a preferred embodiment, a method according to the invention for producing at least two different Ig-like molecules or for producing a heterodimeric Ig-like molecule is provided, wherein said at least two different Ig-like molecules are antibodies, most preferably antibodies of the IgG isotype, even more preferably the IgG1 isotype, as described herein above.

Further provided is an Ig-like molecule, a heterodimeric Ig-like molecule, or a mixture of at least two Ig-like molecules, obtainable by a method according to the present invention. Said (heterodimeric) Ig-like molecule or mixture of Ig-like molecules preferably comprises at least one CH3 mutation as depicted in Table B. An (heterodimeric) Ig-like molecule or a mixture of at least two Ig-like molecules, comprising at least one mutation as depicted in Table B is therefore also herewith provided, as well as a pharmaceutical composition comprising at least one Ig-like molecule, or a mixture of at least two Ig-like molecules, according to the present invention. In one embodiment said Ig-like molecule is a bispecific Ig-like molecule, such as a bispecific antibody. In another embodiment said Ig-like molecule is a monospecific Ig-like molecule, such as a monospecific antibody. One preferred embodiment provides a mixture of at least two different Ig-like molecules obtainable by a method according to the invention, wherein said at least two different Ig-like molecules bind to different epitopes on the same antigen and/or to different epitopes on different antigens. Further provided is a heterodimeric Ig-like molecule obtainable by a method according to the invention, wherein said heterodimeric Ig-like molecule binds to different epitopes on the same antigen and/or to different epitopes on different antigens. Advantages and preferred uses of such mixtures and antibodies are described herein before. The invention also provides a mixture of at least two different Ig-like molecules obtainable by a method according to the invention, wherein said at least two different Ig-like molecules comprise at least one heterodimeric Ig-like molecule. In one embodiment, two of said at least two different Ig-like molecules are heterodimeric Ig-like molecules. Yet another preferred embodiment provides a heterodimeric antibody comprising two CH3 domains, wherein one of said two CH3 domains comprises the amino acid substitutions L351D and L368E and wherein the other of said two CH3 domains comprises the amino acid substitutions T366K and L351K. These amino acid substitutions are preferred means for preferential pairing of said two CH3 domains, as explained before. The amino acid substitutions L351D and L368E in one of said two CH3 domains and the amino acid substitutions T366K and L351K in the other of said two CH3 domains are together dubbed the 'DEKK combination of mutations', 'DEKK variant', 'DEKK pair', 'DEKK engineered CH3 domains', 'DEKK' or alternative names referring to DEKK are used. The CH3 domain that carries the amino acid substitutions L351D and L368E is also dubbed 'the DE-side' and the CH3 domain that carries the amino acid substitutions T366K and L351K is also dubbed 'the KK-side'.

Also provided is a pharmaceutical composition comprising a (heterodimeric) Ig-like molecule, or a mixture of at least two Ig-like molecules obtainable by any method according to the invention. Said (heterodimeric) Ig-like molecule, or said at least two Ig-like molecules according to the invention is/are preferably (an) antibody/antibodies. Said pharmaceutical composition may comprise said (heterodimeric) Ig-like molecule, a mixture comprising monospecific or bispecific Ig-like molecules, or a combination of monospecific and bispecific Ig-like molecules. In addition, a pharmaceutical composition according to the invention comprises a pharmaceutically acceptable carrier. As used herein, such 'pharmaceutically acceptable carrier' includes any and all solvents, salts, dispersion media, coatings, antibacterial and antifungal agents, isotonic and absorption delaying agents, and the like that are physiologically compatible. Depending on the route of administration (e.g., intravenously, subcutaneously, intra-articularly and the like) the Ig-like molecules may be coated in a material to protect the Ig-like molecules from the action of acids and other natural conditions that may inactivate the Ig-like molecules. In one aspect, a pharmaceutical composition comprising a mixture of at least two Ig-like molecules obtainable by any method according to the invention is provided, wherein said at least two different Ig-like molecules have been produced by recombinant host cells according to the present invention. Furthermore, a pharmaceutical composition is provided comprising a heterodimeric Ig-like molecule obtainable by any method according to the invention, wherein said heterodimeric Ig-like molecule has been produced by recombinant host cells according to the present invention.

A nucleic acid molecule encoding a CH3 domain-comprising polypeptide chain that comprises at least one mutation as depicted in Table B is also provided herewith, as well as a recombinant host cell comprising at least one nucleic acid molecule encoding a CH3 domain-comprising polypeptide chain that comprises at least one mutation as depicted in Table B.

The invention is further illustrated by the following examples. These examples are not limiting the invention in any way, but merely serve to clarify the invention.

BRIEF DESCRIPTION OF THE DRAWINGS

FIG. 1: A) schematic representation of construct vector MV1057. The stuffer region is the region into which an antibody VH region is cloned. B) schematic representation of phage display vector MV1043.

FIG. 2: amino acid sequence of wildtype IgG1 Fc (SEQ ID NO: 1), as present in construct vector MV1057 (EU numbering scheme applied).

FIG. 3: nucleotide and amino acid sequences (SEQ ID NOS: 2-7) of VH regions used for cloning into the various constructs.

FIG. 12: Cartoons of interactions in the CH3-CH3 interface; A) L351D/L351'D, B) L351D:S354A:R355D/L351'D: S354'A:R355'D

FIG. 22: Results in serum stability, measured by ELISA using fibrinogen as coated antigen. A) ELISA data with IgG samples diluted to 0.5 µg/ml; B) ELISA data with IgG samples diluted to 0.05 µg/ml. Results are normalized to the T=0 days time point (100%). 1337=2$^{nd}$ parental antibody AA; wildtype=AA, AB, BB; CR=bispecific of charge reversal pair E356K:D399K/K392D:K409D; 3-6 and 9-12=bispecific molecules from combinations 3-6 and 9-12 from Table 15.

FIG. 30: overview of the different forced degradation results on various IgG samples after dilution to 0.2 mg/ml. The colour of the cells indicate the variations between T=0 and after stress: dark grey=large change, light grey=small change and no colour=no change (=stable. * 'combi. #'refers to the combination of mutations as listed in Table 15; ** very small particles by fluorescence microscopy, relevance of these particles unknown; 2d4° C.=2 days at 4° C.; 2d50°

Figure 4:
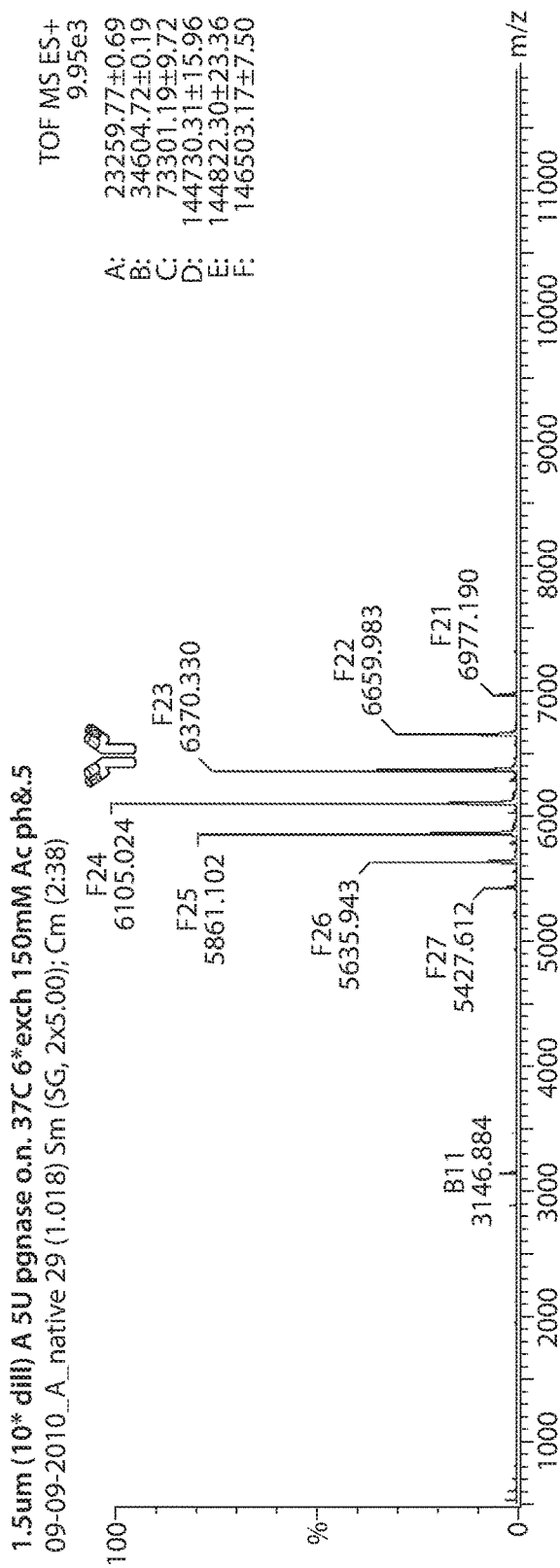
FIG. 4: mass spec data of transfections A, G and H.
Figure 4:
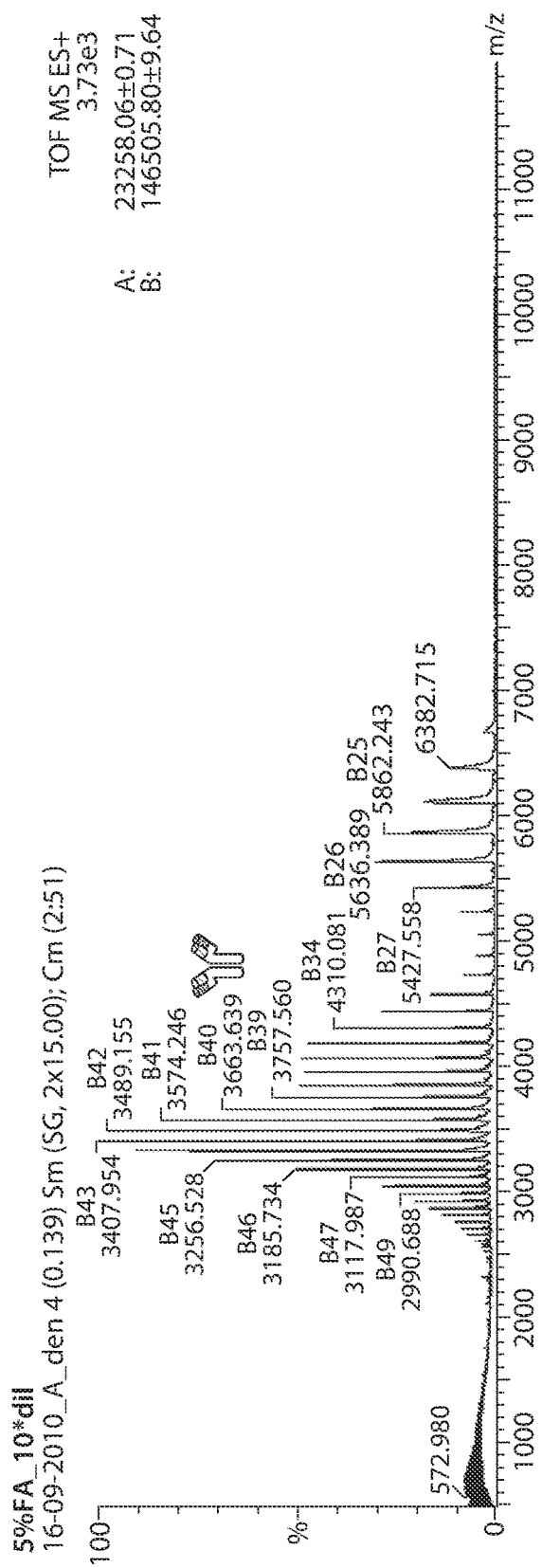
Figure 4:
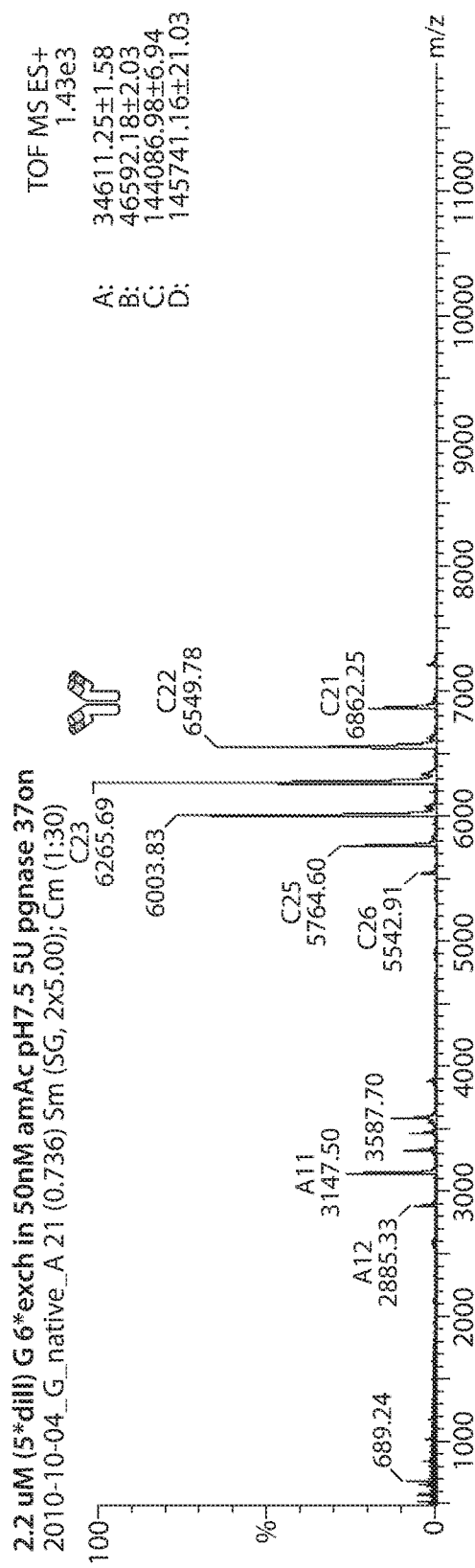
Figure 4:
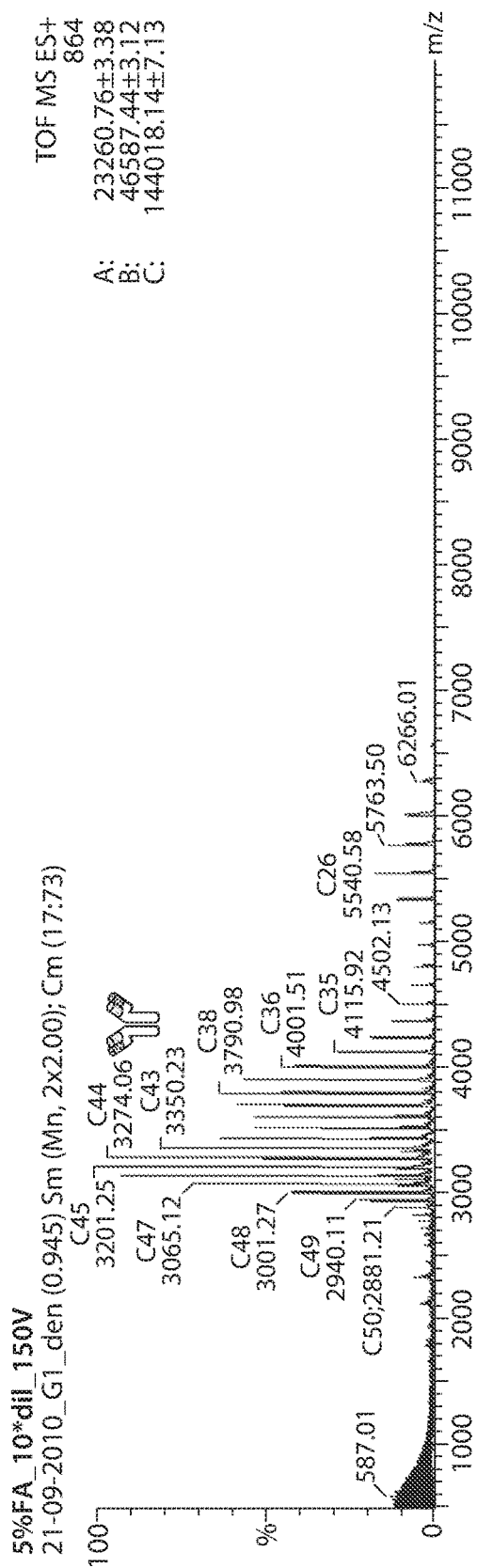
Figure 4:
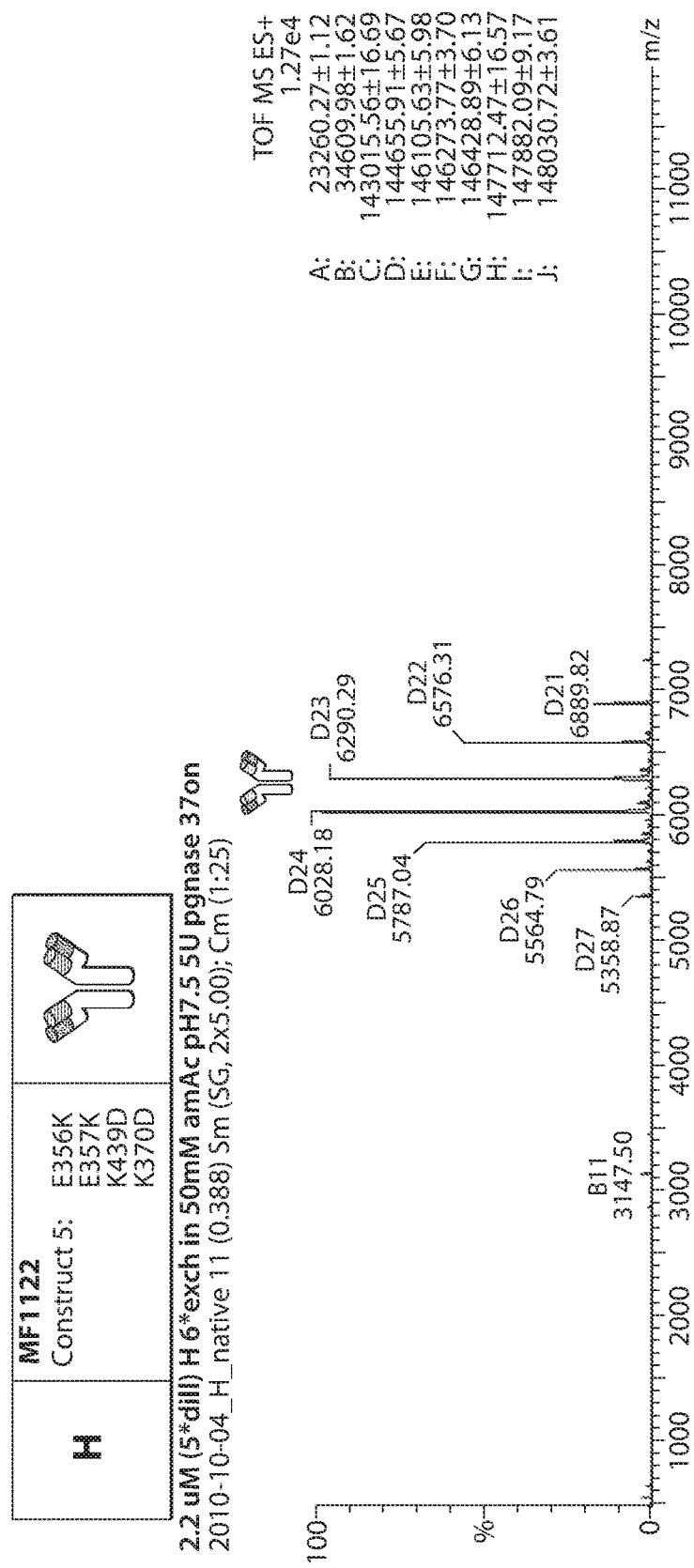
Figure 4:
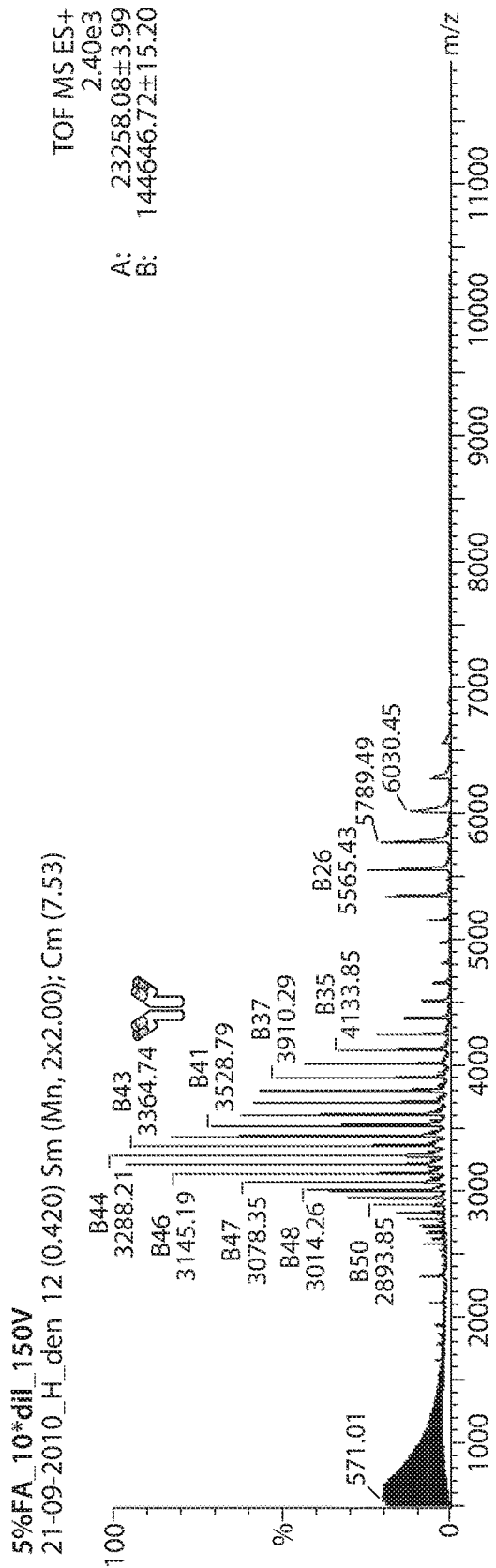

C.=2 days at 50° C.; 2w4° C.=2 weeks at 4° C.; 2w40° C.=2 weeks at 40° C.; T0=start of experiment; 5FT=5 freeze thaw cycles.

FIG. 31: summary of the results of the bispecific ELISA (OD450 values). The greyed cells indicate the expected species for each transfection. Generally, the results meet the expected outcome with view exceptions as indicated in italic or bold.

FIG. 32: overview of masses of the expected species, and the possible contaminants, for each of transfections #9-11 of Table 22. The species are sorted by mass, mass difference is calculated with the mass above. Grey cells: expected (and desired) species; italics: mass difference too small to separate in nMS analysis. *Species: single letters represent half-bodies; two-letter code intact IgG.

EXAMPLES

Example 1

Amino Acid Substitutions to Create Various Different CH3-domains

In order to have a wide variety of Ig-like molecules that differ in their CH3 domains such that pairing of CH3-domain comprising Ig-like molecules is preferentially promoted or inhibited, a number of amino acid substitutions that were known to promote heterodimer formation, as well as a number of alternative amino acid substitutions that were not previously reported nor tested but that were chosen to promote homodimer formation, were introduced into a construct vector (construct vector MV1057; FIG. 1A). The construct vector MV1057 comprises nucleic acid sequences encoding the normal wildtype IgG1 Fc part, as depicted in FIG. 2. Table 1 lists the amino acid substitutions that were introduced in this wildtype Fc, resulting in a series of seven constructs. All constructs were made at Gene art. Constructs 1, 2 and 3, or alternatives thereof, have previously been described to drive heterodimerization (EP01870459, WO2009/089004) as have constructs 6 and 7 (WO98/50431). Constructs 4 and 5 are new and are designed to promote homodimerization.

TABLE 1

| AA substitutions in CH3 | construct # | Will pair with | % bispecific product reported |
|---|---|---|---|
| — (wildtype) | — | — (wildtype) | ~50% |
| E356K, D399K | 1 | Construct 2 or 3 | ~100% |
| K392D, K409D | 2 | Construct 1 | ~100% |
| K392D, K409D, K439D | 3 | Construct 1 | ~100% |
| K392D, D399K, K409D | 4 | Construct 4 | |
| E356K, E357K, K439D, K370D | 5 | Construct 5 | |
| T366W | 6 | Construct 7 | ~86.7% |
| T366S, L368A, Y407V | 7 | Construct 6 | ~86.7% |

Example 2

Cloning of VH into Constructs with CH3 Mutations

Several antibody VH regions with known specificities and known ability to pair with the human IGKV1-39 light chain were used for cloning into these constructs.

As indicated earlier, all CH3 variants can be used in association with other antibody domains to generate full length antibodies that are either bispecific or monospecific. The specificity of the antibody as defined by the VH/VL combinations will not affect the heavy chain dimerization behaviour that is driven by the CH3 domains. Model VH/VL combinations were used throughout the studies, wherein all VLs are based on the germline human IGKV1-39 and VHs vary. FIG. 3 provides full sequences and specificities of the antibody VH regions used throughout the studies. The MF coding refers to internal Merus designation for various VHs, e.g. VH MF1337 has specificity for tetanus toxoid, MF1025 for porcine thyroglobulin, MF1122 for bovine fibrinogen. VH regions present in phage display vector MV1043 (FIG. 1B) are digested with restriction enzymes SfiI and BstEII (New England Biolabs/cat# R0123L and R0162L/according to manufacturer's instructions) that release the VH fragment from this vector. Vector MV1057 is digested with SfiI and BstEII according to standard procedures (according to manufacturer's instructions). Fragments and vector are purified over gel (Promega/cat# V3125/according to manufacturer's instructions) to isolate the cut vector and VH gene inserts. Both are combined by ligation after which the ligation is transformed into E. coli DH5α (Invitrogen/cat#12297-016/according to manufacturer's instructions). After overnight selection single colonies are picked and vectors with a correct insert identified by sequencing.

Example 3

Transfection and Expression of Full IgG in HEK293T Cells

Transfection of the various plasmids encoding the recloned VH variants, and further encoding the common light chain huIGKV1-39, in HEK293T cells was performed according to standard procedures such that IgG could express (de Kruif et al Biotech Bioeng. 2010). After transfection, IgG expression levels in supernatants were measured using the ForteBIO Octet-QK system, which is based on Bio-Layer Interferometry (BLI) and which enables real-time quantitation and kinetic characterization of biomolecular interactions; for details see www.fortebio.com. When expression levels exceeding 5 µg/ml were measured, the IgG was purified using Protein A affinity purification.

Example 4

Purification of IgG

Culture supernatants were purified using protein A columns (GE Healthcare/cat#11-0034-95/according to manufacturer's instructions) and eluted in 0.1 M citrate buffer pH 3.0 and immediately neutralized in an equal volume of 1.0 M Tris-HCL pH 8.0 or directly rebuffered to PBS using a desalting column. Alternatively one could purify IgG using protein A beads (sepharose beads CL-4B, GE healthcare cat #170780-01)

Example 5

Ag-specific ELISA's

Antigen specific ELISAs were performed to establish binding activity against the antigens and capture ELISAs were carried out to demonstrate binding activity of the bispecific antibodies. Biotinylated second antigen was used for detection of the complex. (de Kruif et al Biotech Bioeng. 2010)

Example 6

SDS-PAGE

The purified IgG mixtures were analysed by SDS-PAGE (NuPAGE® 4-12% bis-tris gel/Invitrogen/cat# NP0323BOX) under reduced and non-reducing conditions according to standard procedures, and staining of proteins in gel was carried out with colloidal blue (PageBlue™ protein staining solution/Fermentas/cat# RO571).

Example 7

Enzymatic Deglycosylation of IgG1

As there is heterogeneity in the glycosylation of the IgGs, the proteins were deglycosylated in order to create a single product with a distinct mass, suitable for mass spectrometric analysis. One unit of N-glycosidase F (PNGase F; Roche Diagnostics, Mannheim, Germany) was incubated per 10 μg of IgG1, overnight at 37° C. Buffer exchange using 10 kDa MWCO centrifugal filter columns (Millipore) was performed to remove the original purification buffer (0.1 M citrate buffer pH 3.0/1.0 M Tris-HCL pH 8.0) and to rebuffer to PBS. Similar buffer exchange procedures were performed to remove the detached glycan chains, and to change the buffer to 150 mM ammonium acetate pH 7.5. Filters were washed with 200 μl 150 mM ammonium acetate pH 7.5, for 12 min 11,000 rpm and 4° C. After washing 50 μl deglycosylated IgG was loaded on the filter and 450 μl of 150 mM ammonium acetate pH 7.5 was added, subsequently followed by another centrifugation round of 12 min at 11,000 rpm at 4° C. In total the centrifugation was repeated 5 times, each time fresh 150 mM ammonium acetate pH 7.5 buffer was added to a total volume of 500 μl. After the last centrifugation step the remaining buffer exchanged deglycosylated IgG1, approximately 25 μl, was collected and transferred to an eppendorf tube, ready for mass spectrometric analysis.

Example 8

Native Mass Spectrometric Analysis

Mass Spectrometry was used to identify the different IgG species in the purified IgG mixtures and to establish in what ratios these IgG species are present. Briefly, 2-3 μl at a 1 μM concentration in 150 mM ammonium acetate pH 7.5 of IgG's were loaded into gold-plated borosilicate capillaries made in-house (using a Sutter P-97 puller [Sutter Instruments Co., Novato, Calif., USA] and an Edwards Scancoat six sputter-coater [Edwards Laboratories, Milpitas, Calif., USA]) for analysis on a LCT 1 mass spectrometer (Waters Corp., Milford, Mass., USA), adjusted for optimal performance in high mass detection (Tahallah et al., RCM 2001). A capillary voltage of 1300 V was used and a sampling cone voltage of 200 V; however, these settings were adjusted when a higher resolution of the 'signal-to-noise' ratio was required. The source backing pressure was elevated in order to promote collisional cooling to approximately 7.5 mbar. To measure the IgG1's under denaturing conditions the proteins were sprayed at a 1 μM concentration in 5% formic acid.

Example 9

Data Processing and Quantification

Processing of the acquired spectra was performed using MassLynx 4.1 software (Waters Corp., Milford, Mass., USA). Minimal smoothing was used, after which the spectra were centered. The mass of the species was calculated using each charge state in a series. The corresponding intensities of each charge state were assigned by MassLynx and summed. This approach allowed the relative quantification of all species in a sample. Alternatively, quantification of the peaks can be performed using area-under-the-curve (AUC) methods, known in the art. All analyses were repeated three times to calculate standard deviations of both the masses of the IgG's as well as their relative abundance.

Example 10

Mixtures of 2 or 3 Monospecific Antibodies from a Single Cell

Several antibody VH regions with known specificities and known ability to pair with the human IGKV1-39 light chain (FIG. 3) were used for recloning into the wildtype construct vector MV1057, or in construct 4 or construct 5 of Table 1, resulting in vectors I-III (Table 2). The resulting vectors I, II and III, each containing nucleic acid sequences encoding for the common human light chain as well as an Ig heavy chain with different CH3 region and different VH specificity, were subsequently transfected into cells, either alone to demonstrate formation of intact monospecific antibodies only, or in combination with one or two other construct vectors to obtain mixtures of two monospecific or three monospecific antibodies. Table 3 depicts the transfection schedule and results.

TABLE 2

VH specificity inserted in different constructs

| Vector | VH gene | Antigen specificity | VH mass (Da) | Merus designation | Cloned in construct # |
|---|---|---|---|---|---|
| I | IGHV 1.08 | Tetanus (A) | 13703 | MF1337 | wildtype |
| II | IGHV 3.23 | Thyroglobulin (B) | 12472 | MF1025 | 4 |
| III | IGHV 3.30 | Fibrinogen (C) | 12794 | MF1122 | 5 |

TABLE 3 transfection schedule and results

| # different mono-specifics produced | Transfection of | Transfection code and ratio | Expected species | Calculated mass - 2LYS | Experimental mass | AA found (%) | BB found (%) | CC found (%) | Other molecules (%) |
|---|---|---|---|---|---|---|---|---|---|
| 1 | Only vector I | A | AA | 146521 | 146503 | 100 | | | |
| 1 | Only vector II | G | BB | 144032 | 144087 | | 100 | | |

TABLE 3-continued transfection schedule and results

| # different monospecifics produced | Transfection of | Transfection code and ratio | Expected species | Calculated mass - 2LYS | Experimental mass | AA found (%) | BB found (%) | CC found (%) | Other molecules (%) |
|---|---|---|---|---|---|---|---|---|---|
| 1 | Only vector III | H | CC | 144647 | 144656 | | | 100 | |
| 2 | Vector I and II | M (I:II = 1:1) | AA BB | 146521 144032 | 146518 144030 | 51 | 45 | | 4 |
| 2 | Vector I and III | N (I:III = 1:1) | AA CC | 146521 144647 | 146509 144633 | 88 | | 9 | 3 |
| | | U (I:III = 1:5) | AA CC | 146521 144647 | 146522 144643 | 47 | | 48 | 5 |
| 2 | Vector II and III | nd | BB CC | | | | | | |
| 3 | Vector I, II and III | O (I:II:III = 1:1:1) | AA BB CC | 146521 144032 144647 | 146525 144032 144650 | 66 | 4 | 30 | |
| | | V (I:II:III = 1:1:10) | AA BB CC | 146521 144032 144647 | 146531 144043 144654 | 8 | 81 | 9 | 2 | nd = not done.

It was observed that transfections A, G and H resulted in formation of homodimers only, and 100% of bivalent monospecific AA, BB or CC was retrieved from cells transfected with any one of vectors I, II or III (FIG. 4). Although this was to be expected and previously demonstrated for transfection A, it is actually now shown for the first time that homodimerisation of CH3-engineered Ig heavy chains containing either the triple amino acid substitution of construct 4 (i.e., K392D, D399K, K409D) or the quadruple amino acid substitution of construct 5 (i.e., E356K, E357K, K439D, K370D) is reported (transfections G and H).

Figure 5:
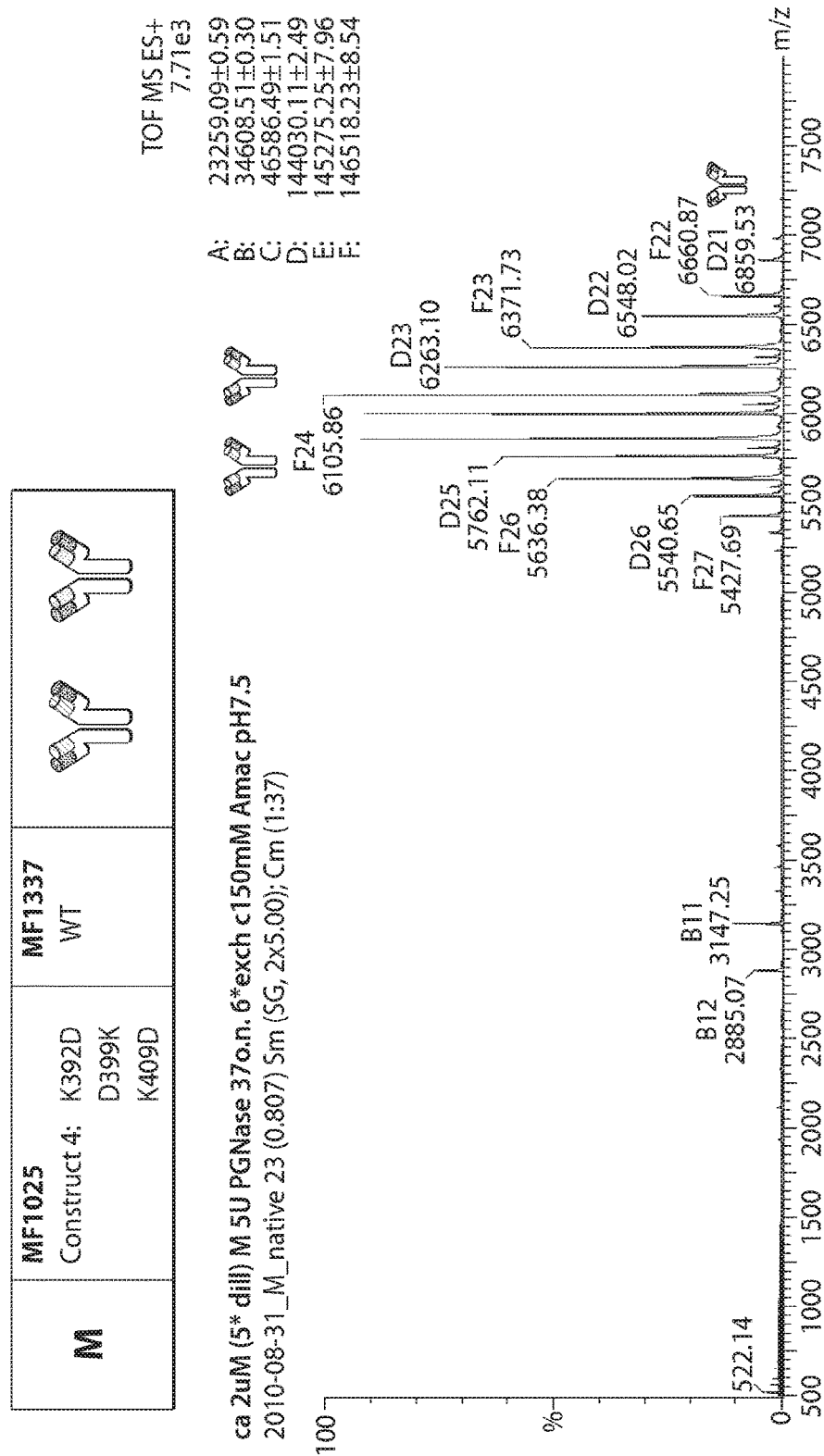
FIG. 5: mass spec data of transfections M and U.
Figure 5:
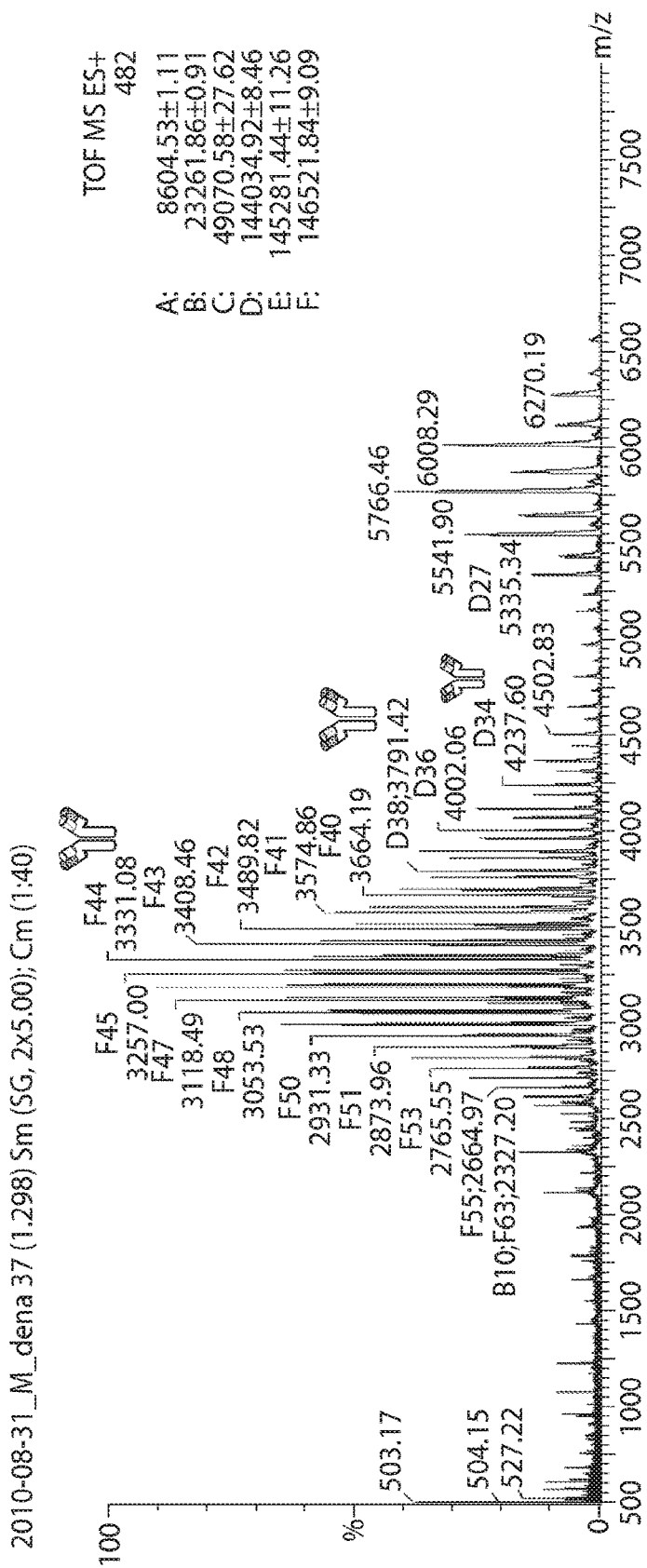
Figure 5:
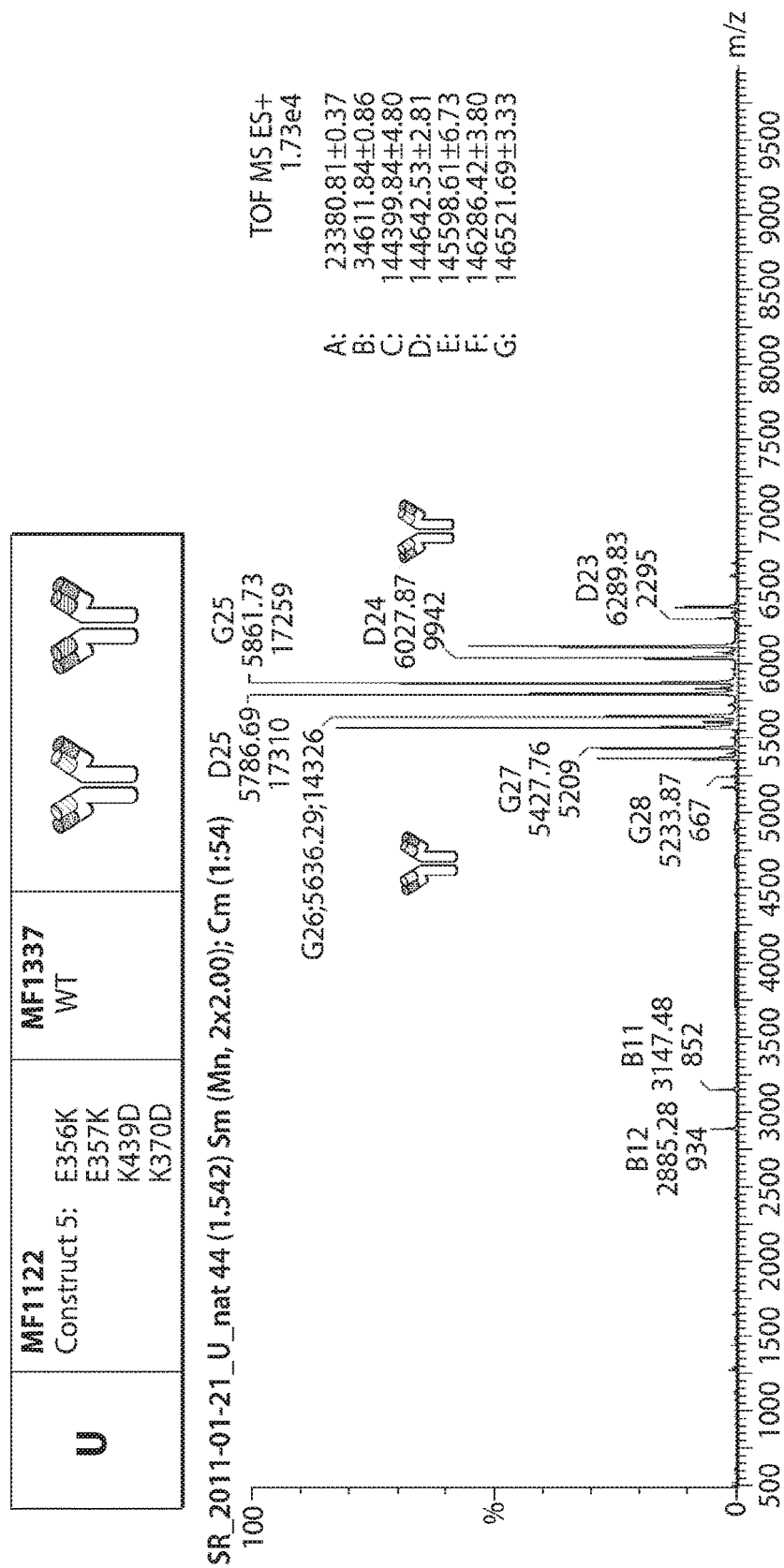
Figure 5:
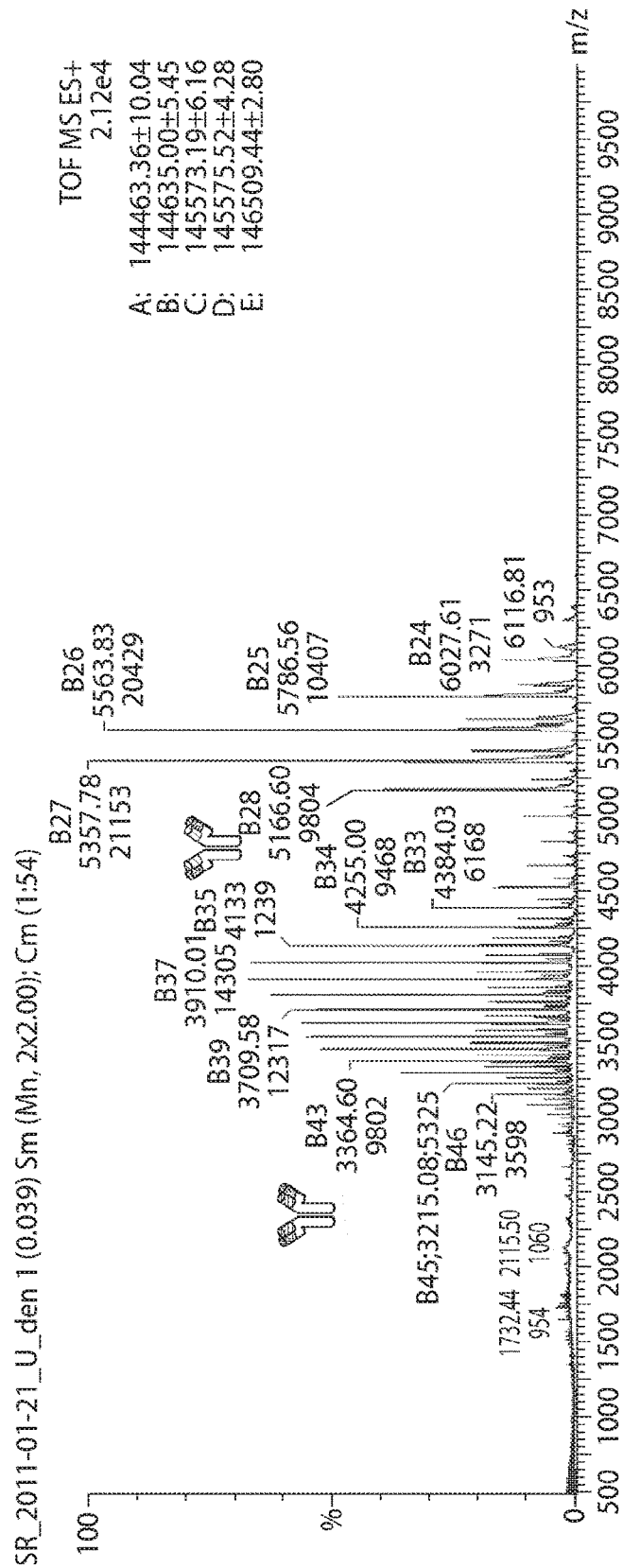

Next, co-expression experiments of two vectors in a single cell were performed. Interestingly, transfections M and N show that wildtype and CH3 engineered Ig heavy chains can be co-expressed in a single cell together with a common light chain resulting in mixtures of two species of monospecific antibodies without the presence of undesired bispecific antibodies and with as little as 4-5% contaminating 'other molecules' present in the mixture. 'Other molecules' is defined as all molecules that do not have the mass of an intact IgG, and includes half molecules consisting of a single heavy and light chain pair. Importantly, the fraction 'other' does not include bispecific product. In transfection M, the ratio of AA:BB was close to 1:1 upon transfection of equal ratios of vector DNA. However, transfection N resulted in an almost 10:1 ratio of AA:CC. Therefore, this transfection was repeated with adjusted ratios of DNA (transfection U). Indeed, a 1:5 ratio of vector DNA I:III equalized the ratio of AA:CC antibody product in the mixture towards an almost 1:1 ratio. Thus, transfections M and U show that it is possible to express two different, essentially pure, monospecific antibodies in a single cell, without undesired by products (i.e., no abundant presence of AC or half molecules A or C) (FIG. 5). The novel CH3 modifications of constructs 4 and 5 differ substantially from wildtype CH3 such that heterodimerization between wildtype and 4, or wildtype and 5, does not occur, which is advantageous for application in large scale production of mixtures of monospecific antibodies from single cells.

Analogous to these results, also transfection of two different CH3 engineered Ig heavy chains (constructs 4 and 5) are expected to result in mixtures of two different monospecific antibodies only, without further undesired species present. It is reasoned that the CH3 modifications of construct 4 differ substantially from the CH3 modifications of constructs 5 such that heterodimerization does not occur. In that case, co-expression of CH3-engineered heavy chains of constructs 4 and 5, together with wildtype CH3 heavy chains in a single cell would results in 3 monospecific antibodies only.

Figure 6:
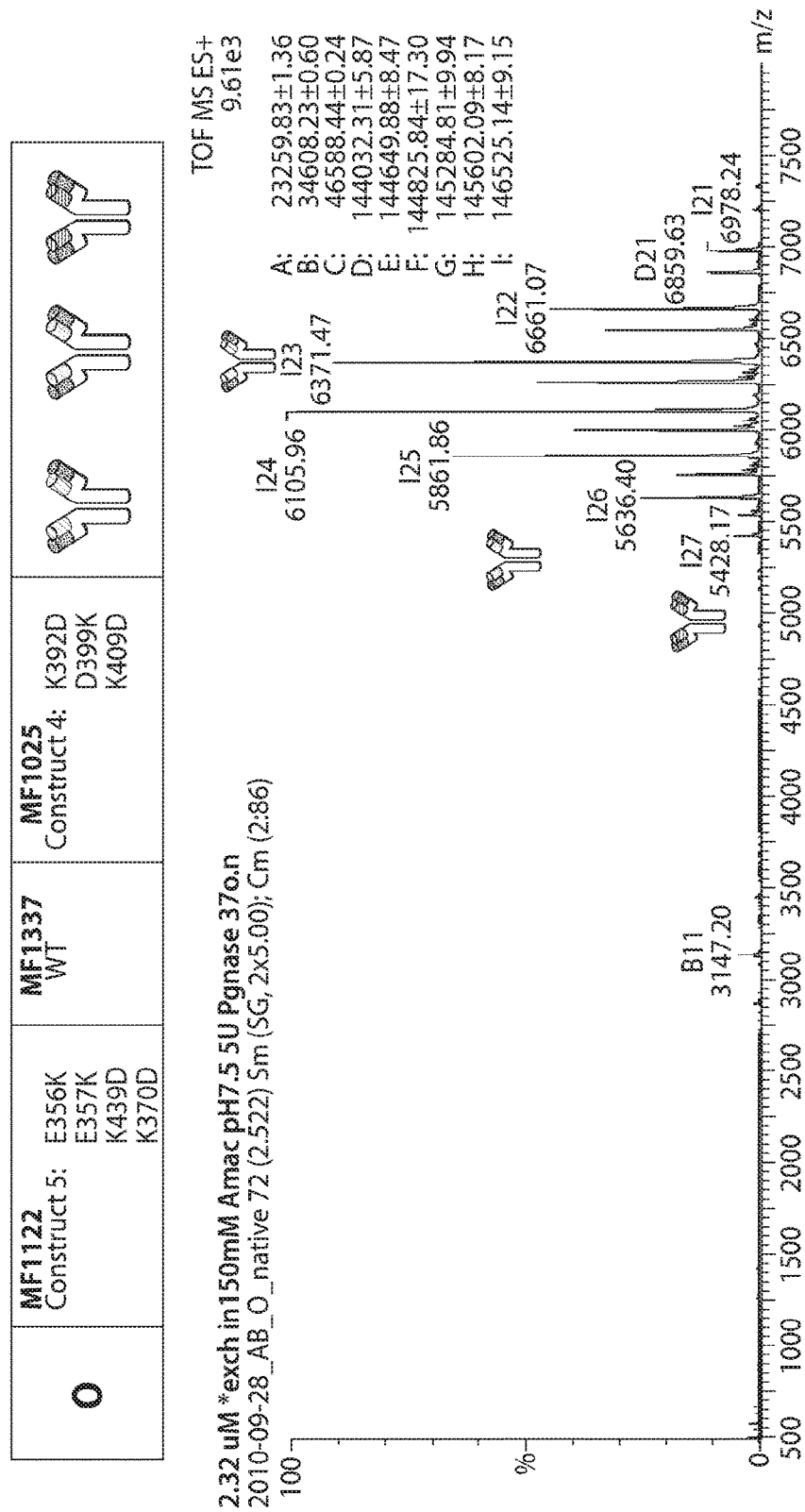
FIG. 6: mass spec data of transfection O.
Figure 6:
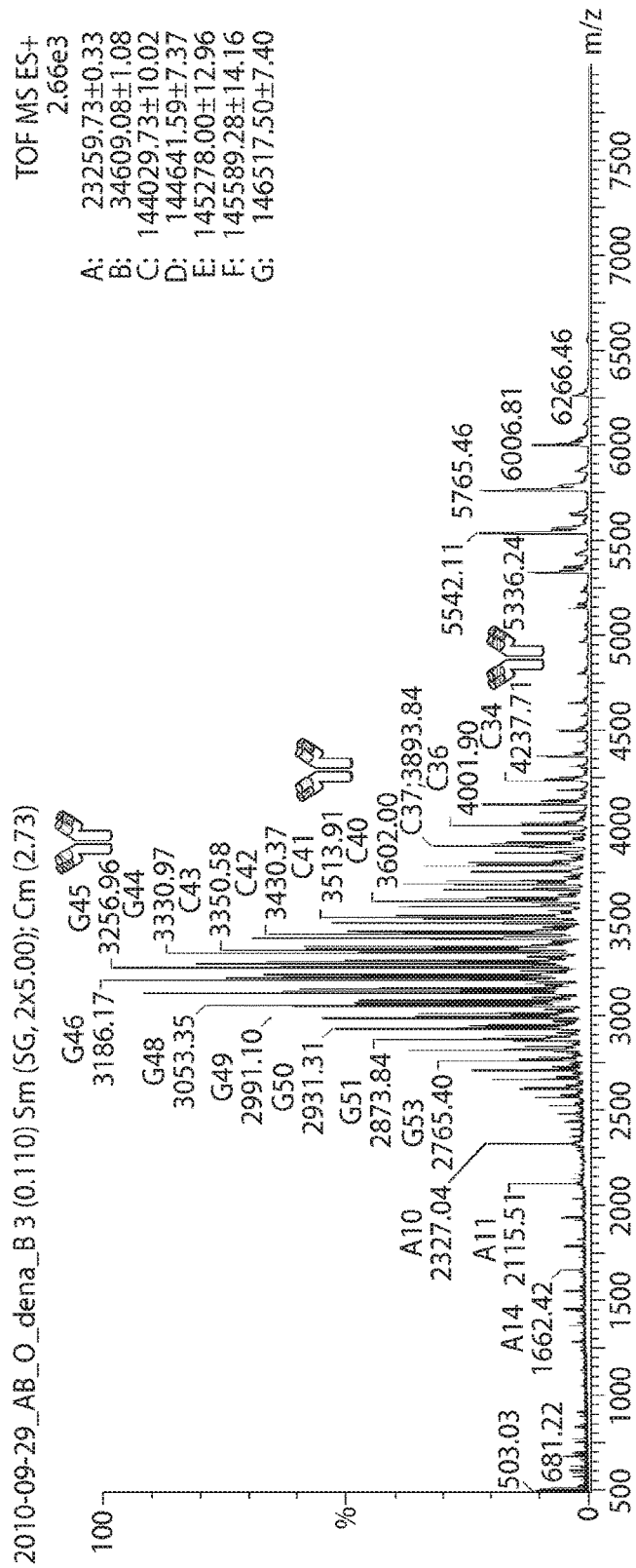

Indeed, this was observed to be the case as it was found that also a mixture of three pure monospecific antibodies could be obtained by expression of three different Ig heavy chains, designed to form homodimers over heterodimers, together with a common light chain in a single cell, with no contaminations present in the mixture (transfection O) (FIG. 6). As is clear from Table 3, with equal ratios of vector DNA used during transfection O, no 1:1:1 ratio of AA:BB:CC antibodies was obtained.

Transfections with altered vector DNA ratios (1:1:10, transfection V) demonstrated that ratios of AA:BB:CC in the mixtures can be steered towards desired ratios. Taken together, these experiments show that two or three essentially pure monospecific antibodies can be expressed in a single cell without undesired by products, offering advantages for large scale production of mixtures of therapeutic monospecific antibodies.

Example 11

Mixtures of 2 Bispecific Antibodies from a Single Cell

Whereas use of CH3-engineered heavy chains for production of single bispecific antibodies has been reported elsewhere, this experiment was designed to investigate whether it is feasible to produce mixtures of 2 different bispecific antibodies from a single cell.

Antibody VH regions with known specificities and known ability to pair with the human IGKV1-39 light chain (FIG. 3) were used for recloning into vectors containing constructs 1-3 or 6-7 of Table 1 resulting in vectors IV-X (Table 4). Vectors IV-X, each containing nucleic acid sequences encoding the common human light chain as well as an Ig heavy chain with different CH3 region and different VH specificity, were subsequently transfected into cells, either alone to demonstrate that formation of intact monospecific antibodies was hampered, or in combination with another construct vector to obtain bispecific antibodies or mixtures of two bispecific antibodies. Table 5 depicts the transfection schedule and results.

TABLE 4

VH specificity inserted in different constructs

| Vector | VH gene | Antigen specificity | VH mass (Da) | Cloned in construct # |
|---|---|---|---|---|
| IV | IGHV 3.23 | Thyroglobulin (B) | 12472 | 1 |
| V | IGHV 3.30 | Fibrinogen (C) | 12794 | 2 |
| VI | IGHV 1.08 | Tetanus (A) | 13703 | 2 |
| VII | IGHV 3.30 | Fibrinogen (C) | 12794 | 3 |
| VIII | IGHV 1.08 | Tetanus (A) | 13703 | 3 |
| IX | IGHV 1.08 | Tetanus (A) | 13703 | 6 |
| X | IGHV 3.23 | Thyroglobulin (B) | 12472 | 7 | strating that the triple charge mutations of construct 3 do not fully impair homodimerisation.

It was furthermore demonstrated that also the 'knob' and 'hole' CH3 variants of constructs 6 and 7 form homodimers (18% homodimers for 'knob-knob' and 42% homodimers for 'hole-hole').

CH3 variants that fully prevent homodimerisation when expressed alone are preferred, to prevent or minimize undesired byproducts (homodimers) upon co-expression with a second CH3 variant for heterodimerization.

Interestingly, the present experiments demonstrate for the first time that also mixtures of bispecific antibodies can be expressed in single cells with virtually no homodimers in the mixture. Transfections K and L clearly show that the expected bispecific species BC+AB are indeed obtained (38%+47% in transfection K, and 16%+60% in transfection L). In both transfections a relatively high percentage of undesired half molecules was observed (15% half molecule A+half molecule C in transfection K, and 24% half molecule A+half molecule C in transfection L). The relatively high percentage of half molecules still present was attributed to

TABLE 5

| # different bispecifics produced | Transfection of | Transfection code and ratio | Expected species | Calculated mass - 2LYS | Experimental mass | Half molecules found (%) | Full IgG found (%) | Bispecific found (%) | Other molecules (%) |
|---|---|---|---|---|---|---|---|---|---|
| 0 | vector IV | B | Half B | 144082 | 144066 | 40 | 60 | | |
| 0 | vector V | C | Half C | 144651 | 144622 | 77 | 23 | | |
| 0 | vector VI | D | Half A | 146469 | 146459 | 23 | 77 | | |
| 0 | vector VII | E | Half C | 144625 | 144643 | 76 | 24 | | |
| 0 | vector VIII | F | Half A | 146443 | 146468 | 64 | 36 | | |
| 0 | vector IX | P | Half A | 146691 | 146677 | 82 | 18 | | |
| 0 | vector X | Q | Half B | 143818 | 143844 | 58 | 42 | | |
| 1 | Vector IV and V | I (1:1) | BC | 144367 | 144352 | | | 96 | 4 |
| 1 | Vector IV and VII | J (1:1) | BC | 144354 | 144382 | | | 96 | 4 |
| 2 | Vector IV, V and VI | K(1:1:1) S(2:1:1) | BC + AB BC + AB | 144367 + 145276 144367 + 145276 | 144351+ 145260 144371 + 145277 | | | 38 + 47 42 + 55 | 15 (A + C) 3 (BB) |
| 2 | Vector IV, VII and VIII | L (1:1:1) T (2:1:1) | BC + AB BC + AB | 144354 + 145263 144354 + 145263 | 144346 + 145255 144385 + 145292 | | | 16 + 60 58 + 39 | 24 (A + C) 3 (BB) |

It was previously demonstrated that CH3-engineered Ig heavy chains encoded by constructs 1 and 2 are still able to form homodimers when expressed alone in single cells (WO2009/089004). However, WO2009/089004 further reports that CH3 domains that are engineered to comprise triple charge pair mutations, such as present in construct 3, are no longer capable of forming homodimers when expressed alone.

In the present study, these findings were only partly confirmed. Indeed, the results of transfections B, C and D demonstrated the presence of full IgGs, in addition to a high proportion of unpaired half molecules, demonstrating some homodimerization of CH3 domains encoded by constructs 1 and 2. Transfections E and F also resulted in production of full IgGs in addition to unpaired half molecules, demonlow amounts of matching heavy chains of vector IV due to unbalanced expression of heavy chains in a matched pair. Therefore, transfections were repeated with an adjusted ratio of vector DNA, 2:1:1, in transfections S and T. This resulted in equal amounts of IgG heavy chains constituting a matched pair and pure mixtures of bispecific IgG without the presence of half IgG molecules and with as little as 3% homodimeric BB present. Ideally, this low proportion of contaminating monospecific product should be reduced to essentially zero. It is therefore desired to find additional CH3-mutants that would result in mixtures of bispecific antibodies with minimal contaminating monospecific antibodies present.

The present study demonstrates for the first time that essentially pure mixtures of two bispecific antibodies recognizing 3 different target epitopes can be produced in a single cell, with minimal presence of monospecific antibodies in the mixture.

Example 12

Varieties of Mixtures

As it was demonstrated that production of mixtures of 2 bispecific antibodies recognizing 3 epitopes from a single cell, or production of mixtures of 2 or 3 monospecific antibodies from a single cell is technically feasible, we next explored the feasibility of controlled production of a variety of other mixtures. A fourth antibody VH region with known specificity and known ability to pair with the human IGKV1-39 light chain will be used for recloning into vectors containing constructs 1-3 or 7 of Table 1, resulting in vectors I', II', III' or X' (the ' indicating a different specificity as compared to corresponding vector numbers). The resulting vectors I'-III', X' and IV-IX, each containing nucleic acid sequences encoding for the common human light chain as well as an Ig heavy chain with different CH3 region and different VH specificity, will subsequently be transfected into cells, in combination with other construct vectors to obtain a variety of mixtures of bispecific and/or monospecific antibodies. The variety of mixtures that will be obtained include mixtures of 2 bispecific antibodies recognizing 4 epitopes, 2 bispecific antibodies and one monospecific antibody, or mixtures of 1 bispecific and one monospecific antibody from a single cell. Table 6 depicts the transfection schedule and expected results.

Although, theoretically, production of all mixtures should be feasible, it is known from previous work by others that large scale production of classical knob-into-hole variants is hampered by instability issues. Mixtures resulting from transfections ZA, ZB, ZL, ZM and ZN are thus expected to become problematic when transferred to larger scale production.

Thus, the current set of constructs present in Table 1 would not allow production of all theoretical mixtures from single cells at a larger scale, as knob-into-hole variants are reported to be unstable, and it cannot be excluded that CH3 domains comprising a 'knob' or a 'hole' will dimerize with either charge variants or wildtype CH3 domains. It is thus desired to design new CH3-variants that are engineered to preferentially form homodimers or heterodimers only and which will not homo-or heterodimerize with constructs 1-5 of Table 1 as to allow for co-expression in single cells.

Example 13

Identification of Novel Charge Pair Mutants

The objective of this study was to engineer the IgG CH3 region to result in the production of only heterodimers or only homodimers upon mixed expression of different IgG heavy chains in a single cell, wherein the novel engineered CH3 domains will not homo-or heterodimerize with known engineered CH3 domains, or with wildtype CH3 domains. Therefore, as a first step in identifying novel engineered CH3 domains that would meet the criteria, many interface contact residues in the IgG CH3 domain were scanned one by one or in groups for substitutions that would result in repulsion of identical heavy chains—i.e., reduced homodimer formation—via electrostatic interactions. The objective was to obtain a list of residues that, when substituted by a charged residue, would result in repulsion of identical chains such that these mutations may be used to drive homo-and/or

TABLE 6

| Variety of mixture | Transfection of | Transfection code and ratio | Expected species | Expected % monospecific IgG | Expected % Bispecific |
|---|---|---|---|---|---|
| 2 BsAbs, 4 epitopes | IV + V + IX + X' | ZA (1:1:1:1) | BC + AD | 0 | 50 + 50 |
| 2 BsAbs, 4 epitopes | IV + VII + IX + X' | ZB (1:1:1:1) | BC + AD | 0 | 50 + 50 |
| 2 bsAbs + 1 mAb | IV + V + VI + wt' | ZC (2:1:1:2) | BC + AB + DD | 33 | 33 + 33 |
| 2 bsAbs + 1 mAb | IV + V + VI + II' | ZD (2:1:1:2) | BC + AB + DD | 33 | 33 + 33 |
| 2 bsAbs + 1 mAb | IV + V + VI + III' | ZE (2:1:1:2) | BC + AB + DD | 33 | 33 + 33 |
| 1 bsAb + 1 mAb | IV + V + wt' | ZF (1:1:2) | BC + DD | 50 | 50 |
| 1 bsAb + 1 mAb | IV + V + II' | ZG (1:1:2) | BC + DD | 50 | 50 |
| 1 bsAb + 1 mAb | IV + V + III' | ZH (1:1:2) | BC + DD | 50 | 50 |
| 1 bsAb + 1 mAb | IV + VII + wt' | ZI (1:1:2) | BC + DD | 50 | 50 |
| 1 bsAb + 1 mAb | IV + VII + II' | ZJ (1:1:2) | BC + DD | 50 | 50 |
| 1 bsAb + 1 mAb | IV + VII + III' | ZK (1:1:2) | BC + DD | 50 | 50 |
| 1 bsAb + 1 mAb | IX + X + wt' | ZL (1:1:2) | AB + DD | 50 | 50 |
| 1 bsAb + 1 mAb | IX + X + II' | ZM (1:1:2) | AB + DD | 50 | 50 |
| 1 bsAb + 1 mAb | IX + X + III' | ZN (1:1:2) | AB + DD | 50 | 50 | heterodimer formation upon mixed expression of different IgG heavy chains, whereby the obtained full length IgGs are stable and are produced with high proportions. In a follow up, the identified substitutions will be used to generate bispecific antibodies or mixtures of bispecific or monospecific antibodies by engineering matched pairs of CH3 residues in one or more IgG heavy chains—CH3 regions. Additionally, newly identified charge mutant pairs may be combined with existing pairs, such that multiple nucleic acid molecules encoding different heavy chains, all carrying different and complementing CH3 mutations, can be used for expression in cells such that mixtures of monospecific antibodies only, or bispecific antibodies only, or mixtures of defined monospecific and bispecific antibodies can preferentially be obtained. The residues to be tested in the present study are contact residues as previously identified (Deisenhofer J., 1981; Miller S., 1990; Padlan, 1996, Gunasekaran, 2010). The rationale for this approach is that repulsive charges are engineered into each available pair of contacting residues. Samples are subsequently analyzed on non-reducing SDS-PAGE to identify pairs in which dimer formation is reduced, as visualized by the presence of bands of approximately 72 kD. All available pairs will be screened as single mutations or in combination with a single other mutation as the repulsive electrostatic interaction between one non-matching pair may or may not be sufficient to result in sufficient amounts of half-molecules for detection by this method, the mutations are also combined.

Amino acid substitutions were introduced in construct vector MV1057 by Geneart according to the table 7 and expression of constructs was performed by transfection in HEK293T cells, according to standard procedures. IgG expression levels were measured in Octet. When production failed twice, the mutation was considered to be detrimental to expression and the mutation was not pursued further.

TABLE 7 list of amino acid substitutions in the various constructs that were made (EU numbering)

| AA substitutions in CH3 | construct # | Effect on homodimer formation (− = no effect; +++ = max. inhibition; NT = not tested on gel) |
|---|---|---|
| Q347K | 8 | − |
| Y349D | 9 | +− |
| Y349K | 10 | +− |
| T350K | 11 | − |
| T350K, S354K | 12 | +− |
| L351K, S354K | 13 | +− |
| L351K, T366K | 14 | ++ |
| L351K, P352K | 15 | +− |
| L351K, P353K | 16 | ++ |
| S354K, Y349K | 17 | ++ |
| D356K | 18 | − |
| E357K | 19 | − |
| S364K | 20 | ++ |
| T366K, L351K | 21 | ++ |
| T366K, Y407K | 22 | +++ |
| L368K | 23 | NT |
| L368K, S364K | 24 | ++ |
| N390K, S400K | 25 | +− |
| T394K, V397K | 26 | + |
| T394K, F405K | 27 | +++ |
| T394K, Y407K | 28 | +++ |
| P395K, V397K | 29 | +− |
| S400K | 30 | − |
| F405K | 31 | +++ |
| Y407K | 32 | ++ |
| Q347K, V397K, T394K | 33 | + |
| Y349D, P395K, V397K | 34 | + |
| T350K, T394K, V397K | 35 | NT |
| L351K, S354K, S400K | 36 | + |
| S354K, Y349K, Y407K | 37 | +− |
| T350K, N390K, S400K | 38 | +− |
| L368K, F405K | 39 | ++ |
| D356K, T366K, L351K | 40 | +++ |
| Q347K, S364K | 41 | +++ |
| L368D, Y407F | 42 | + |
| T366K | 43 | + |
| L351K, S354K, T366K | 44 | + |
| Y349D, Y407D | 45 | + |
| Y349D, S364K, Y407D | 46 | + |
| Y349D, S364K, S400K, T407D | 47 | + |
| D399K | 48 | +− |
| D399R | 49 | +− |
| D399H | 50 | +− |
| K392D | 51 | +− |
| K392E | 52 | +− |
| K409D | 53 | + |

Figure 7:
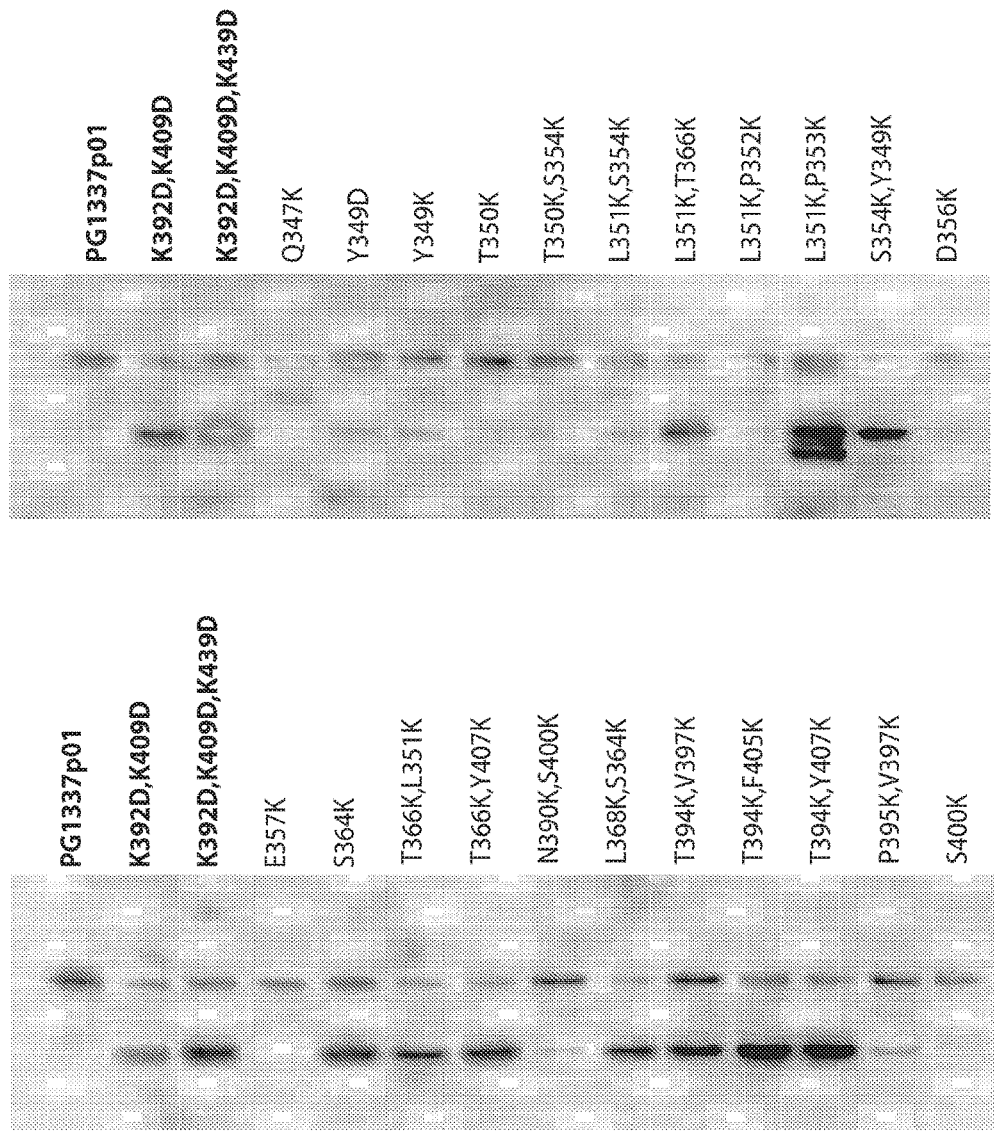
FIG. 7: prevention of homodimerisation by substitution of neutral amino acids for charged amino acids.
Figure 7:
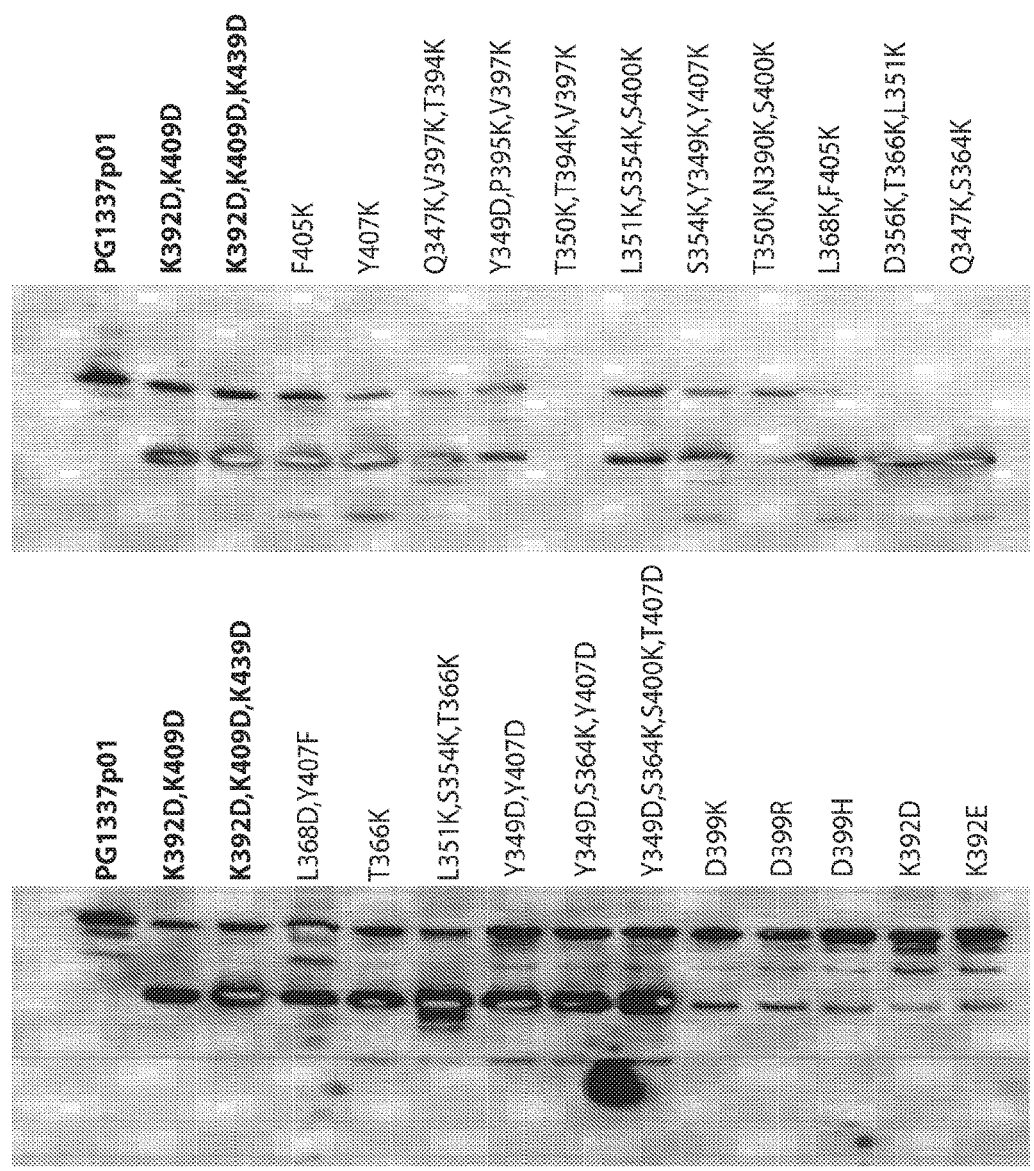

Supernatants containing ≥5 µg/ml IgG were analyzed in SDS-PAGE and IgG was purified using protein A. The proteins were stained using colloidal blue. Homodimers were visible as a band of approximately 150 kD. Smaller bands of approx 75 kD represented the presence of half molecules (see negative control: K392D, K409D). Blots are shown in FIG. 7.

The results of SDS-PAGE gels were analyzed and scored as presented in table 7, right hand column. A number of residues were considered promising for further testing in combination, including residues Q347, S354, Y349, L351, K360, T366, T394, and V397. The choice was based on high scores in the inhibition of formation of homodimers combined with the availability of contacting residues that can be modified without running into issues such as other non-complementary charges. For example, it is known that residues F405 and Y407 have multiple interactions at the CH3-CH3 interface, including interactions with residues that are already charged, which may be problematic after introduction of multiple charge mutations among these interacting residues (see Table A). New constructs were made in vector MV1057 (Table 8), and antibody VH regions with known specificities and known ability to pair with the human IGKV1-39 light chain were used for recloning into vectors containing these new constructs (see Table 9) such that combinations could further be tested. Table 10 depicts the transfection schedules and results.

TABLE 8

| AA substitutions in CH3 | construct # |
|---|---|
| L351K | 61 |
| T394K | 62 |
| L351D | 63 |

TABLE 8-continued

| AA substitutions in CH3 | construct # |
|---|---|
| T366D | 64 |
| S354D, Y349D | 65 |
| V397D | 66 |
| K360D | 67 |

TABLE 9

VH specificity inserted in different constructs

| Vector | VH gene | Antigen specificity | VH mass (Da) | Cloned in construct # |
|---|---|---|---|---|
| XI | IGHV 1.08 | Tetanus (A) | 13703 | 8 |
| XII | IGHV 1.08 | Tetanus (A) | 13703 | 17 |
| XIII | IGHV 1.08 | Tetanus (A) | 13703 | 43 |
| XIV | IGHV 1.08 | Tetanus (A) | 13703 | 61 |
| XV | IGHV 1.08 | Tetanus (A) | 13703 | 62 |
| XVI | IGHV 3.30 | Fibrinogen (C) | 12794 | 63 |
| XVII | IGHV 3.30 | Fibrinogen (C) | 12794 | 64 |
| XVIII | IGHV 3.30 | Fibrinogen (C) | 12794 | 65 |
| XIX | IGHV 3.30 | Fibrinogen (C) | 12794 | 66 |
| XX | IGHV 3.30 | Fibrinogen (C) | 12794 | 67 |

TABLE 10

| Transfection of | Transfection code (ratio) | Expected species | AA found (%) | AC found (%) | CC found (%) | Half A found (%) | Half C found (%) | other (%) |
|---|---|---|---|---|---|---|---|---|
| XIII + XVI | ZO (1:1) | AC | 0 | 69 | 7 | 24 | 0 | 0 |
|  | ZT (3:1) | AC | 10 | 45 | 16 | 27 | 0 | 0 |
|  | ZU (1:1) | AC | 5 | 61 | 10 | 13 | 0 | 0 |
|  | ZV (1:3) | AC | 3 | 61 | 23 | 13 | 0 | 0 |
|  | ZW (1:1) | AC | 0 | 88.3 | 2.4 | 7 | 0 | 2.3 |
| XIV + XVII | ZP | AC | 30 | 52 | 13 | 0 | 0 | 5 |
| XII + XVIII | ZQ | AC | 4 | 51 | 33 | 2 | 1 | 8 |
| XV + XIX | ZR | AC | 20 | 42 | 11 | 0 | 1 | 26 |
| XI + XX | ZS | AC | 34 | 41 | 15 | 0 | 0 | 10 |

Figure 8A:
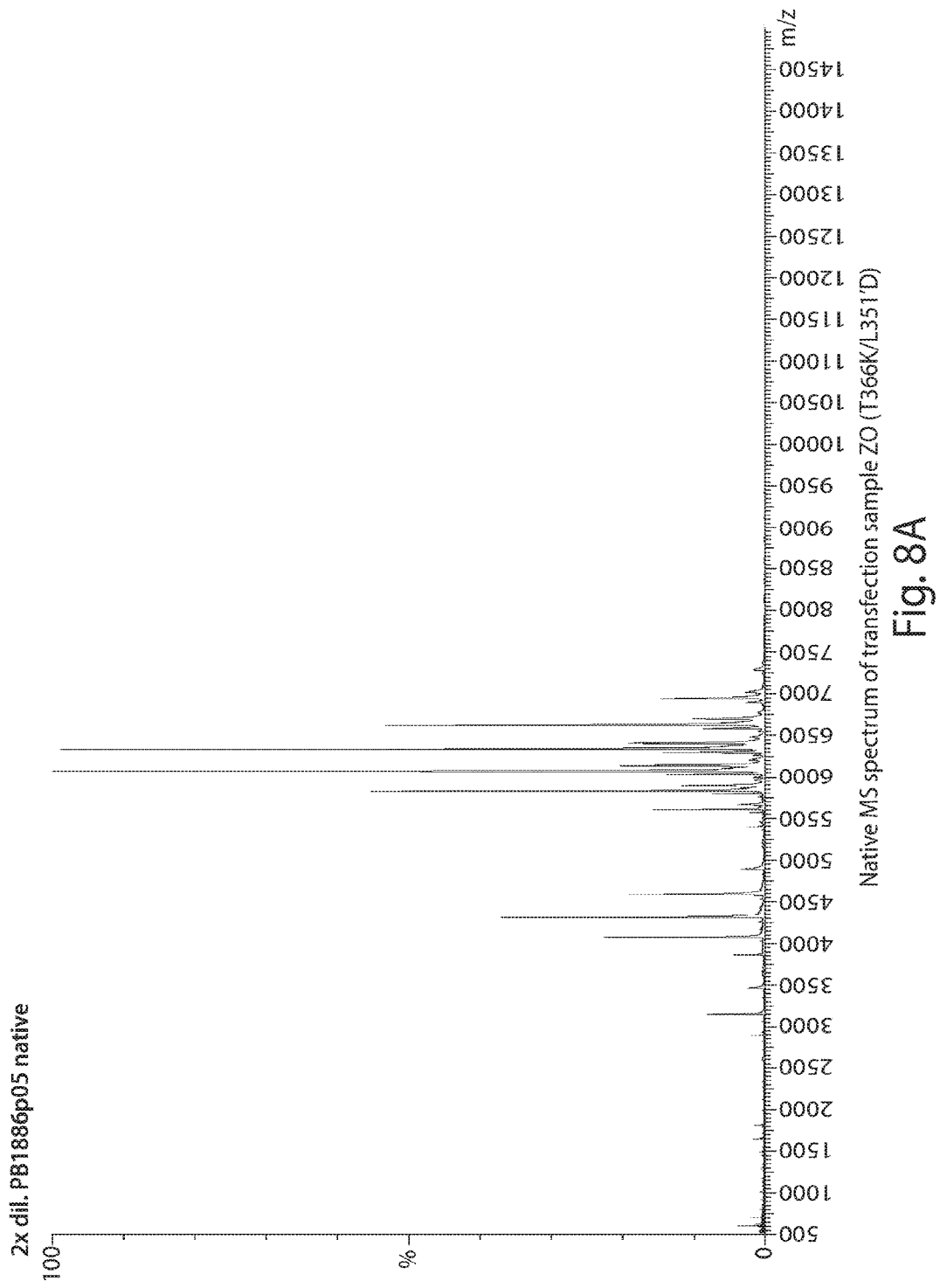
FIG. 8: Native MS spectrum of transfection sample ZO (T366K/L351'D) (A) and Convoluted MS spectrum of transfection sample ZO (T366K/L351'D). The second/main peak represents the bispecific molecule (B).
Figure 8B:
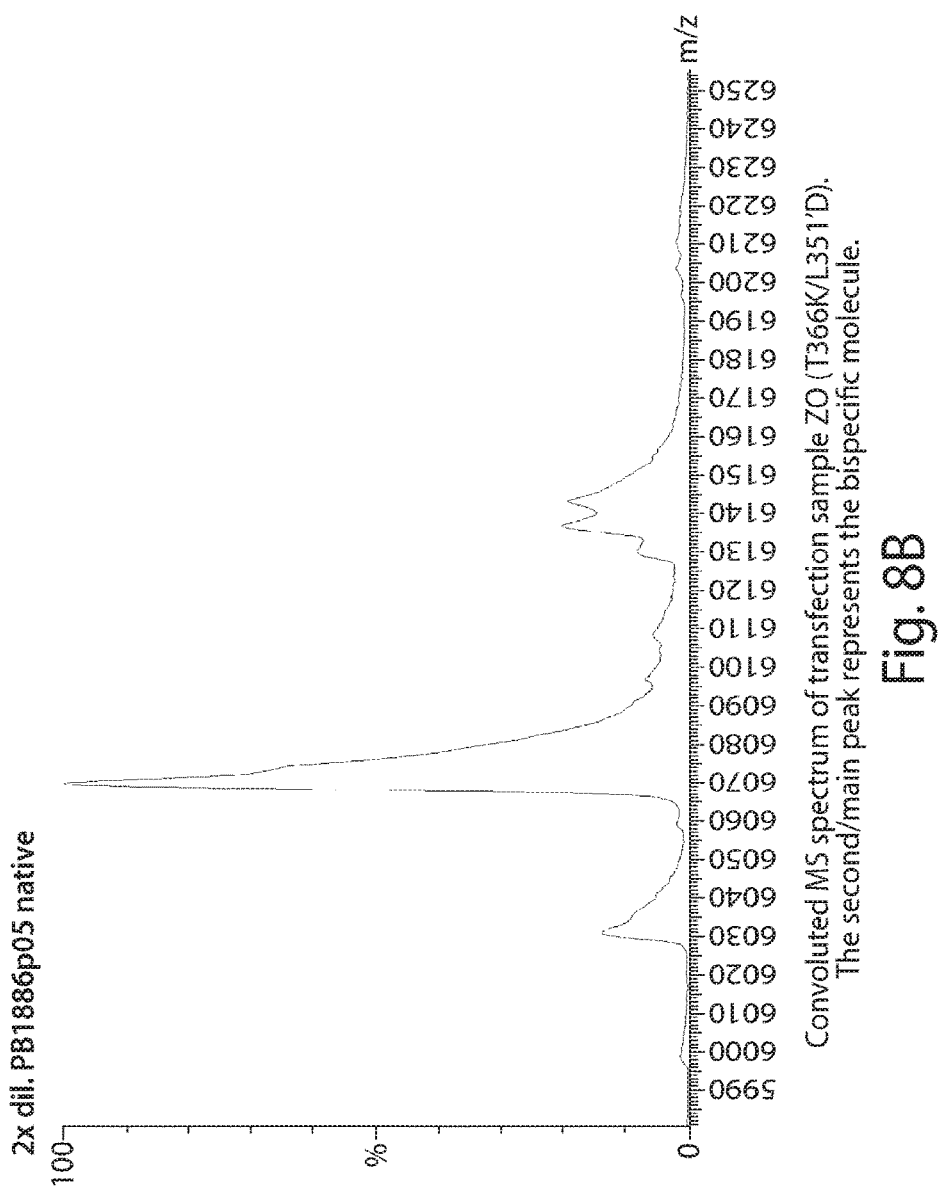

Combinations of CH3 variants were expressed, and analyzed in SDS-PAGE (data not shown) and in native mass spectrometry (MS). Results are summarized in Table 10. The ZO transfection resulted in the highest proportion of heterodimers in the mixtures (69% AC). Interestingly, in the ZO transfection, the AA homodimer was not present whereas the CC homodimer comprised a small proportion (7%). Mass spectrometric analysis unveiled that the remaining protein in the mixture consisted of half A molecules, probably resulting from unequal expression of the A and C heavy chains. The raw MS data from transfection sample ZO are shown in FIG. 8. Surprisingly, whereas transfection ZO resulted in fair amounts of bispecific product, the reverse charge pair of transfection ZP (L351K/T366'D versus T366K/L351'D of ZO) did not result in similar results, and only 52% of bispecific product was observed, with considerable amounts of the two homodimers being present (30% AA and 13% CC). An explanation for this may be that the negatively charged D structurally closely resembles T, hence the T366D may not be potent enough to repulse itself and T366D will thus still form homodimers, as was indeed observed.

It can be envisaged that subtle variants of the newly found T366K/L351'D pair (e.g. by testing all permutations including new constructs T366R and L351E) may result in similar percentages of BsAbs.

Example 14

HADDOCK for Design of New CH3 Mutants to Drive Efficient Heterodimerization

As described in example 13, the newly found charge pair T366K/L351'D increases the proportion of heterodimers in the mixture (69%) with a small fraction of undesired CC homodimers (7%) (L351D/L351'D) and a substantial fraction of half A molecules (24%) 'contaminating' the mixture. In this example, an in silico approach was used to generate further insight in amino acid residues involved CH3 interface interactions, to test complementary substitutions in opposing CH3 regions and to find novel CH3 pairs containing complementary substitutions that further increase efficient heterodimerization while preventing efficient formation of homodimers of the two heavy chains.

HADDOCK (High Ambiguity Driven protein-protein DOCKing) is an information-driven flexible docking approach for the modeling of biomolecular complexes. HADDOCK distinguishes itself from ab-initio docking methods in the fact that it encodes information from identified or predicted protein interfaces in ambiguous interaction restraints (AIRs) to drive the docking process. (de Vries et al., 2010). The input for the HADDOCK web server consists of a protein structure file, which can be a crystal structure, NMR structure cluster or a modeled structure. After the docking or refinement, HADDOCK returns a so-called HADDOCK score, which is a weighted average of VanderWaals energy, electrostatic energy, buried surface area and desolvation energy. The HADDOCK score can be interpreted as an indication of binding energy or affinity, even though a direct translation to experimental data is often hard to achieve. In addition to this, HADDOCK provides structure files for the 'top four' structures that resulted from the docking run. These structure files can be downloaded and visualized, enabling the detailed analysis of the interactions of the individual residues.

In this example, the interactions between the CH3-domains of the IgG1 heavy chains were studied. A high-resolution crystal structure of the Fc part of the IgG (structure 1L6X) was used as starting structure (http://www.rcsb.org/pdb/explore/explore.do?structureId=1l6x; Idusogie, E. E. et al., J. I. 2000 (164)4178-4184).

In example 13, it was found that co-transfection of vectors XIII and XVI resulted in the formation of the CC homodimeric contaminant (Table 10). HADDOCK was used to search for additional mutations to the T366K/L351'D pair that prevent homodimerization.

The HADDOCK output consists of a set of calculated energies, a HADDOCK score (which is a weighted average of the energies) and four structure files corresponding to the four lowest-energy structures found by the program. The HADDOCK-scores are used to compare different structures; the other energies are merely used to get an indication about what is happening in the structures (e.g. good electrostatic interactions, smaller buried surface, high Van der Waals energy). The lower the HADDOCK score, the better. For each mutation pair, the scores were calculated for the AA, AB and BB dimers.

Sets of mutation pairs from example 12 were run in HADDOCK to see whether the calculated energies would correlate to the experimental data. Table 11 presents all theoretical energies, which are visualized in FIG. 9.

TABLE 11

| Construct combinations | HADDOCK Score | VdW energy | Electrostatic energy | Desolvation energy | Buried surface area |
|---|---|---|---|---|---|
| Wildtype-wildtype | −208.2 | −62.8 | −773 | 9.2 | 2505.8 |
| 1-2 (E356KD399K-K392DK409D) | −225.8 | −56.4 | −862 | 3 | 2458.3 |
| 2-2 (K392DK409D-K392DK409D) | −180.3 | −67.9 | −562.1 | 0.1 | 2312.5 |
| 1-1 (E356KD399K-E356KD399K) | −176.7 | −75.5 | −469.3 | −7.3 | 2349.6 |
| 1-3 (E356KD399K-K392DK409DK439D) | −220.6 | −67.9 | −793.8 | 6.1 | 2499.8 |
| 3-3 (K392DK409DK439D-K392DK409DK439D) | −150.1 | −76.6 | −387.6 | 4.1 | 2261.2 |
| 6-7 (T366W-T366SL368AY407V) | −221.3 | −65.8 | −735.5 | −8.3 | 2509.0 |
| 6-6 (T366W-T366W) | 1916.9* | 2072.3 | −681.3 | −19.2 | 2499.9 |
| 7-7 (T366SL368AY407V-T366SL368AY407V) | −191.9 | −55.0 | −683.2 | −0.2 | 2427.2 |
| 43-63 (T366K-L351D) | −210.6 | −64 | −758.4 | 5.1 | 2456.5 |
| 43-43 (T366K-T366K) | −191.7 | −71.2 | −634.1 | 6.3 | 2533.5 |
| 63-63 (L351D-L351D) | −212.5 | −60.4 | −774 | 2.6 | 2445.6 |

Figure 10:
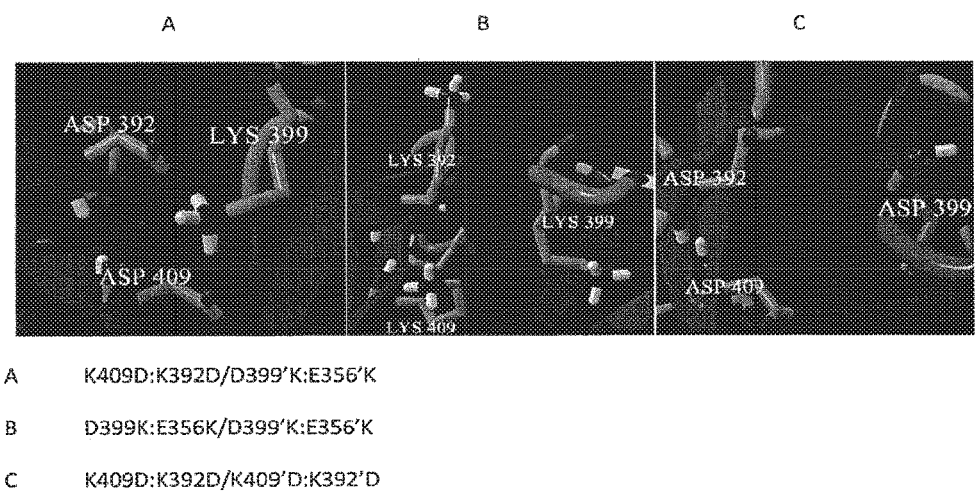
FIG. 10: Cartoons of interactions in the CH3-CH3 interface; A) K409D:K392D/D399'K:E356'K, B) D399K: E356K/D399'K:E356'K, C) K409D:K392D/K409'D: K392'D

*this value is unusually high due to high VanderWaals energy score, probably due to steric clash of T366W/T366'W With 2 wildtype CH3 domains, the HADDOCK scores are the same for AA, AB and BB because the A and B CH3 regions are identical. In most other cases, the AB pair has the lowest score, which is as expected. For the T366K/L351D pair the BB score is slightly better than the AB score (−210.6 vs. −212.5), but this difference is within the error of the calculations. Using HADDOCK, the structures of the heterodimers of these pairs were visualized. For example, the construct combinations 1-2, 1-1 and 2-2 are presented in FIG. 10. From these visualizations it is apparent that salt bridges are formed in the heterodimer (FIG. 10A left hand panel) whereas electrostatic repulsion occurs between residues of identical chains (FIGS. 10B and C, middle and right hand panel). The higher HADDOCK scores for the homodimers can thus be explained by the electrostatic repulsion of the mutated interface residues. These residues have to bend away from each other and don't have interaction with residues on the other chain, causing a drop in the affinity.

Figure 9:
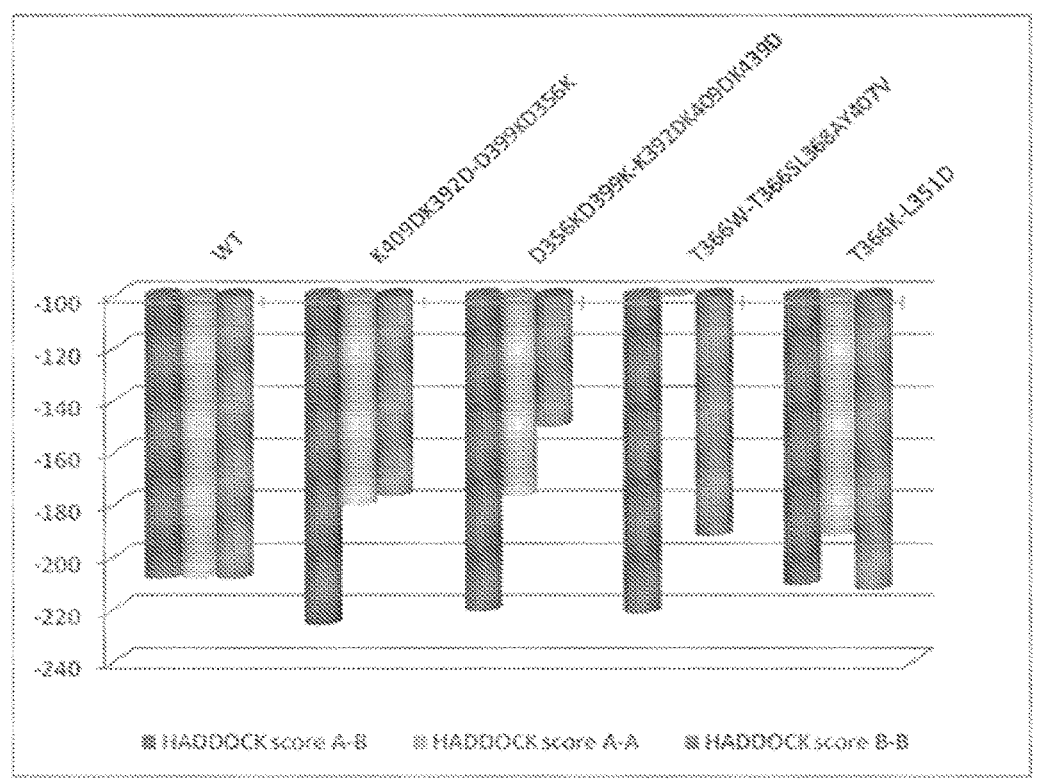
FIG. 9: HADDOCK scores on experimentally verified mutation pairs

Table 11 and FIG. 9 confirm what was observed in example 13. The T366K/L351'D AC heterodimer and the L351D/L351'D CC homodimer form with a similar energy, explaining the presence of both the heterodimer and homodimer in the mixture. The T366K/T366'K AA homodimer, on the other hand, is barely detectable in the mixture although T366K half A molecules are present. Table 11 and FIG. 9 indeed show that the HADDOCK score for the T366K/T366'K AA homodimer is higher than the score for the AC heterodimer; hence formation of this homodimer is energetically less favorable.

Example 15

366/351 Variations

In example 13, it is hypothesized that alternatives for the T366K/L351'D mutant charge pair can be designed that may have similar results in terms of percentage of bispecific antibodies in the mixture. Alternatives may include substitutions T366R, T366D, T366E, L351E, L351K and L351R. The proportion of CC homodimers of L351D/L351'D may be diminished by creating variants of the 366/351 pair. All possible mutation pairs were run in HADDOCK and the resulting scores are presented in Table 12 and visualized in FIG. 11.

TABLE 12

| Construct combinations | HADDOCK Score | VdW energy | Electrostatic energy | Desolvation energy | Buried surface area |
|---|---|---|---|---|---|
| T366K-L351D | −210.6 | −64 | −758.4 | 5.1 | 2456.5 |
| T366K-T366K | −191.7 | −71.2 | −634.1 | 6.3 | 2533.5 |
| L351D-L351D | −212.5 | −60.4 | −774 | 2.6 | 2445.6 |
| T366K-L351E | −216.9 | −55.7 | −854.7 | 9.8 | 2532.7 |
| L351E-L351E | −217.9 | −65.5 | −802.2 | 8 | 2532 |
| T366R-L351D | −210.5 | −68.8 | −760.8 | 10.4 | 2514.5 |
| T366R-T366R | −201.8 | −77.4 | −626.4 | 0.9 | 2608 |
| T366R-L351E | −225.8 | −56.2 | −874.8 | 5.4 | 2579.2 |
| T366D-L351R | −211.2 | −71.3 | −723.6 | 4.8 | 2455.6 |
| T366D-T366D | −198.1 | −58.1 | −713.4 | 2.1 | 2477 |
| L351R-L351R | −220.7 | −75.5 | −806.5 | 16.1 | 2552.2 |
| T366D-L351K | −223.9 | −62.1 | −810.1 | 0.3 | 2487.8 |
| L351K-L351K | −224.2 | −75.6 | −812.1 | 13.6 | 204.5 |
| T366E-L351R | −222.3 | −69 | −783 | 3.4 | 2557.2 |
| T366E-T366E | −201.9 | −57.6 | −741 | 4 | 2487.5 |
| T366E-L351K | −215.9 | −58.4 | −808.9 | 4.3 | 2486 |

When looking at the HADDOCK scores, it was observed that some of the mutations have a similar 'pattern' when compared to T366K/L351'D. For most permutations the AA homodimer was found to have a higher HADDOCK-score than the AB heterodimer, but the BB homodimer appeared as favorable as the AB heterodimer Even though the 351 residue is known to be a 'neighbor' to itself on the other chain, i.e. residue 351 of chain A pairs with residue 351 of chain B at the CH3-CH3 interface, there is barely a negative influence of the identical charges when the BB dimer is formed. Looking at the L351D/L351'D structure this is explained by the aspartic acids bending away from each other and the stabilizing influence of at least the naturally occurring Arginine at position 355 and also some stabilization of negative charge by the naturally occurring Serine at position 354 (see FIG. 12A). Mutation of these residues (S354A and R355D) provides only little improvement. From FIG. 12B it is clear that the backbone-hydrogen of A354 causes stabilization of the homodimer From this series, the T366R/L351'E pair seems to be the most favorable, with the lowest HADDOCK score for the bispecific molecule.

Example 16

Mutations Around T366K/L351'D

Figure 13:
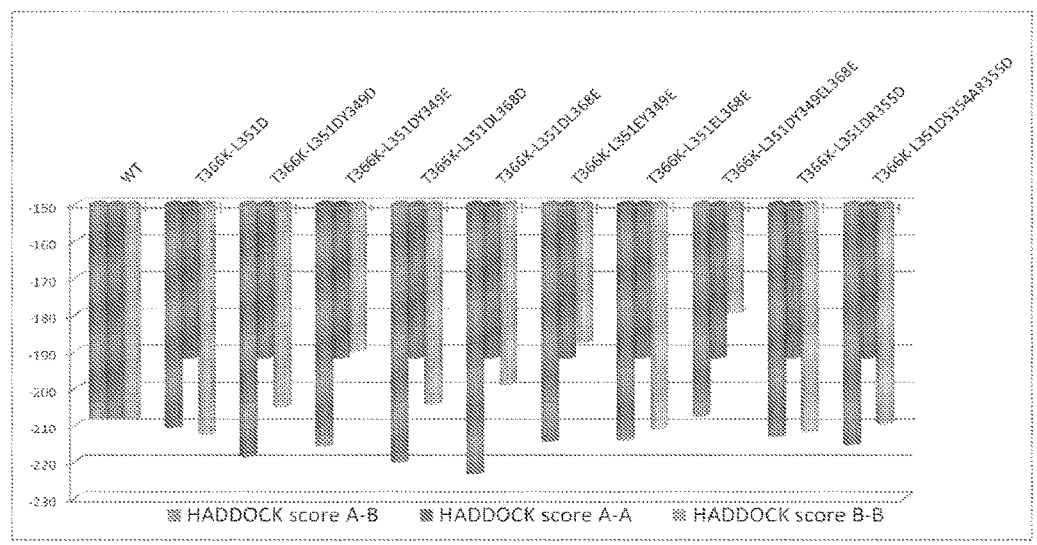
FIG. 13: HADDOCK scores for additional charge mutations around position L351

In the series of HADDOCK analyses in this example, the T366K/L351'D or T366K/L351'E pair were taken as a starting structure. In order to identify additional mutations that would further increase the predicted percentage of bispecifics of these A and B chains, additional mutations on the B-chain were used to calculate the HADDOCK-scores and energies. When the structure of the CH3 domain is studied using a viewer for visualization of protein structures at a molecular level (YASARA, www.yasara.org), one can calculate the distances between individual residues. While doing so, it was observed that the two residues Y349 and L368 are neighboring residues that may contribute positively or negatively to dimer interactions and these have been mutated in this example—in addition to the L351D mutation—to study the result on dimer formation of the homo-and heterodimers (see FIG. 13). Both residues seem to add to the stability of the heterodimer (lower HADDOCK scores) as well as to the destabilization of the BB dimer (higher HADDOCK scores). Glutamic acids (E) on positions 349 and 368 seem to be more favorable than aspartic acids (D). Thus, introduction of a second amino acid substitution in the B-chain, comprising already the amino acid substitution at position 351, seems to favor heterodimerization further.

Figure 14:
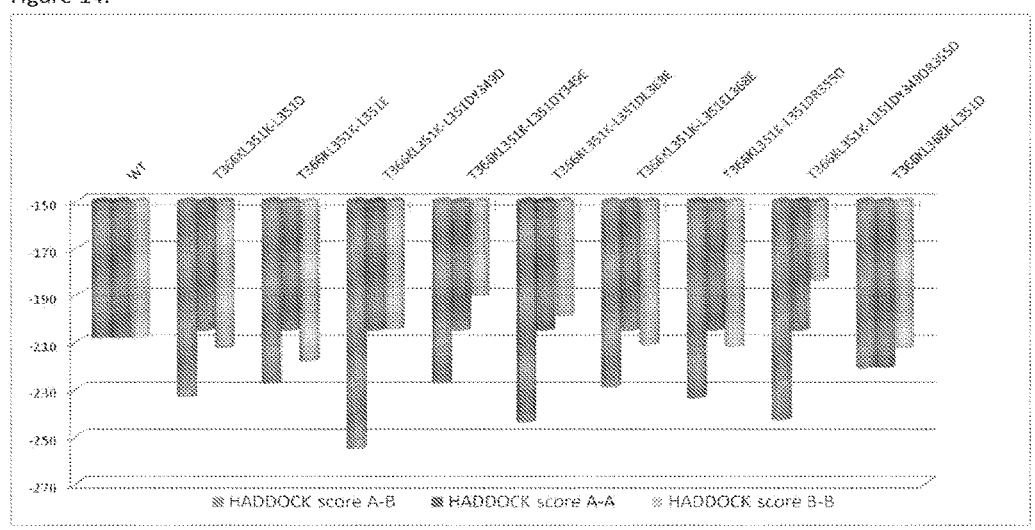
FIG. 14: HADDOCK scores for additional charge mutations around position T366 in chain A and position L351 in chain B.
Figure 15:
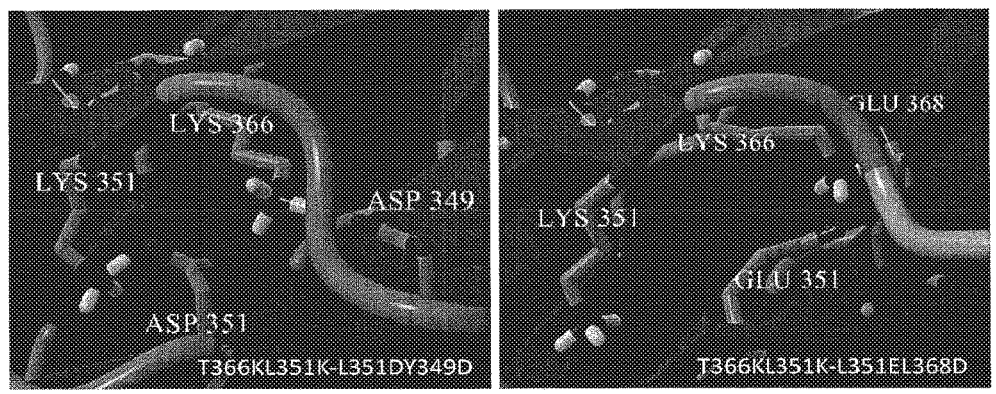
FIG. 15: Cartoons of interactions in the CH3-CH3 interface

In a next set of HADDOCK analyses, the T366K/L351'D pair was again taken as starting structure. In addition to the substitutions in the B chain that further increased heterodimerization (i.e. Y349D/E and L368E), additional mutations were added to the A-chain which already comprises the T366K substitution. As shown in FIG. 14, there are several mutation pairs that seem favorable towards the formation of bispecific heterodimers. In the T366K-L351K/L351'D-Y349'D pair, all four mutated residues are involved in the heterodimeric pairing, which is not de case for T366K-L351K/L351'E-L368'E in which K351 is not directly involved in the binding. However, the HADDOCK-score for this latter heterodimer is −228.9; significantly lower than the −214.2 for the T366K/L351'E-L368'E, which can be explained by hydrogen bonding interactions of the K at position 351 (see FIG. 15). The T366K-L351K/L351'D-Y349'D pair may be further improved by the R355'D mutation in the B-chain, which results in a higher BB-HADDOCK score, but also the AB HADDOCK score is slightly higher. Overall the additional L351K results in lower AB scores and similar AA and BB scores when compared to the sole T366K mutation in the A chain. Theoretically this would result in higher amounts of bispecific heterodimers in the samples.

Figure 11:
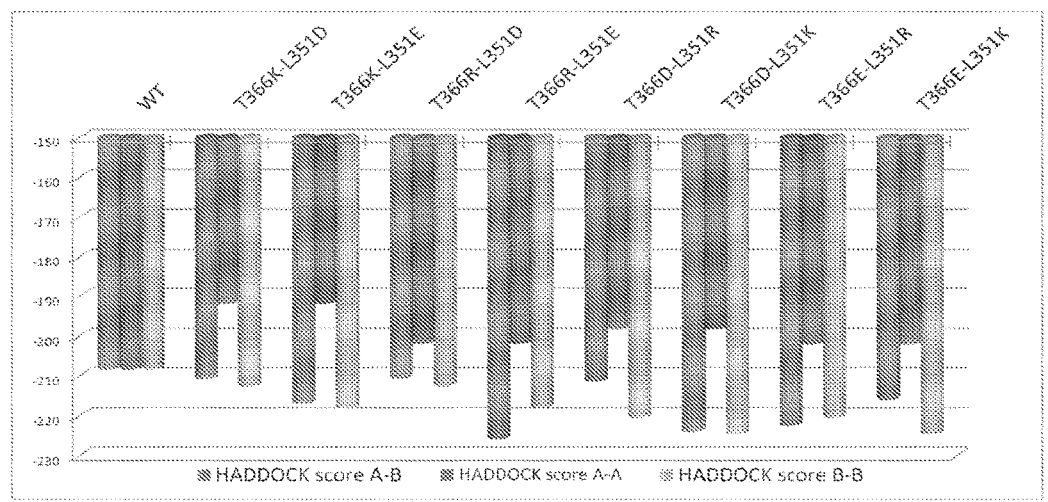
FIG. 11: HADDOCK scores for various 366/351' charge mutants
Figure 16:
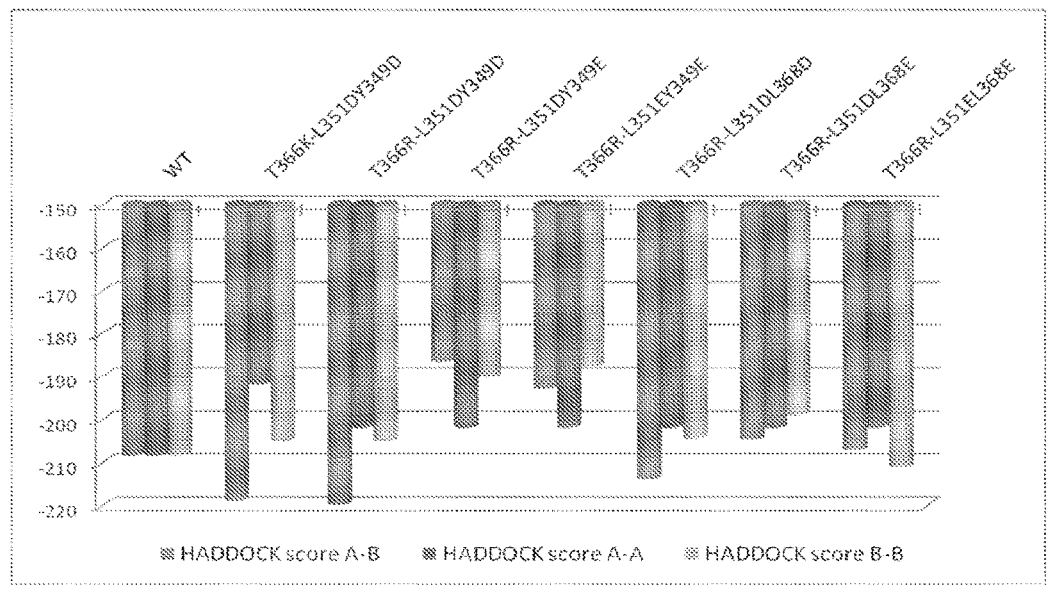
FIG. 16: HADDOCK scores for variants around T366/L351

As is apparent from FIG. 11, having an R rather than a K at position 366 may be more potent in driving heterodimerization. Therefore, some of the HADDOCK analyses shown in FIG. 13 were repeated but now with T366R rather than T366K in the A-chain. It was demonstrated that it is not favourable to combine an R366 in chain A with double mutations in chain B (FIG. 16). This may be due to the large size of this residue, interfering with other interface interactions, even though all the expected salt-bridges with R366 are present in the structures. Also, the HADDOCK score for the AA homodimer is lower for R366 than for K366, which also doesn't contribute favorably to heterodimer formation. Therefore no further HADDOCK analyses were performed using R366 in the interface.

Figure 17:
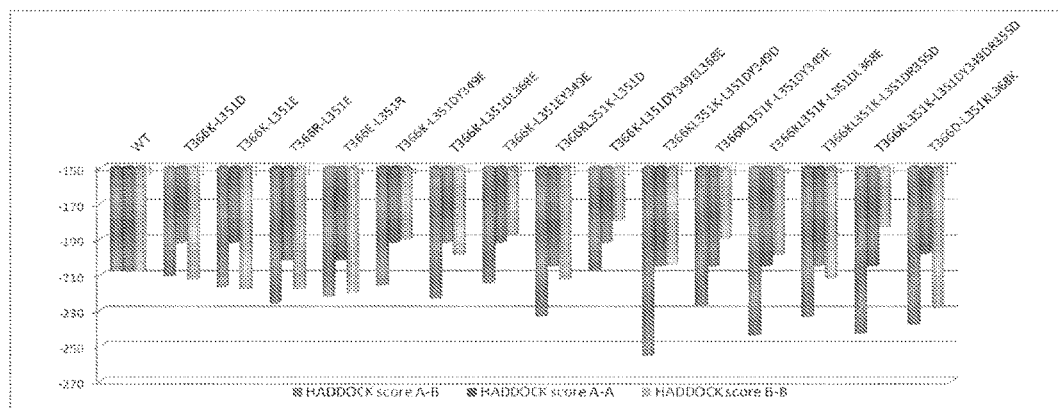
FIG. 17: HADDOCK scores for additional variants around T366/L351

A total of 14 best performing pairs, according to HADDOCK predictions, have been selected (see Table 13 and FIG. 17). In some pairs, an R355D substitution is included to remove the stabilizing influence of the naturally occurring R355 on the L351/L351'D interaction.

TABLE 13

| Construct combinations | HADDOCK Score AB | HADDOCK Score AA | HADDOCK Score BB |
|---|---|---|---|
| Wildtype-wildtype | −208.2 | −208.2 | −208.2 |
| T366K-L351D | −210.6 | −191.7 | −212.5 |
| T366K-L351E | −216.9 | −191.7 | −217.9 |
| T366R-L351E | −225.8 | −201.8 | −217.9 |
| T366E-L351R | −222.3 | −201.9 | −220.3 |
| T366K-L351DY349E | −215.9 | −191.7 | −190 |
| T366K-L351DL368E | −223.3 | −191.7 | −198.9 |
| T366K-L351EY349E | −214.5 | −191.7 | −187.5 |
| T366KL351K-L351D | −233.2 | −205 | −212.5 |
| T366K-L351DY349EL368E | −207.5 | −191.7 | −179.5 |
| T366KL351K-L351DY349D | −255.2 | −205 | −204.3 |
| T366KL351K-L351DY349E | −227.2 | −205 | −190 |
| T366KL351K-L351DL368E | −243.9 | −205 | −198.9 |
| T366KL351K-L351DR355D | −233.6 | −205 | −211.9 |
| T366KL351K-L351DY349DR355D | −242.8 | −205 | −183.5 |
| T366D-L351KY349K | −237.9 | −198.1 | −228.4 |

Example 17

In Vitro Expression of Bispecifics Using CH3 Mutants Based on HADDOCK Predictions The analysis in example 16 suggested that some CH3 variants with additional mutations around the T366K/L351'D pair would yield mixtures with higher proportions of the bispecific component and potentially lower proportions of the homodimeric component. These best performing pairs were selected for production and further analysis. In addition, the constructs T366R and L351E were also generated. Table 14 lists the constructs that were made and which were used for recloning antibody VH regions with known specificities and known ability to pair with the human IGKV1-39 light chain. Expression of the IgGs that contain the individual constructs was previously reported in example 13, and was repeated for the constructs as listed in Table 14. Aim was to assess which of the constructs homodimerize in the absence of a matching heterodimerization partner. Ideally, high percentages of half bodies would be formed and low percentages of homodimers. As a control, constructs containing previously reported charge mutations and constructs containing the previously reported knob-in-hole mutations were also used for expression as whole IgG by recombinant cells. Protein A purified supernatants were analyzed in SDS-PAGE; results were analyzed and scored as presented in Table 14

TABLE 14

| AA substitutions in CH3 | Construct # | % IgG | % half molecule |
|---|---|---|---|
| E356K, D399K | 1 | 64.2 | 35.8 |
| K392D, K409D | 2 | 30.9 | 69.1 |
| K392D, K409D, K439D | 3 | 24.5 | 75.5 |
| T366W | 6 | 27.6 | 72.4 |
| T366S, L368A, Y407V | 7 | 58.6 | 41.4 |
| T366K | 43 | 32.9 | 67.1 |
| L351D | 63 | 89.8 | 10.2 |
| T366D | 64 | 89.6 | 10.4 |
| T366K, L351K | 68 | 34.7 | 65.3 |
| L351D, L368E | 69 | 83.7 | 16.3 |
| L351E, Y349E | 70 | 67.8 | 32.2 |
| L351D, Y349E | 71 | 79.7 | 20.3 |
| L351D, R355D | 72 | 100 | — |
| L351D, Y349E, L368E | 73 | 79.3 | 20.7 |
| L351D, Y349D | 74 | 88.6 | 11.4 |
| L351D, Y349D, R355D | 75 | 89.9 | 10.1 |
| L351K, L368K | 76 | 56.6 | 43.4 |
| L351R | 77 | 100 | — |
| T366E | 78 | 44.4 | 55.6 |
| T366R | 79 | 29.6 | 70.4 |
| L351E | 80 | 100 | — |

The results of co-expression of a common light chain and two different heavy chains carrying the amino acid substitutions of constructs shown in Table 14 or heavy chains carrying the amino acid substitutions of previous constructs are presented in Table 15. Expression of two different heavy chains comprising the amino acid substitutions T366K and L351'D:L368'E respectively resulted in approximately 87% of the bispecific AB heterodimer in the mixture with no AA or BB homodimers present (combination nr. 3 of Table 15). About 12% half molecules (half A) comprising the T366K substitution was observed. Furthermore, it was found that the percentage of bispecific AB heterodimer increased when the additional amino acid substitution L351K was introduced in the first heavy chain. For example, co-expression of two different heavy chains comprising the amino acid substitutions T366K:L351K and L351'D:L368'E respectively resulted in approximately 92% of bispecific AB heterodimer whereas AA and BB homodimers are essentially absent in the mixture (combination nr. 12 of Table 15). Combinations 10 and 11 also resulted in favorable distributions of high percentages heterodimers and virtually absence of homodimers. The absence of homodimers is advantageous, because the fraction containing the intact IgG molecules is composed of AB heterodimer only. For purification and subsequent therapeutic application, the half molecules can be removed by standard approaches such as size exclusion chromatography. Hence, applying these newly identified charge mutants in the production process for generating bispecific antibodies provides advantages over known charge mutants and knobs-into-holes mutants where the presence of 'contaminating' homodimeric antibodies is not excluded. In addition, the T366K/L351'D:L368'E and T366K:L351K/L351'D:L368'E charge pairs have an additional advantage over the previously described E356K:D399K/K392'D:K409'D and E356K:D399K/K392'D:K409'D:K439'D charge reversal pairs, in that the previously described charge variants are based on the reversal of existing charges within the CH3-CH3 interface whereas the newly identified charge variants are adding additional charge pairs (charge-charge interactions) to the CH3-CH3 interface. The introduction of additional charge pairs in the CH3-CH3 interface may further increase the stability of the interface and thereby of the intact antibody. The same holds true for the mutations used in combinations nrs. 4, 5, 6, 9, 10, and 11, which also resulted in favorable proportions of bispecific heterodimer with exceedingly low proportions of AA and BB homodimers present in the mixtures.

TABLE 15

| Combination of 2 different heavy chains | chain A*/ mutations (construct #) | chain B**/ mutations (construct #) | % AA found | % AB found | % BB found | % half A found | % half B found |
|---|---|---|---|---|---|---|---|
| 1 | T366E (78) | L351R (77) | 3 | 81 | 2 | 13 | 0 |
| 2 | T366K (43) | L351D (63) | 0 | 88 | 3 | 9 | 0 |
| 3 | T366K (43) | L351D, L368E (69) | 0 | 87 | 0 | 12 | 0 |
| 4 | T366K (43) | L351E, Y349E (70) | 2 | 85 | 0 | 11 | 0 |
| 5 | T366K (43) | L351D, Y349E (71) | 2 | 92 | 1 | 5 | 0 |
| 6 | T366K (43) | L351D, Y349E, L368E (73) | 0 | 96 | 1 | 4 | 0 |
| 7 | T366K, L351K (68) | L351D (63) | 0 | 77 | 12 | 10 | 1 |
| 8 | T366K, L351K (68) | L351D, R355D (72) | 0 | 79 | 8 | 10 | 1 |
| 9 | T366K, L351K (68) | L351D, Y349D, R355D (75) | 1 | 93 | 2 | 4 | 1 |
| 10 | T366K, L351K (68) | L351D, Y349D (74) | 1 | 95 | 1 | 3 | 0 |
| 11 | T366K, L351K (68) | L351D, Y349E (71) | 1 | 95 | 0 | 3 | 1 |
| 12 | T366K, L351K (68) | L351D, L368E (69) | 0 | 92 | 0 | 8 | 0 |
| 13 | T366K (43) | L351E (80) | 0 | 70 | 10 | 18 | 2 |
| 14 | T366R (79) | L351E (80) | 4 | 38 | 36 | 21 | 1 |
| 15 | T366D (64) | L351K, L368K (76) | 3 | 92 | 2.5 | 2.5 | 0 |
| 16 | T366D (64) | L351R (77) | 30 | 69 | 1 | 0 | 0 |

*chain A carries specificity of MF1337 (=tetanus toxoid);
**chain B carries specificity of MF1122 (=fibrinogen)

Native MS

Figure 18:
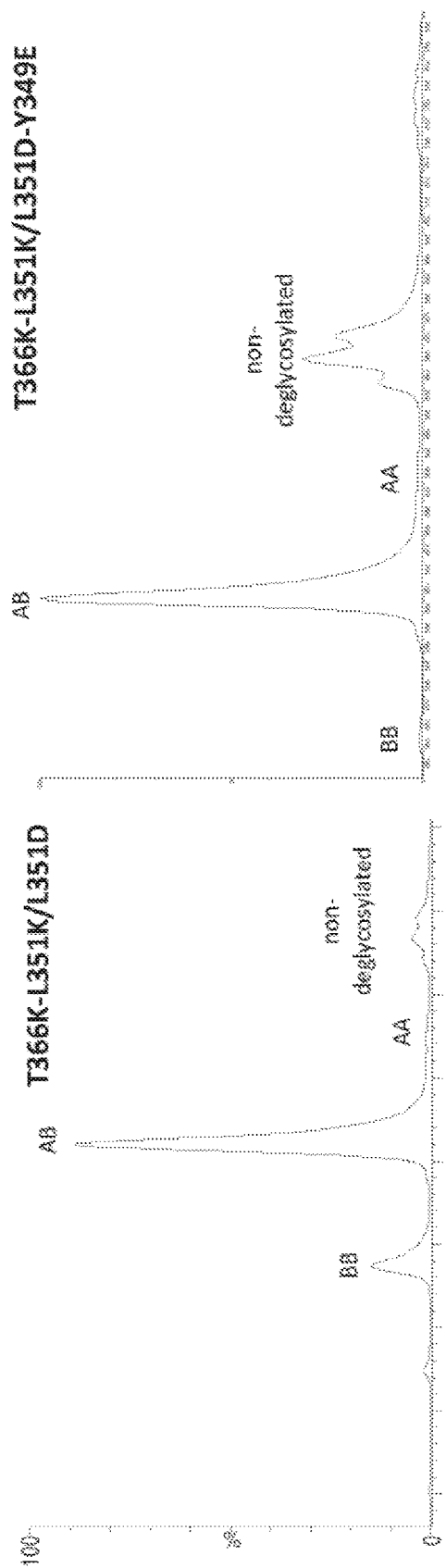
FIG. 18: Examples of nMS spectra for bispecific IgG obtained after the co-expression of construct T366K,L351K with either construct L351D (left hand panel) or L351D, Y349E (right hand panel), zoomed in on a single charge state of the full IgG (half bodies not shown)
Figure 19A:
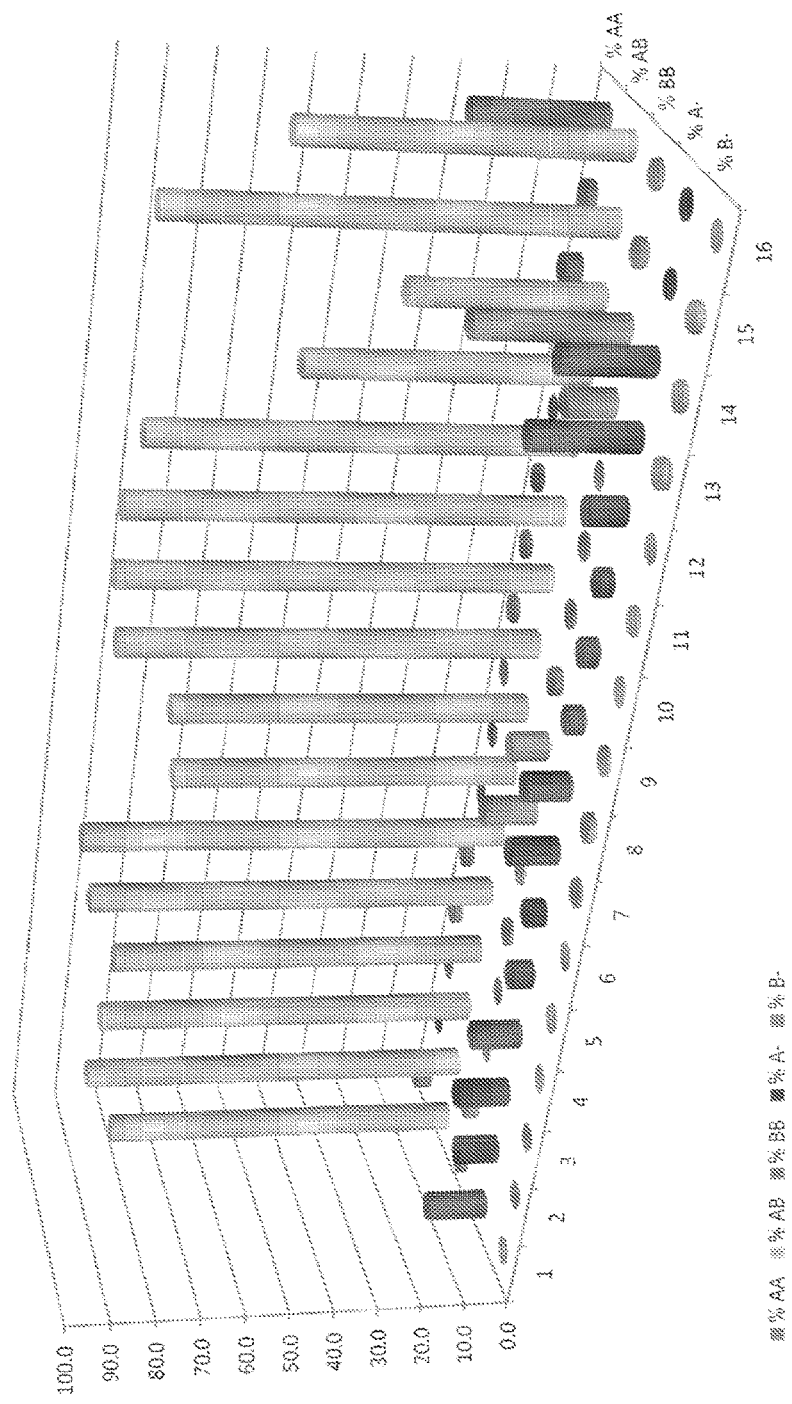
FIG. 19: A) Results of native MS showing relative abundances of AA, AB, BB, A and B (total of all species is 100%); B) idem but now without AB to have a better overview on the undesired species AA, BB, A and B
Figure 19B:
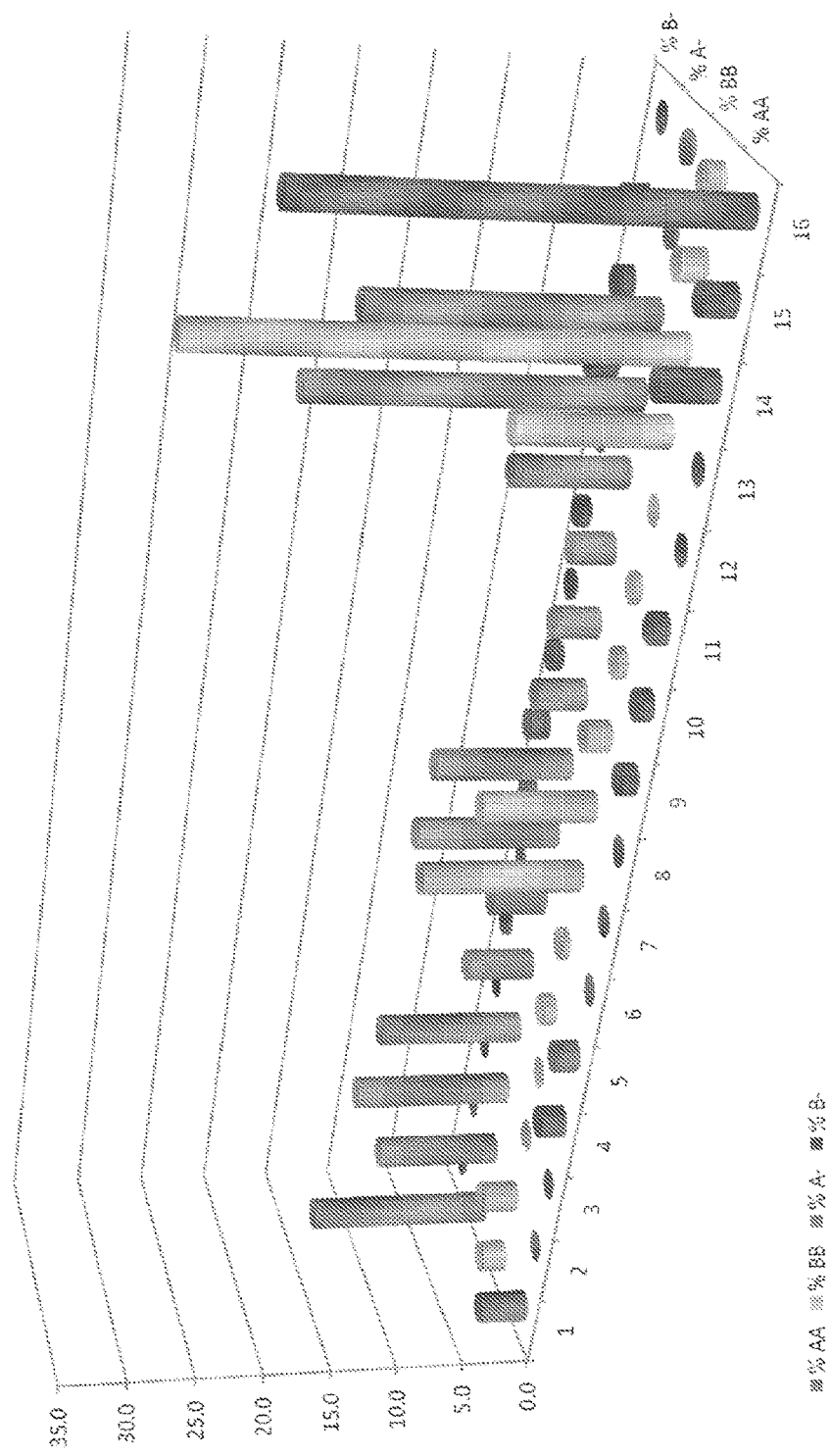

Native MS was performed on all bispecific samples. The obtained graphs were analyzed to determine the relative ratio's of the present species in two ways: by peak height and by peak area. Peak area is the more scientifically correct way of analysis, but since all previous analyses for other studies were done based on peak height, both methods were included in the analysis, for comparison purposes. The differences between the methods were within the error of measurement, and therefore only the peak area values were used for future measurements. Two typical spectra are shown in FIG. 18. An overview of the results is shown graphically in FIG. 19, the numerical values can be found in Table 15. In about half of the samples the total contamination of monospecific IgG is less than 5%, and only in three cases it is >10% while for wt IgG it is expected to find about 50% of monospecific IgG in the mixture.

A panel of ten combinations of 2 different heavy chains was selected from Table 15 for further analyses. These ten combinations included combinations 1, 2, 3, 4, 5, 6, 9, 10, 11 and 12 (Table 15). Selection of these ten was based on low percentages of homodimers present in the mixtures as determined by nMS, but also based on their overall physicochemical properties, including production yields, SDS-PAGE, as well as the number of mutations present in the CH3 domain.

Example 18

IgG Stability Analyses

In this study, a series of CH3 mutation pairs that resulted in high proportions of bispecific heterodimers in the intact IgG fraction and very low amounts (<5%) of parental IgGs will be further analyzed for stability of the Fc part of the IgG molecule. The mutated CH3 domains that are used to promote the heterodimerization of the heavy chains may have unexpected destabilizing effects on the Fc region of the IgG, that may result in undesirable properties such as a reduction of in vivo half life, reduction in effector function and/or an increase in immunogenicity. The newly identified charge pairs will be compared to wildtype bispecifics and a bispecific containing previously identified charge mutations (chain A comprising construct 1 and chain B comprising construct 2). All bispecifics in this study will contain the same heavy and light chain variable regions, ensuring that the observed effects are caused by mutations in the Fc-part of the molecule and not by variation in the variable regions.

A series of stability studies will be performed on these bispecifics. These studies include spectroscopic (UV-Vis absorbance, fluorescence and light-scatter) and microscopic (light and fluorescence microscopy with Nile Red staining) analyses that provide information on the aggregation state of the CH3 variants.

The UV-Vis absorbance spectra will be recorded with a double beam, two monochromators Cary 300 Bio spectrophotometer at 25° C. The spectra will be monitored between 250 and 400 nm using a path length of 1 cm. The absorbance at wavelengths of 320 nm and longer provides information on the aggregation state of the IgG.

Intrinsic fluorescence spectra will be monitored at 25° C. using a FluoroMax spectrofluorimeter. The fluorescence method will be optimized. The fluorescence emission will provide information on conformation and aggregation properties. 90° light-scattering spectra will be monitored at 25° C. using a FluoroMax spectrofluorimeter by running a synchronous scan ($\lambda_{em}=\lambda_{ex}$) between 400 nm and 750 nm with an integration time of 0.01 s. Excitation and emission slits will be optimized. For example, right angle light-scattering can distinguish between IgG samples that have no and 5% dimers.

For fluorescence microscopy with Nile Red staining, just prior to measurements, Nile Red in ethanol will be added to the sample. The samples will be filled in a microscopy slide and analyzed by fluorescence microscopy. Particles will be counted. The lower size limit of the particles that can be observed by fluorescence microscopy is approximately 0.5 µm.

Application of stress such as temperature, pH, mechanical stress or denaturants on proteins might result in a conformation change (e.g. unfolding) and/or aggregation. As it was previously reported that charge-engineered bispecific antibodies have reduced melting temperature of the modified CH3 (Gunasekaran 2010), these studies aim to discriminate between the novel charge mutants of the present invention and existing known charge mutants.

Thermo-stability studies using the Octet are explored, both with Protein A biosensors and by using FcRn binding to IgG. To examine the thermal stability of CH3-engineered IgGs, the samples will be incubated at a concentration of 100 ug/ml (in PBS) at 4, 50, 55, 60, 65, 70 and 75° C. for 1 hour using a PCR machine. Following this the samples will be cooled down slowly during a period of 15 minutes to 25° C. and kept at this temperature for 2 hours, after which they will be stored overnight at 4° C. Precipitated antibodies will be removed by centrifugation, after which the total IgG concentration of soluble antibodies will be determined by Octet using the protein A Biosensor (1/10 dilution in PBS). Assays that measure binding of the CH3 engineered IgG to FcRn using the Octet are being explored. Either protein L biosensors are used to bind the light chain of IgG to the sensor, followed by incubation with FcRn in solution, or anti-penta-HIS biosensors are used to bind His-tagged FcRn protein, followed by incubation with the IgG of interest. These methods may be more sensitive than using the protein A Biosensor and can also be used for thermal stability studies. All samples will also be analyzed for serum stability. Briefly, (engineered) IgG samples will be incubated at 37° C. in human serum, control samples will be kept at 4° C. After 1, 2, 3 and 4 weeks, samples are centrifuged to remove precipitated IgG. Subsequently the sample is titrated in antigen-specific ELISA to determine the relative amounts of functional IgG. Purified control antibody freshly spiked in human serum will be used as a reference.

Example 19

Stability Analyses

In previous experiments, high percentages of bispecific antibodies were obtained by co-expression of two different heavy chains comprising CH3 mutations, and a common light chain (example 17).

A panel of eight combinations of 2 different heavy chains was selected from Table 15 for further analyses. These eight combinations included combinations 3, 4, 5, 6, 9, 10, 11 and 12 (Table 15). In this study, these eight combinations were analyzed, with a strong focus on stability of the Fc part of the IgG. As controls, wildtype bispecifics (i.e. without CH3 mutations) and/or bispecifics based on previously reported CH3 charge mutations were included. Note that for wildtype bispecifics, 2 heavy chains and the common light chain are co-expressed without means for preferential steering towards heterodimers. These 'wildtype bispecifics' thus represent a mixture of AA, AB and BB. All bispecifics in this study were designed to carry the same VH/VL-combinations, ensuring that the observed effects are caused by mutations in the Fc-part of the molecule and not by variation(s) in the Fab parts.

It was hypothesized that the mutational pairs that were used to promote the heterodimeric pairing of the two different heavy chains could be associated with unexpected structural or otherwise destabilizing effects on the Fc region of the IgG. This could subsequently result in undesired issues that would hamper further clinical development, such as a reduction of in vivo half life, a reduced effector function and/or increased immunogenicity due to the presence of these mutations.

Thermo Stability

Figure 20:
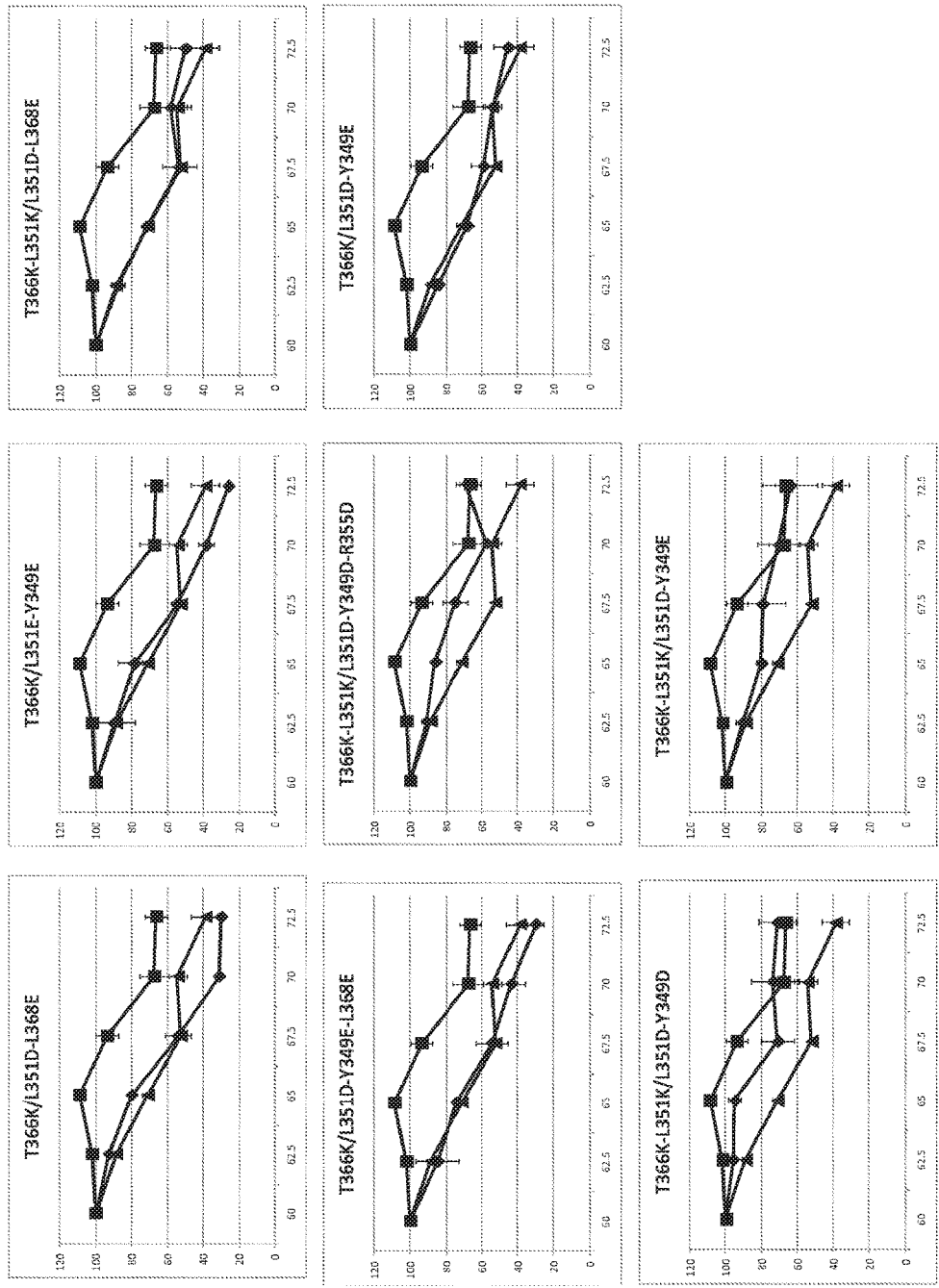
FIG. 20: Results of thermostability assay. Squares:wildtype; triangles:charge reversal pair E356K:D399K/K392D: K409D; circles:mutant CH3 combinations as indicated above each graph.

Application of stress such as increases or decreases in temperature might result in a conformation change (e.g. unfolding) and/or aggregation of proteins. To examine the thermal stability of CH3-engineered IgGs, the bispecific molecules from combinations 3-6 and 9-12 (Table 15), as well as wildtype bispecifics and bispecific molecules obtained when using constructs 1 and 2 (E356K:D399K/K392D':K409D' combination, also dubbed 'charge reversal' pair) were incubated at a concentration of 100 µg/ml (in PBS) at 4, 60, 62.5, 65, 67.5, 70 and 72.5° C. for 1 hour using a PCR machine. Following this the samples were cooled down slowly during a period of 15 minutes to 25° C. and kept at this temperature for 2 hours, after which they were stored overnight at 4° C. The next day, precipitated antibodies were removed by centrifugation (18,000 rpm; 4° C., 20 min), after which the total IgG concentration of soluble antibodies was determined by Octet using the protein A Biosensor (1/10 dilution in PBS). Results are shown in FIG. 20. It was observed that the control CH3 engineered bispecific antibody (the charge reversal E356K:D399K/K392D':K409D' combination (triangles)) has a reduced thermal stability as compared to the wildtype bispecific (squares). The bispecific molecules from combinations 3-6 and 9-12 (diamonds) also demonstrated a reduced thermal stability as compared to wildtype. Remarkably, three combinations, however, demonstrated an improved stability as compared to the control CH3 engineered bispecific antibody. Bispecifics of combinations 9, 10 and 11 are significantly more stable than the other CH3 engineered (charge reversal) bispecifics and are as stable as wildtype bispecifics at the highest temperature measured.

Freeze-thaw Stability

Figure 21:
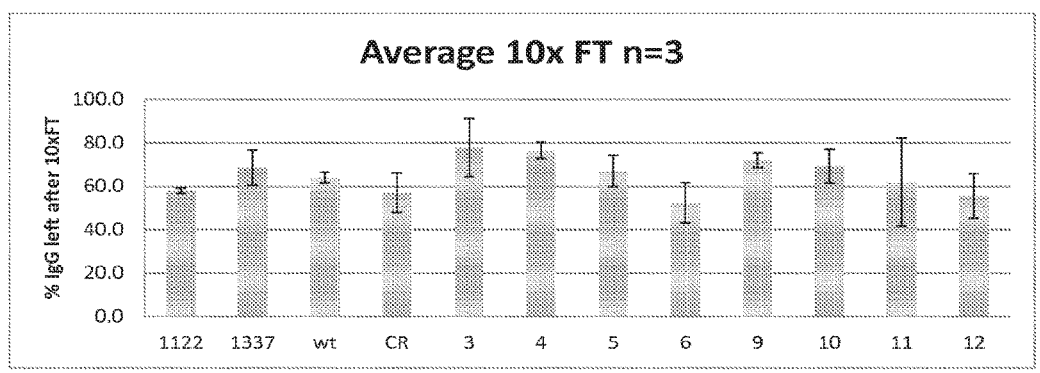
FIG. 21: Results of 10× freeze-thaw experiment. 1122=1$^{st}$ parental antibody BB; 1337=2$^{nd}$ parental antibody AA; wildtype=AA, AB, BB; CR=bispecific of charge reversal pair E356K:D399K/K392D:K409D; 3-6 and 9-12=bispecific molecules from combinations 3-6 and 9-12 from Table 15.

To examine the stability of CH3-engineered IgGs upon repetitive freezing and thawing, the bispecific molecules from combinations 3-6 and 9-12 (Table 15), as well as wildtype bispecifics and bispecific molecules obtained when using constructs 1 and 2 (E356K:D399K/K392D':K409D' combination (charge reversal pair)) were exposed to ten subsequent freeze-thaw cycles by putting the samples at −80° C. for at least 15 minutes until they were completely frozen. Thereafter, samples were thawed at room temperature. When they were completely thawed, the freeze-thaw cycle was repeated. After 10 freeze-thaw cycles, precipitated antibodies were removed by centrifugation (18,000 rpm; 4° C., 20 min), after which the total IgG concentration of soluble antibodies was determined by Octet using the protein A Biosensor (1/10 dilution in PBS). The freeze-thaw stability test was repeated three times Results are shown in FIG. 21. It was observed that the control charge reversal CH3 engineered bispecific antibody seemed to have a slightly reduced stability as compared to the wildtype bispecific. In contrast, the bispecific molecules from combinations 3, 4 and 9 seemed to have a slightly improved stability as compared to the wildtype bispecific. Overall, it can be concluded that the stringent conditions of freeze-thaw cycles do not cause major stability issues for the CH3 engineered variants.

In Vitro Serum Stability

To examine the stability of CH3-engineered IgGs in serum kept at 37° C., the bispecific molecules from combinations 3-6 and 9-12 (Table 15), as well as wildtype bispecifics and the charge reversal bispecific molecules were incubated at 37° C. in 10% human serum. Control samples were kept in human serum at 4° C. After 1, 2 or 5 days, precipitated antibodies were removed by centrifugation. Thereafter, the samples were titrated in a fibrinogen-specific ELISA, to determine the relative amounts of functional IgG. Purified control antibody freshly spiked in human serum was used as reference.

Data of the fibrinogen ELISA show that all samples were quite stable in 10% human serum at 37° C. for 5 days. At the lower IgG concentration bispecific molecules from combinations 4 and 5 seem to be slightly less stable, especially at T=1 and T=2, but the difference is only minimal at the end-point of this experiment (see FIG. 22).

Example 20

Further Stability Tests

A further series of analytical methods was used to assess the stability of the variant IgGs. Bispecific molecules from combinations 3-6 and 9-12 (Table 15), as well as wildtype bispecifics (AA, AB, BB), the individual parental antibodies (AA and BB) and bispecific molecules obtained when using constructs 1 and 2 (E356K:D399K/K392D':K409D' combination (charge reversal pair)) were used as samples in these stability assays. All IgGs were diluted to 0.2 mg/ml and several stress conditions (2 days at 50° C., 2 weeks at 40° C., 5× freeze-thawing) were applied, aiming to be able to discriminate between the different samples. Of note, these high stress levels resulted in conditions in which one of the parental antibodies (the BB parental, carrying two 1122 Fabs) as used in all bispecifics became unstable. At 2 days at 50° C., aggregation of this protein was detected by UV absorbance. This suggested that this stress condition may not differentiate between instability of the Fab and the CH3 in the bispecific and data resulting from the 50° C. incubation should be used cautiously.

The results are summarized in Table 16. Analytical methods that were used included:

- Fluorescence microscopy with Nile Red (Nile Red particles' in Table 16); to observe the amount of particles >0.5 µm after addition of Nile Red dye.
- UV spectrometry at 350 nm (UV 350 nm'); a change in absorption at wavelengths >320 nm gives information about the aggregation state of the protein.
- 90° Light scatter at 400 nm (LS 400 nm'); a sensitive technique to observe changes in protein aggregation, e.g. the difference between monomers and dimers of IgG.
- Intrinsic fluorescence; the fluorescence wavelength maximum and intensity of the aromatic residues in a protein change upon changes in the environment (e.g. unfolding)
- 1,8-ANS fluorescence spectroscopy; 1,8-ANS binds through electrostatic interactions to cationic groups through ion pair formation and changes in protein structure and/or conformation can be detected UV-VIS Spectroscopy UV-Vis absorbance spectra were measured at 25° C. with a double beam, two monochromators Cary 300 Bio spectrophotometer from Varian in different quartz cuvettes (such as black low volume Hellma cuvettes with a pathlength of 1.0 cm and clear Hellma cuvettes of 0.2 cm×1.0 cm). The spectra were monitored between 220 and 450 nm using a pathlength of 1.0 cm. The absorbance around 280 nm provides information on the protein concentration. The region between 320 nm and 450 nm can provide information on the aggregation state of the samples.

90° Light-scattering

The 90° light-scattering spectral method was developed to study protein aggregation and was performed as described in Capelle, 2005; Demeule, 2007a. 90° light-scattering spectra were monitored at 25° C. using a FluoroMax spectrofluorimeter (Spex, Instruments S.A., Inc. U.K.) by running a synchronous scan ($\lambda_{em}=\lambda_{ex}$) between 400 nm and 750 nm with an integration time of 0.01 s. Different slits settings were tested in order to find the optimal conditions. After optimization, the same slit settings were used for all measurements.

Steady-state Fluorescence Emission

The fluorescence emission of tryptophan, tyrosine and phenylalanine residues gives information on the local environment of these fluorophores. Changes or differences in hydrophobicity and/or rigidity are measured. Typically, a more hydrophobic and rigid environment leads to an increase in the fluorescence intensity and a blue shift of the emission maximum. Intrinsic fluorescence spectroscopy can provide information on the current state of the protein and monitor changes in the physical and chemical properties. More information on the fluorescence of tyrosine and tryptophan can be found in the book of Lakowicz [Lakowicz, 2006].

The fluorescence emission and excitation spectra were recorded at 25° C. in different quartz cuvettes. The samples were excited at different wavelengths. Integration times and slit settings were optimized. After optimization, the same integration times and slit settings were applied for all samples.

Fluorescence Microscopy with Nile Red Staining

The Nile Red staining method was developed to visualize protein aggregates and was performed as described in Demeule et al., 2007b.

The microscopy observations were performed on a Leica DM RXE microscope (Leica Microsystems GmbH, Wetzlar, Germany) equipped with a mercury lamp. The images were acquired with a Sony NEX-5 camera and its firmware. The objectives were 10×, 20× and 40×. For microscopy investigations slides with a fixed distance of 0.1 mm between the slide and the cover glass were used. The size of the 4×4 grids is 1 mm×1 mm and corresponds to 0.1 µl.

1,8-ANS Fluorescence Spectroscopy 1-anilinonaphthalene-8-sulfonic acid (1,8-ANS) is an uncharged small hydrophobic fluorescent probe (Mw 299.34 Da) used to study both membrane surfaces and proteins.

1,8-ANS is essentially non-fluorescent in water and only becomes appreciably fluorescent when bound to membranes (quantum yields ~0.25) or proteins (quantum yields ~0.7). This property of 1,8-ANS makes it a sensitive indicator of protein folding, conformational changes and other processes that modify the exposure of the probe to water. References on 1,8-ANS can be found on the Internet home page of Molecular Probes, www.probes.com.

The fluorescence emission spectra of 1,8-ANS were recorded using a FluoroMax spectrometer. A direct comparison of the 1,8-ANS fluorescence between IgGs will not be performed. Each IgG can have different number of 1,8-ANS binding sites and can therefore not be compared. In principle, the lower the 1,8-ANS fluorescence, the less 1,8-ANS molecules are bound to the antibody. The changes in the 1,8-ANS fluorescence intensity and emission wavelength due to stress will be evaluated.

Taken together, these data indicate that the various IgG samples are remarkably stable. Severe stress conditions (e.g. 2 days at 50° C.) were needed to generate measurable differences between the tested samples. Under these conditions, samples of combinations #9 and #10 seem to aggregate more than other samples.

The most discriminating factors for stability between the proteins are the freeze-thaw cycles and increased temperature. Taking into account the very stringent stress factor of incubating at 50° C., the T366K/L351E,Y349E (combi.#4) and T366K,L351K/L351D,Y349E (combi.#11) variants are the two most stable proteins within panel, closely followed by T366K,L351K/L351D,Y349D (combi.#10) and T366K, L351K/L351D,L368E (combi.#12).

Example 21

Native MS on Ratio Experiments; Transfection Ratio's from 1:5 to 5:1

To become more knowledgeable about the behavior of the CH3 mutated IgGs in skewed transfection mixtures, in particular about the T366K:L351K/L351D':L368E' combination (from now on dubbed KK/DE or DEKK), a more elaborate ratio experiment was conducted.

Figure 23:
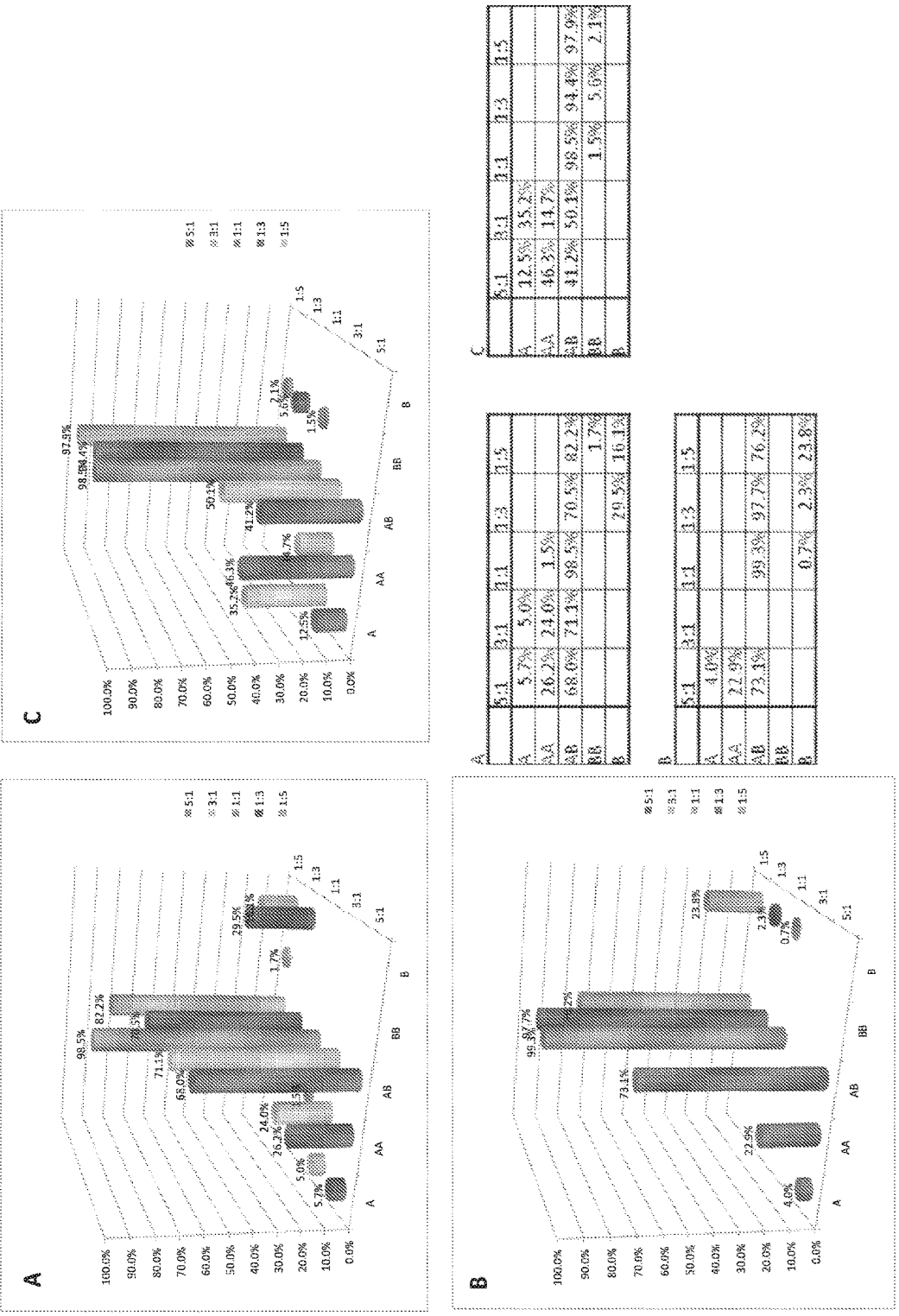
FIG. 23: nMS results of ratio experiments with transfection ratios from 1:5 to 5:1. A) DEKK combination of mutations, with specificity 'A' on the DE-side and 'B' on the KK-side; B) DEKK combination of mutations, with specificity 'C' on the DE-side and B' on the KK-side; C) charge reversal combination of mutations, with specificity 'A' on the E356K:D399K-side and 'B' on the K392D:K409D-side

Previously used antibody VH regions with known ability to pair with the common light chain IGKV1-39 were used for recloning into constructs 1, 2, 68 and 69, resulting in vectors I-V of Table 16. Vectors I-V, each containing nucleic acid sequences encoding the common human light chain as well as an Ig heavy chain with different CH3 region and different antigen specificity, were subsequently transfected into cells with different transfection ratios as indicated in Table 17. Results are shown in FIG. 23.

TABLE 17

| Vector | VH gene | Antigen specificity | VH mass (Da) | Merus designation | Cloned in construct # |
|---|---|---|---|---|---|
| I | IGHV 3.30 | Fibrinogen (A) | 12794 | MF1122 | 69 (L351D, L368E) |
| II | IGHV 3.23 | RSV (C) | 13941 | MF2729 | 69 (L351D, L368E) |
| III | IGHV 1.08 | Tetanus (B) | 13703 | MF1337 | 68 (T366K, L351K) |
| IV | IGHV 3.30 | Fibrinogen (A) | 12794 | MF1122 | 1 (E356K, D399K) |
| V | IGHV 1.08 | Tetanus (B) | 13703 | MF1337 | 2 (K392D, K409D) |

TABLE 18

| Transfection nr | vectors | ratio |
|---|---|---|
| 1 | I and III | 5:1 |
| 2 | I and III | 3:1 |
| 3 | I and III | 1:1 |
| 4 | I and III | 1:3 |
| 5 | I and III | 1:5 |
| 6 | II and III | 5:1 |

TABLE 18-continued

| Transfection nr | vectors | ratio |
|---|---|---|
| 7 | II and III | 3:1* |
| 8 | II and III | 1:1 |
| 9 | II and III | 1:3 |
| 10 | II and III | 1:5 |
| 11 | IV and V | 5:1 |
| 12 | IV and V | 3:1 |
| 13 | IV and V | 1:1 |
| 14 | IV and V | 1:3 |
| 15 | IV and V | 1:5 |

*due to a technical error, this sample has not been measured.

FIGS. 23A and B show that for the DEKK combination of mutations, when an excess of A or C is present (A or C are on the 'DE side' and B is on the 'KK side'), AB or BC is formed but the surplus of A or C is present as a mixture of both homodimers and half bodies in all cases. However, when an excess of B is present (B is on the 'KK side' and A or C are on the 'DE side'), there is a clear difference. AB or BC is still formed but the surplus of B is essentially absent as homodimer and only half bodies are formed. Percentages were again measured by peak height Nota bene: peaks detected in the range of 2% or lower are below the threshold of what the nMS technology as applied can accurately measure. Measurements of <2% are therefore regarded to be within the noise level of analysis and therefore ignored. It is striking that the excess of B results in high percentages of half body B only. Especially at the 1:3 and 1:5 ratios of A:B, high percentages of half body B were observed (FIGS. 23A and 23B) in the absence of homodimer BB, indicating that the CH3 mutations of the KK-side disfavour homodimerization. The absence of homodimers offers a crucial advantage, as this 'KK side' of the DEKK combination can be chosen to incorporate a specificity that may have known adverse effects when present as a homodimer (for example cMET or CD3 antibodies are known to have undesired adverse side effects when present as bivalent homodimers in therapeutic compositions).

The observed findings for the different ratios of DE:KK are in contrast to the control charge reversal CH3 mutations in vectors IV and V. FIG. 23C shows that for the E356K: D399K/K392D':K409D' combination of mutations when an excess of A is present (A is on the 'K392D:K409D side'), the surplus of A is present as a mixture of both homodimers and half bodies in all cases, but also when an excess of B is present (B is on the 'E356K:D399K side'), the surplus of B is present as a mixture of both homodimers and half bodies in all cases. Even at the higher ratios 1:3 and 1:5 no half bodies B are observed although homodimers are present, indicating that the E356K:D399K side does not disfavour homodimerization as much as the KK-side of the DEKK combination.

Taken together, the DEKK combination of mutations offers a clear benefit over the charge reversal CH3 mutations, in that one of the chains of the heterodimer does not form homodimers.

Example 22

Varieties of Mixtures Using the DEKK Combination

As it was demonstrated that the DEKK combination of mutations drives the formation of bispecific IgG molecules ('AB') with high purity, we next explored the feasibility of controlled production of more complex antibody mixtures from one cell, such as 'AB and AA' or 'AB and AC' mixtures. Previously used model Fabs were incorporated in vectors that contain either the 'DE construct' or the 'KK construct' and various combinations of these vectors were co-expressed to create mixtures, to demonstrate the versatility of the technology. Model Fabs MF1337 (tetanus toxoid), MF1122 (fibrinogen) and MF1025 (thyroglobulin) were chosen based on their overall stable behaviour, good expression levels and mass differences between the IgGs containing these Fabs (see Table 18)

TABLE 19

| Specificity | Fab name | IgG mass | Δ-mass MF1122 |
|---|---|---|---|
| Tetanus (A) | (MF)*1337 | 146747.03 | +1842.05 |
| Fibrinogen (B) | (MF)1122 | 144904.98 | 0 |
| Thyroglobulin (C) | (MF)1025 | 144259.87 | −645.11 |

*MF = Merus Fab, designations such as MF1337 and 1337 are both used interchangeably.

TABLE 20

Transfection schedule:

| Tr. # | Heavy chain 1 | Heavy chain 2 | Heavy chain 3 | Tr. ratio | Expected species (%) | Observed species (%) |
|---|---|---|---|---|---|---|
| 1 | 1337-KK | 1122-DE | 1025-DE | 2:1:1 | AB (50%) AC (50%) | AB (43%) AC (57%) |
| 2 | 1337-DE | 1122-KK | 1025-KK | 2:1:1 | AB (50%) AC (50%) | AB (40%) AC (54%) AA (6%) |
| 3 | 1337-KK | 1122-DE | 1025-KK | 1:2:1 | AB (50%) BC (50%) | AB (54%) BC (46%) |
| 4 | 1337-KK | 1122-KK | 1025-DE | 1:1:2 | AC (50%) BC (50%) | AC (66%) BC (33%) CC (1%) |
| 5 | 1337-KK | 1337-DE | 1122-DE | 2:1:1 | AA (50%) AB (50%) | AA (57%) AB (43%) |
| 6 | 1337-KK | 1122-KK | 1122-DE | 1:1:2 | AB (50%) BB (50%) | AB (75%) BB (25%) |
| 7 | 1337-KK | 1337-DE | 1025-DE | 2:1:1 | AA (50%) AC (50%) | AA (46%) AC (54%) |
| 8 | 1337-KK | 1025-KK | 1025-DE | 1:1:2 | AC (50%) CC (50%) | AC (60%) CC (40%) |
| 9 | 1337-KK | 1122-DE | | 1:1 | AB (100%) | AB (>98%) |
| 10 | 1337-KK | 1025-DE | | 1:1 | AC (100%) | AC (>98%) |
| 11 | 1122-KK | 1025-DE | | 1:1 | BC (100%) | AC (>98%) |

SDS-PAGE analysis demonstrated that most samples consisted of predominantly full IgGs and in some cases half bodies were present at small percentages. Furthermore, many of the samples showed two bands at ca. 150 kDa on non-reduced gels, reflecting the presence of two distinct IgG species in the sample. Also on the reduced gels, two heavy chain bands were visible in some samples (data not shown).

Figure 24:
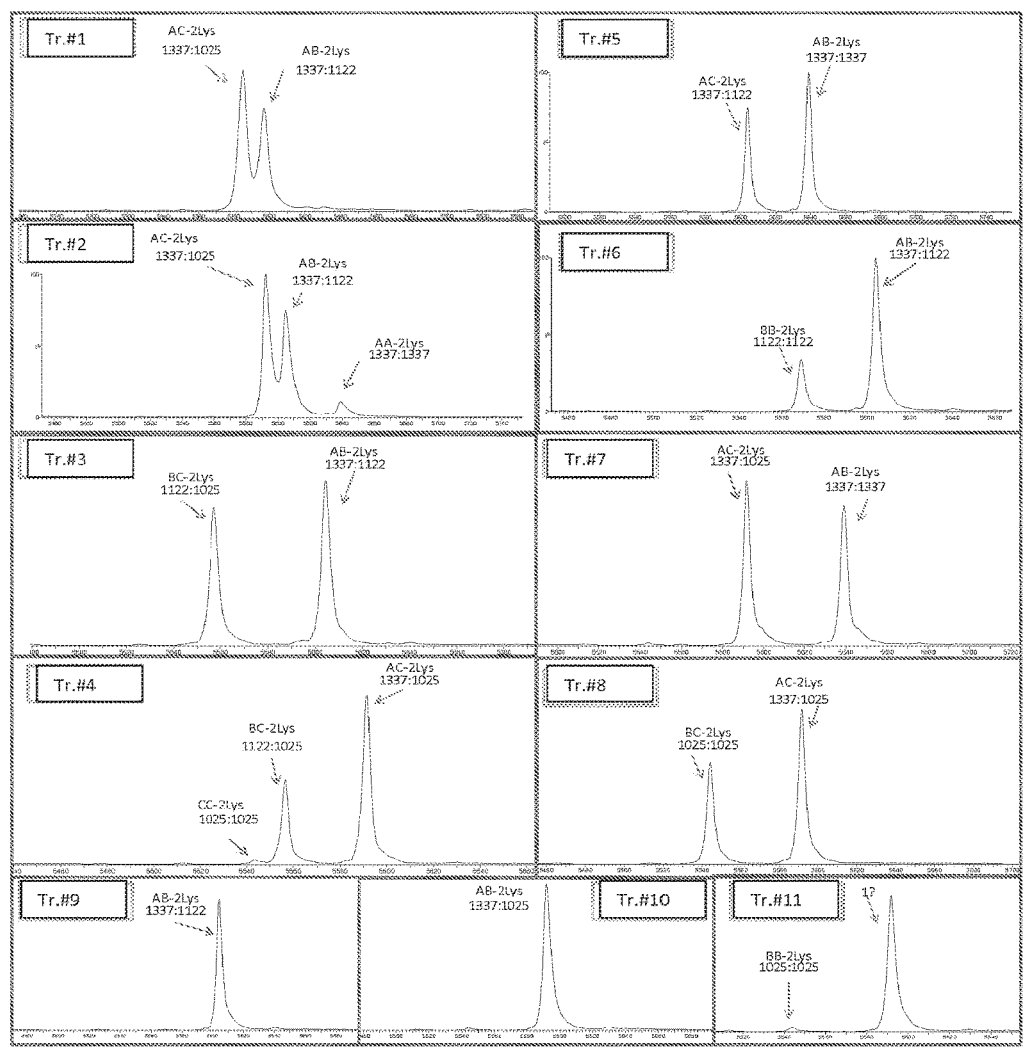
FIG. 24: nMS results of transfections #1-11 from Table 20.

Native MS was performed on all samples and the percentages of observed species were calculated based on peak height (% of observed species in Table 19). Results are presented in FIG. 24. In all eight samples where three heavy chains were co-expressed, two main peaks were observed which corresponded to the expected species. In two of these samples (transfections 2 and 4), and in transfection 11, a small amount of contaminating DE-DE homodimer was observed. Half bodies were detected in very small amounts in most of the samples (less than 2%), which are not problematic as they can be easily separated from the full length IgG fraction as discussed previously. After nMS it was discovered that the observed mass of the IgG in sample 11 corresponded to a different species than expected, and it was concluded that this was due to an transfection error, i.e. in sample 11 apparently 1025-DE was co-transfected with 1337-KK instead of 1122-KK.

The IgG samples were further tested in a sandwich ELISA to confirm the functional presence of the desired specificities. Coating of ELISA plates was done with fibrinogen or thyroglobulin and detection was performed with fluorescein-labelled thyroglobulin or—tetanus toxoid. The detection antigens were labelled with fluorescein (Pierce NHS-fluorescin Antibody Labeling kit, cat. #53029) according to the manufacturer's instructions. Fluorescein-labeled antigens could subsequently be detected by a FITC-conjugated anti-fluorescein antibody (Roche diagnostics, cat. #11426346910). Results of the bispecific ELISA (0D450 values) are summarized in FIG. 31. The greyed cells indicate the expected species for each transfection. Generally, the results meet the expected outcome with view exceptions as indicated in italic or bold. In transfections 1-3, the supposed 'negative' well for species BC (tr. #1 and 2) or AC (tr.#3) demonstrated a significant background signal. It is known from previous studies that bispecific ELISAs may suffer from high background levels. These background levels may also be caused by the potential presence of half-bodies in the sample. Of note is that the results of bispecific ELISA indeed confirmed that an error had occurred in transfection #11, as the species AC (bold value) was detected rather than BC.

Example 23

Improved Mixtures of Two Bispecific Antibodies Recognizing 4 Different Epitopes (AB and CD) from a Single Cell In example 12 it was hypothesized that mixtures resulting from transfections ZA or ZB are expected to become problematic when transferred to larger scale production, as knob-into-hole variants are reported to be unstable and it cannot be excluded that CH3 domains comprising a 'knob' or a 'hole' will dimerize with charge-engineered CH3 domains. As it was demonstrated in the above examples that novel charge pair mutants have been found that preferentially drive heterodimerization with virtually no formation of homodimers, CH3 domain-comprising polypeptide chains comprising these novel charge pair mutants can be expressed in cells together with previously known charge-engineered CH3 domain-comprising polypeptide chains or potentially with SEED bodies, and are likely to result in the preferential formation of two bispecific molecules only.

From the above examples it was clear that the DEKK combination of mutations is excellent for the production of one bispecific (AB) or two bispecifics (AB plus AC) by clonal cells where dimerization of the heavy chains is driven by the CH3 domains. However, using only one vector set of complementary CH3 mutations limits the number of possibilities of mixture-varieties that can be produced. It would be possible to produce more complex mixtures of IgGs and/or bispecifics, such as 'AB and CD' or 'AB and CC' mixtures if a second 'orthogonal' vector set could be used in combination with DEKK. When combining two vector sets, an important requirement is that the heavy chains expressed from the two different sets of CH3 engineered vectors cannot make 'crossed' dimers, which is that the heavy chains produced by one of the vector sets dimerize into full IgG with heavy chains expressed by the other vector set.

To test for such potential formation of 'crossed' dimers, an in silico analysis was performed using HADDOCK to obtain further insights whether possible pairing between wildtype CH3 domains and CH3 domains containing DE-or KK-mutations would occur. Similarly, potential pairings between wildtype CH3 domains and CH3 domains containing E356K,D399K or K392D,K409D mutations were analyzed, as well as potential pairings between wildtype CH3 domains and CH3 domains containing knob-into-hole mutations and any combination of the above. Combinations of CH3-mutants that were analyzed in HADDOCK are listed in Table 22 and the resulting HADDOCK scores are summarized in FIG. 25.

TABLE 22

CH3 variants analyzed in HADDOCK, with one letter codes for assigned for each CH3-variant carrying heavy chain.

| CH3 combination | Mutations | One letter code in HADDOCK |
| --- | --- | --- |
| DEKK | Chain 1: T366K, L351K | A |
|  | Chain 2: L351D, L368E | B |
| Wildtype (WT) | Chain 1: none | C* |
|  | Chain 2: none | D* |
| Charge reversal | Chain 1: K392D, K409D | A/C** |
| (CR) | Chain 2: E356K, D399K | B/D** |
| Knob-into-hole | Chain 1: T366W | C |
| (KIH) | Chain 2: T366S, L368A, Y407V | D |

*Wildtype chains are designated 'C' and 'D' for matters of consistency;
**The charge reversal variants are designated 'A and B' when combined with knob-into-hole variants, and are designated 'C and D' when combined with DE/KK variants.

Figure 25:
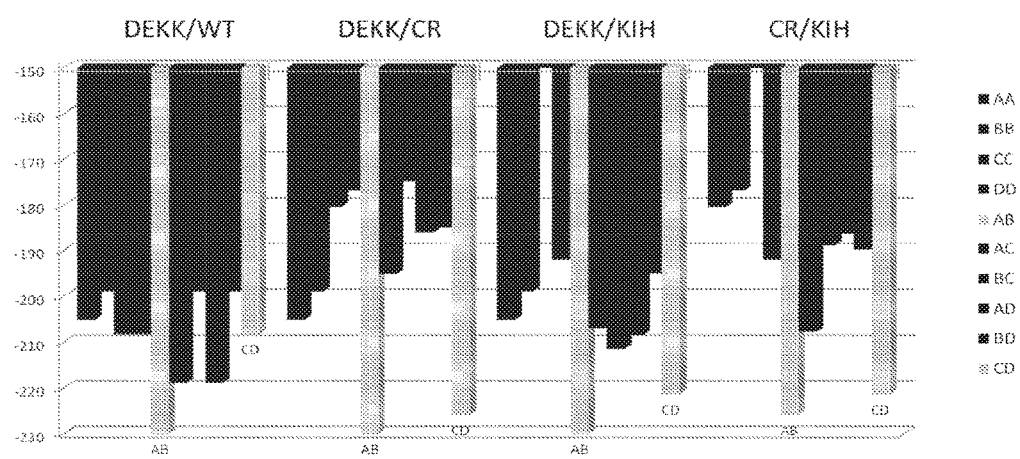
FIG. 25: HADDOCK scores for dimers with different CH3 engineered vectors. Grey bars: Desired species AB and CD; black bars: undesired species AA, BB, CC, DD, AC, BC, AD, BD.

FIG. 25 shows that, based on these HADDOCK predictions, combining the CH3 combinations of DEKK with charge reversal CH3 combinations is most likely to be successful in forming the desired combination of two bispecifics (AB and CD) without contaminating by-products (especially AC, AD, BC, BD) when co-transfected in a single cell. As can be seen from FIG. 25, these undesired bispecific species AC, AD, BC, and BD have relatively high HADDOCK scores, whereas the desired AB and CD species have the lowest HADDOCK scores. Of course, when either the CH3 combinations of DEKK or charge reversal will be put into a construct carrying the same specificity (e.g. 'C' on the DE-side, 'C' on the KK-side, 'A' on the E356K,D399K-side and 'B' on the E356K,D399K-side, or 'A' on the DE-side, 'B' on the KK-side, 'C' on the E356K,D399K-side and 'C' on the E356K,D399K-side) this will result in the production of predominantly CC and AB upon co-expression in a cell.

In contrast, when looking at the predictions for co-expressing DEKK with wildtype, it can be seen that the HADDOCK scores for AC and AD are lower than the HADDOCK score for CD, which indicates that AC and AD are very likely contaminants when trying to produce a mixture of AB and CD by co-expression of vectors encoding for CH3 combinations of DEKK together with vectors encoding wildtype CH3. Lastly, the predictions for co-expressing either DEKK or charge reversal variants together with the knob-into-hole variants results in undesired bispecific variants with relatively low HADDOCK scores, i.e. a high likelihood that these undesired species will be produced upon co-expression.

the heavy chains produced by one of the vector sets dimerize into full IgG with heavy chains expressed by the other vector set. To test for such potential formation of 'crossed' dimers between heavy chains containing charge reversal mutations and heavy chains containing DE or KK mutations, control transfections were performed.

TABLE 24

| Tr. # | 1st VH/ construct # | 2nd VH/ construct # | Expected species |
|---|---|---|---|
| 1 | D/68 | A/68 | mismatch 'KK' with 'KK'; Mostly half-bodies expected |
| 2 | D/68 | A/69 | match 'KK' with 'DE'; AD product expected |
| 3 | D/68 | A/1 | Expected mismatch 'KK' with 'E356K:D399K' |
| 4 | D/68 | A/2 | Expected mismatch 'KK' with 'K392D:K409D' |
| 5 | D/69 | A/68 | match 'DE' with 'KK'; AD product expected |
| 6 | D/69 | A/69 | mismatch 'DE' with 'DE'; mixture of half-bodies, AA, AD and DD expected |
| 7 | D/69 | A/1 | Expected mismatch 'DE' with 'E356K:D399K' |
| 8 | D/69 | A/2 | Expected mismatch 'DE' with 'K392D:K409D' |

| Tr. # | 1st VH/ construct # | 2nd VH/ construct # | 3rd VH/ construct # | 4th VH/ construct # | Expected species |
|---|---|---|---|---|---|
| 9 | A/68 | B/69 | C/1 | D/2 | AB and CD |
| 10 | A/68 | A/69 | C/1 | D/2 | AA and CD |
| 11 | A/68 | B/69 | C/1 | C/2 | AB and CC |

It is thus concluded that combining the CH3 combinations of DEKK with charge reversal CH3 combinations (E356K, D399K/K392'D,K409D') is ideally suited for obtaining essentially pure 'AB and CD' and/or 'AB and CC' mixtures of antibodies.

Next, mixtures of 2 bispecifics recognizing 4 targets/epitopes (AB and CD) and mixtures of one bispecific and 1 monospecific antibody recognizing 3 targets/epitopes (AB and CC) were created by putting the above into practice. These mixtures were created using 4 different VHs that are all capable of pairing with the common light chain IGVK1-39, but the individual VH/VL combinations all have different specificities. To enable native MS analysis, the mass difference between the (expected) species has to be sufficient, i.e. >190 Da. Four individual VHs have been selected and the masses of these were such that the expected species upon co-transfection could be identified and separated by nMS. Furthermore, the mass differences between the 4 selected VHs are also large enough to identify most of the possible contaminants in the mixtures, in addition to the two desired species. Selected VHs are listed in Table 21.

TABLE 23

| VH (target) | Mass as wt IgG |
|---|---|
| A (RTK1) | 146736.78 |
| B (Tetanus toxoid) | 146106.20 |
| C (Fibrinogen) | 144904.98 |
| D (RTK2) | 145421.37 |

The 4 different VHs were cloned into vectors containing the 'DE' or 'KK' constructs or the charge reversal constructs, and several co-transfections were performed as indicated in Table 22. NB: as always, all vectors also contained the nucleic acid encoding the common light chain IGKV1-39. As previously indicated, when combining two vector sets, an important requirement is that the heavy chains expressed from the two different sets of CH3 engineered vectors cannot make 'crossed' dimers, which is that FIG. 32 provides a further overview of masses of the expected species, and the possible contaminants, of transfections #9-11 of Table 22.

Figure 26:
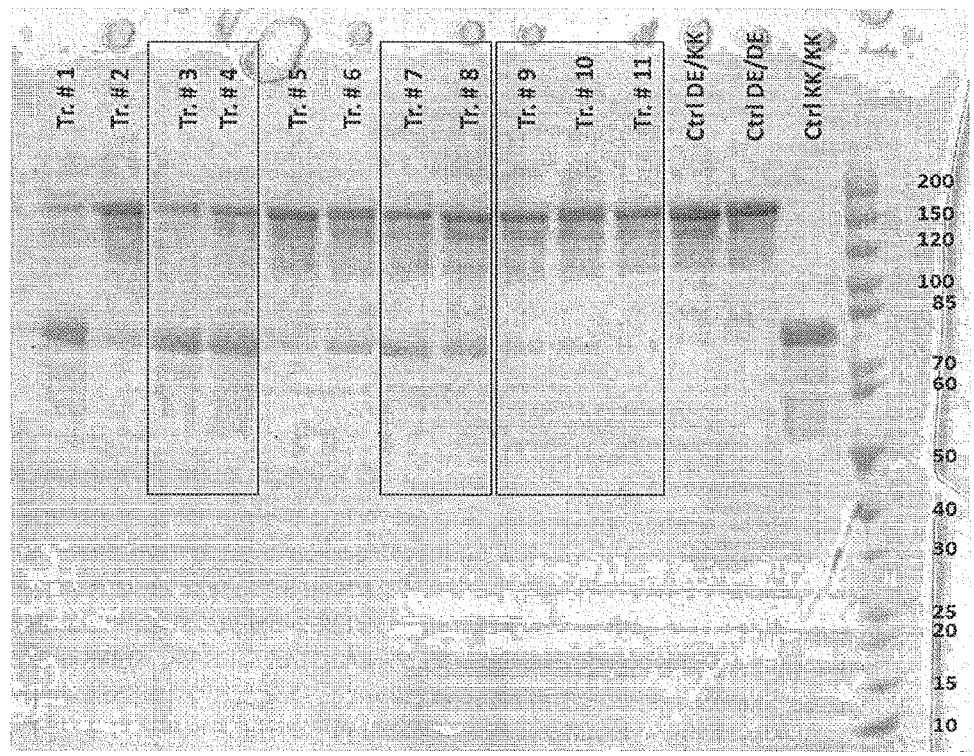
FIG. 26: SDS-PAGE of transfections #1-11 from Table 20. Control samples DE/KK, DE/DE and KK/KK are also included.

All purified protein samples obtained from transfections #1-11 were analyzed on SDS-PAGE, and three control samples were included (FIG. 26). In addition, nMS analysis was performed on protein samples from transfections #9-11 to identify all species in the samples. As can be seen from FIG. 26, transfections #3 and #4 resulted in the expected mismatch between 'KK' constructs and either 'E356K:D399K' or 'K392D:K409D' and the amount of half bodies in protein samples from these transfections exceeded the amount of full IgG molecules. Transfections #7 and #8 resulted in protein samples wherein both half bodies and full IgG is present in about equal amounts. However, from SDS-PAGE it cannot be deduced whether the full IgG represents a DE/DE dimer, a DE/E356K:D399K dimer or a DE/K392D:K409D dimer Remarkably, virtually no half bodies were observed in samples from transfections #9-11.

Figure 27A:
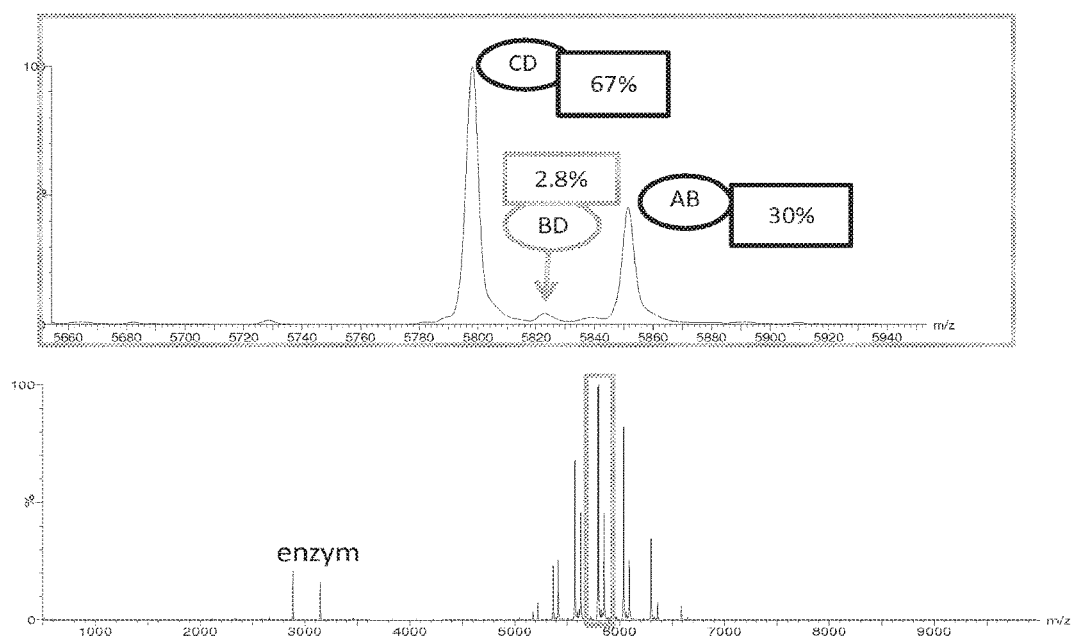
FIG. 27: nMS of transfections #9 (A) and #11 (B).

In FIG. 27, the nMS analysis of transfections #9 and #11 are presented. Percentages of expected species and contaminating species were calculated by peak height. It was demonstrated that, for transfection #9, the expected species 'AB and CD' are represented for 97% in the mixture (30% AB and 67% CD) whereas only as little of about 3% of contaminating BD is present (FIG. 27A). For transfection #11, the expected species 'AB and CC' are represented for 94% in the mixture (33% AB and 61% CC) whereas only as little of about 6% of contaminating BC (4.1%) and AC (1.8%) is present (FIG. 27B). These data show that it is indeed possible to produce more complex mixtures of IgGs and/or bispecifics, such as 'AB and CD' or 'AB and CC' mixtures when a second 'orthogonal' vector set is used in combination with DEKK. Combination of the charge reversal constructs together with the DEKK constructs results in only very limited formation of 'crossed' dimers. By adjusting the transfection ratio's it is expected that the low percentages of these contaminating by-products can be even further reduced.

Example 24

Single Dose Pharmacokinetic Study in Mice

To study the pharmacokinetic (pK) behavior of bispecific antibodies carrying the DEKK combination of mutations in their CH3 regions, in this study the pK parameters for three different IgG batches were determined and compared.

The three IgG batches included 1) wildtype anti-tetanus toxoid parental antibody 1337:1337 (two MF1337 Fabs on a wildtype Fc backbone); 2) wildtype anti-tetanus toxoid parental antibody 1516:1516 (two MF1516 Fabs on a wildtype Fc backbone); 3) CH3 engineered bispecific anti-tetanus toxoid antibody 1516:1337 that carries the DEKK combination of mutations in its Fc region (MF1516 Fab on DE-side, MF1337 Fab on KK-side).

The parental antibodies 1337:1337 and 1516:1516 were chosen as specificities to be included in the DEKK-bispecific product, as it was known based on previous studies that no pre-dose serum response against these antibodies was present in several mice strains. NB: the presence of a pre-dose serum response would of course invalidate the study. In addition, there is sufficient mass difference between the parental antibodies to enable the identification of 1337:1337 (wt Fc), 1516:1337 (DEKK Fc) and 1516:1516 (wt Fc) species by nMS. The three IgG batches were prepared as previously described, but the DNA used for transfection was made using an endo-free maxiprep kit to ensure that the amount of endotoxins is as low as possible. The batches were subsequently tested for protein concentration, aggregate levels, endotoxin levels and percentage bispecific product. It was demonstrated that the acceptance criteria for subsequent use of the IgG batches in a pK study were met, i.e. the IgG concentration after gel filtration was >0.3 mg/ml, aggregate levels were <5%, endotoxin levels were <3 EU/mg protein and the DEKK batch contained >90% bispecific IgG.

Figure 28:
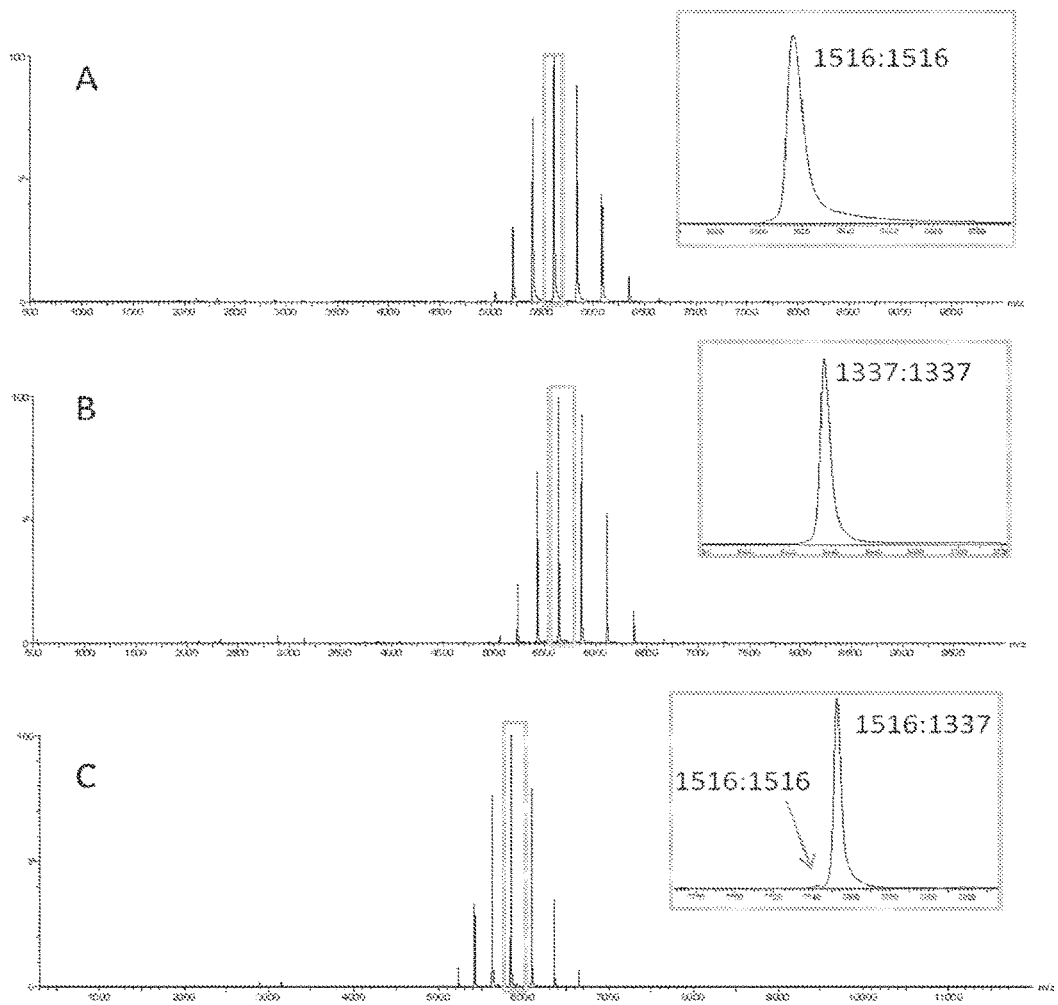
FIG. 28: nMS of gel filtrated samples 1516:1516 (A), 1337:1337 (B) and 1516:1337 (C).

Native mass spectrometry of the gel filtrated samples showed that the expected species were present in high percentages. In sample 1516:1337 a small amount of the DE:DE homodimer is detected, which is estimated to be ca. 2% (FIG. 28). It was concluded that the 3 IgG batches are qualified to be used in the pK study.

For comparison of pK parameters between the three batches, 3 groups of female C57BL/6J mice (Harlan, The Netherlands) were dosed at 1 mg/kg human IgG (5 ml/kg immunoglobulin solution/kg body weight). At dosing time, the animals were between 7-8 weeks of age and had a body weight of about 18-20 grams. Blood samples were collected pre-dose and at 15, 60 minutes, and 2, 4, 8, 24, 48, 96, 168, 268 and 336 h after dosing. Serum samples were prepared and stored at <−20° C. until analysis. Each group consisted of 3 subgroups of 4 mice, i.e. 12 mice/group. From each mice 6 time points were sampled. The welfare of the animals was maintained in accordance with the general principles governing the use of animals in experiments of the European Communities (Directive 86/609/EEC) and Dutch legislation (The Experiments on Animals Act, 1997). This study was also performed in compliance with the Standards for Humane Care and Use of Laboratory Animals, as issued by the Office of Laboratory Animal Welfare of the U.S. National Institutes of Health under identification number 45859-01 (expiration date: 30 Apr. 2015).

Mice of Group 1 received the full length monospecific IgG 1516:1516 antibody (triangles); Mice of Group 2 received the full length monospecific IgG 1337:1337 antibody (squares); Mice of Group 3 received the full length bispecific IgG 1516:1337 antibody (diamonds), with DEKK engineered CH3 regions (1516 on the DE-side and 1337 on the KK-side).

Figure 29:
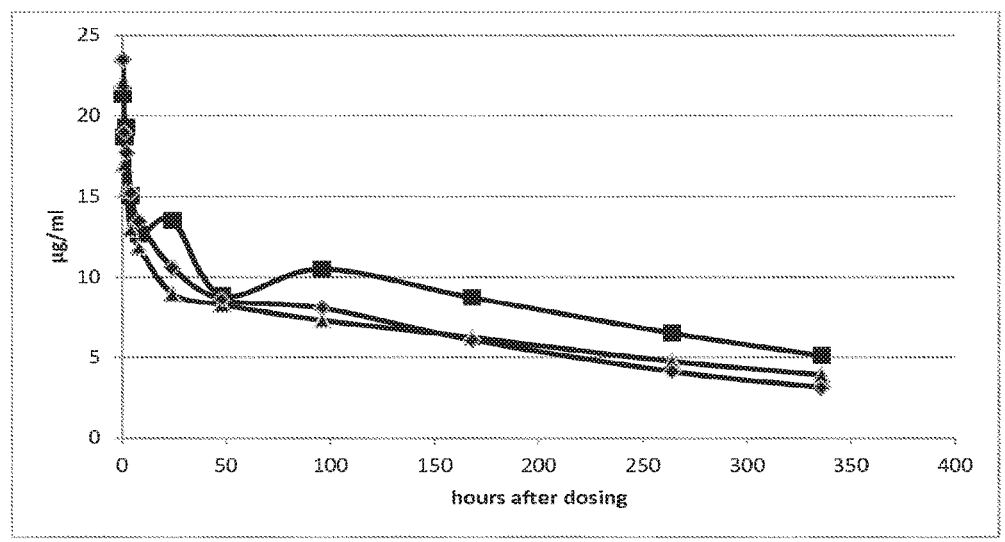
FIG. 29: serum levels of samples of DEKK engineered antibody and its two parental antibodies (pK study).

An ELISA assay was applied for the quantitative analysis of monoclonal human antibodies in mouse serum using a quantitative human IgG ELISA (ZeptoMetrix, NY USA; ELISA kit nr. 0801182). Briefly, the ELISA assay is based on the principle that the human monoclonal antibody binds to anti-human IgG coated in a 96-wells ELISA plate. Bound antibody was subsequently visualized using a polyclonal antihuman IgG antibody conjugated with horseradish peroxidase (HRP). The optical density (OD) of each well is directly proportional to the amount of antibody in the serum sample. Results are shown in FIG. 29, and it was observed that serum levels of both the bispecific full length IgG antibody carrying the DEKK combination of mutations and its parental monospecific antibodies are strikingly similar. It is concluded that the CH3 mutations as present in the DEKK-bispecific antibody does not alter stability nor half life, and the DEKK variant is behaving as wildtype IgG.

REFERENCES

Deisenhofer J., Biochemistry 1981 (20)2361-2370;
Miller S., J. Mol. Biol. 1990 (216)965-973;
Padlan, Advances in Protein Chemistry 1996 (49) 57-133
Ellerson J R., et al., J. Immunol 1976 (116) 510-517;
Lee and Richards J. Mol. Biol. 1971 (55)379.
Gunasekaran et al J. Biol. Chem. 2010 (285)19637-19646
De Vries Nature Protocols 2010 (5)883
Kabat et al, (1991)
Mammalian Cell Biotechnology: a Practical Approach (M. Butler, ed., IRL Press, 1991
Merchant Nature biotechnology 1998 (16)677
Ridgeway Protein Engineering 1996 (9)617-621.
Davis J H. Et al., Protein Engineering, Design & Selection 2010 (23)195-202
Papadea and Check. Crit Rev Clin Lab Sci. 1989; 27 (1):27-58.
Tissue Culture, Academic Press, Kruse and Paterson, editors (1973)
Ionescu et al., J. Pharm. Sci. 2008 (97)1414)
Current protocols in Protein Science 1995, coligan J E et al., Wingfield P T, ISBN 0-471-11184-8, Bendig 1988.
Capelle, M. A. H., Brugger, P., Arvinte, T. Vaccine 23 (2005), 1686-1694.
Demeule, B., Lawrence, M. J., Drake, A. F., Gurny, R., Arvinte, T. Biochim. Biophys. Acta 1774 (2007a), 146-153.
Demeule, B., Gurny, R., Arvinte, T., Int. J. Pharm 329 (2007b), 37-45.
Lakowicz, J. R., Principles of fluorescence spectroscopy; Second Edition Kluwer Academic/Plenum Publishers, New York, Boston, Dordrecht, London, Moscow, (2006) ISBN 0-306-46093-9.

The invention claimed is:

1. A method of producing at least two different antibodies in a single host cell, the method comprising:
a. providing a host cell comprising:
(i) a first nucleic acid molecule encoding a $1^{st}$ antibody heavy chain comprising at least one substitution of a neutral amino acid residue in the CH3 domain by a positively charged amino acid residue,
(ii) a second nucleic acid molecule encoding a $2^{nd}$ antibody heavy chain comprising at least one substitution of a neutral amino acid residue in the CH3 domain by a negatively charged amino acid residue,
(iii) a third nucleic acid molecule encoding a $3^{rd}$ antibody heavy chain, and
(iv) a fourth nucleic acid molecule encoding a $4^{th}$ antibody heavy chain;
b. culturing the host cell and allowing for expression of the four nucleic acid molecules to produce the $1^{st}$ antibody heavy chain, the $2^{nd}$ antibody heavy chain, the $3^{rd}$ antibody heavy chain and the $4^{th}$ antibody heavy chain, wherein the CH3 domain of the $1^{st}$ antibody heavy chain preferentially pairs with the CH3 domain of the $2^{nd}$ antibody heavy chain, and the CH3 domain of the $3^{rd}$ antibody heavy chain preferentially pairs with the CH3 domain of the $4^{th}$ antibody heavy chain to produce antibodies containing the $1^{st}$ and $2^{nd}$ antibody heavy chains and the $3^{rd}$ and $4^{th}$ antibody heavy chains; and
c. harvesting the at least two different antibodies from the culture.

2. The method of claim 1, further comprising providing the host cell with a nucleic acid molecule encoding a common light chain.

3. The method of claim 1, wherein the $1^{st}$ antibody heavy chain comprises a substitution of the amino acid residue at position 366 in the CH3 domain according to the EU numbering system by a lysine (K) residue, and wherein the $2^{nd}$ antibody heavy chain comprises a substitution of the amino acid residue at position 351 in the CH3 domain according to the EU numbering system by an aspartic acid (D) residue.

4. The method of claim 3, wherein the CH3-domain of the $1^{st}$ antibody heavy chain further comprises a substitution of the amino acid residue at position 351 according to the EU numbering system by a lysine (K) residue.

5. The method of claim 4, wherein the CH3 domain of the $2^{nd}$ antibody heavy chain further comprises amino acid substitution(s) selected from the group consisting of
(i) a substitution of the amino acid residue at position 349 according to the EU numbering system by a glutamic acid (E) residue;
(ii) a substitution of the amino acid residue at position 349 according to the EU numbering system by an aspartic acid (D) residue;
(iii) a substitution of the amino acid residue at position 368 according to the EU numbering system by a glutamic acid (E) residue;
(iv) a substitution of the amino acid residue at position 349 according to the EU numbering system by an aspartic acid (D) residue, and a substitution of the amino acid residue at position 368 according to the EU numbering system by a glutamic acid (E) residue; and
(v) substitution of the amino acid residues at positions 349 and 355 according to the EU numbering system by aspartic acid (D) residues.

6. The method of claim 5, wherein the CH3 domain of the $2^{nd}$ antibody heavy chain comprises the substitution of the amino acid residue at position 368 according to the EU numbering system by a glutamic acid (E) residue.

7. The method of claim 1, wherein the CH3 domain of the $1^{st}$ antibody heavy chain comprises substitutions of the amino acid residues at positions 366 and 351 according to the EU numbering system by a lysine (K) residue, and the CH3 domain of the $2^{nd}$ antibody heavy chain comprises a substitution of the amino acid residue at position 351 according to the EU numbering system by an aspartic acid (D) residue and a substitution of the amino acid residue at position 368 according to the EU numbering system by a glutamic acid (E) residue.

8. The method of claim 1, wherein the CH3 domain of the $3^{rd}$ antibody heavy chain comprises the substitution of the amino acid residue at position 356 according to the EU numbering system by a lysine (K) reside and the substitution of the amino acid residue at position 399 according to the EU numbering system by a lysine (K) residue, and the $4^{th}$ antibody heavy chain comprises the substitution of the amino acid residue at position 392 according to the EU numbering system by an aspartic acid (D) residue, and the substitution of the amino acid residue at position 409 according to the EU numbering system by an aspartic (D) residue.

9. The method of claim 1, wherein at least two of the variable regions of the $1^{st}$, $2^{nd}$, $3^{rd}$ and $4^{th}$ antibody heavy chains recognize different target epitopes.

10. The method of claim 1, wherein each of the variable regions of the $1^{st}$, $2^{nd}$, $3^{rd}$ and $4^{th}$ antibody heavy chains recognize different target epitopes.

11. The method of claim 9, wherein the variable regions of the $1^{st}$ and the $2^{nd}$ antibody heavy chains recognize different target epitopes, whereas the variable regions of the $3^{rd}$ and the $4^{th}$ antibody heavy chains recognize the same target epitope.

12. The method of claim 9, wherein the target epitope recognized by the variable regions of the $3^{rd}$ and $4^{th}$ antibody heavy chain is the same as one of the target epitopes recognized by the variable region of the $1^{st}$ or the $2^{nd}$ antibody heavy chain.

13. The method of claim 11, wherein the target epitope recognized by the variable regions of the $3^{rd}$ and $4^{th}$ antibody heavy chain is different from the target epitope recognized by the variable region of the $1^{st}$ or the $2^{nd}$ antibody heavy chain.

14. The method of claim 1, wherein the variable regions of the $1^{st}$ and the $2^{nd}$ antibody heavy chains recognize the same target epitope, whereas the variable regions of the $3^{rd}$ and the $4^{th}$ antibody heavy chains recognize a second target epitope which differs from the target epitope recognized by the $1^{st}$ and $2^{nd}$ variable regions.

15. The method of claim 9, wherein the at least two different target epitopes are located on the same target molecule.

16. The method of claim 15, wherein the target molecule is a soluble molecule.

17. The method of claim 15 wherein the target molecule is a membrane-bound molecule.

18. The method of claim 9, wherein the at least two different target epitopes are located on different target molecules.

19. The method of claim 18, wherein the different target molecules are expressed on the same cells.

20. The method of claim 18, wherein the different target molecules are expressed on different cells.

21. The method of claim 18, wherein the different target molecules are soluble molecules.

22. The method of claim 18, wherein one target molecule is a soluble molecule whereas the second target molecule is a membrane bound molecule.

23. The method of claim 1, wherein
  a. the CH3 domain of the $3^{rd}$ and $4^{th}$ antibody heavy chains are both wild type;
  b. the CH3 domain of the $3^{rd}$ antibody heavy chain comprises a substitution of the amino acid residues at positions 356 and 399 according to the EU numbering system by a lysine (K) residue, and the CH3 domain of the $4^{th}$ antibody heavy chain comprises a substitution of the amino acid residues at positions 392 and 409 according to the EU numbering system by an aspartic acid (D) residue;
  c. the CH3 domain of the $3^{rd}$ antibody heavy chain comprises a substitution of the amino acid residues at positions 356 and 399 according to the EU numbering system by a lysine (K) residue, and the CH3 domain of the $4^{th}$ antibody heavy chain comprises a substitution of the amino acid residues at positions 392, 409 and 439 according to the EU numbering system by an aspartic acid (D) residue;
  d. the CH3 domain of the $3^{rd}$ antibody heavy chain comprises a substitution of the amino acid residues at positions 392 and 409 according to the EU numbering system by an aspartic acid (D) residue and a substitution of the amino acid residue at position 399 according to the EU numbering system by a lysine (K) residue, and the CH3 domain of the $4^{th}$ antibody heavy chain comprises a substitution of the amino acid residues at positions 392 and 409 according to the EU numbering system by an aspartic acid (D) residue and a substitution of the amino acid residue at position 399 according to the EU numbering system by a lysine (K) residue;
  e. the CH3 domain of the $3^{rd}$ antibody heavy chain comprises a substitution of the amino acid residues at position 356 and 357 according to the EU numbering system by a lysine (K) residue, and a substitution of the amino acid residues at position 439 and 370 according to the EU numbering system by an aspartic acid (D) residue, and the CH3 domain of the $4^{th}$ antibody heavy chain comprises a substitution of the amino acid residues at position 356 and 357 according to the EU numbering system by a lysine (K) residue, and a substitution of the amino acid residues at position 439 and 370 according to the EU numbering system by an aspartic acid (D) residue; or
  f. the CH3 domain of the $3^{rd}$ antibody heavy chain comprises a substitution of the amino acid residue at position 366 according to the EU numbering system by a tryptophan (W) residue, and the CH3 domain of the $4^{th}$ antibody heavy chain comprises a substitution of the amino acid residue at position 366 according to the EU numbering system by a serine (S) residue, a substitution of the amino acid residue at position 368 according to the EU numbering system by an alanine (A) residue and a substitution of the amino acid residue at position 407 according to the EU numbering system by a valine (V) residue.

24. The method of claim 9, wherein at least one of the target epitopes is located on a tumor cell.

25. The method of claim 9, wherein at least one of the target epitopes is located on an effector cell.

26. The method of claim 25, wherein the effector cell is an NK cell, a T cell, a B cell, a monocyte, a macrophage, a dendritic cell or a neutrophilic granulocyte.

27. The method of claim 25, wherein the target epitope is located on a CD3, CD16, CD25, CD28, CD64, CD89, NKG2D or a NKp46 molecule.

28. A mixture of at least two different antibodies obtained by the method of claim 1.

29. The mixture of claim 28, wherein the at least two different antibodies bind to different epitopes on the same antigen.

30. The mixture of claim 28, wherein the mixture comprises at least one heterodimeric antibody.

31. The mixture of claim 28, wherein two of the at least two different antibodies are heterodimeric antibodies.

32. A recombinant host cell comprising nucleic acids encoding:
  (i) a first nucleic acid molecule encoding a $1^{st}$ antibody heavy chain comprising at least one substitution of a neutral amino acid residue in the CH3 domain by a positively charged amino acid residue,
  (ii) a second nucleic acid molecule encoding a $2^{nd}$ antibody heavy chain comprising at least one substitution of a neutral amino acid residue in the CH3 domain by a negatively charged amino acid residue,
  (iii) a third nucleic acid molecule encoding a $3^{rd}$ antibody heavy chain, and
  (iv) a fourth nucleic acid molecule encoding a $4^{th}$ antibody heavy chain,
wherein expression of the $1^{st}$, $2^{nd}$, $3^{rd}$ and $4^{th}$ antibody heavy chains results in preferential pairing of the $1^{st}$ antibody heavy chain with the $2^{nd}$ antibody heavy chain, and preferential pairing of the $3^{rd}$ antibody heavy chain with the $4^{th}$ antibody heavy chain.

33. The recombinant host cell of claim 32, wherein the $1^{st}$ antibody heavy chain comprises a substitution of the amino acid residue at position 366 in the CH3 domain according to the EU numbering system by a lysine (K) residue, and wherein the $2^{nd}$ antibody heavy chain comprises a substitution of the amino acid residue at position 351 in the CH3 domain according to the EU numbering system by an aspartic acid (D) residue.

34. The recombinant host cell of claim 32, wherein the host cell further comprises a nucleic acid sequence encoding a common light chain.

35. A pharmaceutical composition comprising of the mixture of claim 28, and a pharmaceutically acceptable carrier.

36. A method for making a host cell which produces at least two different antibodies, the method comprising the step of introducing into the host cell nucleic acids encoding a $1^{st}$ antibody heavy chain comprising at least one substitution of a neutral amino acid residue in the CH3 domain by a positively charged amino acid residue, a $2^{nd}$ antibody heavy chain comprising at least one substitution of a neutral amino acid residue in the CH3 domain by a negatively charged amino acid residue, a $3^{rd}$ antibody heavy chain and a $4^{th}$ antibody heavy chain, wherein the nucleic acids are introduced consecutively or concomitantly, and wherein expression of the $1^{st}$, $2^{nd}$, $3^{rd}$ and $4^{th}$ antibody heavy chains in the host cell results in preferential pairing of the $1^{st}$ antibody heavy chain with the $2^{nd}$ antibody heavy chain, and preferential pairing of the $3^{rd}$ antibody heavy chain with the $4^{th}$ antibody heavy chain.

37. The method of claim 36, further comprising the step of introducing into the host cell a nucleic acid sequence encoding a common light chain.

38. The method of claim 36, wherein the $1^{st}$ antibody heavy chain comprises a substitution of the amino acid residue at position 366 in the CH3 domain according to the EU numbering system by a lysine (K) residue, and wherein the $2^{nd}$ antibody heavy chain comprises a substitution of the amino acid residue at position 351 in the CH3 domain according to the EU numbering system by an aspartic acid (D) residue.

39. The method of claim 1, wherein at least 90% of the antibodies produced comprising the $1^{st}$ antibody heavy chain further comprise the $2^{nd}$ antibody heavy chain, and at least 90% of the antibodies produced comprising the $3^{rd}$ antibody heavy chain further comprise the $4^{th}$ antibody heavy chain.

40. The method of claim 1, wherein the $1^{st}$ and $2^{nd}$ antibody heavy chains are IgG.

41. The method of claim 40, wherein the $1^{st}$ and $2^{nd}$ antibody heavy chains are IgG1.

42. The method of claim 1, wherein the $3^{rd}$ and $4^{th}$ antibody heavy chains are IgG.

43. The method of claim 42, wherein the $3^{rd}$ and $4^{th}$ antibody heavy chains are IgG1.

* * * * *